United States Patent
Parsy et al.

(10) Patent No.: US 9,284,307 B2
(45) Date of Patent: Mar. 15, 2016

(54) MACROCYCLIC SERINE PROTEASE INHIBITORS

(75) Inventors: Christophe Claude Parsy, Jacou (FR); Francois-Rene Alexandre, Montpellier (FR); Frederic Leroy, Montarnaud (FR); Thierry Convard, Sathonay-Camp (FR); Dominique Surleraux, Wauthier-Braine (BE)

(73) Assignee: Idenix Pharmaceuticals LLC, Cambridge, MA (US)

( * ) Notice: Subject to any disclaimer, the term of this patent is extended or adjusted under 35 U.S.C. 154(b) by 764 days.

(21) Appl. No.: 12/850,534

(22) Filed: Aug. 4, 2010

(65) Prior Publication Data
US 2011/0129443 A1 Jun. 2, 2011

Related U.S. Application Data

(60) Provisional application No. 61/231,636, filed on Aug. 5, 2009.

(51) Int. Cl.
| | |
|---|---|
| *A61K 31/4709* | (2006.01) |
| *A61K 38/21* | (2006.01) |
| *A61P 31/14* | (2006.01) |
| *C07D 417/14* | (2006.01) |
| *C12N 5/00* | (2006.01) |
| *C12N 7/06* | (2006.01) |
| *C12N 9/99* | (2006.01) |
| *A61K 31/403* | (2006.01) |

(52) U.S. Cl.
CPC ............ *C07D 417/14* (2013.01); *A61K 31/403* (2013.01); *A61K 31/4709* (2013.01)

(58) Field of Classification Search
CPC . A61K 31/403; A61K 31/4079; C07D 417/14
See application file for complete search history.

(56) References Cited

U.S. PATENT DOCUMENTS

| | | | |
|---|---|---|---|
| 5,538,865 A | 7/1996 | Reyes et al. |
| 5,990,276 A | 11/1999 | Zhang et al. |
| 6,004,933 A | 12/1999 | Spruce et al. |
| 6,143,715 A | 11/2000 | Llinas-Brunet et al. |
| 6,265,380 B1 | 7/2001 | Tung et al. |
| 6,268,207 B1 | 7/2001 | Bailey |
| 6,323,180 B1 | 11/2001 | Llinas-Brunet et al. |
| 6,329,379 B1 | 12/2001 | Llinas-Brunet et al. |
| 6,329,417 B1 | 12/2001 | Llinas-Brunet et al. |
| 6,410,531 B1 | 6/2002 | Llinas-Brunet et al. |
| 6,420,380 B2 | 7/2002 | Llinas-Brunet et al. |
| 6,448,281 B1 | 9/2002 | Beaulieu et al. |
| 6,479,508 B1 | 11/2002 | Beaulieu et al. |
| 6,534,523 B1 | 3/2003 | Llinas-Brunet et al. |
| 6,608,027 B1 | 8/2003 | Tsamtzops et al. |
| 6,642,204 B2 | 11/2003 | Llinas-Brunet et al. |
| 6,653,295 B2 | 11/2003 | Glunz et al. |
| 6,727,366 B2 | 4/2004 | Han et al. |
| 6,767,991 B1 | 7/2004 | Llinas-Brunet et al. |
| 6,794,404 B2 | 9/2004 | Beaulieu et al. |
| 6,838,475 B2 | 1/2005 | Arasappan et al. |
| 6,841,566 B2 | 1/2005 | Beaulieu et al. |

(Continued)

FOREIGN PATENT DOCUMENTS

| | | |
|---|---|---|
| CA | 2370400 | 8/2003 |
| DE | 19914474 | 10/1999 |

(Continued)

OTHER PUBLICATIONS

Attwood et al., "The Design and Synthesis of Potent Inhibitors of I Iepatitis C Virus NS3-4A Proteinase," *Antiviral Chemistry and Chemotherapy* 1999, vol. 10, pp. 259-273.

(Continued)

*Primary Examiner* — Suzanne Ziska
*Assistant Examiner* — Thurman Wheeler
(74) *Attorney, Agent, or Firm* — John C. Todaro; Keith D. MacMillan

(57) ABSTRACT

Provided herein are macrocyclic serine protease inhibitor compounds, for example, of Formula Ia or Ib, pharmaceutical compositions comprising the compounds, and processes of preparation thereof. Also provided are methods of their use for the treatment of an HCV infection in a host in need thereof.

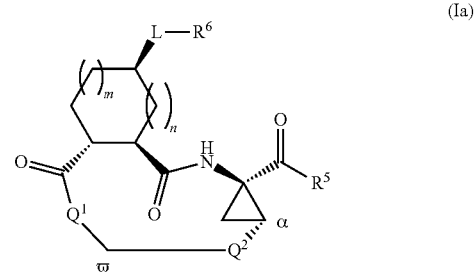

(Ia)

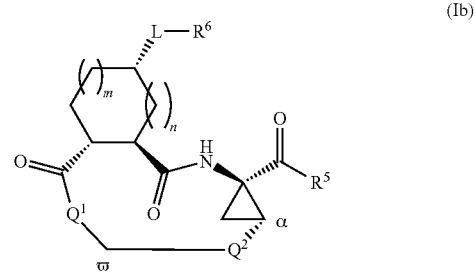

(Ib)

18 Claims, No Drawings

(56) References Cited

U.S. PATENT DOCUMENTS

| | | |
|---|---|---|
| 6,846,802 B2 | 1/2005 | Chen et al. |
| 6,867,185 B2 | 3/2005 | Campbell et al. |
| 6,869,964 B2 | 3/2005 | Campbell et al. |
| 6,872,805 B2 | 3/2005 | Campbell et al. |
| 6,878,722 B2 | 4/2005 | Campbell et al. |
| 6,908,901 B2 | 6/2005 | Bailey et al. |
| 6,911,428 B2 | 6/2005 | Zhu et al. |
| 6,919,423 B2 | 7/2005 | Llinas-Brunet et al. |
| 6,995,174 B2 | 2/2006 | Wang et al. |
| 7,012,066 B2 | 3/2006 | Saksena et al. |
| 7,041,698 B2 | 5/2006 | Ripka et al. |
| 7,091,184 B2 | 8/2006 | Llinas-Brunet et al. |
| 7,109,344 B2 | 9/2006 | Arlt |
| 7,119,072 B2 | 10/2006 | Llinas-Brunet et al. |
| 7,125,845 B2 | 10/2006 | Wu et al. |
| 7,132,504 B2 | 11/2006 | Scola et al. |
| 7,135,462 B2 | 11/2006 | Scola et al. |
| 7,148,347 B2 | 12/2006 | Brandenburg et al. |
| 7,169,760 B2 | 1/2007 | Saksena et al. |
| 7,173,004 B2 | 2/2007 | McPhee et al. |
| 7,176,208 B2 | 2/2007 | Nakajima et al. |
| 7,183,302 B2 | 2/2007 | Romine et al. |
| 7,183,374 B2 | 2/2007 | Brenner et al. |
| 7,189,844 B2 | 3/2007 | Gallou et al. |
| 7,208,600 B2 | 4/2007 | Cottrell et al. |
| 7,253,160 B2 | 8/2007 | Njoroge et al. |
| 7,268,211 B2 | 9/2007 | Gallou et al. |
| 7,273,851 B2 | 9/2007 | Miao et al. |
| 7,309,708 B2 | 12/2007 | Tu et al. |
| 7,323,447 B2 | 1/2008 | Sin et al. |
| 7,351,825 B2 | 4/2008 | Inaba et al. |
| 7,368,452 B2 | 5/2008 | Nakajima et al. |
| RE40,525 E | 9/2008 | Llinas-Brunet et al. |
| 7,439,258 B2 | 10/2008 | Beaulieu et al. |
| 7,442,695 B2 | 10/2008 | Njoroge et al. |
| 7,449,479 B2 | 11/2008 | Wang et al. |
| 7,449,591 B2 | 11/2008 | Brenner et al. |
| 7,470,664 B2 | 12/2008 | Holloway et al. |
| 7,482,501 B2 | 1/2009 | Leitner et al. |
| 7,491,794 B2 | 2/2009 | Blatt et al. |
| 7,504,378 B2 | 3/2009 | Llinas-Brunet et al. |
| 7,511,157 B2 | 3/2009 | Bailey et al. |
| 8,003,659 B2 | 8/2011 | Parsy et al. |
| 8,377,962 B2 | 2/2013 | Parsy et al. |
| 2002/0016294 A1 | 2/2002 | Venkatraman et al. |
| 2002/0016442 A1 | 2/2002 | Llinas-Brunet et al. |
| 2002/0032175 A1 | 3/2002 | Tung et al. |
| 2002/0037998 A1 | 3/2002 | Llinas-Brunet et al. |
| 2002/0065418 A1 | 5/2002 | Beaulieu et al. |
| 2002/0111313 A1 | 8/2002 | Campbell et al. |
| 2003/0181363 A1 | 9/2003 | Llinas-Brunet et al. |
| 2003/0186895 A1 | 10/2003 | Llinas-Brunet et al. |
| 2003/0187018 A1 | 10/2003 | Llinas-Brunet et al. |
| 2003/0191067 A1 | 10/2003 | Llinas-Brunet et al. |
| 2003/0224977 A1 | 12/2003 | Llinas-Brunet et al. |
| 2003/0232816 A1 | 12/2003 | Beaulieu et al. |
| 2003/0236251 A1 | 12/2003 | Beaulieu et al. |
| 2004/0002448 A1 | 1/2004 | Tsantrizos et al. |
| 2004/0033959 A1 | 2/2004 | Chen et al. |
| 2004/0038872 A1 | 2/2004 | Campbell et al. |
| 2004/0048802 A1 | 3/2004 | Ripka et al. |
| 2004/0072761 A1 | 4/2004 | Campbell et al. |
| 2004/0077551 A1 | 4/2004 | Campbell et al. |
| 2004/0106559 A1 | 6/2004 | Wang et al. |
| 2004/0110126 A1 | 6/2004 | Kukolj et al. |
| 2004/0180815 A1 | 9/2004 | Nakajima et al. |
| 2004/0224900 A1 | 11/2004 | Bailey et al. |
| 2004/0224955 A1 | 11/2004 | Beaulieu et al. |
| 2004/0229777 A1 | 11/2004 | Cerreta et al. |
| 2004/0229818 A1 | 11/2004 | Llinas-Brunet et al. |
| 2004/0248779 A1 | 12/2004 | Dersch et al. |
| 2004/0266668 A1 | 12/2004 | Nakajima et al. |
| 2005/0020503 A1 | 1/2005 | Llinas-Brunet et al. |
| 2005/0049187 A1 | 3/2005 | Brandenburg et al. |
| 2005/0065073 A1 | 3/2005 | Wu et al. |
| 2005/0069522 A1 | 3/2005 | Colonno et al. |
| 2005/0075279 A1 | 4/2005 | Llinas-Brunet et al. |
| 2005/0080005 A1 | 4/2005 | Llinas-Brunet et al. |
| 2005/0090432 A1 | 4/2005 | McPhee et al. |
| 2005/0090450 A1 | 4/2005 | Farmer et al. |
| 2005/0096364 A1 | 5/2005 | Romine et al. |
| 2005/0119453 A1 | 6/2005 | Brenner et al. |
| 2005/0137140 A1 | 6/2005 | Cottrell et al. |
| 2005/0143316 A1 | 6/2005 | Tu et al. |
| 2005/0143580 A1 | 6/2005 | Arlt |
| 2005/0153877 A1 | 7/2005 | Miao et al. |
| 2005/0154186 A1 | 7/2005 | Gallou et al. |
| 2005/0164921 A1 | 7/2005 | Njoroge et al. |
| 2005/0176648 A1 | 8/2005 | Saksena et al. |
| 2005/0187165 A1 | 8/2005 | Scola et al. |
| 2005/0192212 A1 | 9/2005 | Llinas-Brunet et al. |
| 2005/0209135 A1 | 9/2005 | Busacca et al. |
| 2005/0215423 A1 | 9/2005 | Brenner et al. |
| 2005/0261200 A1 | 11/2005 | Miao et al. |
| 2005/0267018 A1 | 12/2005 | Blatt et al. |
| 2005/0267040 A1 | 12/2005 | Scola et al. |
| 2005/0267151 A1 | 12/2005 | Busacca et al. |
| 2006/0009667 A1 | 1/2006 | Herweck et al. |
| 2006/0019905 A1 | 1/2006 | Bailey et al. |
| 2006/0046956 A1 | 3/2006 | Sannigrahi et al. |
| 2006/0046965 A1 | 3/2006 | Bailey et al. |
| 2006/0063915 A1 | 3/2006 | Gallou et al. |
| 2006/0089300 A1 | 4/2006 | Llinas-Brunet et al. |
| 2006/0122123 A1 | 6/2006 | Chaudhary et al. |
| 2006/0172950 A1 | 8/2006 | Wang et al. |
| 2006/0183694 A1 | 8/2006 | Sin et al. |
| 2006/0199773 A1 | 9/2006 | Sausker et al. |
| 2006/0199826 A1 | 9/2006 | Inaba et al. |
| 2006/0252951 A1 | 11/2006 | Leitner et al. |
| 2006/0258868 A1 | 11/2006 | Bailey et al. |
| 2007/0010455 A1 | 1/2007 | Hewawasam et al. |
| 2007/0021330 A1 | 1/2007 | Wu et al. |
| 2007/0021351 A1 | 1/2007 | White et al. |
| 2007/0027071 A1 | 2/2007 | Holloway et al. |
| 2007/0049536 A1 | 3/2007 | Venkatraman et al. |
| 2007/0054842 A1 | 3/2007 | Blatt et al. |
| 2007/0060510 A1 | 3/2007 | Nakajima et al. |
| 2007/0060565 A1 | 3/2007 | Meanwell et al. |
| 2007/0072809 A1 | 3/2007 | Cho et al. |
| 2007/0078081 A1 | 4/2007 | Casarez et al. |
| 2007/0078122 A1 | 4/2007 | Bergstrom et al. |
| 2007/0078130 A1 | 4/2007 | Ansorge et al. |
| 2007/0093414 A1 | 4/2007 | Carini et al. |
| 2007/0093430 A1 | 4/2007 | Chen et al. |
| 2007/0099825 A1 | 5/2007 | D'Andrea et al. |
| 2007/0099929 A1 | 5/2007 | Thede et al. |
| 2007/0105781 A1 | 5/2007 | Lyons et al. |
| 2007/0161574 A1 | 7/2007 | Rosenquist et al. |
| 2007/0161575 A1 | 7/2007 | Miao et al. |
| 2007/0161789 A1 | 7/2007 | Cottrell et al. |
| 2007/0179167 A1 | 8/2007 | Cottrell et al. |
| 2007/0203072 A1 | 8/2007 | Rosenquist et al. |
| 2007/0237818 A1 | 10/2007 | Alton et al. |
| 2007/0243166 A1 | 10/2007 | Llinas-Brunet et al. |
| 2007/0249637 A1 | 10/2007 | Collins et al. |
| 2007/0258947 A1 | 11/2007 | Njoroge et al. |
| 2007/0265281 A1 | 11/2007 | Cottens et al. |
| 2007/0281884 A1 | 12/2007 | Sun et al. |
| 2007/0281885 A1 | 12/2007 | Sun et al. |
| 2007/0299078 A1 | 12/2007 | Niu et al. |
| 2008/0008681 A1 | 1/2008 | Niu et al. |
| 2008/0014173 A1 | 1/2008 | Scola et al. |
| 2008/0019942 A1 | 1/2008 | Seiwert et al. |
| 2008/0032936 A1 | 2/2008 | Gai et al. |
| 2008/0038225 A1 | 2/2008 | Sun et al. |
| 2008/0039375 A1 | 2/2008 | Moore et al. |
| 2008/0039470 A1 | 2/2008 | Niu et al. |
| 2008/0045530 A1 | 2/2008 | Brandl et al. |
| 2008/0107623 A1 | 5/2008 | D'Andrea et al. |
| 2008/0107624 A1 | 5/2008 | D'Andrea et al. |
| 2008/0107625 A1 | 5/2008 | D'Andrea et al. |
| 2008/0108632 A1 | 5/2008 | Lin et al. |
| 2008/0119461 A1 | 5/2008 | Sin et al. |
| 2008/0125444 A1 | 5/2008 | Sun et al. |

(56) References Cited

U.S. PATENT DOCUMENTS

| | | |
|---|---|---|
| 2008/0145334 A1 | 6/2008 | Wang et al. |
| 2008/0152619 A1 | 6/2008 | Sin et al. |
| 2008/0152622 A1 | 6/2008 | Nakajima et al. |
| 2008/0159982 A1 | 7/2008 | Wang et al. |
| 2008/0177029 A1 | 7/2008 | Busacca et al. |
| 2008/0181868 A1 | 7/2008 | Sun et al. |
| 2008/0187516 A1 | 8/2008 | Sun et al. |
| 2008/0200497 A1 | 8/2008 | Bailey et al. |
| 2008/0200503 A1 | 8/2008 | Simmen et al. |
| 2008/0242835 A1 | 10/2008 | Shu |
| 2008/0261994 A1 | 10/2008 | Inaba et al. |
| 2008/0262058 A1 | 10/2008 | Simmen et al. |
| 2008/0267916 A1 | 10/2008 | Gai et al. |
| 2008/0267917 A1 | 10/2008 | Niu et al. |
| 2008/0267918 A1 | 10/2008 | Gai et al. |
| 2008/0269228 A1 | 10/2008 | Moore et al. |
| 2008/0269502 A1 | 10/2008 | Gantz et al. |
| 2008/0274080 A1 | 11/2008 | Or et al. |
| 2008/0274082 A1 | 11/2008 | Gai et al. |
| 2008/0279821 A1 | 11/2008 | Niu et al. |
| 2008/0286233 A1 | 11/2008 | Sun et al. |
| 2008/0287449 A1 | 11/2008 | Niu et al. |
| 2008/0292587 A1 | 11/2008 | Sun et al. |
| 2008/0306258 A1 | 12/2008 | Inaba et al. |
| 2008/0311077 A1 | 12/2008 | Chaudhary et al. |
| 2008/0317712 A1 | 12/2008 | Niu et al. |
| 2009/0005387 A1 | 1/2009 | Niu et al. |
| 2009/0023758 A1 | 1/2009 | Wahling et al. |
| 2009/0035267 A1 | 2/2009 | Moore et al. |
| 2009/0035268 A1 | 2/2009 | Sun et al. |
| 2009/0035271 A1 | 2/2009 | Sun et al. |
| 2009/0035272 A1 | 2/2009 | Moore et al. |
| 2009/0041721 A1 | 2/2009 | Niu et al. |
| 2009/0047244 A1 | 2/2009 | Parsy et al. |
| 2009/0047248 A1 | 2/2009 | Sun et al. |
| 2009/0047252 A1 | 2/2009 | Cai et al. |
| 2009/0048297 A1 | 2/2009 | Phadke et al. |
| 2009/0062311 A1 | 3/2009 | Simmen et al. |
| 2009/0075869 A1 | 3/2009 | Holloway et al. |
| 2009/0082261 A1 | 3/2009 | Chen et al. |
| 2009/0111969 A1 | 4/2009 | Blatt et al. |
| 2009/0111982 A1 | 4/2009 | Blatt et al. |
| 2009/0123425 A1 | 5/2009 | Moore et al. |
| 2009/0130059 A1 | 5/2009 | Sun et al. |
| 2009/0148407 A1 | 6/2009 | Blatt et al. |
| 2009/0149491 A1 | 6/2009 | Liu et al. |
| 2009/0156800 A1 | 6/2009 | Wagaw et al. |
| 2009/0169510 A1 | 7/2009 | Blatt et al. |
| 2009/0175822 A1 | 7/2009 | Moore et al. |
| 2009/0180981 A1 | 7/2009 | Niu et al. |
| 2009/0202480 A1 | 8/2009 | Parsy et al. |
| 2010/0260710 A1 | 10/2010 | Parsy et al. |
| 2011/0129443 A1 | 6/2011 | Parsy et al. |
| 2012/0207703 A1 | 8/2012 | Parsy et al. |

FOREIGN PATENT DOCUMENTS

| | | |
|---|---|---|
| EP | 1881002 | 1/2008 |
| WO | WO 98/17679 | 4/1998 |
| WO | WO 98/22496 | 5/1998 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/04425 | 1/2002 |
| WO | WO 02/08187 | 1/2002 |
| WO | WO 02/08198 | 1/2002 |
| WO | WO 02/08251 | 1/2002 |
| WO | WO 02/08256 | 1/2002 |
| WO | WO 02/48116 | 6/2002 |
| WO | WO 02/48157 | 6/2002 |
| WO | WO 02/48172 | 6/2002 |
| WO | WO 02/060926 | 8/2002 |
| WO | WO 02/070739 | 9/2002 |
| WO | WO 03/007945 | 1/2003 |
| WO | WO 03/053349 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/014313 | 2/2004 |
| WO | WO 2004/014852 | 2/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/089974 | 10/2004 |
| WO | WO 2004/092203 | 10/2004 |
| WO | WO 2004/093798 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/053735 | 6/2005 |
| WO | WO 2005/053843 | 6/2005 |
| WO | WO 2005/054430 | 6/2005 |
| WO | WO 2005/056182 | 6/2005 |
| WO | WO 2005/058884 | 6/2005 |
| WO | WO 2005/070955 | 8/2005 |
| WO | WO 2005/073195 | 8/2005 |
| WO | WO 2005/073216 | 8/2005 |
| WO | WO 2005/075502 | 8/2005 |
| WO | WO 2005/090383 | 9/2005 |
| WO | WO 2005/095403 | 10/2005 |
| WO | WO 2005/116054 | 12/2005 |
| WO | WO 2006/000085 | 1/2006 |
| WO | WO 2006/005479 | 1/2006 |
| WO | WO 2006/007700 | 1/2006 |
| WO | WO 2006/007708 | 1/2006 |
| WO | WO 2006/020276 | 2/2006 |
| WO | WO 2006/026352 | 3/2006 |
| WO | WO 2006/033851 | 3/2006 |
| WO | WO 2006/043145 | 4/2006 |
| WO | WO 2006/075021 | 7/2006 |
| WO | WO 2006/086381 | 8/2006 |
| WO | WO 2006/119061 | 11/2006 |
| WO | WO 2006/122188 | 11/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/011658 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015855 | 2/2007 |
| WO | WO 2007/016441 | 2/2007 |
| WO | WO 2007/017144 | 2/2007 |
| WO | WO 2007/025307 | 3/2007 |
| WO | WO 2007/030656 | 3/2007 |
| WO | WO 2007/044933 | 4/2007 |
| WO | WO 2007/056120 | 5/2007 |
| WO | WO 2007/015824 | 8/2007 |
| WO | WO 2007/088571 | 8/2007 |

(56) References Cited

FOREIGN PATENT DOCUMENTS

| | | |
|---|---|---|
| WO | WO 2007/120595 | 10/2007 |
| WO | WO 2007/121124 | 10/2007 |
| WO | WO 2007/121125 | 10/2007 |
| WO | WO 2007/131966 | 11/2007 |
| WO | WO 2007/143694 | 12/2007 |
| WO | WO 2007/145894 | 12/2007 |
| WO | WO 2007/146695 | 12/2007 |
| WO | WO 2007/148135 | 12/2007 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | 2008002924 A2 | 3/2008 |
| WO | WO 2008/033389 | 3/2008 |
| WO | WO 2008/125594 | 4/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/070733 | 6/2008 |
| WO | WO 2008/086161 | 7/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106058 | 9/2008 |
| WO | WO 2008/106130 | 9/2008 |
| WO | WO 2008/106139 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/005676 | 1/2009 |
| WO | WO 2009/005677 | 1/2009 |
| WO | WO 2009/005690 | 1/2009 |
| WO | WO 2009/010804 | 1/2009 |
| WO | WO 2009/014730 | 1/2009 |
| WO | WO 2009/042668 | 4/2009 |
| WO | WO 2009/053828 | 4/2009 |
| WO | WO 2009/058856 | 5/2009 |
| WO | WO 2009/073713 | 6/2009 |
| WO | WO 2009/073780 | 6/2009 |
| WO | WO 2009/080542 | 7/2009 |
| WO | WO 2009/082697 | 7/2009 |
| WO | WO 2009/082701 | 7/2009 |
| WO | WO 2009/085978 | 7/2009 |
| WO | 2009/099596 | 8/2009 |
| WO | 2010/090976 | 8/2010 |
| WO | WO 2010/090976 | 8/2010 |
| WO | 2011017389 A1 | 10/2011 |

OTHER PUBLICATIONS

Boyer et al., "Pathogenesis, Diagnosis and Management of Hepatitis C," *J. Hepatol.* 2000, vol. 32(Suppl. 1), pp. 98-112.
Chaloin et al., "Synthesis of Enantiopure Di(*tert*-butyl))(2S,4S)-4-hydroxy-6-oxo-1,2-piperidinedicarboxylate. A Useful Building Block for the Preparation of 4-Hydroxypipecolate Derivatives," *Organic Synthesis* 2008, vol. 85, p. 147.
Chu et al., "Isolation and Structure of Sch 351633: A Novel Hepatitis C Virus (HCV) NS3 Protease Inhibitor from the Fungus," *Bioorganic and Medicinal Chemistry Letters* 1999, vol. 9, pp. 1949-1952.
Chu et al., "Structure of Sch 68631: A New Hepatitis C Virus Proteinase Inhibitor from *Streptomyces* sp.," *Tetrahedron Letters* 1996, vol. 37, pp. 7229-7232.
Di Besceglie et al., "The Unmet Challenges of Hepatitis C," *Scientific American* 1999, vol. 281, pp. 80-85.
Fried et al., "Peginterferon alfa-2a Plus Ribavirin for Chronic Hepatitis C Virus Infection," *N. Engl. J. Med.* 2002, vol. 347, pp. 975-982.
Fliche et al., "Enantioselective Synthesis of (1R,2S) and (1S,2S) Dehydrocoronamic Acids," *Synthetic Communications* 1994, vol. 24, pp. 2873-2876.
Hadziyannis et al., "Peginterferon-α2a and Ribavirin Combination Therapy in Chronic Hepatitis C," *Ann. Intern. Med.* 2004, vol. 140, pp. 346-355.
Hays et al., "Synthesis of Cis-4-(phosphonooxy)-2-piperidinecarboxylic acid, an N-Methyl-D-aspartate Antagonist," *J. Org. Chem.* 1991, vol. 56, pp. 4084-4086.
Kakiuchi, et al., "Non-peptide Inhibitors of HCV Serine Proteinase," *FEBS Lett.* 1998, vol. 421, pp. 217-220.
Kato et al., "Molecular Cloning of the Human Hepatitis C Cirus Genome from Japanese Patients with Non-A, Non-B Hepatitis," *Proc. Natl. Acad. Sci. USA* 1990, vol. 87, pp. 9524-9528.
Kato, "Molecular Virology of Hepatitis C Virus," *Acta Medica Okayama* 2001, vol. 55, pp. 133-159.
Kuo et al., "An Assay for Circulating Antibodies to a Major Etiologic Virus of Human Non-A, Non-B Hepatitis," *Science* 1989, vol. 244, pp. 362-364.
Llinas-Brunet et al., "Peptide-based Inhibitors of the Hepatitis C Virus Serine Protease," *Bioorg. Med. Chem. Lett.* 1998, vol. 8, pp. 1713-1718.
Manns et al., "Peginterferon alfa-2b Plus Ribavirin Compared with Interferon alfa-2b Plus Ribavirin for Initial Treatment of Chronic Hepatitis C: a Randomised Trial," *Lancet* 2001, vol. 358, pp. 958-965.
Marin et al., "Synthesis of Enantiopure 4-Hydroxypipecolate and 4-Hydroxylysine Derivatives from a Common 4,6-Dioxopiperidinecarboxylate Precursor," *J. Org. Chem.* 2004, vol. 69, pp. 130-141.
Poynard et al., "Randomised Trial of Interferon α2b Plus Ribavirin for 48 Weeks or for 24 Weeks Versus Interferon α2b Plus Placebo for 48 Weeks for Treatment of Chronic Infection with Hepatitis C Virus," *Lancet* 1998, vol. 352, pp. 1426-1432.
Qasim et al., "Interscaffolding Additivity. Association of $P^1$ Variants of Eglin C and of Turkey Ovomucoid Third Domain with Serine Proteinases," *Biochemistry* 1997, vol. 36, pp. 1598-1607.
Steinkuhler et al., "Product Inhibition of the Hepatitis C Virus NS3 Protease," *Biochemistry* 1998, vol. 37, pp. 8899-8905.
Sudo et al., "Establishment of an In Vitro Assay System for Screening Hepatitis C Virus Protease Inhibitors Using High Performance Liquid Chromatography," *Antiviral Research* 1996, vol. 32, pp. 9-18.
Sudo et al., "Novel Hepatitis C Virus Protease Inhibitors: Thiazolidine Derivatives," *Biochem. Biophys. Res. Commun.* 1997, vol. 238, pp. 643-647.
Takeshita, et al., "An Enzyme-linked Immunosorbent Assay for Detecting Proteolytic Activity of Hepatitis C Virus Proteinase," *Analytical Biochemistry* 1997, vol. 247, pp. 242-246.
Thomas, "Hepatitis C Epidemiology," *Curr. Top. Microbiol. Immunol.* 2000, vol. 242, pp. 25-41.
Velazquez et al., "Design, Synthesis, and Evaluation of Oxygen-Containing Macrocyclic Peptidomimetics as Inhibitors of HCV NS3 Protease," *J. Med. Chem.* 2009, vol. 52, pp. 700-708.
Zeng et al., "Epimerization Reaction of a Substituted Vinylcyclopropane Catalyzed by Ruthenium Carbenes: Mechanistic Analysis," *J. Org. Chem.* 2006, vol. 71, pp. 8864-8875.

(56) References Cited

OTHER PUBLICATIONS

Good et al., "Preclinical Pharmacokinetic Profile of IDX320, A Novel and Potent HCV Protease Inhibitor," *The International Liver Congress 2010, 45th Annual Meeting of the European Associate for the Study of the Liver*, Apr. 14-18, 2010.

Lacolla et al., "A Triple Combination of Direct-acting Antiviral Agents Demonstrates Robust Anti-HCV Activity in vitro," *The International Liver Congress 2010, 45th Annual Meeting of the European Associate for the Study of the Liver*, Apr. 14-18, 2010.

Lallos et al., "In vitro Antiviral Activity of IDX320, A Novel and Potent Macrocyclic HCV Protease Inhibitor," *The International Liver Congress 2010, 45th Annual Meeting of the European Associate for the Study of the Liver*, Apr. 14-18, 2010.

Taremi, et al., "Construction, Expression, and Characterization of a Novel Fully Activated Recombinant Single-chain Hepatitis C Virus Protease," Protein Science 1998, vol. 7, pp. 2143-2149.

Wakita, et al., "Production of Infectious Hepatitis C Virus in Tissue Culture from a Cloned Viral Genome," Nat. Med. 2005, vol. 11, pp. 791-796.

Sayle et al., "Electrostatic evaluation of isometric analogues," J. Comput Aided Mol Des (2006), pp. 191-208, vol. 20.

Örtqvista et al., "Phenylglycine as a novel P2 scaffold in hepatitis C virus NS3 protease inhibitors," Bioorganic & Medicinal Chemistry, (2007), pp. 1448-1474. vol. 15, No. 3.

International Searching Authority, "International Search Report for International Application No. PCT/US2008/008997," (Mailed Oct. 21, 2008), 2 pages.

International Searching Authority, "International Search Report for International Application No. PCT/US2009/000688," (Mailed Oct. 22, 2009), 5 pages.

International Searching Authority, "International Search Report for International Application No. PCT/US2010/030156," (Mailed Sep. 1, 2010), 4 pages.

International Searching Authority, "International Search Report for International Application No. PCT/US2010/044334," (Mailed Dec. 7, 2010), 3 pages.

International Searching Authority, "International Search Report for International Application No. PCT/US2012/024389", (Mailed Apr. 23, 2012), 5 pages.

MACROCYCLIC SERINE PROTEASE INHIBITORS

CROSS REFERENCE TO RELATED APPLICATION

This application claims priority to U.S. Provisional Application No. 61/231,636, filed Aug. 5, 2009, the disclosure of which is incorporated herein by reference in its entirety.

FIELD

Provided herein are macrocyclic serine protease inhibitor compounds, pharmaceutical compositions comprising the compounds, and processes of preparation thereof. Also provided are methods of their use for the treatment of an HCV infection in a host in need thereof.

BACKGROUND

Hepatitis C virus (HCV) is known to cause at least 80% of posttransfusion hepatitis and a substantial proportion of sporadic acute hepatitis (Kuo et al., *Science* 1989, 244, 362-364; Thomas, *Curr. Top. Microbiol. Immunol.* 2000, 25-41). Preliminary evidence also implicates HCV in many cases of "idiopathic" chronic hepatitis, "cryptogenic" cirrhosis, and probably hepatocellular carcinoma unrelated to other hepatitis viruses, such as hepatitis B virus (Di Besceglie et al., *Scientific American,* 1999, October, 80-85; Boyer et al., *J. Hepatol.* 2000, 32, 98-112).

HCV is an enveloped virus containing a positive-sense single-stranded RNA genome of approximately 9.4 kb (Kato et al., *Proc. Natl. Acad. Sci. USA* 1990, 87, 9524-9528; Kato, *Acta Medica Okayama,* 2001, 55, 133-159). The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as an internal ribosome entry. This mechanism involves the binding of ribosomes to an RNA sequence known as the internal ribosome entry site (IRES). An RNA pseudoknot structure has recently been determined to be an essential structural element of the ICV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

Presently, the most effective HCV therapy employs a combination of alpha-interferon and ribavirin, leading to sustained efficacy in about 40% of patients (Poynard et al., *Lancet* 1998, 352, 1426-1432). Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load (Maims et al, *Lancet* 2001, 358, 958-965; Fried et al., *N. Engl. J. Med.* 2002, 347, 975-982; Hadziyannis et al., *Ann. Intern. Med.* 2004, 140, 346-355). Thus, there is a clear and unmet need to develop effective therapeutics for treatment of HCV infection.

SUMMARY OF THE DISCLOSURE

Provided herein are macrocyclic serine protease inhibitor compounds, pharmaceutical compositions comprising the compounds, and processes of preparation thereof. Also provided are methods of their use for the treatment of an HCV infection in a host in need thereof.

In one embodiment, provided herein is a compound of Formula Ia or Ib:

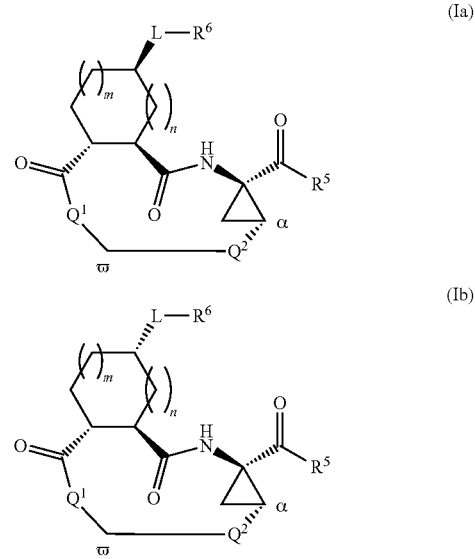

or a single enantiomer, a racemic mixture, a mixture of diastereomers, or an isotopic variant thereof; or a pharmaceutically acceptable salt, solvate, or prodrug thereof;

wherein:

$R^5$ is —OH, —$NR^8R^9$, —$NHS(O)_2R^8$, —$NHS(O)_2NR^8R^9$, —$NHC(O)R^8$, —$NHC(O)NR^8R^9$, —$C(O)R^8$, or —$C(O)NR^8R^9$; wherein:

each $R^8$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, $C_{1-6}$ alkyl-$C_{3-7}$ cycloalkylene, —$CH_2NR^{8a}R^{8b}$, —$CH(R^{8c})NR^{8a}R^{8b}$, —$CHR^{8c}CHR^{8d}NR^{8a}$, $R^{8b}$, or —$CH_2CR^{8c}R^{8d}NR^{8a}R^{8b}$, wherein:

each $R^{8a}$, $R^{8c}$, and $R^{8d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; and each $R^{8b}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, heterocyclyl, —$C(O)R^{11}$, —$C(O)OR^{11}$, —$C(O)NR^{11}R^{12}$, —$C(=NR^{13})NR^{11}R^{12}$, —$S(O)R^{11}$, —$S(O)_2R^{11}$, —$S(O)NR^{11}R^{12}$, or —$S(O)_2NR^{11}R^{12}$, wherein each $R^{11}$, $R^{12}$, and $R^{13}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{11}$ and $R^{12}$ together with the N atom to which they are attached form heterocyclyl; or $R^{8a}$ and $R^{8b}$ together with the N atom to which they are attached form heterocyclyl; and each $R^9$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^8$ and $R^9$ together with the N atom to which they are attached form heterocyclyl;

$R^6$ and L are (i) or (ii):

(i) $R^6$ is hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; and L is a bond, $C_{1-6}$ alkylene, $C_{2-6}$ alkenylene, $C_{2-6}$ alkynylene, $C_{3-7}$ cycloalkylene, —X—, or —$(CR^{6a}R^{6b})_p$X—; wherein p is an integer of 1, 2, or 3; $R^{6a}$ and $R^{6b}$ are each independently hydrogen, halo, cyano, hydroxyl, or alkoxy; and X is —C(O)—, —C(O)O—, —C(O)NR$^{14}$—, —C(=NR$^{14}$)NR$^{15}$—, —O—, —OC(O)O—, —OC(O)NR$^{14}$—, —OC(=NR$^{14}$)NR$^{15}$—, —OP(O)(OR$^{14}$)—, —NR$^{14}$—, —NR$^{14}$C(O)NR$^{15}$—, —NR$^{14}$C(=NR$^{15}$)NR$^{16}$—, —NR$^{14}$S(O)NR$^{15}$—, —NR$^{14}$S(O)$_2$NR$^{15}$—, —S—, S(O)—, —S(O)$_2$—, —S(O)NR$^{14}$—, —S(O)$_2$NR$^{14}$—, or —P(O)(OR$^{14}$)—, where each $R^{14}$, $R^{15}$, and $R^{16}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (ii) -L-$R^6$ is —O—N=$CR^{6c}R^{6d}$, wherein each $R^{6c}$ and $R^{6d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{6c}$ and $R^{6d}$ together with the C atom to which they are attached form $C_{3-15}$ cycloalkylidene, $C_{6-14}$ arylidene, heteroarylidene, or heterocyclylidene;

$Q^1$ is —O—, —N($R^{17}$)—, —C($R^{18}R^{19}$)—, or —$CR^{17}$($NR^{18}R^{19}$)—; wherein:

each $R^{17}$ and $R^{18}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; and each $R^{19}$ is independently —$R^{20}$, —C(O)$R^{20}$, —C(O)OR$^{20}$, —C(O)NR$^{21}R^{22}$, —C(=NR$^{20}$)NR$^{21}R^{22}$, —S(O)$R^{20}$, or —S(O)$_2R^{20}$; where each $R^{20}$, $R^{21}$, and $R^{22}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{21}$ and $R^{22}$ together with the N atom to which they are attached form heterocyclyl; or $R^{18}$ and $R^{19}$ together with the C or N atom to which they are attached form $C_{3-7}$ cycloalkyl or heterocyclyl;

$Q^2$ is $C_{3-9}$ alkylene, $C_{3-9}$ alkenylene, or $C_{3-9}$ alkynylene, each optionally containing one to three heteroatoms in the chain, independently selected from O, N, and S; and m is an integer of 0 or 1; and n is an integer of 1 or 2; with the proviso that the sum of m and n is 2 or 3;

wherein each alkyl, alkylene, alkenyl, alkenylene, alkynyl, alkynylene, cycloalkyl, cycloalkylene, aryl, aralkyl, heterocyclyl, and heteroaryl is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (c) —C(O)$R^a$, —C(O)OR$^a$, —C(O)NR$^bR^c$, —C(NR$^a$)NR$^bR^c$, —OR$^a$, —OC(O)$R^1$, —OC(O)OR$^a$, —OC(O)NR$^bR^c$, —OC(=NR$^a$)NR$^bR^c$, —OS(O)$_2R^a$, —OS(O)NR$^bR^c$, —OS(O)$_2$NR$^bR^c$, —NR$^bR^c$, —NR$^a$C(O)$R^d$, —NR$^a$C(O)OR$^d$, —NR$^a$C(O)NR$^bR^c$, —NR$^a$C(=NR$^d$)NR$^bR^c$, —NR$^a$S(O)$R^d$, —NR$^a$S(O)$_2R^d$, —NR$^a$S(O)NR$^bR^c$, —NR$^a$S(O)$_2$NR$^bR^c$, —SR$^a$, —S(O)$R^a$, —S(O)$_2R^a$, —S(O)NR$^bR^c$, and —S(O)$_2$NR$^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) $R^b$ and $R^c$ together with the N atom to which they are attached form heterocyclyl, optionally substituted with one or more, in one embodiment, one, two, three, or four, substituents Q;

wherein each Q is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)OR$^e$, —C(O)NR$^fR^g$, —C(NR$^e$)NR$^fR^g$, —OC(O)$R^e$, —OC(O)OR$^e$, —OC(O)NR$^fR^g$, —OC(=NR$^e$)NR$^fR^g$, —OS(O)$R^e$, —OS(O)$_2R^e$, —OS(O)NR$^fR^g$, —OS(O)$_2$NR$^fR^g$, —NR$^fR^g$, —NR$^e$C(O)$R^h$, —NR$^e$C(O)OR$^f$, —NR$^e$C(O)NR$^fR^g$, —NR$^e$C(=NR$^h$)NR$^fR^g$, —NR$^e$S(O)$R^h$, NR$^e$S(O)$_2R^h$, —NR$^e$S(O)NR$^fR^g$, —NR$^e$S(O)$_2$NR$^fR^g$, —SR$^2$, —S(O)$R^e$, —S(O)$_2R^e$, —S(O)NR$^fR^g$, and —S(O)$_2$NR$^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ ether with the N atom to which they are attached form heterocyclyl.

Also provided herein are pharmaceutical compositions comprising a compound disclosed herein, e.g., a compound of Formula I, including a single enantiomer, a racemic mixture, a mixture of diastereomers, or an isotopic variant thereof; or a pharmaceutically acceptable salt, solvate, or prodrug thereof; in combination with one or more pharmaceutically acceptable excipients or carriers.

Further provided herein is a method for treating or preventing an HCV infection, which comprises administering to a subject a therapeutically effective amount of a compound disclosed herein, e.g., a compound of Formula I, including a single enantiomer, a racemic mixture, a mixture of diastereomers, or an isotopic variant thereof; or a pharmaceutically acceptable salt, solvate, or prodrug thereof.

Additionally provided herein is a method for treating, preventing, or ameliorating one or more symptoms of a liver disease or disorder associated with an HCV infection, comprising administering to a subject a therapeutically effective amount of a compound disclosed herein, e.g., a compound of Formula I, including a single enantiomer, a racemic mixture, a mixture of diastereomers, or an isotopic variant thereof; or a pharmaceutically acceptable salt, solvate, or prodrug thereof.

Provided herein is a method for inhibiting replication of a virus in a host, which comprises administering to the host a therapeutically effective amount of a compound disclosed herein, e.g., a compound of Formula I, including a single enantiomer, a racemic mixture, a mixture of diastereomers, or an isotopic variant thereof; or a pharmaceutically acceptable salt, solvate, or prodrug thereof Provided herein is a method for inhibiting the activity of a serine protease, which comprises contacting the serine protease with a compound disclosed herein, e.g., a compound of Formula I, including a single enantiomer, a racemic mixture, a mixture of diastereomers, or an isotopic variant thereof; or a pharmaceutically acceptable salt, solvate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The term "host" refers to a unicellular or multicellular organism in which a virus can replicate, including, but not limited to, a cell, cell line, and animal, such as human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "$IC_{50}$" or "$EC_{50}$" refers an amount, concentration, or dosage of a compound that is required for 50% inhibition of a maximal response in an assay that measures such response.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "monocyclic" refers to a group having a single ring that is bonded to the rest of a molecule through one of its ring atoms. In one embodiment, a monocyclic group can be substituted with one or more substituents that are cyclic.

The term "bicyclic" refers to a group containing two rings fused together. Bicyclic groups are bonded to the rest of a molecule through one of the ring atoms of the two fused rings. In certain embodiments, the two fused rings share a common bond. In certain embodiments, the two fused rings share two or more common ring atoms to form a bridged ring compound. In certain embodiments, the two fused rings share a common ring atom to form a spirocyclic compound.

The term "alkyl" refers to a linear or branched saturated monovalent hydrocarbon radical, wherein the alkyl may optionally be substituted as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkylene" refers to a linear or branched saturated divalent hydrocarbon radical, wherein the alkylene may optionally be substituted as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms).

The term "alkenyl" refers to a linear or branched monovalent hydrocarbon radical, which contains one or more, in one embodiment, one to five, in another embodiment, one, carbon-carbon double bond(s). The alkenyl may be optionally substituted as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one to five, in another embodiment, one, carbon-carbon double bond(s). The alkenylene may be optionally substituted as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$) or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 or 6 ($C_{3-6}$) carbon atoms. Examples of alkenylene groups include, but are not limited to, ethenylene, allylene, propenylene, butenylene, and 4-methylbutenylene.

The term "alkynyl" refers to a linear or branched monovalent hydrocarbon radical, which contains one or more, in one embodiment, one to five, in another embodiment, one, carbon-carbon triple bond(s). The alkynyl may be optionally substituted as described herein. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "alkynylene" refers to a linear or branched divalent hydrocarbon radical, which contains one or more, in one embodiment, one to five, in another embodiment, one, carbon-carbon triple bond(s). The alkynylene may be optionally substituted as described herein. For example, $C_{2-6}$ alkynylene refers to a linear unsaturated divalent hydrocarbon radical of 2 to 6 carbon atoms or a branched unsaturated divalent hydrocarbon radical of 3 to 6 carbon atoms. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynylene groups include, but are not limited to, ethynylene, propynylene (including all isomeric forms, e.g., 1-propynylene and propargylene), butynylene (including all isomeric forms, e.g., 1-butyn-1-ylene and 2-butyn-1-ylene), pentynylene (including all isomeric forms, e.g., 1-pentyn-1-ylene and 1-methyl-2-butyn-1-ylene), and hexynylene (including all isomeric forms, e.g., 1-hexyn-1-ylene).

The term "cycloalkyl" refers to a cyclic monovalent hydrocarbon radical, which may be optionally substituted as described herein. In one embodiment, cycloalkyl groups may be saturated or unsaturated but non-aromatic, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "cycloalkylene" refers to a cyclic divalent hydrocarbon radical, which may be optionally substituted as described herein. In one embodiment, cycloalkyl groups may be saturated or unsaturated but non-aromatic, and/or bridged, and/or non-bridged, and/or fused bicyclic groups. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene (e.g., 1,1-cyclopropylene and 1,2-cyclopropylene), cyclobutylene (e.g., 1,1-cyclobutylene, 1,2-cyclobutylene, or 1,3-cyclobutylene), cyclopentylene (e.g., 1,1-cyclopentylene, 1,2-cyclopentylene, or 1,3-cyclopentylene), cyclohexylene (e.g., 1,1-cyclohexylene, 1,2-cyclohexylene, 1,3-cyclohexylene, or 1,4-cyclohexylene), cycloheptylene (e.g., 1,1-cycloheptylene, 1,2-cycloheptylene, 1,3-cycloheptylene, or 1,4-cycloheptylene), decalinylene, and adamantylene.

The term "aryl" refers to a monovalent monocyclic aromatic group and/or monovalent multicyclic aromatic group that contain at least one aromatic carbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, aralkyl are optionally substituted with one or more substituents as described herein.

The term "heteroaryl" refers to a monovalent monocyclic aromatic group or monovalent multicyclic aromatic group that contain at least one aromatic ring, wherein at least one aromatic ring contains one or more heteroatoms independently selected from O, S, and N in the ring. Heteroaryl groups are bonded to the rest of a molecule through the aromatic ring. Each ring of a heteroaryl group can contain one or two P atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "heterocyclyl" or "heterocyclic" refers to a monovalent monocyclic non-aromatic ring system or monovalent multicyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "halogen", "halide" or "halo" refers to fluorine, chlorine, bromine, and/or iodine.

The suffix "-ylidene" means that two hydrogen atoms of a compound are replaced by a double bond. In certain embodiments, the suffix "-ylidene" refers to carbene. Examples of $C_{3-15}$ cycloalkylidene, $C_{6-15}$ arylidene, heteroalkylidene, and heterocyclylidene include, but are not limited to, 9H-fluoren-9-ylidene, 9H-xanth-9-ylidene, anthracen-9(10H)-one-10-ylidene, 9,10-dihydroacridin-9-ylidene, 1,8-diaza-9H-fluoren-9-ylidene, 4,5-diaza-9H-fluoren-9-ylidene, 10,11-dihydro-5H-bibenzo[1,2-d]cyclohept-5-ylidene, 2,3-dihydro-1H-inden-1-ylidene, 1,2,3,4-tetrahydronaphth-1-ylidene, 5,6,7,8-tetrahydroquinolin-5-ylidene, 5,6,7,8-tetrahydroquinolin-8-ylidene, chroman-4-ylidene, and thiochroman-4-ylidene.

The term "optionally substituted" is intended to mean that a group, such as an alkyl, alkenyl, alkynyl, cycloalkyl, aryl, aralkyl, heteroaryl, or heterocyclyl group, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q: and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(═NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(═NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^e$, wherein each R$^a$, R$^b$, R$^e$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) R$^b$ and R$^c$ together with the N atom to which they are attached form heteroaryl or heterocyclyl, optionally substituted with one or more, in one embodiment, one, two, three, or four, substituents Q. As used herein, all groups that can be substituted are "optionally substituted," unless otherwise specified.

In one embodiment, each Q is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(═NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(═NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^1H$), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1H$), deuterium ($^2H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^2H$, for example, or any carbon can be $^{13}C$, as example, or any nitrogen can be $^{15}N$, as example, and any oxygen can be $^{18}O$, where feasible according to the judgment of one of skill. In certain embodiments, an "isotopic variant" of a compound contains unnatural proportions of deuterium.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a single enantiomer, a racemic mixture, a mixture of diastereomers, or an isotopic variant thereof; or a pharmaceutically acceptable salt, solvate, or prodrug thereof" has the same meaning as the phrase "a single enantiomer, a racemic mixture, a mixture of diastereomers, or an isotopic variant of the compound referenced therein; or a pharmaceutically acceptable salt, solvate, or prodrug of the compound referenced therein, or a single enantiomer, a racemic mixture, a mixture of diastereomers, or an isotopic variant of the compound referenced therein."

Compounds

HCV has a single positive-stranded RNA genome having about 9.6 kb in length that encodes a large polyprotein having about 3010 amino acids. This precursor polyprotein is then processed into a range of structural proteins, including core protein, C, and envelope glycoproteins, E1 and E2; and non-structural proteins, including NS2, NS3, NS4A, NS4B, NS5A, and NS5B, by host signal peptidases and two viral proteases, NS2-3 and NS3. The NS3 protein contains a trypsin-like serine protease domain at its N-terminus, while its C-terminal domain has helicase activity. Because of its vital role in viral replication, HCV NS3 serine protease has been actively pursued as a drug target for developing a new anti-HCV therapy.

Inhibitors of HCV NS3 protease that have been reported include linear and cyclic peptides and peptide mimetics, and non-peptide molecules (Llinàs-Brunet et al., *Bioorg. Med. Chem. Lett.* 1998, 8, 1713-1718; Steinkühler et al., *Biochemistry* 1998, 37, 8899-8905; U.S. Pat. Nos. 5,538,865; 5,990,276; 6,143,715; 6,265,380; 6,323,180; 6,329,379; 6,410,531; 6,420,380; 6,534,523; 6,608,027; 6,642,204; 6,653,295; 6,727,366; 6,838,475; 6,846,802; 6,867,185; 6,869,964; 6,872,805; 6,878,722; 6,908,901; 6,911,428; 6,995,174; 7,012,066; 7,041,698; 7,091,184; 7,169,760; 7,176,208; 7,208,600; and 7,491,794; U.S. Pat. Appl. Publ. Nos. 2002/0016294, 2002/0016442; 2002/0032175; 2002/0037998; 2004/0229777; 2005/0090450; 2005/0153877; 2005/176648; 2006/0046956; 2007/0021330; 2007/0021351; 2007/0049536; 2007/0054842; 2007/0060510; 2007/0060565; 2007/0072809; 2007/0078081; 2007/0078122; 2007/0093414; 2007/0093430; 2007/0099825; 2007/0099929; 2007/0105781, 2008/0152622, 2009/0035271, 2009/0035272, 2009/0111969, 2009/0111982, 2009/0123425, 2009/0130059, 2009/148407, 2009/0156800, 2009/0169510, 2009/0175822, and 2009/0180981; and International Pat. Appl. Publ. Nos. WO 98/17679; WO 98/22496; WO 99/07734; WO 00/09543; WO 00/59929; WO 02/08187; WO 02/08251; WO 02/08256; WO 02/08198; WO 02/48116; WO 02/48157; WO 02/48172; WO 02/60926; WO 03/53349; WO 03/64416; WO 03/64455; WO 03/64456; WO 03/66103; WO 03/99274; WO 03/99316; WO 2004/032827; WO 2004/043339; WO 2005/037214; WO 2005/037860; WO 2006/000085; WO 2006/119061; WO 2006/122188; WO 2007/001406; WO 2007/014925; WO 2007/014926; WO 2007/015824, WO 2007/056120, WO 2008/019289, WO 2008/021960, WO 2008/022006, WO 2008/086161, WO 2009/053828, WO 2009/058856, WO 2009/073713, WO 2009/073780, WO 2009/080542, WO 2009/082701, WO 2009/082697, and WO 2009/085978). However, citation of any reference herein is not an admission that such reference is prior art to the present disclosure.

Provided herein are compounds which are useful for the treatment of HCV infection, which, in one embodiment, can have activity as HCV serine protease inhibitors. Also provided herein are pharmaceutical compositions that comprise the compounds, methods of manufacture of the compounds, and methods of use of the compounds for the treatment of HCV infection in a host in need of treatment.

In one embodiment, provided herein is a compound of Formula Ia or Ib:

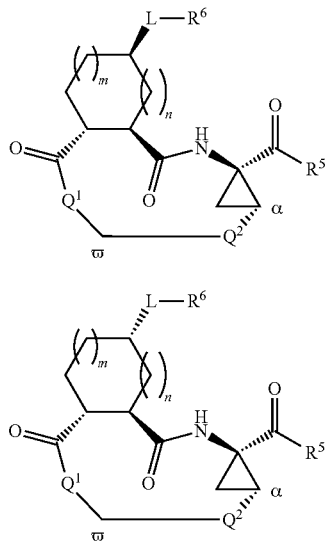

or a single enantiomer, a racemic mixture, a mixture of diastereomers, or an isotopic variant thereof; or a pharmaceutically acceptable salt, solvate, or prodrug thereof; wherein:

$R^5$ is —OH, —$NR^8R^9$, —$NHS(O)_2R^8$, —$NHS(O)_2NR^8R^9$, —$NHC(O)R^8$, —$NHC(O)NR^8R^9$, —$C(O)R^8$, or —$C(O)NR^8R^9$; wherein:

each $R^8$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, $C_{1-6}$ alkyl-$C_{3-7}$ cycloalkylene, —$CH_2NR^{8a}R^{8b}$, —$CH(R^{8c})NR^{8a}R^{8b}$, —$CHR^{8c}CHR^{8d}NR^{8a}R^{8b}$, or —$CH_2CR^{8c}R^{8d}NR^{8a}R^{8b}$, wherein:

each $R^{8a}$, $R^{8c}$, and $R^{8d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; and each $R^{8b}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, heterocyclyl, —$C(O)R^{11}$, —$C(O)OR^{11}$, —$C(O)NR^{11}R^{12}$, —$C(=NR^{13})NR^{11}R^{12}$, —$S(O)R^{11}$, —$S(O)_2R^{11}$, —$S(O)NR^{11}R^{12}$, or —$S(O)_2NR^{11}R^{12}$, wherein each $R^{11}$, $R^{12}$, and $R^{13}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{11}$ and $R^{12}$ together with the N atom to which they are attached form heterocyclyl; or $R^{8a}$ and $R^{8b}$ together with the N atom to which they are attached form heterocyclyl; and each $R^9$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^8$ and $R^9$ together with the N atom to which they are attached form heterocyclyl;

$R^6$ and L are (i) or (ii):

(i) $R^6$ is hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; and L is a bond, $C_{1-6}$ alkylene, $C_{2-6}$ alkenylene, $C_{2-6}$ alkynylene, $C_{3-7}$ cycloalkylene, —X—, or —$(CR^{6a}R^{6b})_pX$—; wherein p is an integer of 1, 2, or 3; $R^{6a}$ and $R^{6b}$ are each independently hydrogen, halo, cyano, hydroxyl, or alkoxy; and X is —C(O)—, —C(O)O—, —C(O)NR^{14}—, —C(=NR^{14})NR^{15}—, —O—, —OC(O)O—, —OC(O)NR^{14}—, —OC(=NR^{14})NR^{15}—, —OP(O)(OR^{14})—, —NR^{14}—, —NR^{14}C(O)NR^{15}—, —NR^{14}C(=NR^{15})NR^{16}—, —NR^{14}S(O)NR^{15}—, —NR^{14}S(O)_2NR^{15}—, —S—, —S(O)—, —S(O)_2—, —S(O)NR^{14}—, —S(O)_2NR^{14}—, or —P(O)(OR^{14})—, where each $R^{14}$, $R^{15}$, and $R^{16}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (ii) -L-$R^6$ is —O—N=$CR^{6c}R^{6d}$, wherein each $R^{6c}$ and $R^{6d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{6c}$ and $R^{6d}$ together with the C atom to which they are attached form $C_{3-15}$ cycloalkylidene, $C_{6-14}$ arylidene, heteroarylidene, or heterocyclylidene;

$Q^1$ is —O—, —N($R^{17}$)—, —$C(R^{18}R^{19})$—, or —$CR^{17}(NR^{18}R^{19})$—; wherein:

each $R^{17}$ and $R^{18}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; and each $R^{19}$ is independently —$R^{20}$, —$C(O)R^{20}$, —$C(O)OR^{20}$, —$C(O)NR^{21}R^{22}$, —$C(=NR^{20})NR^{21}R^{22}$, —$S(O)R^{20}$, or —$S(O)_2R^{20}$; where each $R^{20}$, $R^{21}$, and $R^{22}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{21}$ and $R^{22}$ together with the N atom to which they are attached form heterocyclyl; or $R^{18}$ and $R^{19}$ together with the C or N atom to which they are attached form $C_{3-7}$ cycloalkyl or heterocyclyl;

$Q^2$ is $C_{3-9}$ alkylene, $C_{3-9}$ alkenylene, or $C_{3-9}$ alkynylene, each optionally containing one to three heteroatoms in the chain, independently selected from O, N, and S; and m is an integer of 0 or 1; and n is an integer of 1 or 2; with the proviso that the sum of m and n is 2 or 3;

wherein each alkyl, alkylene, alkenyl, alkenylene, alkynyl, alkynylene, cycloalkyl, cycloalkylene, aryl, aralkyl, heterocyclyl, and heteroaryl is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (c) —$C(O)R^a$, —$C(O)OR^a$, —$C(O)NR^bR^c$, —$C(NR^a)NR^bR^c$, —$OR^a$, —$OC(O)R^a$, —$OC(O)OR^a$, —$OC(O)NR^bR^c$, —$OC(=NR^a)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^d$, —$NR^aC(O)OR^d$, —$NR^aC(O)NR^bR^c$, —$NR^aC(=NR^d)NR^bR^c$, —$NR^aS(O)R^d$, —$NR^aS(O)_2R^d$, —$NR^aS(O)NR^bR^c$, —$NR^aS(O)_2NR^bR^c$, —$SR^a$, —$S(O)R^a$, —$S(O)_2R^a$, —$S(O)NR^bR^c$, and —$S(O)_2NR^bR^c$, wherein each $R^1$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) $R^b$ and $R^c$ together with the N atom to which they are attached form heterocyclyl, optionally substituted with one or more, in one embodiment, one, two, three, or four, substituents Q;

wherein each Q is independently selected from the group consisting of (a) cyano, halo, and nitro; (b) $C_{1-6}$ alkyl, $C_{2-6}$ alkenyl, $C_{2-6}$ alkynyl. $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OC(O)R$^e$, —OC(O)OR$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In another embodiment, provided herein is a compound of Formula IIa or IIb:

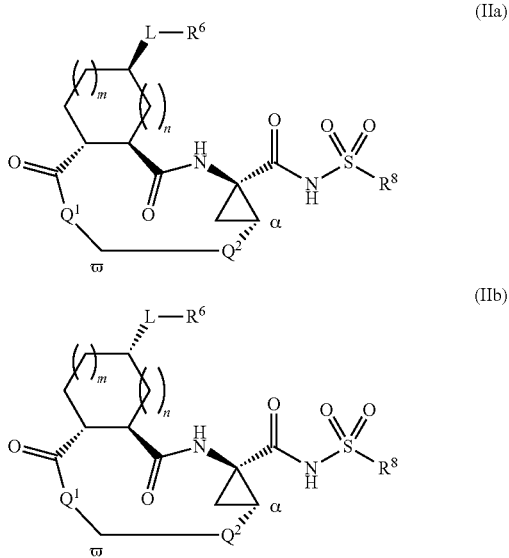

(IIa)

(IIb)

or a single enantiomer, a racemic mixture, a mixture of diastereomers, or an isotopic variant thereof; or a pharmaceutically acceptable salt, solvate, or prodrug thereof; wherein R$^6$, R$^8$, L, Q$^1$, Q$^2$, m, and n are each as defined herein.

In another embodiment, provided herein is a compound of Formula IIIa or IIIb:

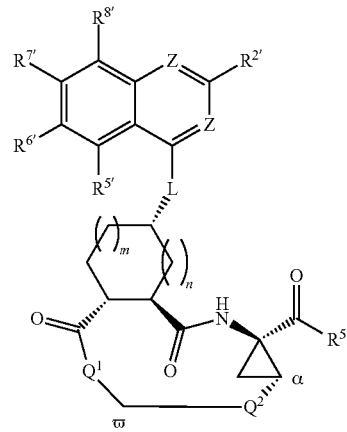

(IIIa)

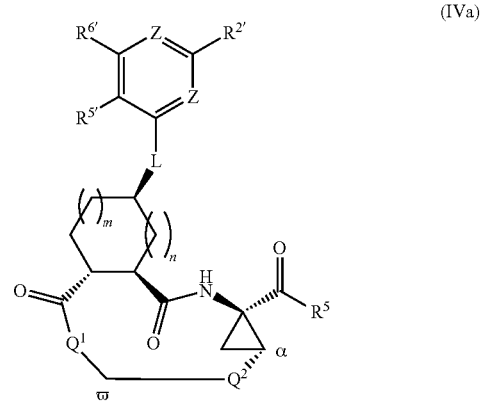

(IIIb)

or a single enantiomer, a racemic mixture, a mixture of diastereomers, or an isotopic variant thereof; or a pharmaceutically acceptable salt, solvate, or prodrug thereof;
wherein:
R$^5$, L, Q$^1$, Q$^2$, m, and n are each as defined herein;
each Z is independently CR$^{3'}$ or N; and
R$^{2'}$, R$^{3'}$, R$^{5'}$, R$^{6'}$, R$^{7'}$, and R$^{8'}$ are each independently:
hydrogen, halo, cyano, trifluoromethyl, or nitro;
C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more substituents as described herein; or
—C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$; —S(O)NR$^b$R$^c$, or —S(O)$_2$NR$^b$R$^c$; wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more substituents as described herein; or (iii) R$^b$ and R$^c$ together with the N atom to which they are attached form heterocyclyl, optionally substituted with one or more substituents as described herein.

In yet another embodiment, provided herein is a compound of Formula IVa or IVb:

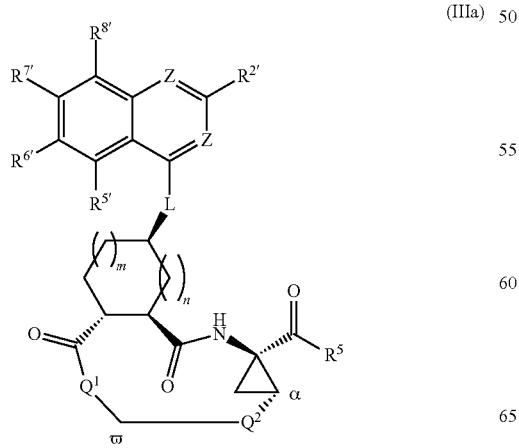

(IVa)

-continued

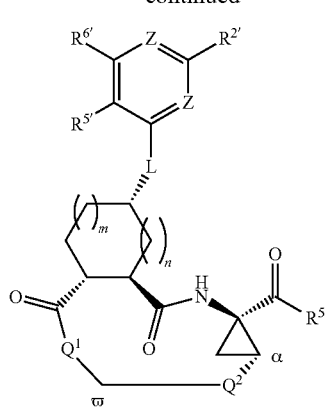

(IVb)

or a single enantiomer, a racemic mixture, a mixture of diastereomers, or an isotopic variant thereof; or a pharmaceutically acceptable salt, solvate, or prodrug thereof; wherein $R^5$, $R^{2'}$, $R^{5'}$, $R^{6'}$, L, $Q^1$, $Q^2$, Z, m, and n are each as defined herein.

In yet another embodiment, provided herein is a compound of Formula Va or Vb:

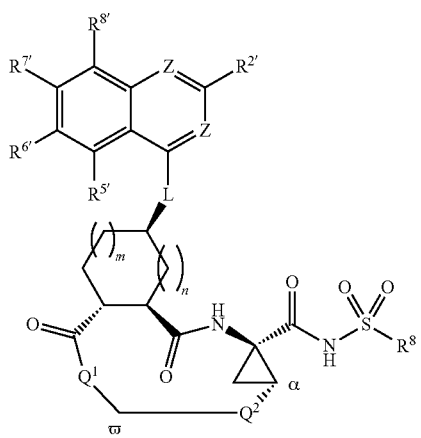

(Va)

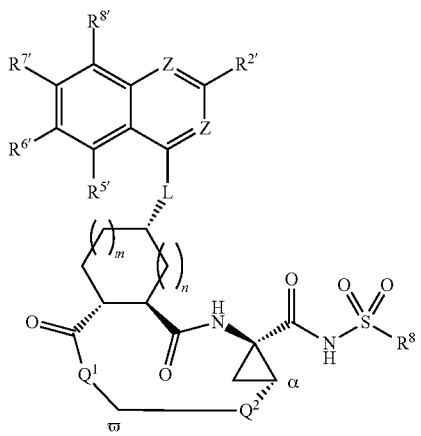

(Vb)

or a single enantiomer, a racemic mixture, a mixture of diastereomers, or an isotopic variant thereof; or a pharmaceutically acceptable salt, solvate, or prodrug thereof; wherein $R^8$, $R^{2'}$, $R^{5'}$, $R^{6'}$, $R^{7'}$, $R^{8'}$, L, $Q^1$, $Q^2$, Z, m, and n are each as defined herein.

In yet another embodiment, provided herein is a compound of Formula VIa or VIb:

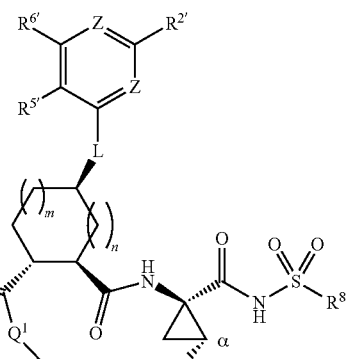

(VIa)

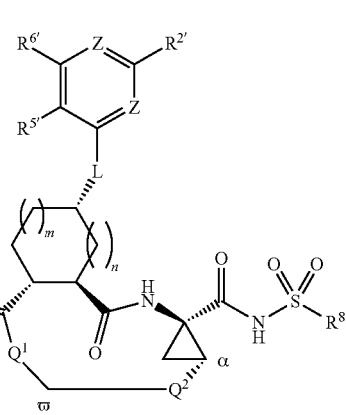

(VIb)

or a single enantiomer, a racemic mixture, a mixture of diastereomers, or an isotopic variant thereof; or a pharmaceutically acceptable salt, solvate, or prodrug thereof; wherein $R^8$, $R^{2'}$, $R^{5'}$, $R^{6'}$, L, $Q^1$, $Q^2$, Z, m, and n are each as defined herein.

In Formula Ia, Ib, IIa, IIb, IIIa, IIIb, IVa, IVb, Va, Vb, VIa, or VIb, in one embodiment, m and n are each 1; in another embodiment, m is 0, and n is 2.

In certain embodiments, $Q^2$ is $C_{3-9}$ alkylene. In certain embodiments, $Q^2$ is $C_{3-9}$ alkenylene. In certain embodiments, $Q^2$ is $C_{3-9}$ alkenylene having one carbon-carbon double bond in either cis or trans configuration. In certain embodiments, $Q^2$ is $C_{3-9}$ alkenylene having one carbon-carbon double bond in cis configuration. In certain embodiments, $Q^2$ is $C_{3-9}$ alkynylene.

In certain embodiments, $Q^2$ has the structure of:

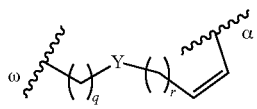

wherein:

Y is a bond, —O—, —S—, S(O)—, —S(O)$_2$—, or —N($R^Y$)—, wherein $R^Y$ is hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, —C(O)$R^{Ya}$, —C(O)O$R^{Ya}$, —C(O)NR$^{Yb}$R$^{Yc}$, —S(O)$_2$NR$^{Yb}$R$^{Yc}$, or —S(O)$_2$R$^{Ya}$;

each $R^{Ya}$, $R^{Yb}$, and $R^{Yc}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

q is an integer of 0, 1, 2, 3, or 4; and r is an integer of 0, 1, 2, 3, or 4;

wherein each alkyl, alkenyl, alkynyl, cycloalkyl, aryl, aralkyl, heteroaryl, and heterocyclyl is optionally substituted with one or more substituents as described herein.

In one embodiment, provided herein is a compound of Formula VIIa or VIIb:

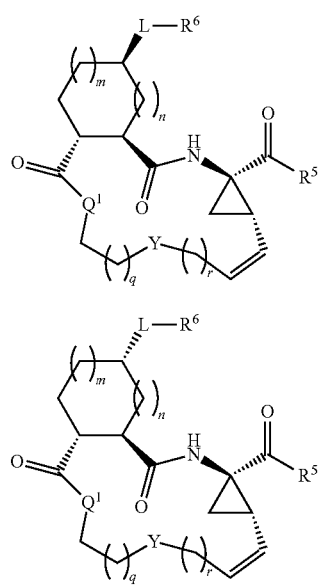

(VIIa)

(VIIb)

or a single enantiomer, a racemic mixture, a mixture of diastereomers, or an isotopic variant thereof; or a pharmaceutically acceptable salt, solvate, or prodrug thereof; wherein $R^5$, $R^6$, L, $Q^1$, Y, m, n, q, and r are each as defined herein.

In Formula VIIa or VIIb, in one embodiment, m and n are each 1; in another embodiment, m is 0, and n is 2; in yet another embodiment, Y is a bond, q is 1, and r is 2; in yet another embodiment, Y is —O—, and q and r are each 1; in yet another embodiment, Y is a bond, m, n, and q are each 1, and r is 2: in yet another embodiment, Y is —O—, and m, n, q, and r are each 1; in still another embodiment, Y is a bond, m is 0, n is 2, q is 1, and r is 2.

In another embodiment, provided herein is a compound of Formula VIIIa or VIIIb:

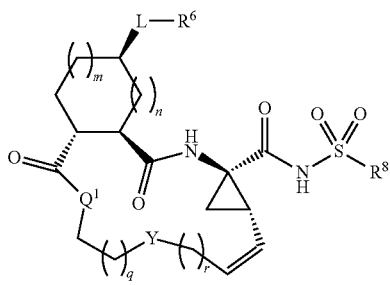

(VIIIa)

(VIIIb)

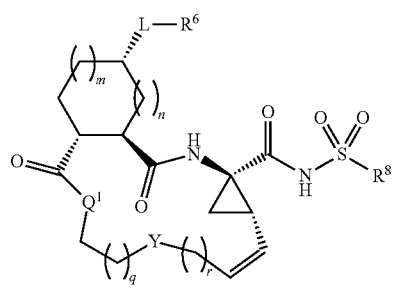

or a single enantiomer, a racemic mixture, a mixture of diastereomers, or an isotopic variant thereof; or a pharmaceutically acceptable salt, solvate, or prodrug thereof; wherein $R^6$, $R^8$, L, $Q^1$, Y, m, n, q, and r are each as defined herein.

In Formula VIIIa or VIIIb, in one embodiment, m and n are each 1; in another embodiment, m is 0, and n is 2; in yet another embodiment, Y is a bond, q is 1, and r is 2; in yet another embodiment, Y is —O—, and q and r are each 1; in yet another embodiment, Y is a bond, m, n, and q are each 1, and r is 2; in yet another embodiment, Y is —O—, and m, n, q, and r are each 1; in still another embodiment, Y is a bond, m is 0, n is 2, q is 1, and r is 2.

In yet another embodiment, provided herein is a compound of Formula IXa or IXb:

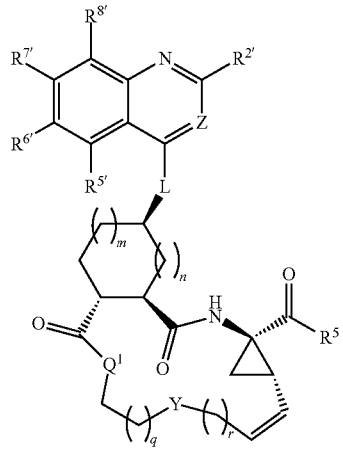

(IXa)

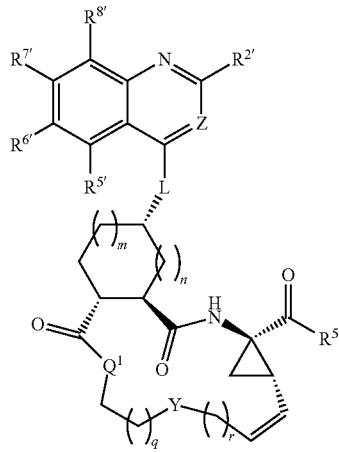

(IXb)

or a single enantiomer, a racemic mixture, a mixture of diastereomers, or an isotopic variant thereof; or a pharmaceutically acceptable salt, solvate, or prodrug thereof; wherein R⁵, R²', R⁵', R⁶', R⁷', R⁸', L, Q¹, Y, Z, m, n, q, and r are each as defined herein.

In yet another embodiment, provided herein is a compound of Formula Xa or Xb:

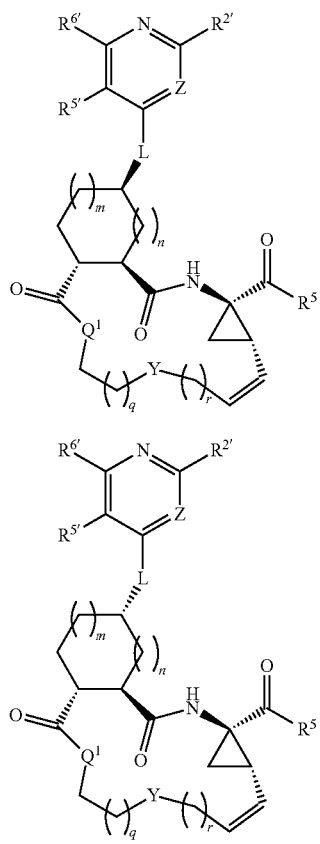

or a single enantiomer, a racemic mixture, a mixture of diastereomers, or an isotopic variant thereof; or a pharmaceutically acceptable salt, solvate, or prodrug thereof; wherein R⁵, R²', R⁵', R⁶', L, Q', Y, Z, m, n, q, and r are each as defined herein.

In Formula Xa or Xb, in one embodiment, m and n are each 1; in another embodiment, m is 0, and n is 2; in yet another embodiment, Y is a bond, q is 1, and r is 2; in yet another embodiment, Y is —O—, and q and r are each 1; in yet another embodiment, Z is CH; in yet another embodiment, Z is N; in yet another embodiment, Y is a bond, m, n, and q are each 1, and r is 2; in yet another embodiment, Y is —O—, and m, n, q, and r are each 1; in yet another embodiment, Y is a bond, m is 0, n is 2, q is 1, and r is 2; in yet another embodiment, Y is a bond, Z is CH, m, n, and q are each 1, and r is 2; in yet another embodiment, Y is —O—, Z is CH, and m, n, q, and r are each 1; in yet another embodiment, Y is a bond, Z is CH, m is 0, n is 2, q is 1, and r is 2; in yet another embodiment, Y is a bond, Z is N, m, n, and q are each 1, and r is 2; in yet another embodiment, Y is —O—, Z is N, and m, n, q, and r are each 1; in still another embodiment, Y is a bond, Z is N, m is 0, n is 2, q is 1, and r is 2.

In yet another embodiment, provided herein is a compound of Formula XIa or XIb:

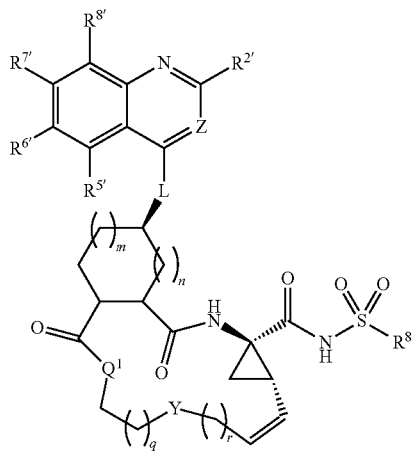

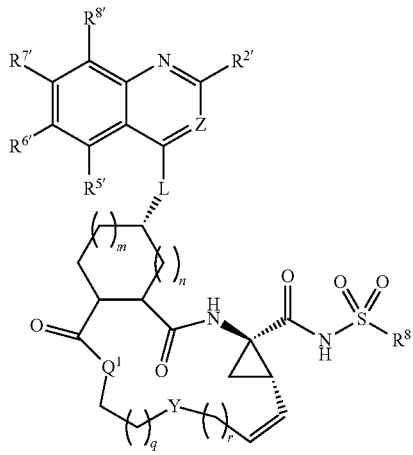

or a single enantiomer, a racemic mixture, a mixture of diastereomers, or an isotopic variant thereof; or a pharmaceutically acceptable salt, solvate, or prodrug thereof; wherein R⁸, R²', R⁵', R⁶', R⁷', R⁸', L, Q¹, Y, Z, m, n, q, and r are each as defined herein.

In yet another embodiment, provided herein is a compound of Formula XIIa or XIIb:

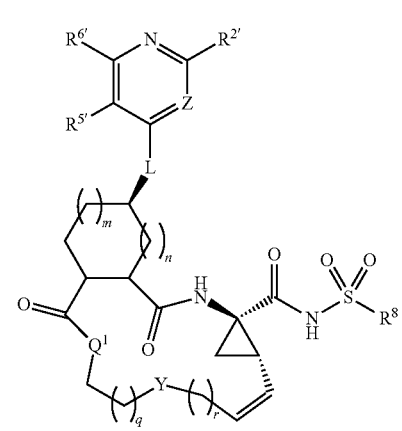

(XIIb)

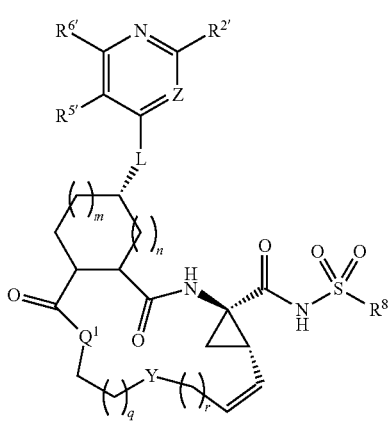

or a single enantiomer, a racemic mixture, a mixture of diastereomers, or an isotopic variant thereof; or a pharmaceutically acceptable salt, solvate, or prodrug thereof; wherein $R^8$, $R^{2'}$, $R^{5'}$, $R^{6'}$, L, $Q^1$, Y, Z, m, n, q, and r are each as defined herein.

In Formula XIIa or XIIb, in one embodiment, m and n are each 1; in another embodiment, m is 0, and n is 2; in yet another embodiment, Y is a bond, q is 1, and r is 2; in yet another embodiment, Y is —O—, and q and r are each 1; in yet another embodiment, Z is CH; in yet another embodiment, Z is N; in yet another embodiment, Y is a bond, m, n, and q are each 1, and r is 2; in yet another embodiment, Y is —O—, and m, n, q, and r are each 1; in yet another embodiment, Y is a bond, m is 0, n is 2, q is 1, and r is 2; in yet another embodiment, Y is a bond, Z is CH, m, n, and q are each 1, and r is 2; in yet another embodiment, Y is —O—, Z is CH, and m, n, q, and r are each 1; in yet another embodiment, Y is a bond, Z is CH, m is 0, n is 2, q is 1, and r is 2; in yet another embodiment, Y is a bond, Z is N, m, n, and q are each 1, and r is 2; in yet another embodiment, Y is —O—, Z is N, and m, n, q, and r are each 1; in still another embodiment, Y is a bond, Z is N, m is 0, n is 2, q is 1, and r is 2.

In one embodiment, provided herein is a compound of Formula XIIIa or XIIIb:

(XIIIa)

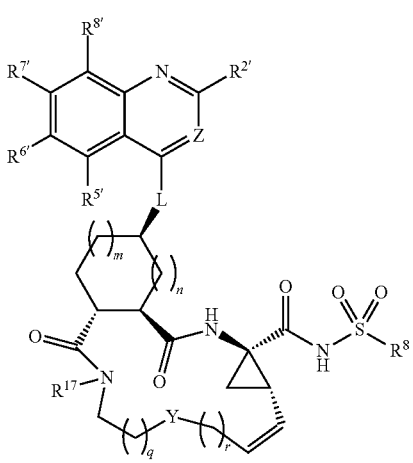

(XIIIb)

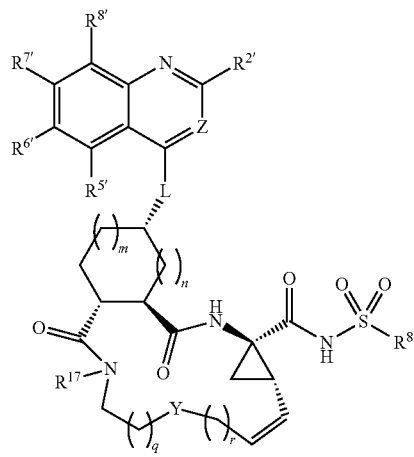

or a single enantiomer, a racemic mixture, a mixture of diastereomers, or an isotopic variant thereof; or a pharmaceutically acceptable salt, solvate, or prodrug thereof; wherein $R^8$, $R^{17}$, $R^{2'}$, $R^{5'}$, $R^{6'}$, $R^{7'}$, $R^{8'}$, L, Y, Z, m, n, q, and r are each as defined herein.

In another embodiment, provided herein is a compound of Formula XIVa or XIVb:

(XIVa)

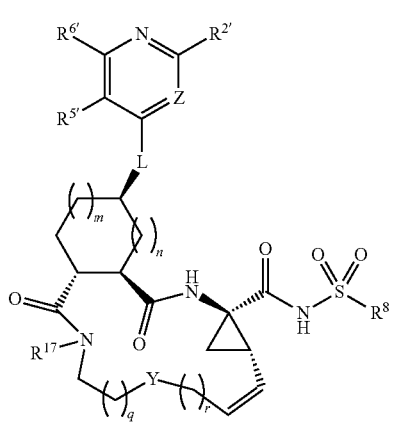

(XIVb)

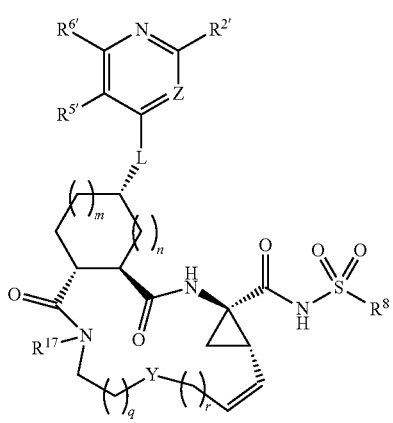

or a single enantiomer, a racemic mixture, a mixture of diastereomers, or an isotopic variant thereof; or a pharmaceutically acceptable salt, solvate, or prodrug thereof; wherein $R^8$, $R^{17}$, $R^{2'}$, $R^{5'}$, $R^{6'}$, $R^{7'}$, $R^{8'}$, L, Y, Z, m, n, q, and r are each as defined herein.

In Formula XIIIa, XIIIb, XIVa, or XIVb, in one embodiment, m and n are each 1; in another embodiment, m is 0, and n is 2; in yet another embodiment, Y is a bond, q is 1, and r is 2; in yet another embodiment, Y is —O—, q is 1, and r is 1; in yet another embodiment, Z is CH; in yet another embodiment, Z is N; in yet another embodiment, Y is a bond, m, n, and q are each 1, and r is 2; in yet another embodiment, Y is —O—, and m, n, q, and r are each 1; in yet another embodiment, Y is a bond, m is 0, n is 2, q is 1, and r is 2; in yet another embodiment, Y is a bond, Z is CH, m, n, and q are each 1, and r is 2; in yet another embodiment, Y is —O—, Z is CH, and m, n, q, and r are each 1; in yet another embodiment, Y is a bond, Z is CH, m is 0, n is 2, q is 1, and r is 2; in yet another embodiment, Y is a bond, Z is N, m, n, and q are each 1, and r is 2; in yet another embodiment, Y is —O—, Z is N, and m, n, q, and r are each 1; in still another embodiment, Y is a bond, Z is N, m is 0, n is 2, q is 1, and r is 2.

The groups, $R^5$, $R^6$, $R^8$, $R^{2'}$, $R^{3'}$, $R^{5'}$, $R^{6'}$, $R^{7'}$, $R^{8'}$, L, $Q^1$, $Q^2$, Y, Z, m, n, q, and r in formulae described herein, including Formulae Ia, Ib, IIa, IIb, IIIc, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, and XIVb, are further defined herein. All combinations of the embodiments provided herein for such groups are within the scope of this disclosure.

In certain embodiments, $R^6$ is hydrogen. In certain embodiments, $R^6$ is $C_{1-6}$ alkyl, optionally substituted with one or more substituents as described herein. In certain embodiments, $R^6$ is $C_{2-6}$ alkenyl, optionally substituted with one or more substituents as described herein. In certain embodiments, $R^6$ is $C_{2-6}$ alkynyl, optionally substituted with one or more substituents as described herein. In certain embodiments, $R^6$ is $C_{3-7}$ cycloalkyl, optionally substituted with one or more substituents as described herein. In certain embodiments, $R^6$ is $C_{6-14}$ aryl, optionally substituted with one or more substituents as described herein. In certain embodiments, $R^6$ is heteroaryl, optionally substituted with one or more substituents as described herein. In certain embodiments, $R^6$ is heterocyclyl, optionally substituted with one or more substituents as described herein.

In certain embodiments, $R^6$ is selected from the group consisting of:

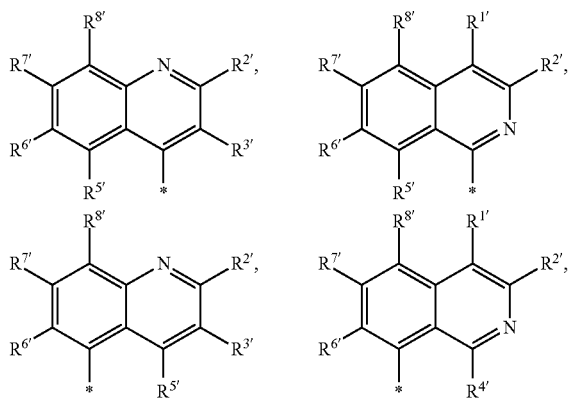

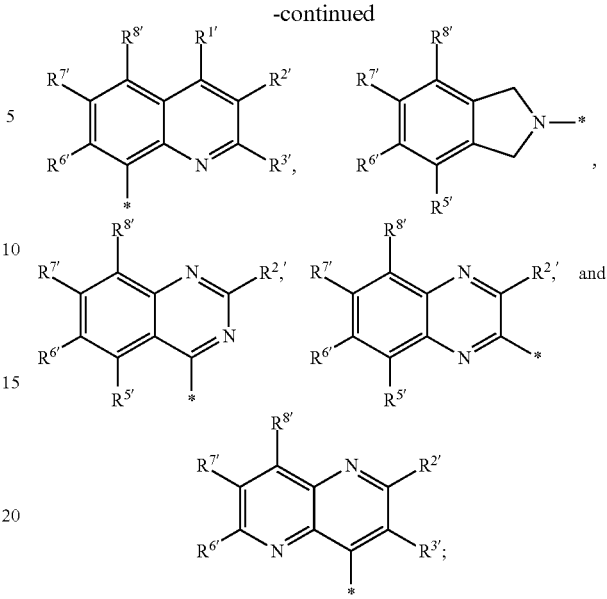

wherein:
$R^{2'}$, $R^{3'}$, $R^{5'}$, $R^{6'}$, $R^{7'}$, and $R^{8'}$ are each as defined herein;
$R^{1'}$ is independently:
hydrogen, halo, cyano, trifluoromethyl, or nitro;
$C_{1-6}$ alkyl, $C_{2-6}$ alkenyl, $C_{2-6}$ alkynyl, $C_{3-7}$ cycloalkyl, $C_{6-14}$ aryl, $C_{7-15}$ aryl, heteroaryl, or heterocyclyl, each optionally substituted with one or more substituents as described herein; or
—C(O)$R^a$, —C(O)O$R^a$, —C(O)N$R^bR^c$, —C(N$R^a$)N$R^b$ $R^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2$ $R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$; —S(O)N$R^bR^c$, or —S(O)$_2$N$R^bR^c$; wherein each $R^a$, $R^b$, $R^c$, and $R^d$ is independently (i) hydrogen; (ti) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents as described herein; or (iii) $R^b$ and $R^c$ together with the N atom to which they are attached form heterocyclyl, optionally substituted with one or more substituents as described herein; and
each star (*) represents the point of attachment.

In certain embodiments, $R^6$ is bicyclic $C_{3-7}$ cycloalkyl, optionally substituted with one or more substituents as described herein. In certain embodiments, $R^6$ is 2,3-dihydro-1H-indenyl, optionally substituted with one or more substituents as defined herein. In certain embodiments, $R^6$ is 4-chloro-2,3-dihydro-1H-inden-2-yl, 4-vinyl-2,3-dihydro-1H-inden-2-yl, or 5-(2-dimethylaminoethoxy)-2,3-dihydro-1H-inden-2-yl. Further examples of 2,3-dihydro-1H-indenyl groups and their syntheses can be found, e.g., in U.S. Pat. Appl. Publ. No. 2009/0169510; and International Pat. Appl. No. WO 2009/082701, the disclosure of which is incorporated herein by reference in its entirety.

In certain embodiments, $R^6$ is bicyclic $C_{6-14}$ aryl, optionally substituted with one or more substituents as described herein. In certain embodiments, $R^6$ is naphthyl, optionally substituted with one or more substituents as described herein. In certain embodiments, $R^6$ is 1-naphthyl or, 2-naphthyl.

In certain embodiments, $R^6$ is bicyclic heteroaryl, optionally substituted with one or more substituents as described herein. In certain embodiments, $R^6$ is bicyclic heteroaryl, optionally substituted with one or more substituents, each substituent independently selected from halo, $C_{1-6}$ alkyl, $C_{6-14}$ aryl, heteroaryl, —$OR^a$, and —$NR^aS(O)_2R^d$; wherein the alkyl, aryl, and heteroaryl are each further optionally substituted with one or more substituents as described herein, and $R^a$ and $R^d$ are each as defined herein.

In certain embodiments, $R^6$ is quinolinyl, optionally substituted with one or more substituents, each of which is independently selected from (i) fluoro, chloro, and bromo; and (i) methyl, trifluoromethyl, phenyl, pyrazolyl, isoxazolyl, thiazolyl, methoxy, difluoromethoxy, trifluoromethoxy, and methanesulfonamido, each of which is further optionally substituted with one or more substituents, each of which is independently selected from fluoro, cyano, methyl, isopropyl, trifluoromethyl, ethenyl, ethynyl, cyclopropyl, cyclobutyl, and isopropylamino.

In certain embodiments, $R^6$ is quinolinyl, each optionally substituted with one or more substituents, each of which is independently selected from fluoro, chloro, bromo, methyl, trifluoromethyl, methoxy, difluoromethoxy, trifluoromethoxy, methanesulfonamido, phenyl, fluorophenyl, cyanothiazolyl, methylthiazolyl, isopropylthiazolyl, trifluoromethyl-thiazolyl, ethenylthiazolyl, ethynylthiazolyl, cyclopropylthiazolyl, cyclobutylthiazolyl, isopropylaminothiazolyl, isopropylisoxazolyl, isopropyl-1H-pyrazolyl, and trifluoromethyl-1H-pyrazolyl In certain embodiments, $R^6$ is quinolinyl, optionally substituted with one or more substituents, each of which is independently selected from fluoro, chloro, bromo, methyl, trifluoromethyl, methoxy, difluoromethoxy, trifluoromethoxy, methanesulfonamido, phenyl, 4-fluorophenyl, 2-isopropylthiazol-4-yl, 2-trifluoromethylthiazol-4-yl, 4-cyano-thiazol-2-yl, 4-methylthiazol-2-yl, 4-isopropylthiazol-2-yl, 4-ethenylthiazol-2-yl, 4-ethynyl-thiazol-2-yl, 4-trifluoromethylthiazol-2-yl, 4-cyclopropylthiazol-2-yl, 4-cyclobutylthiazol-2-yl, 2-isopropylamino-thiazol-4-yl, 5-isopropylisoxazol-3-yl, 3-isopropyl-1H-pyrazol-1-yl, and 3-trifluoromethyl-1H-pyrazol-1-yl.

In certain embodiments, $R^6$ is methoxy-(isopropylthiazolyl)quinolinyl, methoxy-fluoro-(isopropylthiazolyl)quinolinyl, methoxy-chloro-(isopropylthiazolyl)quinolinyl, methoxy-bromo-(isopropylthiazolyl)quinolinyl, methoxy-methyl-(isopropylthiazolyl)quinolinyl, dimethoxy-(isopropylthiazolyl)quinolinyl, difluoromethyl-chloro-(isopropylthiazolyl)quinolinyl, difluoromethyl-methyl-(isopropylthiazolyl)quinolinyl, trifluoromethyl-methyl-(isopropyl-thiazolyl)quinolinyl, methanesulfonamido-chloro-(isopropylthiazolyl)quinolinyl, methanesulfonamido-methyl-(isopropylthiazolyl)quinolinyl, methoxy-(trifluoromethylthiazolyl)-quinolinyl, methoxy-fluoro-(trifluoromethylthiazolyl)quinolinyl, methoxy-chloro-(trifluoromethylthiazolyl)-quinolinyl, methoxy-bromo-(trifluoromethylthiazolyl)quinolinyl, methoxy-methyl-(trifluoromethylthiazolyl)quinolinyl, dimethoxy-(trifluoromethylthiazolyl)quinolinyl, methanesulfonamido-methyl-(trifluoromethylthiazolyl)quinolinyl, methoxy-chloro-(ethenylthiazolyl)quinolinyl, methoxy-chloro-(ethynylthiazolyl)quinolinyl, methoxy-methyl-(ethynylthiazolyl)quinolinyl, methoxy-chloro-(cyanothiazolyl)quinolinyl, methoxy-chloro-(methylthiazolyl)quinolinyl, methoxy-chloro-(cyclopropylthiazolyl)quinolinyl, methoxy-chloro-(cyclobutylthiazolyl)quinolinyl, methoxy-phenyl-quinolinyl, chloro-methoxy-(isopropyl-1H-pyrazolyl) quinolinyl, methyl-methoxy-(isopropyl-1H-pyrazolyl) quinolinyl, chloro-methoxy-(trifluoromethyl-1H-pyrazolyl)-quinolinyl, methyl-methoxy-(trifluoromethyl-1H-pyrazolyl) quinolinyl, methoxy-(isopropyl-isoxazolyl)quinolinyl, methoxy-fluoro-(isopropylisoxazolyl)quinolinyl, methoxy-chloro-(isopropylisoxazolyl)quinolinyl, methoxy-bromo-(isopropylisoxazolyl)quinolinyl, methoxy-methyl-(isopropylisoxazolyl)quinolinyl, dimethoxy-(isopropylisoxazolyl)quinolinyl, or methoxy-(isopropylaminothiazolyl) quinolinyl.

In certain embodiments, $R^6$ is quinolin-3-yl, quinolin-6-yl, quinolin-7-yl, quinolin-8-yl, 7-methoxy-2-(4-isopropylthiazol-2-yl)quinolin-4-yl, 7-methoxy-8-fluoro-2-(4-isopropylthiazol-2-yl)quinolin-4-yl, 7-methoxy-8-chloro-2-(4-isopropylthiazol-2-yl)quinolin-4-yl, 7-methoxy-8-bromo-2-(4-isopropylthiazol-2-yl)quinolin-4-yl, 7-methoxy-8-methyl-2-(4-isopropylthiazol-2-yl)quinolin-4-yl, 5,7-dimethoxy-2-(4-isopropylthiazol-2-yl)quinolin-4-yl, 6-chloro-7-methoxy-2-(4-isopropylthiazol-2-yl)quinolin-4-yl, 6-methoxy-7-chloro-2-(4-isopropylthiazol-2-yl)quinolin-4-yl, 6-methoxy-8-methyl-2-(4-isopropylthiazol-2-yl)quinolin-4-yl, 6-methoxy-8-chloro-2-(4-isopropylthiazol-2-yl)quinolin-4-yl, 7-difluoromethyl-8-methyl-2-(4-isopropylthiazol-2-yl)quinolin-4-yl, 7-difluoromethyl-8-chloro-2-(4-isopropylthiazol-2-yl)quinolin-4-yl, 6-trifluoromethyl-8-methyl-2-(4-isopropylthiazol-2-yl)quinolin-4-yl, 7-trifluoromethyl-8-methyl-2-(4-isopropylthiazol-2-yl)quinolin-4-yl, 7-trifluoromethyl-8-chloro-2-(4-isopropylthiazol-2-yl) quinolin-4-yl, 7-methanesulfonamido-8-methyl-2-(4-isopropylthiazol-2-yl)quinolin-4-yl, 7-methanesulfonamido-8-chloro-2-(4-isopropylthiazol-2-yl)quinolin-4-yl, 6-methyl-8-difluoromethyl-2-(4-isopropylthiazol-2-yl)quinolin-4-yl, 2,2-difluoro-6-(4-isopropylthiazol-2-yl)-[1,3]dioxolo[4,5-g]quinolin-8-yl, 2,2-difluoro-8-(4-isopropylthiazol-2-yl)-[1,3]dioxolo[4,5-h]quinolin-6-yl, 7-methoxy-2-(4-trifluoromethylthiazol-2-yl)quinolin-4-yl, 7-methoxy-8-fluoro-2-(4-trifluoromethylthiazol-2-yl)quinolin-4-yl, 7-methoxy-8-chloro-2-(4-trifluoromethylthiazol-2-yl)quinolin-4-yl, 7-methoxy-8-bromo-2-(4-trifluoromethylthiazol-2-yl) quinolin-4-yl, 7-methoxy-8-methyl-2-(4-trifluoromethyl-2-yl)quinolin-4-yl, 5,7-dimethoxy-2-(4-trifluoromethylthiazol-2-yl)quinolin-4-yl, 6-methoxy-7-chloro-2-(4-trifluoromethylthiazol-2-yl)quinolin-4-yl, 6-methoxy-8-methyl-2-(4-trifluoromethylthiazol-2-yl)quinolin-4-yl, 7-methanesulfonamido-8-methyl-2-(4-trifluoromethylthiazol-2-yl)quinolin-4-yl, 7-methoxy-8-chloro-2-(4-ethenylthiazol-2-yl)quinolin-4-yl, 7-methoxy-8-chloro-2-(4-ethynylthiazol-2-yl)quinolin-4-yl, 7-methoxy-8-methyl-2-(4-ethynylthiazol-2-yl)quinolin-4-yl, 7-methoxy-8-chloro-2-(4-cyanothiazol-2-yl)quinolin-4-yl, 7-methoxy-8-chloro-2-(4-methylthiazol-2-yl)quinolin-4-yl, 7-methoxy-8-chloro-2-(4-cyclopropylthiazol-2-yl)quinolin-4-yl, 7-methoxy-8-chloro-2-(4-cyclobutylthiazol-2-yl)quinolin-4-yl, 7-methoxy-2-(2-isopropylthiazol-4-yl)quinolin-4-yl, 7-methoxy-8-fluoro-2-(2-isopropylthiazol-4-yl)quinolin-4-yl, 7-methoxy-8-chloro-2-(2-isopropylthiazol-4-yl)quinolin-4-yl, 7-methoxy-8-bromo-2-(2-isopropylthiazol-4-yl)quinolin-4-yl, 7-methoxy-8-methyl-2-(2-isopropylthiazol-4-yl)quinolin-4-yl, 5,7-dimethoxy-2-(2-isopropylthiazol-4-yl)quinolin-4-yl, 6-methoxy-7-chloro-2-(2-isopropylthiazol-4-yl)quinolin-4-yl, 6-methoxy-8-methyl-2-(2-isopropylthiazol-4-yl)quinolin-4-yl, 7-methoxy-8-chloro-2-(2-trifluoromethylthiazol-4-yl)quinolin-4-yl, 7-methoxy-8-methyl-2-(2-trifluoromethylthiazol-4-yl)quinolin-4-yl, 8-chloro-7-methoxy-2-(3-isopropyl-1H-pyrazol-1-yl)quinolin-4-yl, 8-methyl-7-methoxy-2-(3-isopropyl-1H-pyrazol-1-yl)quinolin-4-yl, 8-chloro-7-methoxy-2-(3-trifluoromethyl- 1H-pyrazol-1-yl)quinolin-4-yl, 8-methyl-7-methoxy-2-(3-trifluoromethyl-1H-pyrazol-1-yl)quinolin-4-yl, 7-methoxy-2-(5-isopropylisoxazol-3-yl)quinolin-4-yl, 7-methoxy-8-fluoro-2-(5-isopropylisoxazol-3-yl)quinolin-4-yl, 7-methoxy-8-chloro-2-(5-isopropylisoxazol-3-yl)quinolin-4-yl, 7-methoxy-8-bromo-2-(5-isopropylisoxazol-3-yl)quinolin-4-yl, 7-methoxy-8-methyl-2-(5-isopropylisoxazol-3-yl)quinolin-4-yl, 5,7-dimethoxy-2-(5-isopropylisoxazol-3-yl)quinolin-4-yl, 6-methoxy-7-chloro-2-(5-isopropylisoxazol-3-yl)quinolin-4-yl, 6-methoxy-8-methyl-2-(5-isopropylisoxazol-3-yl)quinolin-4-yl, 7-methoxy-2-phenyl-quinolinyl, or 7-methoxy-2-(2-isopropylaminothiazol-4-yl)quinolinyl.

In certain embodiments, $R^6$ is quinazolinyl, optionally substituted with one or more substituents, each of which is independently selected from (i) fluoro, chloro, and bromo; and (i) methyl, trifluoromethyl, phenyl, pyrazolyl, isoxazolyl, thiazolyl, methoxy, difluoromethoxy, trifluoromethoxy, and methanesulfonamido, each of which is further optionally substituted with one or more substituents, each of which is independently selected from fluoro, cyano, methyl, isopropyl, trifluoromethyl, ethenyl, ethynyl, cyclopropyl, cyclobutyl, and isopropylamino.

In certain embodiments, $R^6$ is quinazolinyl, each optionally substituted with one or more substituents, each of which is independently selected from fluoro, chloro, bromo, methyl, trifluoromethyl, methoxy, difluoromethoxy, trifluoromethoxy, methanesulfonamido, phenyl, fluorophenyl, cyanothiazolyl, methylthiazolyl, isopropylthiazolyl, trifluoromethyl-thiazolyl, ethenylthiazolyl, ethynylthiazolyl, cyclopropylthiazolyl, cyclobutylthiazolyl, isopropylaminothiazolyl, isopropylisoxazolyl, isopropyl-1H-pyrazolyl, and trifluoromethyl-1H-pyrazolyl In certain embodiments, $R^6$ is quinazolinyl, optionally substituted with one or more substituents, each of which is independently selected from fluoro, chloro, bromo, methyl, trifluoromethyl, methoxy, difluoromethoxy, trifluoromethoxy, methanesulfonamido, phenyl, 4-fluorophenyl, 2-isopropylthiazol-4-yl, 2-trifluoromethylthiazol-4-yl, 4-cyano-thiazol-2-yl, 4-methylthiazol-2-yl, 4-isopropylthiazol-2-yl, 4-ethenylthiazol-2-yl, 4-ethynyl-thiazol-2-yl, 4-trifluoromethylthiazol-2-yl, 4-cyclopropylthiazol-2-yl, 4-cyclobutylthiazol-2-yl, 2-isopropylamino-thiazol-4-yl, 5-isopropylisoxazol-3-yl, 3-isopropyl-1H-pyrazol-1-yl, and 3-trifluoromethyl-1H-pyrazol-1-yl.

In certain embodiments, $R^6$ is methoxy-(isopropylthiazolyl)quinazolinyl, methoxy-fluoro-(isopropylthiazolyl) quinazolinyl, methoxy-chloro-(isopropylthiazolyl) quinazolinyl, methoxy-bromo-(isopropylthiazolyl)-quinazolinyl, methoxy-methyl-(isopropylthiazolyl) quinazolinyl, dimethoxy-(isopropyl-thiazolyl)quinazolinyl, methoxy-chloro-(isopropylthiazolyl)quinazolinyl, methoxy-methyl-(isopropylthiazolyl)-quinazolinyl, methoxy-chloro-(trifluoromethyl-1H-pyrazolyl)-quinazolinyl, or methoxy-chloro-(fluorophenyl)quinazolinyl.

In certain embodiments, $R^6$ is 7-methoxy-2-(4-isopropylthiazol-2-yl)quinazolin-4-yl, 7-methoxy-8-fluoro-2-(4-isopropylthiazol-2-yl)quinazolin-4-yl, 7-methoxy-8-chloro-2-(4-isopropylthiazol-2-yl)quinazolin-4-yl, 7-methoxy-8-bromo-2-(4-isopropylthiazol-2-yl)quinazolin-4-yl, 7-methoxy-8-methyl-2-(4-isopropylthiazol-2-yl)quinazolin-4-yl, 5,7-dimethoxy-2-(4-isopropylthiazol-2-yl)quinazolin-4-yl, 6-methoxy-7-chloro-2-(4-isopropylthiazol-2-yl)quinazolin-4-yl, 6-methoxy-8-methyl-2-(4-isopropylthiazol-2-yl)quinazolin-4-yl, 7-methoxy-8-chloro-2-(3-trifluoromethyl-1H-pyrazol-1-yl)quinazolin-4-yl, or 7-methoxy-8-chloro-2-(4-fluorophenyl)quinazolin-4-yl.

In certain embodiments, $R^6$ is quinoxalinyl, optionally substituted with one or more substituents as defined herein. In certain embodiments, $R^6$ is quinoxalin-2-yl, 3-chloroquinoxalin-2-yl, 3-ethylquinoxalin-2-yl, 3-propargylquinoxalin-2-yl, 3-(thien-3-yl-methyl)quinoxalin-2-yl, 3-(1H-imidazol-2-ylmethyl)quinoxalin-2-yl, 3-(1H-indol-3-yl)methylquinoxalin-2-yl, 3-(2-(3,4-dimethoxyphenyl)ethenyl)quinoxalin-2-yl, 3-(2-thien-2-yl-ethenyl)quinoxalin-2-yl, 3-(2-pyridin-3-yl-ethenyl)quinoxalin-2-yl, 3-(2-pyridin-3-yl-ethynyl)quinoxalin-2-yl, 3-phenylquinoxalin-2-yl, 3-(4-fluorophenyl)quinoxalin-2-yl, 3-(4-t-butylphenyl)quinoxalin-2-yl, 3-(4-methoxyphenyl)quinoxalin-2-yl, 3-(4-ethoxyphenyl)quinoxalin-2-yl, 3-(3,4-dimethoxyphenyl)quinoxalin-2-yl, 7-(2-fluorophenyl)quinoxalin-2-yl, 3-benzylquinoxalin-2-yl, 3-methoxyquinoxalin-2-yl, 3-(2-furanyl)quinoxalin-2-yl, 3-(1-methyl-pyrrol-2-yl)quinoxalin-2-yl, 3-(oxazol-2-yl)quinoxalin-2-yl, 3-(thiazol-2-yl)quinoxalin-2-yl, 3-(pyridin-2-yl)quinoxalin-2-yl, 3-(pyridin-4-yl)quinoxalin-2-yl, 3-(1,3-dihydro-isoindol-2-yl)quinoxalin-2-yl, 3-(2-phenylacetamido)-quinoxalin-2-yl, 3-(2-thienyl)quinoxalin-2-yl, 3-(2-thienyl)-7-methoxy-quinoxalin-2-yl, 3-(2-thienyl)-6-methylamino-quinoxalin-2-yl, 3-(2-thienyl)-6,7-dimethoxy-quinoxalin-2-yl, 3-(2-thienyl)-6-cyano-quinoxalin-2-yl, 3-(2-thienyl)-6-(tetrazol-5-yl)-quinoxalin-2-yl, 3-(2-thienyl)-6-methanesulfonyl-quinoxalin-2-yl, 3-(2-thienyl)-6-hydroxysulfonyl-quinoxalin-2-yl, 3-(2-thienyl)-6-hydroxymethyl-quinoxalin-2-yl, 3-(2-thienyl)-6-(1-piperidylmethyl)-quinoxalin-2-yl, 3-(2-thienyl)-6-nitroquinoxalin-2-yl, 3-(2-thienyl)-6-amino-quinoxalin-2-yl, 3-(2-thienyl)-6-(2-phenylacetamido)-quinoxalin-2-yl, 3-(2-thienyl)-6-(dimethylamino)-quinoxalin-2-yl, 3-(2-thienyl)-6-hydroxy-quinoxalin-2-yl, 3-(2-thienyl)-6-benzoxy-quinoxalin-2-yl, 3-(2-thienyl)-6-carboxy-quinoxalin-2-yl, 3-(2-thienyl)-6-(2-phenylacetyl)-quinoxalin-2-yl, 3-(2-thienyl)-6-(benzylaminocarbonyl)-quinoxalin-2-yl, 3-(2-thienyl)-6-(2-phenylethyl)-quinoxalin-2-yl, 3-(2-thienyl)-6-bromo-quinoxalin-2-yl, 3-(2-thienyl)-6-(2-thiazolyl)-quinoxalin-2-yl, 3-(2-thienyl)-6-phenyl-quinoxalin-2-yl, 3-(2-thienyl)-6-(2-pyridin-3-yl-ethynyl)-quinoxalin-2-yl, 3-(2-thienyl)-6-(pyrazol-1-yl)-quinoxalin-2-yl, 3-(5-bromothien-2-yl)quinoxalin-2-yl, 3-(thien-3-yl)quinoxalin-2-yl, 3-tetrazolylquinoxalin-2-yl, 3-(pyridin-3-yl)quinoxalin-2-yl, 3-(2-formamidothiazol-4-yl)-7-methoxy-quinoxalin-2-yl, 3-(indol-2-yl)quinoxalin-2-yl, 3-(1H-benzoimidazol-2-yl)quinoxalin-2-yl, 3-(2,3-dihydrobenzofuran-5-yl)quinoxalin-2-yl, or 3-(morpholin-4-yl)quinoxalin-2-yl. In certain embodiments, $R^6$ is 3-(thien-2-yl)-quinoxalin-2-yl. Further examples of quinoxalinyl groups and their syntheses can be found, e.g., in U.S. Pat. Appl. Publ. Nos. 2008/0152622, 2009/0175822, and 2009/0180981; and International Pat. Appl. No. WO 2009/053828, the disclosure of which is incorporated herein by reference in its entirety.

In certain embodiments, $R^6$ is isoquinolinyl, optionally substituted with one or more substituents as defined herein. In certain embodiments, $R^6$ is isoquinolin-1-yl, 7-bromo-isoquinolin-1-yl, 6-cyclopropyl-isoquinolin-1-yl, 7-cyclopropyl-isoquinolin-1-yl, 7-ethenyl-isoquinolin-1-yl, 7-(thien-2-yl)-isoquinolin-1-yl, 6-methoxy-isoquinolin-1-yl, 7-methoxy-isoquinolin-1-yl, or 6-isopropoxy-isoquinolin-1-yl. Further examples of isoquinolinyl groups and their syntheses can be found, e.g., in International Pat. Appl. No. WO 2009/082697; the disclosure of which is incorporated herein by reference in its entirety.

In certain embodiments, $R^6$ is indolyl, optionally substituted with one or more substituents as defined herein. In certain embodiments, $R^6$ is indol-2-yl, 5-fluoro-indol-2-yl, 5-chloro-indol-2-yl, 1-methyl-indol-2-yl, 5-trifluoromethylindol-2-yl, 5-methoxy-indol-2-yl, or 5,6-dimethoxy-indol-2-yl, or indol-6-yl. Further examples of indolyl groups and their syntheses can be found, e.g., in U.S. Pat. Appl. Publ. Nos. 2009/0111982, the disclosure of which is incorporated herein by reference in its entirety.

In certain embodiments, $R^6$ is benzofuranyl, optionally substituted with one or more substituents as defined herein. In certain embodiments, $R^6$ is benzofuran-2-yl, 5-chloro-benzofuran-2-yl, 5-methoxy-benzofuran-2-yl, or 7-methoxy-benzofuran-2-yl. Further examples of benzofuranyl groups and their syntheses can be found, e.g., in U.S. Pat. Appl. Publ. Nos. 2009/0111982, the disclosure of which is incorporated herein by reference in its entirety.

In certain embodiments, $R^6$ is benzo[b]thienyl, optionally substituted with one or more substituents as defined herein. In certain embodiments, $R^6$ is benzo[b]thien-2-yl, 3-chloro-benzo[b]thien-2-yl, 3,4-dichloro-benzo[b]thien-2-yl, or 3-chloro-6-fluoro-benzo[b]thien-2-yl. Further examples of benzo[b]thienyl groups and their syntheses can be found, e.g., in U.S. Pat. Appl. Publ. Nos. 2009/0111982, the disclosure of which is incorporated herein by reference in its entirety.

In certain embodiments, $R^6$ is pyrido[2,3-b]pyrazinyl, thieno[3,2-d]pyrimidinyl, thieno[2,3-b]pyrazinyl, benzothiazolyl, benzoimidazolyl, or 2H-benzo[d][1,2,3]triazolyl, each optionally substituted with one or more substituents as defined herein. In certain embodiments, $R^6$ is pyrido[2,3-b]pyrazin-3-yl, 2-(thien-2-yl)pyrido[2,3-b]pyrazin-3-yl, 2-(pyridin-2-yl)thieno[3,2-d]pyrimidin-4-yl, thieno[2,3-b]pyrazin-3-yl, benzothiazol-2-yl, benzoimidazol-2-yl, 5,6-dimethyl-2H-benzo[d][1,2,3]triazol-2-yl, or 4,5-dimethyl-6-thien-3-yl-2H-benzo[d][1,2,3]triazol-2-yl.

In certain embodiments, $R^6$ is bicyclic heterocyclyl; optionally substituted with one or more substituents as described herein. In certain embodiments, $R^6$ is 1,3-dihydro-isoindolyl, optionally substituted with one or more substituents as described herein. In certain embodiments. $R^6$ is 1,3-dihydro-isoindol-2-yl, optionally substituted with one or more substituents as described herein. In certain embodiments, $R^6$ is 1,3-dihydro-isoindol-2-yl, 5-cyano-1,3-dihydro-isoindol-2-yl, 4-fluoro-1,3-dihydro-isoindol-2-yl, 5-fluoro-1,3-dihydro-isoindol-2-yl, 4,7-difluoro-1,3-dihydro-isoindol-2-yl, 4-fluoro-7-chloro-1,3-dihydro-isoindol-2-yl, 4-chloro-1,3-dihydro-isoindol-2-yl, 5-chloro-1,3-dihydro-isoindol-2-yl, 4,7-dichloro-1,3-dihydro-isoindol-2-yl, 5,6-dichloro-1,3-dihydro-isoindol-2-yl, 4-bromo-1,3-dihydro-isoindol-2-yl, 5-bromo-1,3-dihydro-isoindol-2-yl, 5-hydroxy-1,3-dihydro-isoindol-2-yl, 5-trifluoromethyl-1,3-dihydro-isoindol-2-yl, 4-vinyl-1,3-dihydro-isoindol-2-yl, 5-methoxy-1,3-dihydro-isoindol-2-yl, 4-amino-1,3-dihydro-isoindol-2-yl, 5-amino-1,3-dihydro-isoindol-2-yl, 5-isopropylamino-1,3-dihydro-isoindol-2-yl, 5-carboxy-1,3-dihydro-isoindol-2-yl, 5-methoxycarbonyl-1,3-dihydro-isoindol-2-yl, 5-ethylaminocarbonyl-1,3-dihydro-isoindol-2-yl, 5-(2-dimethylaminoethoxy)-1,3-dihydro-isoindol-2-yl, 5-(2-isopropylaminoethoxy)-1,3-dihydro-isoindol-2-yl, 5-(2-cyclopropylaminoethoxy)-1,3-dihydro-isoindol-2-yl, 5-(2-morpholin-4-ylethoxy)-1,3-dihydro-isoindol-2-yl, 5-(2-morpholin-4-ylcarbonyloxyethoxy)-1,3-dihydro-isoindol-2-yl, 5-(2-imidazol-1-ylethoxy)-1,3-dihydro-isoindol-2-yl, 5-(2-pyrazol-1-ylethoxy)-1,3-dihydro-isoindol-2-yl, 5-(2-methyl-thiazol-4-yl)-1,3-dihydro-isoindol-2-yl, 5-(2-isopropylamino-thiazol-4-yl)-1,3-dihydro-isoindol-2-yl, 4-(morpholin-4-yl)-1,3-dihydro-isoindol-2-yl, 5-(morpholin-4-yl)-1,3-dihydro-isoindol-2-yl, or 5-(4-methyl-piperazin-1-yl)-1,3-dihydro-isoindol-2-yl. In certain embodiments, $R^6$ is 4-fluoro-1,3-dihydro-isoindol-2-yl. Further examples of 1,3-dihydro-isoindolyl groups and their syntheses can be found, e.g., in U.S. Pat. No. 7,491,794; U.S. Pat. Appl. Publ. Nos. 2009/0111969, 2009/0111982, 2009/0148407, 2009/0169510, and 20090175822; and International Pat. Appl. Nos. WO 2008/086161, WO 2009/053828, WO 2009/080542, and WO 2009/082701; the disclosure of which is incorporated herein by reference in its entirety.

In certain embodiments, $R^6$ is 3,4-dihydro-1H-isoquinolinyl, optionally substituted with one or more substituents as described herein. In certain embodiments, $R^6$ is 3,4-dihydro-1H-isoquinolin-2-yl, 5-fluoro-3,4-dihydro-1H-isoquinolin-2-yl, 6-fluoro-3,4-dihydro-1H-isoquinolin-2-yl, 5-chloro-3,4-dihydro-1H-isoquinolin-2-yl, 7-chloro-3,4-dihydro-1H-isoquinolin-2-yl, 5,8-difluoro-3,4-dihydro-1H-isoquinolin-2-yl, 5,8-dichloro-3,4-dihydro-1/1-isoquinolin-2-yl, 5-fluoro-8-chloro-3,4-dihydro-1H-isoquinolin-2-yl, 5-amino-3,4-dihydro-1H-isoquinolin-2-yl, 6-amino-3,4-dihydro-1H-isoquinolin-2-yl, 7-amino-3,4-dihydro-1H-isoquinolin-2-yl, 5-dimethylamino-3,4-dihydro-1H-isoquinolin-2-yl, 4-methyl-3,4-dihydro-1H-isoquinolin-2-yl, 4(R)-methyl-3,4-dihydro-1H-isoquinolin-2-yl, 4(S)-methyl-3,4-dihydro-1H-isoquinolin-2-yl, 4,4-dimethyl-3,4-dihydro-1H-isoquinolin-2-yl, 6-trifluoromethyl-3,4-dihydro-1H-isoquinolin-2-yl, 8-trifluoromethyl-3,4-dihydro-1H-isoquinolin-2-yl, 6,7-dimethoxy-3,4-dihydro-1H-isoquinolin-2-yl, 1-(piperidin-1-ylmethyl)-3,4-dihydro-1H-isoquinolin-2-yl, 1(R)-(piperidin-1-ylmethyl)-3,4-dihydro-1H-isoquinolin-2-yl, 1(S)-(piperidin-1-ylmethyl)-3,4-dihydro-1H-isoquinolin-2-yl, 1-(piperidin-1-ylmethyl)-6-methoxy-3,4-dihydro-1H-isoquinolin-2-yl, 1-(morpholin-4-ylmethyl)-3,4-dihydro-1H-isoquinolin-2-yl, 1-(morpholin-4-ylmethyl)-6-methoxy-3,4-dihydro-1H-isoquinolin-2-yl, 1-methoxymethyl-5-fluoro-3,4-dihydro-1H-isoquinolin-2-yl, 1-methoxymethyl-6-methoxy-3,4-dihydro-1H-isoquinolin-2-yl, 1-dimethyaminomethyl-3,4-dihydro-1H-isoquinolin-2-yl, or 1-dimethyaminomethyl-6-methoxy-3,4-dihydro-1H-isoquinolin-2-yl. Further examples of 3,4-dihydro-1H-isoquinolinyl groups and their syntheses can be found, e.g., in U.S. Pat. No. 7,491,794; and U.S. Pat. Appl. Publ. Nos. 2009/0111969, 2009/0111982, 2009/0148407, and 2009/0169510; the disclosure of which is incorporated herein by reference in its entirety.

In certain embodiments, $R^6$ is 4,5,6,7-tetrahydrothiazolo[5,4-c]pyridinyl, optionally substituted with one or more substituents as described herein. In certain embodiments, $R^6$ is 2-amino-4,5,6,7-tetrahydrothiazolo[5,4-c]pyridin-5-yl, 2-tert-butylamino-4,5,6,7-tetrahydrothiazolo[5,4-c]pyridin-5-yl, 2-phenylamino-4,5,6,7-tetrahydrothiazolo[5,4-c]pyridin-5-yl, 2-methyl-4,5,6,7-tetrahydrothiazolo[5,4-c]pyridin-5-yl, or 2-acetamino-4,5,6,7-tetrahydrothiazolo[5,4-c]pyridin-5-yl. Further examples of 4,5,6,7-tetrahydrothiazolo[5,4-c]pyridin-5-yl groups and their syntheses can be found, e.g., in U.S. Pat. No. 7,491,794; and U.S. Pat. Appl. Publ. Nos. 2009/0111969 and 2009/0111982; the disclosure of which is incorporated herein by reference in its entirety.

In certain embodiments, $R^6$ is 5,6,7,8-tetrahydropyrido[4,3-d]pyrimidinyl. In certain embodiments, $R^6$ is 5,6,7,8-tetrahydropyrido[4,3-d]pyrimidin-6-yl.

In certain embodiments, $R^6$ is

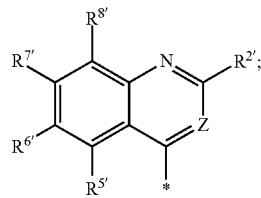

wherein R², R³', R⁵', R⁶', R⁷', R⁸', and Z are each as defined herein.

In certain embodiments, R⁶ is

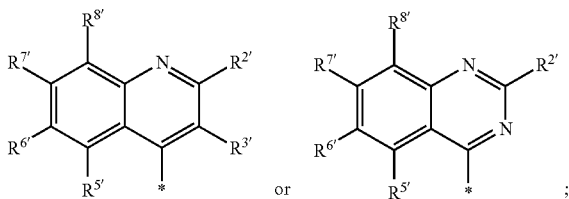

wherein R²', R³', R⁵', R⁶', R⁷', and R⁸' are each as defined herein.

In certain embodiments, R⁶ is polycyclic aryl or heteroaryl, optionally substituted with one or more substituents as defined herein. In certain embodiments, R⁶ is [1,3]dioxolo[4,5-g]quinoxalinyl, benzo[g]quinoxalinyl, 4,4-spirocyclobutyl-3,4-dihydro-1H-isoquinolinyl, 2,3,4,9-tetrahydro-1H-pyrido[3,4-b]indolyl, each optionally substituted with one or more substituents as defined herein. In certain embodiments, R⁶ is [1,3]dioxolo[4,5-g]quinoxalin-6-yl, benzo[g]quinoxalin-6-yl, 4,4-spirocyclobutyl-3,4-dihydro-1H-isoquinolin-2-yl, 4,4-spirocyclobutyl-3,4-dihydro-1H-isoquinolin-2-yl, 2,3,4,9-tetrahydro-1H-pyrido[3,4-b]indol-2-yl, 6-methoxy-2,3,4,9-tetrahydro-1H-pyrido[3,4-b]indol-2-yl, 3H-pyridazino[4,5-b]indol-4(5H)-on-3-yl, benzofuro[3,2-d]pyridazin-4(3H)-on-3-yl, 9-anthracenyl, 9H-xanth-9-yl, or 10,11-dihydro-5H-bibenzo[1,2-d]cyclohept-5-yl.

In certain embodiments, R⁶ is monocyclic $C_{3-7}$ cycloalkyl, optionally substituted with one or more substituents as described herein. In certain embodiments, R⁶ is monocyclic $C_{6-14}$ aryl, optionally substituted with one or more substituents as described herein. In certain embodiments, R⁶ is phenyl, optionally substituted with one or more substituents as described herein. In certain embodiments, R⁶ is phenyl, 3-cyanophenyl, 4-cyanophenyl, 3,4-difluorophenyl, 4-chlorophenyl, 3-bromophenyl, 3,4-dichlorophenyl, 2,4,6-trifluorophenyl, 4-ethylphenyl, 2-phenylphenyl, 3-phenylphenyl, 4-phenylphenyl, 3-thien-2-yl-phenyl, 4-(1H-imidazol-1-yl)phenyl, 3-methoxyphenyl, 4-methoxyphenyl, 4-methoxy-3-trifluoromethylphenyl, 4-dimethylaminophenyl, 4-aminocarbonylphenyl, or 4-aminosulfonylphenyl. Further examples of monocyclic aryl groups and their syntheses can be found, e.g., in U.S. Pat. No. 7,491,794 and U.S. Pat. Appl. Publ. No. 2009/0111982; the disclosure of each of which is incorporated herein by reference in its entirety.

In certain embodiments, R⁶ is 5- or 6-membered heteroaryl or heterocyclyl, each of which independently contains one, two, three, or four heteroatoms independently selected from nitrogen, oxygen, and sulfur.

In certain embodiments. R⁶ is monocyclic heterocyclyl, optionally substituted with one or more substituents as described herein. In certain embodiments, R⁶ is monocyclic 5- or 6-membered heterocyclyl, optionally substituted with one or more substituents as described herein.

In certain embodiments, R⁶ is pyridazinonyl, optionally substituted with one or more substituents as defined herein. In certain embodiments, R⁶ is 4,5-dibromopyridazin-6-on-1-yl, 4-phenyl-5-bromopyridazin-6-on-1-yl, 4,5-diphenyl-pyridazin-6-on-1-yl, 3-phenyl-5-(4-fluorophenyl)pyridazin-6-on-1-yl, 3-phenyl-4-(piperidin-1-yl)pyridazin-6-on-1-yl, 4,5-bis(3-fluorophenyl)pyridazin-6-on-1-yl, 3-(4-chlorophenyl)-5-(4-fluorophenyl)pyridazin-6-on-1-yl, 4-(3-fluorophenyl)-5-methoxypyridazin-6-on-1-yl, 4-(1-naphthyl)pyridazin-6-on-1-yl, 4-(1-naphthyl)-5-bromopyridazin-6-on-1-yl, 4,5-bis(1-naphthyl)pyridazin-6-on-1-yl, 4-(1-naphthyl)-5-methoxypyridazin-6-on-1-yl, 4-(5-fluoronaphth-1-yl)-5-methoxypyridazin-6-on-1-yl, 5-(1-naphthyl)-4-methoxypyridazin-6-on-1-yl, 4-(1-naphthyl)-5-isopropoxypyridazin-6-on-1-yl, 4-(1-naphthyl)-5-methylaminopyridazin-6-on-1-yl, 4-(1-naphthyl)-5-dimethylamino-pyridazin-6-on-1-yl, 4,5-bis(thien-3-yl)pyridazin-6-on-1-yl, 4-(pyrrolidin-1-yl)-5-bromo-pyridazin-6-on-1-yl, 4-(pyrrolidin-1-yl)-5-(thien-3-yl)pyridazin-6-on-1-yl, 4-(benzofuran-4-yl)-5-methoxypyridazin-6-on-1-yl, 4-(benzothien-4-yl)-5-methoxypyridazin-6-on-1-yl, 4-(quinolin-4-yl)-5-methoxypyridazin-6-on-1-yl, 4-(quinoxalin-5-yl)-5-methoxypyridazin-6-on-1-yl, 4-(pyrimidin-2-ylthio)-5-bromo-pyridazin-6-on-1-yl, 4,5-bis(pyrimidin-2-ylthio)-pyridazin-6-on-1-yl, 4-(pyrimidin-2-ylthio)-5-(thien-3-yl)pyridazin-6-on-1-yl, 4,5-bis(imidazol-1-yl))pyridazin-6-on-1-yl, 5-(imidazol-1-yl)-4-methoxypyridazin-6-on-1-yl, 4,5-bis(thiazol-2-yl))pyridazin-6-on-1-yl, 4-(tetrazol-2-yl)-5-(thien-3-yl)pyridazin-6-on-1-yl, 3-phenyl-4-(thien-3-yl)pyridazin-6-on-1-yl, 4-phenyl-5-(thien-3-yl)pyridazin-6-on-1-yl, 4,5-bis(4-dimethylaminophenyl)pyridazin-6-on-1-yl, 4,5-bis(4-cyanophenyl)pyridazin-6-on-1-yl, 4,5-bis(4-trifluoromethoxyphenyl)pyridazin-6-on-1-yl, or 4,5-bis(pyridin-3-yl)pyridazin-6-on-1-yl. Further examples of pyridazinonyl groups and their syntheses can be found, e.g., in U.S. Pat. Appl. Publ. No. 2009/0035272, the disclosure of which is incorporated herein by reference in its entirety.

In certain embodiments, R⁶ is piperidinyl, optionally substituted with one or more substituents as defined herein. In certain embodiments, R⁶ is 4-(2-methoxyphenyl)-piperidin-1-yl. Further examples of piperidinyl groups and their syntheses can be found, e.g., in U.S. Pat. Appl. Publ. No. 2009/0111982; the disclosure of which is incorporated herein by reference in its entirety.

In certain embodiments, R⁶ is monocyclic heteroaryl, optionally substituted with one or more substituents as described herein. In certain embodiments, R⁶ is monocyclic 5-membered heteroaryl, optionally substituted with one or more substituents as described herein.

In certain embodiments, R⁶ is triazolyl, optionally substituted with one or more substituents as defined herein. In certain embodiments, R⁶ is 4-(4-methoxyphenyl)-triazol-2-yl, 4-phenyl-5-bromo-triazol-2-yl, 4-phenyl-5-propyl-triazol-2-yl, 4,5-diphenyl-triazol-2-yl, 4-phenyl-5-(thiazol-2-yl)-triazol-2-yl, 4-phenyl-5-(thien-2-yl)triazol-2-yl, 4-phenyl-5-(thien-3-yl)triazol-2-yl, 4-phenyl-5-(quinolin-8-yl)triazol-2-yl, 4-phenyl-5-(2-fluoropyridin-3-yl)triazol-2-yl, 4-phenyl-5-(2-fluoropyridin-4-yl)triazol-2-yl, 4-phenyl-5-(naphth-2-yl)triazol-2-yl, 4-phenyl-5-(2-methoxypyrimidin-5-yl)triazol-2-yl, 4-phenyl-5-(2-(4-fluorophenylaminocarbonyl)phenyl)-triazol-2-yl, 4-phenyl-5-(3-(furan-2-yl-methylamino-carbonyl)phenyl)triazol-2-yl, 4-phenyl-5-(4-cyanomethylphenyl)triazol-2-yl, 4-phenyl-5-(2-methoxypyridin-5-yl)triazol-2-yl, 4-phenyl-5-(2-trifluoromethoxypyridin-5-yl)triazol-2-yl, 4-phenyl-5-(3-acetylphenyltriazol-2-yl, 4-phenyl-5-(3-(morpholin-4-ylcarbonyl)phenyl)-triazol-2-yl, 4-phenyl-5-(4-phenoxyphenyl)triazol-2-yl, 4-(4-methoxyphenyl)-5-(thiazol-2-yl)-triazol-2-yl, 4-(4-methoxyphenyl)-5-(3-bromophenyl)triazol-2-yl, 4-(4-methoxyphenyl)-5-(1-naphthyl)triazol-2-yl, 4-(4-methoxyphenyl)-5-(thien-2-yl)triazol-2-yl, or 4-phenyl-5-(2-phenylethenyl)triazol-2-yl. Further examples of triazolyl groups and their syntheses can be found, e.g., in International Pat. Appl. No. WO 2008/021960, the disclosure of which is incorporated herein by reference in its entirety.

In certain embodiments, $R^6$ is tetrazolyl, optionally substituted with one or more substituents as defined herein. In certain embodiments, $R^6$ is 5-(3-bromophenyl)-2H-tetrazol-2-yl, 5-(3,4-difluorophenyl)-2H-tetrazol-2-yl, 5-(3,5-difluorophenyl)-2H-tetrazol-2-yl, 5-(3,5-dichlorophenyl)-2H-tetrazol-2-yl, 5-(4-trifluoromethylphenyl)-2H-tetrazol-2-yl, 5-(2-(2-phenylethenyl)phenyl)-2H-tetrazol-2-yl, 5-(3-phenylphenyl)-2H-tetrazol-2-yl, 5-benzyl-2H-tetrazol-2-yl, 5-(3-thien-2-yl-phenyl)-2H-tetrazol-2-yl, 5-(5-bromothien-2-yl)-2H-tetrazol-2-yl, 5-(4-methoxyphenyl)-2H-tetrazol-2-yl, 5-(4-ethoxyphenyl)-2H-tetrazol-2-yl, 5-(3-bromo-4-methoxy-phenyl)-2H-tetrazol-2-yl, 5-(3-chloro-4-methoxy-phenyl)-2H-tetrazol-2-yl, 5-(1-naphthyl)-2H-tetrazol-2-yl, 5-(2-naphthyl)-2H-tetrazol-2-yl, 5-ethoxy-2H-tetrazol-2-yl, 2-(2-naphthyl)-2H-tetrazol-5-yl, 2-(4-methoxyphenyl)-2H-tetrazol-5-yl, 2-benzyl-2H-tetrazol-5-yl, or 2-(2-naphthylmethyl)-2H-tetrazol-5-yl. In certain embodiments, $R^6$ is 5-(4-methoxyphenyl)-2H-tetrazol-2-yl. Further examples of tetrazolyl groups and their syntheses can be found, e.g., in U.S. Pat. Appl. Publ. Nos. 2009/0035271, 2009/0130059, and 2009/0175822, the disclosure of each of which is incorporated herein by reference in its entirety.

In certain embodiments, $R^6$ is pyrazolyl, furanyl, thienyl, or thiazolyl, each optionally substituted with one or more substituents as defined herein. In certain embodiments, $R^6$ is 1-phenyl-5-trifluoromethyl-pyrazol-4-yl, 5-(4-chlorophenyl)furan-2-yl, 2-(4-chlorophenyl)thien-4-yl, 2-isopropylamino-thiazol-4-yl, 2-phenylthiazol-4-yl, 2-(2-chlorophenyl)thiazol-4-yl, or 2-(4-chlorophenyl)thiazol-4-yl. Further examples of pyrazolyl, furanyl, thienyl, and thiazolyl groups and their syntheses can be found, e.g., in U.S. Pat. No. 7,491,794 and U.S. Pat. Appl. Publ. No. 2009/0111982, the disclosure of each of which is incorporated herein by reference in its entirety.

In certain embodiments, $R^6$ is monocyclic 6-membered heteroaryl, optionally substituted with one or more substituents as described herein. In certain embodiments, $R^6$ is monocyclic 6-membered heteroaryl, optionally substituted with one or more substituents, each substituent independently selected from —$NR^bR^c$, —$OR^a$, halo, $C_{6-14}$ aryl, heteroaryl, and heterocyclyl; wherein the aryl and heteroaryl are each further optionally substituted with one or more substituents as described herein, and $R^a$, $R^b$, and $R^c$ are each as defined herein.

In certain embodiments, $R^6$ is pyridinyl, optionally substituted with one or more substituents as described herein. In certain embodiments, $R^6$ is pyridinyl, optionally substituted with one or more substituents, each substituent independently selected from —$OR^a$, —$NR^bR^c$, halo, $C_{6-14}$ aryl, heteroaryl, and heterocyclyl; wherein the aryl, heteroaryl, and heterocyclyl are each further optionally substituted with one or more substituents as described herein, and $R^a$, $R^b$, and $R^c$ are each as defined herein. In certain embodiments, $R^6$ is pyridinyl, optionally substituted with one or more substituents, each of which is independently selected from fluoro, methoxy, phenoxy, dimethylamino, phenyl, furanyl, thienyl, oxazolyl, isoxazolyl, imidazolyl, thiazolyl, pyrazolyl, and morpholinyl, each of which is further optionally substituted with one or more substituents, each of which is independently selected from fluoro, chloro, cyano, methoxy, methyl, ethyl, isopropyl, trifluoromethyl, ethynyl, phenyl, benzyl, and pyrrolidinyl.

In certain embodiments, $R^6$ is pyridinyl, optionally substituted with one or more substituents, each of which is independently selected from fluoro, methoxy, phenoxy, dimethylamino, phenyl, fluorophenyl, chlorophenyl, methoxyphenyl, furanyl, thienyl, cyanothienyl, methoxythienyl, methylthienyl, dimethylthienyl, (trifluoromethyl)thienyl, phenylthienyl, thiazolyl, methylthiazolyl, trifluoromethylthiazolyl, isopropylthiazolyl, dimethylthiazolyl, ethynylthiazolyl, pyrrolidinyl-thiazolyl, methyl-1H-pyrazolyl, ethyl-1H-pyrazolyl, trifluoromethyl-pyrazolyl, methyl-(trifluoromethyl)-1H-pyrazolyl, benzyl-1H-pyrazolyl, trimethyl-1H-pyrazolyl, methyl-1H-imidazolyl, phenyl-oxazolyl, dimethylisoxazolyl, and morpholinyl.

In certain embodiments, $R^6$ is pyridinyl, optionally substituted with one or more substituents, each of which is independently selected from fluoro, methoxy, phenoxy, dimethylamino, phenyl, 4-fluorophenyl, 3-chlorophenyl, 4-chlorophenyl, 4-methoxyphenyl, furan-2-yl, thien-2-yl, 4-cyanothien-2-yl, 5-methoxythien-2-yl, 3-methoxy-thien-2-yl, 3-methylthien-2-yl, 5-methylthien-2-yl, 3,5-dimethylthien-2-yl, 5-(trifluoromethyl)-thien-2-yl, 5-phenylthien-2-yl, thien-3-yl, 2-methylthien-3-yl, 4-methyl-thien-3-yl, 2,5-dimethylthien-3-yl, 2-cyano-thien-3-yl, thiazol-2-yl, 4-methyl-thiazol-2-yl, 4-isopropylthiazol-2-yl, 4-trifluoromethyl-thiazol-2-yl, 4-ethynyl-thiazol-2-yl, 5-methyl-thiazol-2-yl, 4,5-dimethylthiazol-2-yl, 2-(pyrrolidin-1-yl)thiazol-4-yl, thiazol-5-yl, 2,4-dimethylthiazol-5-yl, thiazol-4-yl, 2-methoxythiazol-4-yl, 3-trifluoromethyl-pyrazol-1-yl, 1-methyl-3-(trifluoromethyl)-1H-pyrazol-4-yl, 1-methyl-1H-pyrazol-4-yl, 1-ethyl-1H-pyrazol-4-yl, 1-benzyl-1H-pyrazol-4-yl, 1,3,5-trimethyl-1H-pyrazol-4-yl, 1-methyl-1H-imidazol-2-yl, 1-methyl-1H-imidazol-5-yl, 2-phenyloxazol-5-yl, 3,5-dimethylisoxazol-4-yl, and morpholin-4-yl.

In certain embodiments, $R^6$ is 5-fluoropyridin-2-yl, 2-dimethylaminopyridin-5-yl, 2-(4-fluorophenyl)-6-(4-isopropylthiazol-2-yl)pyridin-4-yl, 2-(4-trifluoromethyl-thiazol-2-yl)-6-(4-(trifluoromethypthiazol-2-yl)pyridin-4-yl, 2-(4-ethynyl-thiazol-2-yl)-6-(4-(trifluoromethypthiazol-2-yl)pyridin-4-yl, or 2-(morpholin-4-yl)pyridin-5-yl. In certain embodiments, $R^6$ is 5-fluoro-pyridin-2-yl. Further examples of pyridinyl groups and their syntheses can be found, e.g., in U.S. Pat. No. 7,491,794; and U.S. Pat. Appl. Publ. Nos. 2009/0111982 and 2009/0169510; the disclosure of each of which is incorporated herein by reference in its entirety.

In certain embodiments, $R^6$ is pyrimidinyl, optionally substituted with one or more substituents as described herein. In certain embodiments, $R^6$ is pyrimidinyl, optionally substituted with one or more substituents, each substituent independently selected from —$OR^a$, —$NR^bR^c$, halo, $C_{6-14}$ aryl, heteroaryl, and heterocyclyl; wherein the aryl, heteroaryl, and heterocyclyl are each further optionally substituted with one or more substituents as described herein, and $R^a$, $R^b$, and $R^c$ are each as defined herein. In certain embodiments, $R^6$ is pyrimidinyl, optionally substituted with one or more substituents, each of which is independently selected from fluoro, methoxy, phenoxy, dimethylamino, phenyl, furanyl, thienyl, oxazolyl, isoxazolyl, imidazolyl, thiazolyl, pyrazolyl, and morpholinyl, each of which is further optionally substituted with one or more substituents, each of which is independently selected from fluoro, chloro, cyano, methoxy, methyl, ethyl, isopropyl, trifluoromethyl, ethynyl, phenyl, benzyl, and pyrrolidinyl.

In certain embodiments, $R^6$ is pyrimidinyl, optionally substituted with one or more substituents, each of which is independently selected from fluoro, methoxy, phenoxy, dimethylamino, phenyl, fluorophenyl, chlorophenyl, methoxyphenyl, furanyl, thienyl, cyanothienyl, methoxythienyl, methylthienyl, dimethylthienyl, (trifluoromethyl)thienyl, phenylthienyl, thiazolyl, methylthiazolyl, trifluoromethylthiazolyl, isopropylthiazolyl, dimethylthiazolyl, ethynylthiazolyl, pyrrolidinyl-thiazolyl, methyl-1H-pyrazolyl, ethyl-1H-pyrazolyl, trifluoromethyl-pyrazolyl, methyl-(trifluoromethyl)-1H-pyrazolyl, benzyl-1H-pyrazolyl, trimethyl-1H-pyrazolyl, methyl-1H-imidazolyl, phenyl-oxazolyl, dimethylisoxazolyl, and morpholinyl.

In certain embodiments, $R^6$ is pyrimidinyl, optionally substituted with one or more substituents, each of which is independently selected from fluoro, methoxy, phenoxy, dimethylamino, phenyl, 4-fluorophenyl, 3-chlorophenyl, 4-chlorophenyl, 4-methoxyphenyl, furan-2-yl, thien-2-yl, 3-cyanothien-2-yl, 4-cyanothien-2-yl, 5-methoxythien-2-yl, 3-methoxy-thien-2-yl, 3-methylthien-2-yl, 5-methylthien-2-yl, 3,5-dimethylthien-2-yl, 5-(trifluoromethyl-thien-2-yl, 5-phenylthien-2-yl, thien-3-yl, 2-methylthien-3-yl, 4-methyl-thien-3-yl, 2,5-dimethylthien-3-yl, 2-cyano-thien-3-yl, thiazol-2-yl, 4-methyl-thiazol-2-yl, 4-isopropylthiazol-2-yl, 4-trifluoromethyl-thiazol-2-yl, 4-ethynyl-thiazol-2-yl, 5-methyl-thiazol-2-yl, 4,5-dimethylthiazol-2-yl, 2-(pyrrolidin-1-yl)thiazol-4-yl, thiazol-5-yl, 2,4-dimethylthiazol-5-yl, thiazol-4-yl, 2-methoxythiazol-4-yl, 3-trifluoromethyl-pyrazol-1-yl, 1-methyl-3-(trifluoromethyl)-1H-pyrazol-4-yl, 1-methyl-1H-pyrazol-4-yl, 1-ethyl-1H-pyrazol-4-yl, 1-benzyl-1H-pyrazol-4-yl, 1,3,5-trimethyl-1H-pyrazol-4-yl, 1-methyl-1H-imidazol-2-yl-1-methyl-1H-imidazol-5-yl, 2-phenyloxazol-5-yl, 3,5-dimethylisoxazol-4-yl, and morpholin-4-yl.

In certain embodiments, $R^6$ is 6-methoxy-2-(4-isopropylthiazol-2-yl)pyrimidin-4-yl, 5-phenoxy-2-(4-(trifluoromethyl)thiazol-2-yl)pyrimidin-4-yl; 6-phenoxy-2-(4-(trifluoromethyl)thiazol-2-yl)pyrimidin-4-yl; 6-(4-fluorophenyl)-2-(4-isopropylthiazol-2-yl)pyrimidin-4-yl, 6-(furan-2-yl)-2-(4-(trifluoromethyl)thiazol-2-yl)pyrimidin-4-yl, 6-(thien-2-yl)-2-(4-(trifluoromethypthiazol-2-yl)pyrimidin-4-yl, 6-(3-cyanothien-2-yl)-2-(4-(trifluoromethyl)thiazol-2-yl)pyrimidin-4-yl, 6-(4-cyanothien-2-yl)-2-(4-(trifluoromethypthiazol-2-yl)pyrimidin-4-yl, 6-(5-methoxythien-2-yl)-2-(4-(trifluoromethyl)thiazol-2-yl)pyrimidin-4-yl, 6-(3-methoxy-thien-2-yl)-2-(4-(trifluoromethyl)thiazol-2-yl)pyrimidin-4-yl, 6-(3-methylthien-2-yl)-2-(4-(trifluoromethypthiazol-2-yl)pyrimidin-4-yl, 6-(5-methylthien-2-yl)-2-(4-(trifluoromethyl)-thiazol-2-yl)pyrimidin-4-yl, 6-(3,5-dimethylthien-2-yl)-2-(4-(trifluoromethypthiazol-2-yl)pyrimidin-4-yl, 6-(5-(trifluoromethyl)thien-2-yl)-2-(4-(trifluoromethypthiazol-2-yl)pyrimidin-4-yl, 6-(5-phenylthien-2-yl)-2-(4-(trifluoromethyl)thiazol-2-yl)pyrimidin-4-yl, 6-(thien-3-yl)-2-(4-(trifluoromethyl)thiazol-2-yl)pyrimidin-4-yl, 6-(2-methylthien-3-yl)-2-(4-(trifluoromethypthiazol-2-yl)pyrimidin-4-yl, 6-(4-methylthien-3-yl)-2-(4-(trifluoromethyl)-thiazol-2-yl)pyrimidin-4-yl, 6-(2,5-dimethylthien-3-yl)-2-(4-(trifluoromethypthiazol-2-yl)pyrimidin-4-yl, 6-(2-cyano-thien-3-yl)-2-(4-(trifluoromethyl)thiazol-2-yl)pyrimidin-4-yl, 6-(thiazol-2-yl)-2-(4-(trifluoromethyl)thiazol-2-yl)pyrimidin-4-yl, 6-(4-methyl-thiazol-2-yl)-2-(4-(trifluoromethypthiazol-2-yl)pyrimidin-4-yl, 6-(5-methyl-thiazol-2-yl)-2-(4-(trifluoromethypthiazol-2-yl)pyrimidin-4-yl, 6-(4-trifluoromethyl-thiazol-2-yl)-2-(4-(trifluoromethyl)thiazol-2-yl)pyrimidin-4-yl, 6-(4-ethynyl-thiazol-2-yl)-2-(4-(trifluoromethypthiazol-2-yl)pyrimidin-4-yl, 2-(4-ethynyl-thiazol-2-yl)-6-(4-(trifluoromethyl)thiazol-2-yl)pyrimidin-4-yl, 6-(4,5-dimethylthiazol-2-yl)-2-(4-(trifluoromethypthiazol-2-yl)pyrimidin-4-yl, 6-(2-(pyrrolidin-1-yl)thiazol-4-yl)-2-(4-(trifluoromethyl)thiazol-2-yl)pyrimidin-4-yl, 6-(thiazol-5-yl)-2-(4-(trifluoromethyl)thiazol-2-yl)pyrimidin-4-yl, 6-(2,4-dimethylthiazol-5-yl)-2-(4-(trifluoromethyl)thiazol-2-yl)pyrimidin-4-yl, 6-(thiazol-4-yl)-2-(4-(trifluoromethyl)thiazol-2-yl)pyrimidin-4-yl, 6-(2-methoxythiazol-4-yl)-2-(4-(trifluoromethyl)thiazol-2-yl)pyrimidin-4-yl, 6-(1-methyl-3-(trifluoromethyl)-1H-pyrazol-4-yl)-2-(4-(trifluoromethyl)thiazol-2-yl)pyrimidin-4-yl, 6-(1-methyl-1H-pyrazol-4-yl)-2-(4-(trifluoromethyl)thiazol-2-yl)pyrimidin-4-yl, 6-(1-ethyl-1H-pyrazol-4-yl)-2-(4-(trifluoromethyl)thiazol-2-yl)pyrimidin-4-yl, 6-(1-benzyl-1H-pyrazol-4-yl)-2-(4-(trifluoromethyl)thiazol-2-yl)pyrimidin-4-yl, 6-(1,3,5-trimethyl-1H-pyrazol-4-yl)-2-(4-(trifluoromethypthiazol-2-yl)pyrimidin-4-yl, 6-(1-methyl-1H-imidazol-2-yl)-2-(4-(trifluoromethyl)thiazol-2-yl)pyrimidin-4-yl, 6-(1-methyl-1H-imidazol-5-yl)-2-(4-(trifluoromethyl)thiazol-2-yl)pyrimidin-4-yl, 6-(2-phenyloxazol-5-yl)-2-(4-(trifluoromethyl)-thiazol-2-yl)pyrimidin-4-yl, 6-(3,5-dimethylisoxazol-4-yl)-2-(4-(trifluoromethyl)thiazol-2-2-(3-trifluoromethylpyrazol-1-yl)pyrimidin-4-yl, 6-phenyl-2-(3-trifluoromethylpyrazol-1-yl)pyrimidin-4-yl, 6-(4-methylphenyl)-2-(3-trifluoromethylpyrazol-1-yl) pyrimidin-4-yl, 6-(4-methoxyphenyl)-2-(3-trifluoromethylpyrazol-1-yl) pyrimidin-4-yl, 6-(3-chlorophenyl)-2-(3-trifluoromethylpyrazol-1-yl) pyrimidin-4-yl, 6-(4-chlorophenyl)-2-(3-trifluoromethylpyrazol-1-yl) pyrimidin-4-yl, 6-(4-fluorophenyl)-2-(3-trifluoromethylpyrazol-1-yl) pyrimidin-4-yl, or 6-(4-isopropyl-thiazol-2-yl)-2-(3-trifluoromethylpyrazol-1-yl) pyrimidin-4-yl.

In certain embodiments, $R^6$ is pyrazinyl, optionally substituted with one or more substituents as described herein. In certain embodiments, $R^6$ is pyrazinyl, optionally substituted with one or more substituents, each substituent independently selected from —$OR^a$, $C_{6-14}$ aryl, and heteroaryl, wherein the aryl and heteroaryl are each further optionally substituted with one or more substituents as described herein, and $R^a$ is as defined herein.

In certain embodiments, $R^6$ is pyrazin-2-yl or 5,6-bis(thien-3-yl)-pyrazin-2-yl. Further examples of pyrazinyl groups and their syntheses can be found, e.g., in U.S. Pat. Appl. Publ. No.: 2009/0152622; the disclosure of which is incorporated herein by reference in its entirety.

In certain embodiments, $R^6$ is selected from the group consisting of:

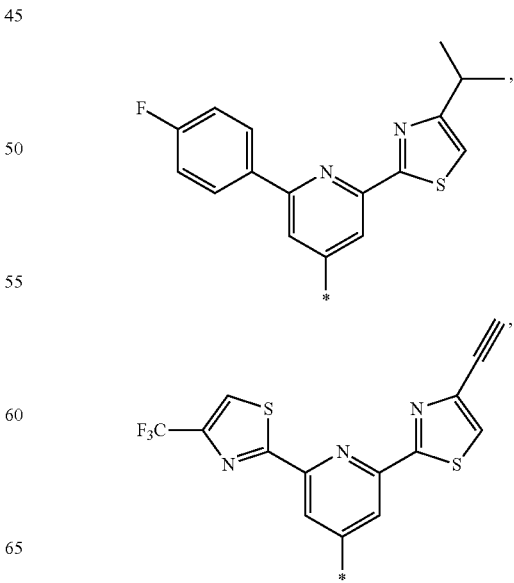

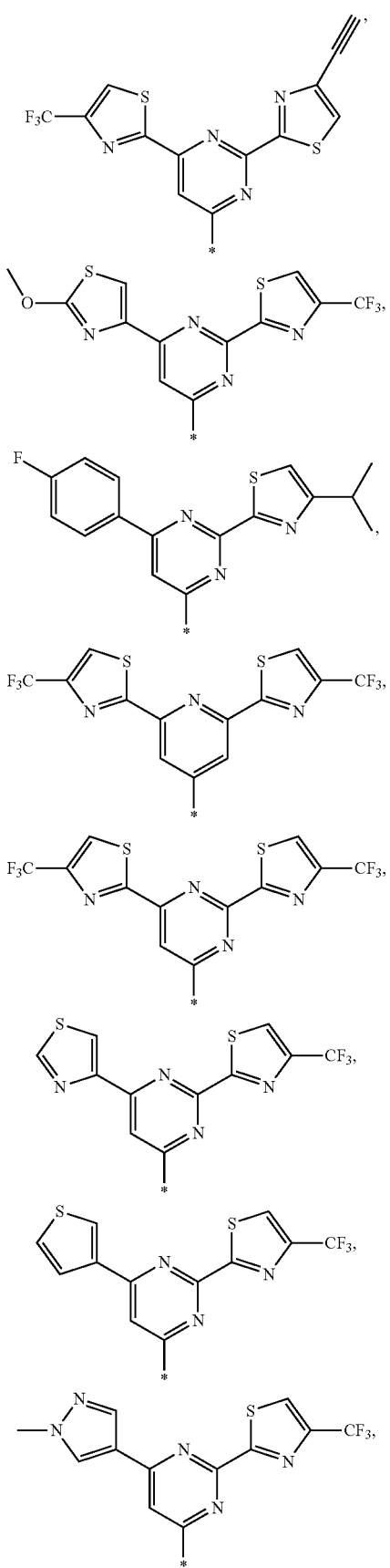
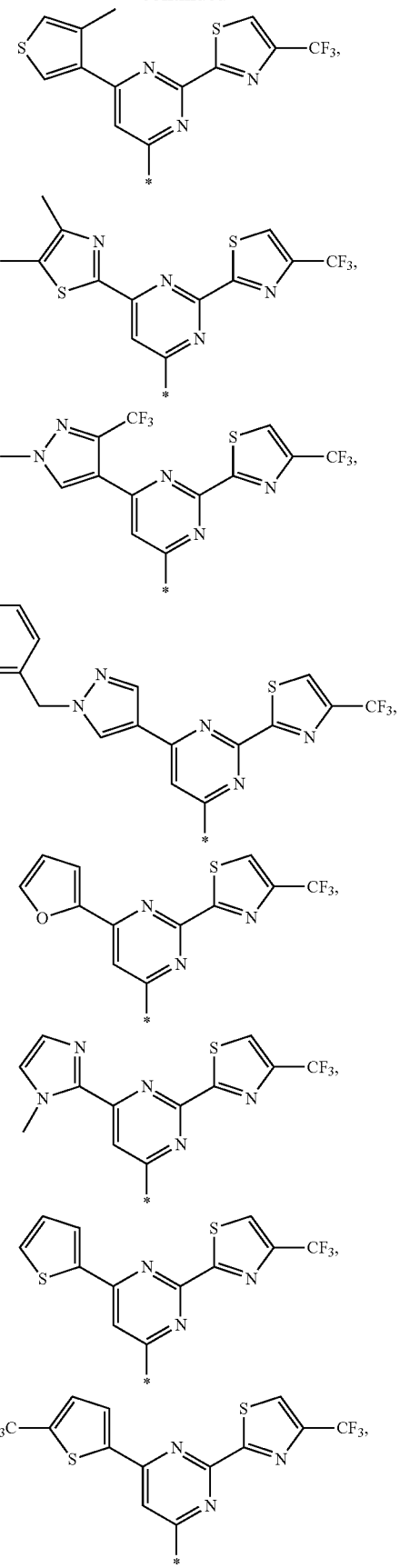

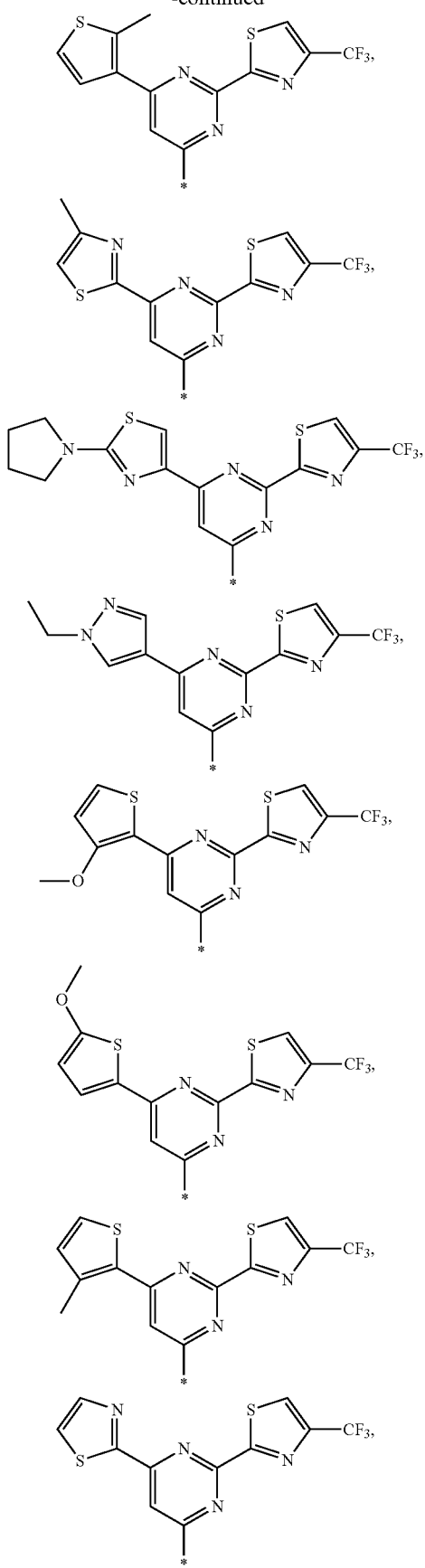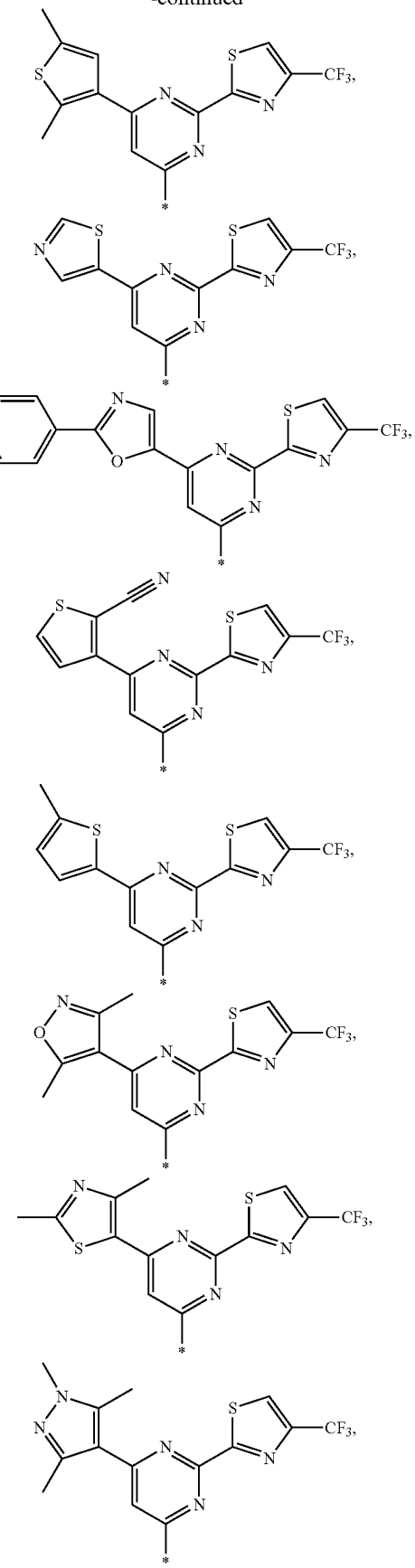

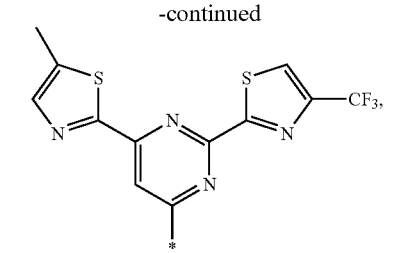
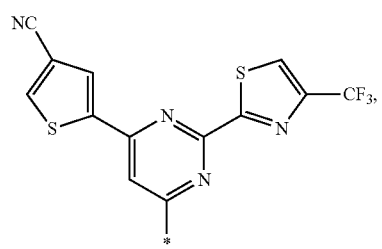
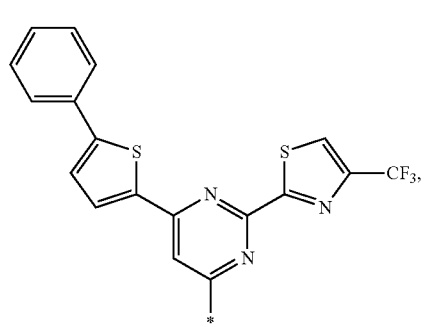
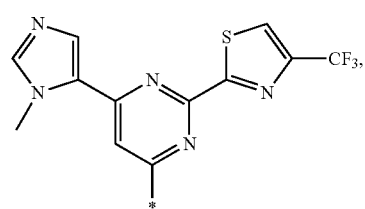
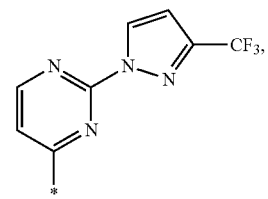
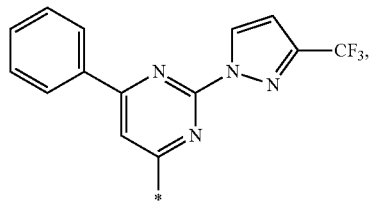
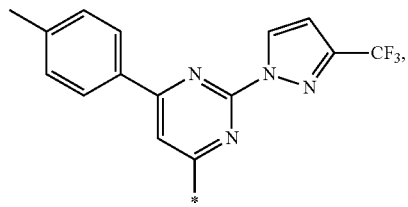
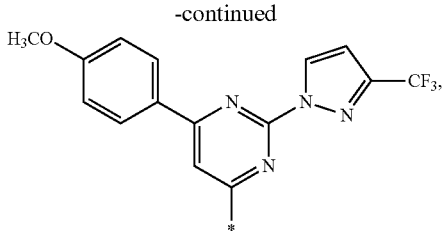
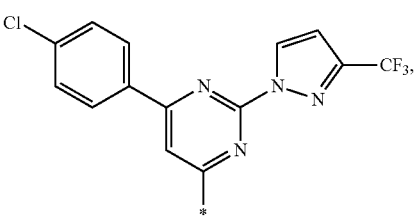
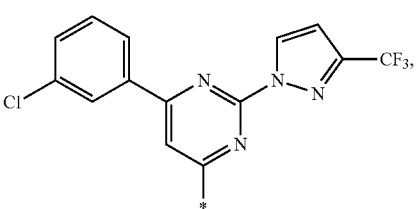
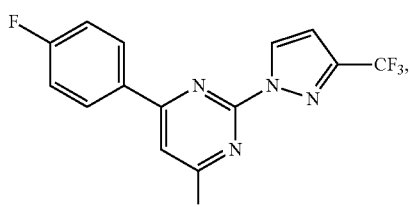
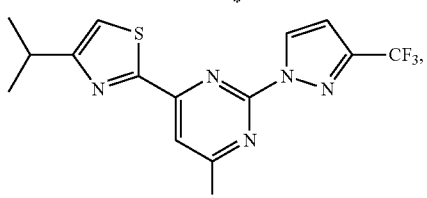
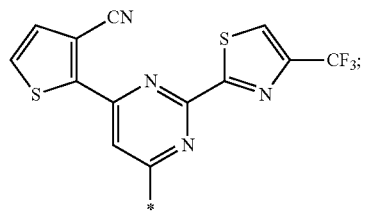
wherein the symbol * indicates the point of attachment.
In certain embodiments, $R^6$ is
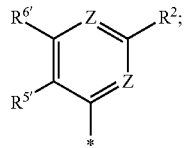
wherein $R^{2'}$, $R^{5'}$, $R^{6'}$, and Z are each as defined herein.

In certain embodiments, $R^6$ is

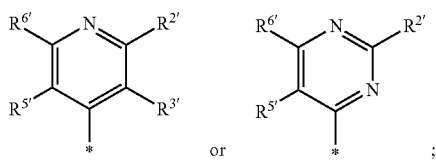 or 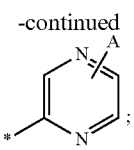 ;

wherein $R^{2'}$, $R^{5'}$, $R^{6'}$, and Z are each as defined herein.

In certain embodiments, $R^{2'}$ is hydrogen. In certain embodiments, $R^{2'}$ is $C_{1-6}$ alkyl, optionally substituted with one or more substituents as described herein. In certain embodiments, $R^{2'}$ is $C_{2-6}$ alkenyl, optionally substituted with one or more substituents as described herein. In certain embodiments, $R^{2'}$ is $C_{7-6}$ alkynyl, optionally substituted with one or more substituents as described herein. In certain embodiments, $R^{2'}$ is $C_{3-7}$ cycloalkyl, optionally substituted with one or more substituents as described herein. In certain embodiments, $R^{2'}$ is $C_{6-14}$ aryl, optionally substituted with one or more substituents as described herein. In certain embodiments, $R^{2'}$ is heteroaryl, optionally substituted with one or more substituents as described herein. In certain embodiments, $R^{2'}$ is heterocyclyl, each optionally substituted with one or more substituents as described herein. In certain embodiments, $R^{2'}$ is —$OR^a$, where $R^a$ is as defined herein. In certain embodiments, $R^{2'}$ is —$OR^a$, where $R^a$ is $C_{1-6}$ alkyl or $C_{6-14}$ aryl, each optionally substituted with one or more substituents as described herein.

In certain embodiments, $R^{2'}$ is selected from the group consisting of:

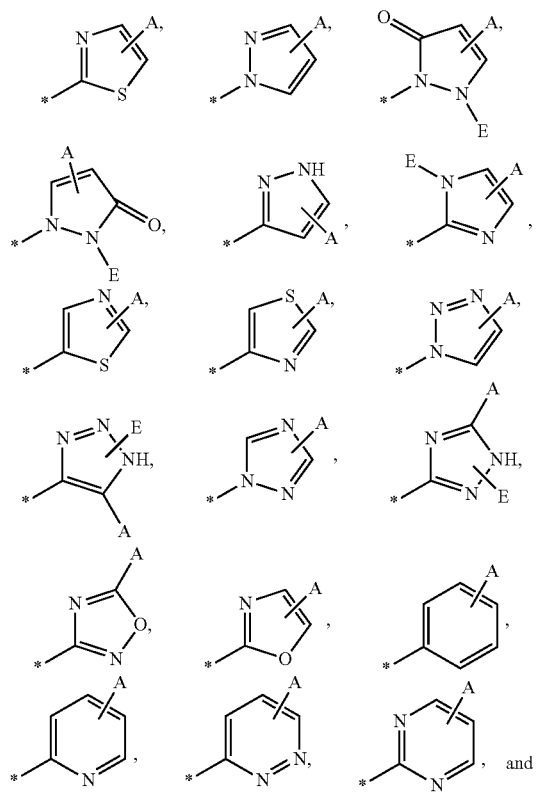

, and

-continued wherein
each A and E is independently (a) hydrogen, halo, cyano, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{6-14}$ aralkyl, heteroaryl, or heterocyclyl, each optionally substituted with one or more substituents as described herein; or (c) —$C(O)R^a$, —$C(O)OR^a$, —$C(O)NR^bR^c$, —$C(NR^a)NR^bR^c$, —$OR^a$, —$OC(O)R^a$, —$OC(O)OR^a$, —$OC(O)NR^bR^c$, —$OC(=NR^a)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^d$, —$NR^aC(O)OR^d$, —$NR^aC(O)NR^bR^c$, —$NR^aC(=NR^d)NR^bR^c$, —$NR^aS(O)R^d$, —$NR^aS(O)_2R^d$, —$NR^aS(O)NR^bR^c$, —$NR^aS(O)_2NR^bR^c$, —$SR^a$, —$S(O)R^a$, —$S(O)_2R^a$; —$S(O)NR^bR^c$, or —$S(O)_2NR^bR^c$; wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents as described herein; or (iii) $R^b$ and $R^c$ together with the N atom to which they are attached form heterocyclyl, optionally substituted with one or more substituents as described herein; and
each star (*) is the point of attachment.

In certain embodiments, A is hydrogen. In certain embodiments, A is halo. In certain embodiments, A is fluoro or chloro. In certain embodiments, A is cyano. In certain embodiments, A is nitro. In certain embodiments, A is $C_{1-6}$ alkyl, optionally substituted with one or more substituents as described herein. In certain embodiments, A is methyl, ethyl, propyl (e.g., n-propyl, isopropyl, or 2-propyl), butyl (e.g., n-butyl, isobutyl, sec-butyl, or tert-butyl), pentyl (n-pentyl, 2-pentyl, 3-pentyl, isopentyl, 2-methyl-1-butyl, tert-pentyl, 3-methyl-2-propyl, or 2,2-dimethyl-1-propyl), optionally substituted with one or more substituents as described herein. In certain embodiments, A is fluoromethyl, including monofluoromethyl, difluoromethyl, and trifluoromethyl. In certain embodiments, A is methyl, ethyl, propyl, isopropyl, isobutyl, isopentyl, trifluoromethyl, or (morpholinyl)ethyl (including 2-(4-morpholinyl)ethyl). In certain embodiments, A is $C_{2-6}$ alkenyl, optionally substituted with one or more substituents as described herein. In certain embodiments, A is ethenyl. In certain embodiments, A is $C_{2-6}$ alkynyl, optionally substituted with one or more substituents as described herein. In certain embodiments, A is ethynyl. In certain embodiments, A is $C_{3-7}$ cycloalkyl, optionally substituted with one or more substituents as described herein. In certain embodiments, A is cyclopropyl or cyclobutyl.

In certain embodiments, A is $C_{6-14}$ aryl, optionally substituted with one or more substituents as described herein. In certain embodiments, A is phenyl. In certain embodiments, A is $C_{7-15}$ aralkyl, optionally substituted with one or more substituents as described herein. In certain embodiments, A is benzyl. In certain embodiments, A is heteroaryl, optionally substituted with one or more substituents as described herein. In certain embodiments, A is heterocyclyl, optionally substituted with one or more substituents as described herein. In certain embodiments, A is pyrrolidinyl.

In certain embodiments, A is —$OR^a$, where $R^a$ is as defined herein. In certain embodiments, A is $C_{1-6}$ alkoxy (i.e., —$OR^a$, where $R^a$ is $C_{1-6}$ alkyl), optionally substituted with one or more substituents as described herein. In certain embodiments, A is $C_{3-10}$ cycloalkoxy (i.e., —$OR^a$, where $R^a$ is $C_{3-10}$ cycloalkyl), optionally substituted with one or more substituents as described herein. In certain embodiments, A is methoxy, ethoxy, or cyclopropoxy. In certain embodiments, A is —NR$^b$R$^c$, where R$^b$ and R$^c$ are each as defined herein. In certain embodiments, A is C$_{1-6}$ alkylamine (i.e., —NR$^b$R$^c$, where R$^b$ is hydrogen and R$^c$ is C$_{1-6}$ alkyl), optionally substituted with one or more substituents as described herein. In certain embodiments, A is C$_{3-10}$ cycloalkylamine (i.e., —NR$^b$R$^c$, where R$^b$ is hydrogen and R$^c$ is C$_{3-10}$ cycloalkyl), optionally substituted with one or more substituents as described herein. In certain embodiments, A is di(C$_{1-6}$ alkyl) amino (i.e., —NR$^b$R$^c$, where R$^b$ and R$^c$ are each independently C$_{1-6}$ alkyl), optionally substituted with one or more substituents as described herein. In certain embodiments, A is propylamino (e.g., n-propylamino, isopropylamino, or 2-propylamino). In certain embodiments, A is isopropylamino.

In certain embodiments, E is hydrogen. In certain embodiments, E is halo. In certain embodiments, E is fluoro or chloro. In certain embodiments, E is cyano. In certain embodiments, E is nitro. In certain embodiments, E is C$_{1-6}$ alkyl, optionally substituted with one or more substituents as described herein. In certain embodiments, E is methyl, ethyl, propyl (e.g., n-propyl, isopropyl, or 2-propyl), butyl (e.g., n-butyl, isobutyl, sec-butyl, or tert-butyl), pentyl (n-pentyl, 2-pentyl, 3-pentyl, isopentyl, 2-methyl-1-butyl, tert-pentyl, 3-methyl-2-propyl, or 2,2-dimethyl-1-propyl), optionally substituted with one or more substituents as described herein. In certain embodiments, E is fluoromethyl, including monofluoromethyl, difluoromethyl, and trifluoromethyl. In certain embodiments, E is methyl, ethyl, propyl, isopropyl, isobutyl, isopentyl, trifluoromethyl, or (morpholinyl)ethyl (including 2-(4-morpholinyl)ethyl). In certain embodiments, E is C$_{2-6}$ alkenyl, optionally substituted with one or more substituents as described herein. In certain embodiments, E is ethenyl. In certain embodiments, E is C$_{2-6}$ alkynyl, optionally substituted with one or more substituents as described herein. In certain embodiments, E is ethynyl. In certain embodiments, E is C$_{3-7}$ cycloalkyl, optionally substituted with one or more substituents as described herein. In certain embodiments, E is cyclopropyl or cyclobutyl.

In certain embodiments, E is C$_{6-14}$ aryl, optionally substituted with one or more substituents as described herein. In certain embodiments, E is phenyl. In certain embodiments, E is C$_{7-15}$ aralkyl, optionally substituted with one or more substituents as described herein. In certain embodiments, E is benzyl. In certain embodiments, E is heteroaryl, optionally substituted with one or more substituents as described herein. In certain embodiments, E is heterocyclyl, optionally substituted with one or more substituents as described herein. In certain embodiments, E is pyrrolidinyl.

In certain embodiments, E is —OR$^a$, where R$^a$ is as defined herein. In certain embodiments, E is C$_{1-6}$ alkoxy (i.e., —OR$^a$, where R$^a$ is C$_{1-6}$ alkyl), optionally substituted with one or more substituents as described herein. In certain embodiments, E is C$_{3-10}$ cycloalkoxy (i.e., —OR$^a$, where R$^a$ is C$_{3-10}$ cycloalkyl), optionally substituted with one or more substituents as described herein. In certain embodiments, E is methoxy, ethoxy, or cyclopropoxy. In certain embodiments, E is —NR$^b$R$^c$, where R$^b$ and R$^c$ are each as defined herein. In certain embodiments, E is C$_{1-6}$ alkylamine (i.e., —NR$^b$R$^c$, where R$^b$ is hydrogen and R$^c$ is C$_{1-6}$ alkyl), optionally substituted with one or more substituents as described herein. In certain embodiments, E is C$_{3-10}$ cycloalkylamine (i.e., —NR$^b$R$^c$, where R$^b$ is hydrogen and R$^c$ is C$_{3-10}$ cycloalkyl), optionally substituted with one or more substituents as described herein. In certain embodiments, E is di(C$_{1-6}$ alkyl) amino (i.e., —NR$^b$R$^c$, where R$^b$ and R$^c$ are each independently C$_{1-6}$ alkyl), optionally substituted with one or more substituents as described herein. In certain embodiments, E is propylamino (e.g., n-propylamino, isopropylamino, or 2-propylamino). In certain embodiments, E is isopropylamino.

In certain embodiments, R$^{2'}$ is methoxy, phenoxy, phenyl, furanyl, pyrazolyl, thienyl, thiazolyl, oxadiazolyl, or triazolyl, each of which is optionally substituted with one to four substituents, each of which is independently selected from fluoro, cyano, methyl, ethyl, propyl, isopropyl, isobutyl, isopentyl, trifluoromethyl, (morpholinyl)ethyl, ethenyl, ethynyl, cyclopropyl, cyclobutyl, phenyl, benzyl, pyrrolidinyl, methoxy, ethoxy, cyclopropoxy, and isopropylamino.

In certain embodiments, R$^{2'}$ is methoxy, phenoxy, phenyl, fluorophenyl, furanyl, thienyl, cyanothienyl, methoxythienyl, methylthienyl, dimethylthienyl, (trifluoromethyl)-thienyl, phenylthienyl, thiazolyl, cyanothiazolyl, methylthiazolyl, isopropylthiazolyl, (trifluoromethyl)thiazolyl, ethenylthiazolyl, ethynylthiazolyl, cyclopropylthiazolyl, cyclobutylthiazolyl, dimethylthiazolyl, isopropylaminothiazolyl, methoxythiazolyl, ethoxythiazolyl, cyclopropoxythiazolyl, pyrrolidinylthiazolyl, methyl-1H-pyrazolyl, ethyl-1H-pyrazolyl, propyl-1H-pyrazolyl, isopropyl-1H-pyrazolyl, isobutyl-1H-pyrazolyl, isopentyl-1H-pyrazolyl, trifluoromethyl-1H-pyrazolyl, (morpholinyl)ethyl-1H-pyrazolyl, methyl-(trifluoromethyl)-1H-pyrazolyl, trimethyl-1H-pyrazolyl, benzyl-1H-pyrazolyl, methyl-1H-imidazolyl, phenyloxazolyl, isopropylisoxazolyl, dimethylisoxazolyl, ethyl-triazolyl, isopropyl-triazolyl, trifluoromethyl-triazolyl, methoxy-triazolyl, or isopropyl-oxadiazolyl.

In certain embodiments, R$^{2'}$ is methoxy, phenoxy, phenyl, 4-fluorophenyl, furan-2-yl, thien-2-yl, 4-cyanothien-2-yl, 5-methoxythien-2-yl, 3-methoxy-thien-2-yl, 3-methylthien-2-yl, 5-methylthien-2-yl, 3,5-dimethylthien-2-yl, 5-(trifluoromethyl)thien-2-yl, 5-phenylthien-2-yl, thien-3-yl, 2-methylthien-3-yl, 4-methylthien-3-yl, 2,5-dimethylthien-3-yl, 2-cyano-thien-3-yl, thiazol-2-yl, 4-cyano-thiazol-2-yl, 4-methyl-thiazol-2-yl, 4-isopropyl-thiazol-2-yl, 4-isobutyl-thiazol-2-yl, 4-trifluoromethyl-thiazol-2-yl, 4-cyclopropyl-thiazol-2-yl, 4-cyclobutyl-thiazol-2-yl, 4-ethenyl-thiazol-2-yl, 4-ethynyl-thiazol-2-yl, 5-methyl-thiazol-2-yl, 4,5-dimethylthiazol-2-yl, thiazol-4-yl, 2-isopropyl-thiazol-4-yl, 2-trifluoromethyl-thiazol-4-yl, 2-isopropylamino-thiazol-4-yl, 2-methoxy-thiazol-4-yl, 2-ethoxy-thiazol-4-yl, 2-2-methoxythiazol-4-yl, thiazol-5-yl, 2-cyclopropyl-thiazol-5-yl, 2-ethoxy-thiazol-5-yl, 2-cyclopropoxy-thiazol-5-yl, 2,4-dimethylthiazol-5-yl, 3-isopropyl-1H-pyrazol-1-yl, 3-trifluoromethyl-1H-pyrazol-1-yl, 1-ethyl-1H-pyrazol-3-yl, 1-propyl-1H-pyrazol-3-yl, 1-isobutyl-1H-pyrazol-3-yl, 1-3-isopentyl-1H-pyrazol-3-yl, 2-(4-morpholinyl)ethyl-1H-pyrazol-3-yl, 1-benzyl-1H-pyrazol-3-yl, 1-methyl-1H-pyrazol-4-yl, 1-ethyl-1H-pyrazol-4-yl, 1-benzyl-1H-pyrazol-4-yl, 1,3,5-trimethyl-1H-pyrazol-4-yl, 1-methyl-3-(trifluoromethyl)-1H-pyrazol-4-yl, 1-methyl-3-(trifluoromethyl)-1H-pyrazol-5-yl, 1-methyl-1H-imidazol-2-yl, 1-methyl-1H-imidazol-5-yl, 2-phenyloxazol-5-yl, 3,5-dimethylisoxazol-4-yl, 5-isopropylisoxazol-3-yl, 4-isopropyl-1,2,3-triazol-1-yl, 4-trifluoromethyl-1,2,3-triazol-1-yl, 1-isopropyl-1,2,3-triazol-4-yl, 3-ethyl-1,2,4-triazol-1-yl, isopropyl-1,2,4-triazol-1-yl, 3-methoxy-1,2,4-triazol-1-yl, 1-isopropyl-1,2,4-triazol-3-yl, or 5-isopropyl-1,2,4-oxadiazol-3-yl. In certain embodiments, R$^2$ is 4-isopropylthiazol-2-yl or 4-(trifluoromethyl)thiazol-2-yl.

In certain embodiments, R$^{1'}$ is hydrogen. In certain embodiments, R$^{1'}$ is hydroxyl. In certain embodiments, R$^{1'}$ is cyano. In certain embodiments, R$^{1'}$ is halo. In certain embodiments, R$^{1'}$ is C$_{1-6}$ alkyl, optionally substituted with one or more substituents as described herein. In certain embodiments, $R^{1'}$ is $C_{2-6}$ alkenyl, optionally substituted with one or more substituents as described herein. In certain embodiments, $R^{1'}$ is $C_{2-6}$ alkynyl, optionally substituted with one or more substituents as described herein. In certain embodiments, $R^{1'}$ is $C_{3-7}$ cycloalkyl, optionally substituted with one or more substituents as described herein. In certain embodiments, $R^{1'}$ is $C_{6-14}$ aryl, optionally substituted with one or more substituents as described herein. In certain embodiments, $R^{1'}$ is $C_{7-15}$ aralkyl, optionally substituted with one or more substituents as described herein. In certain embodiments, $R^{1'}$ is heteroaryl, optionally substituted with one or more substituents as described herein. In certain embodiments, $R^{1'}$ is heterocyclyl, optionally substituted with one or more substituents as described herein. In certain embodiments, $R^{1'}$ is —$OR^a$, wherein $R^a$ is as defined herein. In certain embodiments, $R^{1'}$ is hydrogen, fluoro, chloro, or methoxy.

In certain embodiments, $R^{3'}$ is hydrogen. In certain embodiments, $R^{3'}$ is hydroxyl. In certain embodiments, $R^{3'}$ is cyano. In certain embodiments, $R^{3'}$ is halo. In certain embodiments, $R^{3'}$ is fluoro or chloro. In certain embodiments, $R^{3'}$ is $C_{1-6}$ alkyl, optionally substituted with one or more substituents as described herein. In certain embodiments, $R^{3'}$ is $C_{2-6}$ alkenyl, optionally substituted with one or more substituents as described herein. In certain embodiments, $R^{3'}$ is $C_{2-6}$ alkynyl, optionally substituted with one or more substituents as described herein. In certain embodiments, $R^{3'}$ is $C_{3-7}$ cycloalkyl, optionally substituted with one or more substituents as described herein. In certain embodiments, $R^{3'}$ is $C_{6-14}$ aryl, optionally substituted with one or more substituents as described herein. In certain embodiments, $R^{3'}$ is $C_{7-15}$ aralkyl, optionally substituted with one or more substituents as described herein. In certain embodiments, $R^{3'}$ is heteroaryl, optionally substituted with one or more substituents as described herein. In certain embodiments, $R^{3'}$ is heterocyclyl, optionally substituted with one or more substituents as described herein. In certain embodiments, $R^{3'}$ is —$OR^a$, wherein $R^a$ is as defined herein.

In certain embodiments, $R^{5'}$ is hydrogen. In certain embodiments, $R^{5'}$ is hydroxyl. In certain embodiments, $R^{5'}$ is cyano. In certain embodiments, $R^{5'}$ is halo. In certain embodiments, $R^{5'}$ is fluoro or chloro. In certain embodiments, $R^{5'}$ is $C_{1-6}$ alkyl, optionally substituted with one or more substituents as described herein. In certain embodiments, $R^{5'}$ is $C_{2-6}$ alkenyl, optionally substituted with one or more substituents as described herein. In certain embodiments, $R^{5'}$ is $C_{2-6}$ alkynyl, optionally substituted with one or more substituents as described herein. In certain embodiments, $R^{5'}$ is $C_{3-7}$ cycloalkyl, optionally substituted with one or more substituents as described herein. In certain embodiments, $R^{5'}$ is $C_{6-14}$ aryl, optionally substituted with one or more substituents as described herein. In certain embodiments, $R^{5'}$ is $C_{7-15}$ aralkyl, optionally substituted with one or more substituents as described herein. In certain embodiments, $R^{5'}$ is heteroaryl, optionally substituted with one or more substituents as described herein. In certain embodiments, $R^{5'}$ is heterocyclyl, optionally substituted with one or more substituents as described herein. In certain embodiments, $R^{5'}$ is —$OR^a$, wherein $R^a$ is as defined herein. In certain embodiments, $R^{5'}$ is methoxy or phenoxy.

In certain embodiments, $R^{6'}$ is hydrogen. In certain embodiments, $R^{6'}$ is hydroxyl. In certain embodiments, $R^{6'}$ is cyano. In certain embodiments, $R^{6'}$ is halo. In certain embodiments, $R^{6'}$ is fluoro or chloro. In certain embodiments, $R^{6'}$ is $C_{1-6}$ alkyl, optionally substituted with one or more substituents as described herein. In certain embodiments, $R^{6'}$ is trifluoromethyl. In certain embodiments, $R^{6'}$ is $C_{2-6}$ alkenyl, optionally substituted with one or more substituents as described herein. In certain embodiments, $R^{6'}$ is $C_{2-6}$ alkynyl, optionally substituted with one or more substituents as described herein. In certain embodiments, $R^{6'}$ is $C_{3-7}$ cycloalkyl, optionally substituted with one or more substituents as described herein. In certain embodiments, $R^{6'}$ is $C_{6-14}$ aryl, optionally substituted with one or more substituents as described herein. In certain embodiments, $R^{6'}$ is $C_{7-15}$ aralkyl, optionally substituted with one or more substituents as described herein. In certain embodiments, $R^{6'}$ is heteroaryl, optionally substituted with one or more substituents as described herein. In certain embodiments, $R^{6'}$ is heterocyclyl, optionally substituted with one or more substituents as described herein. In certain embodiments, $R^{6'}$ is —$OR^a$, wherein $R^a$ is as defined herein.

In certain embodiments, $R^{6'}$ is methoxy, phenoxy, phenyl, furanyl, pyrazolyl, thienyl, thiazolyl, oxadiazolyl, or triazolyl, each of which is optionally substituted with one to four substituents, each of which is independently selected from fluoro, chloro, cyano, methyl, ethyl, propyl, isopropyl, isobutyl, isopentyl, trifluoromethyl, (morpholinyl)ethyl, ethenyl, ethynyl, cyclopropyl, cyclobutyl, phenyl, benzyl, pyrrolidinyl, methoxy, ethoxy, cyclopropoxy, and isopropylamino.

In certain embodiments, $R^{6'}$ is trifluoromethyl, methoxy, phenoxy, phenyl, fluorophenyl, chlorophenyl, methylphenyl, methoxyphenyl, isopropylthiazolyl, (trifluoromethyl)thiazolyl, furanyl, thienyl, cyanothienyl, methoxythienyl, methylthienyl, dimethylthienyl, (trifluoromethyl)thienyl, phenylthienyl, thiazolyl, cyano-thiazolyl, methylthiazolyl, isopropyl-thiazolyl, trifluoromethyl-thiazolyl, ethenyl-thiazolyl, ethynyl-thiazolyl, cyclopropyl-thiazolyl, dimethylthiazolyl, isopropylamino-thiazolyl, methoxy-thiazolyl, ethoxy-thiazolyl, cyclopropoxy-thiazolyl, cyclobutyl-thiazolyl, pyrrolidinyl-thiazolyl, methyl-1H-pyrazolyl, ethyl-1H-pyrazolyl, propyl-1H-pyrazolyl, isopropyl-1H-pyrazolyl, isobutyl-1H-pyrazolyl, isopentyl-1H-pyrazolyl, trifluoromethyl-1H-pyrazolyl, (morpholinyl)ethyl-1H-pyrazolyl, methyl-(trifluoromethyl)-1H-pyrazolyl, trimethyl-1H-pyrazolyl, benzyl-1H-pyrazolyl, methyl-1H-imidazolyl, phenyloxazolyl, dimethylisoxazolyl, ethyl-triazolyl, isopropyl-triazolyl, trifluoromethyl-triazolyl, methoxy-triazolyl, or isopropyl-oxadiazolyl.

In certain embodiments, $R^6$ is pyrrolidinyl, methoxy, phenoxy, phenyl, 4-fluorophenyl, 3-chlorophenyl. 4-chlorophenyl, 4-methylphenyl, 4-methoxyphenyl, 4-isopropylthiazol-2-yl, 4-(trifluoromethyl)thiazol-2-yl, furan-2-yl, thien-2-yl, 3-cyanothien-2-yl, 4-cyanothien-2-yl, 5-methoxythien-2-yl, 3-methoxy-thien-2-yl, 3-methylthien-2-yl, 5-methylthien-2-yl, 3,5-dimethylthien-2-yl, 5-(trifluoromethyl)thien-2-yl, 5-phenylthien-2-yl, thien-3-yl, 2-methylthien-3-yl, 4-methylthien-3-yl, 2,5-dimethylthien-3-yl, 2-cyano-thien-3-yl, thiazol-2-yl, 4-cyano-thiazol-2-yl, 4-methyl-thiazol-2-yl, 4-isopropyl-thiazol-2-yl, 4-isobutyl-thiazol-2-yl, 4-trifluoromethyl-thiazol-2-yl, 4-cyclopropyl-thiazol-2-yl, 4-cyclobutyl-thiazol-2-yl, 4-ethenyl-thiazol-2-yl, 4-ethynyl-thiazol-2-yl, 5-methyl-thiazol-2-yl, 4,5-dimethylthiazol-2-yl, thiazol-4-yl, 2-trifluoromethyl-thiazol-4-yl, 2-isopropylamino-thiazol-4-yl, 2-methoxy-thiazol-4-yl, 2-ethoxy-thiazol-4-yl, 2-(pyrrolidin-1-yl)thiazol-4-yl, 2-methoxythiazol-4-yl, thiazol-5-yl, 2-cyclopropyl-thiazol-5-yl, 2-ethoxy-thiazol-5-yl, 2-cyclopropoxy-thiazol-5-yl, 2,4-dimethylthiazol-5-yl, 3-isopropyl-1H-pyrazol-1-yl, 3-trifluoromethyl-1H-pyrazol-1-yl, 1-ethyl-1H-pyrazol-3-yl, 1-propyl-1H-pyrazol-3-yl, 1-isobutyl-1H-pyrazol-3-yl, 1-3-isopentyl-1H-pyrazol-3-yl, 2-(4-morpholinyl)ethyl-1H-pyrazol-3-yl, 1-benzyl-1H-pyrazol-3-yl, 1-methyl-1H-pyrazol-4-yl, 1-ethyl-1H-pyrazol-4-yl, 1-benzyl-1H-pyrazol-4- yl, 1,3,5-trimethyl-1H-pyrazol-4-yl, 1-methyl-3-(trifluoromethyl)-1H-pyrazol-4-yl, 1-methyl-3-(trifluoromethyl)-1H-pyrazol-5-yl, 1-methyl-1H-imidazol-2-yl, 1-methyl-1H-imidazol-5-yl, 2-phenyloxazol-5-yl, 3,5-dimethylisoxazol-4-yl, 4-isopropyl-1,2,3-triazol-1-yl, 4-trifluoromethyl-1,2,3-triazol-1-yl, 1-isopropyl-1,2,3-triazol-4-yl, 3-ethyl-1,2,4-triazol-1-yl, 3-isopropyl-1,2,4-triazol-1-yl, 3-methoxy-1,2,4-triazol-1-yl, 1-isopropyl-1,2,4-triazol-3-yl, or 5-isopropyl-1,2,4-oxadiazol-3-yl.

In certain embodiments, $R^{7'}$ is hydrogen. In certain embodiments, $R^{7'}$ is hydroxyl. In certain embodiments, $R^{7'}$ is cyano. In certain embodiments, $R^{7'}$ is halo. In certain embodiments, $R^{7'}$ is fluoro or chloro. In certain embodiments, $R^{7'}$ is $C_{1-6}$ alkyl, optionally substituted with one or more substituents as described herein. In certain embodiments, $R^{7'}$ is $C_{2-6}$ alkenyl, optionally substituted with one or more substituents as described herein. In certain embodiments, $R^{7'}$ is $C_{2-6}$ alkynyl, optionally substituted with one or more substituents as described herein. In certain embodiments, $R^{7'}$ is $C_{3-7}$ cycloalkyl, optionally substituted with one or more substituents as described herein. In certain embodiments, $R^{7'}$ is $C_{6-14}$ aryl, optionally substituted with one or more substituents as described herein. In certain embodiments, $R^{7'}$ is $C_{7-15}$ aralkyl, optionally substituted with one or more substituents as described herein. In certain embodiments, $R^{7'}$ is heteroaryl, optionally substituted with one or more substituents as described herein. In certain embodiments, $R^{7'}$ is heterocyclyl, optionally substituted with one or more substituents as described herein. In certain embodiments, $R^{7'}$ is —$OR^a$, wherein $R^a$ is as defined herein. In certain embodiments, $R^{7'}$ is methoxy, difluoromethoxy, or trifluoromethoxy. In certain embodiments, $R^{7'}$ is —$NR^aS(O)_2R^d$, wherein $R^a$ and $R^d$ are each as defined herein. In certain embodiments, $R^{7'}$ is methanesulfonamido.

In certain embodiments, $R^{6'}$ is —$OR^a$ and $R^{7'}$ is hydrogen, wherein $R^a$ is as defined herein. In certain embodiments, $R^{6'}$ is methoxy and $R^{7'}$ is hydrogen. In certain embodiments, $R^{6'}$ is hydrogen and $R^{7'}$ is —$OR^a$, wherein $R^a$ is as defined herein. In certain embodiments, $R^{6'}$ is hydrogen and $R^{7'}$ is methoxy.

In certain embodiments, $R^{8'}$ is hydrogen. In certain embodiments, $R^{8'}$ is hydroxyl. In certain embodiments, $R^{8'}$ is cyano. In certain embodiments, $R^{8'}$ is halo. In certain embodiments, $R^{8'}$ is fluoro, chloro, or bromo. In certain embodiments, $R^{8'}$ is $C_{1-6}$ alkyl, optionally substituted with one or more substituents as described herein. In certain embodiments, $R^{8'}$ is methyl. In certain embodiments, $R^{8'}$ is $C_{2-6}$ alkenyl, optionally substituted with one or more substituents as described herein. In certain embodiments, $R^{8'}$ is $C_{2-6}$ alkynyl, optionally substituted with one or more substituents as described herein. In certain embodiments, $R^{8'}$ is $C_{3-7}$ cycloalkyl, optionally substituted with one or more substituents as described herein. In certain embodiments, $R^{8'}$ is $C_{6-14}$ aryl, optionally substituted with one or more substituents as described herein. In certain embodiments, $R^{8'}$ is $C_{7-15}$ aralkyl, optionally substituted with one or more substituents as described herein. In certain embodiments, $R^{8'}$ is heteroaryl, optionally substituted with one or more substituents as described herein. In certain embodiments, $R^{8'}$ is heterocyclyl, optionally substituted with one or more substituents as described herein. In certain embodiments, $R^{8'}$ is —$OR^a$, wherein $R^a$ is as defined herein. In certain embodiments, $R^{8'}$ is difluoromethoxy.

In certain embodiments, $R^{5'}$ is hydrogen or methoxy; $R^{6'}$ is hydrogen or methoxy; $R^{7'}$ is hydrogen, chloro, or methoxy; and $R^{8'}$ is hydrogen, chloro, fluoro, bromo, or methyl. In certain embodiments, $R^{5'}$ is methoxy, and $R^{7'}$ is fluoro. In certain embodiments, $R^{6'}$ is methoxy, and $R^{7'}$ is chloro. In certain embodiments, $R^{6'}$ is methoxy, and $R^{8'}$ is methyl. In certain embodiments, $R^{7'}$ is methoxy, and $R^{8'}$ is fluoro. In certain embodiments, $R^{7'}$ is methoxy, and $R^{8'}$ is chloro. In certain embodiments, $R^{7'}$ is methoxy, and $R^{8'}$ is bromo. In certain embodiments, $R^{7'}$ is methoxy, and $R^{8'}$ is methyl.

In certain embodiments, $R^a$ is $C_{1-6}$ alkyl, optionally substituted with one or more substituents as described herein. In certain embodiments, $R^a$ is $C_{2-6}$ alkenyl, optionally substituted with one or more substituents as described herein. In certain embodiments, $R^a$ is $C_{2-6}$ alkynyl, optionally substituted with one or more substituents as described herein. In certain embodiments, $R^a$ is $C_{3-7}$ cycloalkyl, optionally substituted with one or more substituents as described herein. In certain embodiments, $R^a$ is $C_{6-14}$ aryl, optionally substituted with one or more substituents as described herein. In certain embodiments, $R^a$ is $C_{7-15}$ aralkyl, optionally substituted with one or more substituents as described herein. In certain embodiments, $R^a$ is heteroaryl, optionally substituted with one or more substituents as described herein. In certain embodiments, $R^a$ is heterocyclyl, optionally substituted with one or more substituents as described herein.

In certain embodiments, $R^{2'}$ is 4-fluorophenyl, 2-isopropylthiazol-4-yl, 2-trifluoromethylthiazol-4-yl, 4-cyanothiazol-2-yl, 4-methylthiazol-2-yl, 4-isopropylthiazol-2-yl, 4-ethenylthiazol-2-yl, 4-ethynylthiazol-2-yl, 4-trifluoromethylthiazol-2-yl, 4-cyclopropylthiazol-2-yl, 4-cyclobutylthiazol-2-yl, 5-isopropylisoxazol-3-yl, 3-isopropyl-1H-pyrazol-1-yl, or 3-trifluoromethyl-1H-pyrazol-1-yl; $R^{3'}$ is hydrogen; $R^{5'}$ is hydrogen or methoxy; $R^{6'}$ is hydrogen, chloro, methoxy, or trifluoromethyl; $R^{7'}$ is hydrogen, chloro, methoxy, methanesulfonamido, difluoromethoxy, or trifluoromethoxy; and $R^{8'}$ is hydrogen, fluoro, chloro, bromo, methyl, or difluoromethoxy.

In certain embodiments, L is a bond. In certain embodiments, L is $C_{1-6}$ alkylene, optionally substituted with one or more substituents as described herein. In certain embodiments, L is $C_{2-6}$ alkenylene, optionally substituted with one or more substituents as described herein. In certain embodiments, L is $C_{2-6}$ alkynylene, optionally substituted with one or more substituents as described herein. In certain embodiments, L is $C_{3-7}$ cycloalkylene, optionally substituted with one or more substituents as described herein.

In certain embodiments, —X—, wherein X is as defined herein. In certain embodiments, L is —O—. In certain embodiments, L is —OC(O)O—. In certain embodiments, L is —C(O)—. In certain embodiments, L is —C(O)O—. In certain embodiments, L is —C(O)NR$^{14}$—, wherein R$^{14}$ is as defined herein. In certain embodiments, L is —C(=NR$^{14}$)NR$^{15}$—, wherein R$^{14}$ and R$^{15}$ are each as defined herein. In certain embodiments, L is —NR$^{14}$—, wherein R$^{14}$ is as defined herein. In certain embodiments, L is —NR$^{14}$C(O)NR$^{15}$—, wherein R$^{14}$ and R$^{15}$ are each as defined herein. In certain embodiments, L is —NR$^{14}$C(=NR$^{15}$)NR$^{16}$—, wherein R$^{14}$, R$^{15}$, and R$^{16}$ are each as defined herein. In certain embodiments, L is —NR$^{14}$S(O)NR$^{15}$—, wherein R$^{14}$ and R$^{15}$ are each as defined herein. In certain embodiments, L is —NR$^{14}$S(O)$_2$NR$^{15}$—, wherein R$^{14}$ and R$^{15}$ are each as defined herein. In certain embodiments, L is —S—. In certain embodiments, L is —S(O)—. In certain embodiments, L is —S(O)$_2$—. In certain embodiments, L is —S(O)NR$^{14}$—, wherein R$^{14}$ is as defined herein. In certain embodiments, L is —S(O)$_2$NR$^{14}$—, wherein R$^{14}$ is as defined herein. In certain embodiments, L is —P(O)(OR$^{14}$)—, wherein R$^{14}$ is as defined herein. In certain embodiments, L is —OP(O)(OR$^{14}$)—, wherein R$^{14}$ is as defined herein.

In certain embodiments, R$^{14}$ is hydrogen. In certain embodiments, R$^{14}$ is $C_{1-6}$ alkyl, optionally substituted with one or more substituents as described herein. In certain embodiments, $R^{14}$ is $C_{2-6}$ alkenyl, optionally substituted with one or more substituents as described herein. In certain embodiments, $R^{14}$ is $C_{2-6}$ alkynyl, optionally substituted with one or more substituents as described herein. In certain embodiments, $R^{14}$ is $C_{3-7}$ cycloalkyl, optionally substituted with one or more substituents as described herein. In certain embodiments, $R^{14}$ is $C_{6-14}$ aryl, optionally substituted with one or more substituents as described herein. In certain embodiments, $R^{14}$ is $C_{7-15}$ aralkyl, optionally substituted with one or more substituents as described herein. In certain embodiments, $R^{14}$ is heteroaryl, optionally substituted with one or more substituents as described herein. In certain embodiments, $R^{14}$ is heterocyclyl, optionally substituted with one or more substituents as described herein.

In certain embodiments, $R^{15}$ is hydrogen. In certain embodiments, $R^{15}$ is $C_{1-6}$ alkyl, optionally substituted with one or more substituents as described herein. In certain embodiments, $R^{15}$ is $C_{2-6}$ alkenyl, optionally substituted with one or more substituents as described herein. In certain embodiments, $R^{15}$ is $C_{2-6}$ alkynyl, optionally substituted with one or more substituents as described herein. In certain embodiments, $R^{15}$ is $C_{3-7}$ cycloalkyl, optionally substituted with one or more substituents as described herein. In certain embodiments, $R^{15}$ is $C_{6-14}$ aryl, optionally substituted with one or more substituents as described herein. In certain embodiments, $R^{15}$ is $C_{7-15}$ aralkyl, optionally substituted with one or more substituents as described herein. In certain embodiments, $R^{15}$ is heteroaryl, optionally substituted with one or more substituents as described herein. In certain embodiments, $R^{15}$ is heterocyclyl, optionally substituted with one or more substituents as described herein.

In certain embodiments, L is —$(CR^{6a}R^{6b})_p$X—, wherein $R^{6a}$, $R^{6b}$, X, and p are each as defined herein. In certain embodiments, L is —$(CR^{6a}R^{6b})_p$C(O)—, wherein $R^{6a}$, $R^{6b}$, and p are each as defined herein. In certain embodiments, L is —$(CR^{6a}R^{6b})_p$C(O)O—, wherein $R^{6a}$, $R^{6b}$, and p are each as defined herein. In certain embodiments, L is —$(CR^{6a}R^{6b})_p$OC(O)—, wherein $R^{6a}$, $R^{6b}$, and p are each as defined herein. In certain embodiments, L is —$(CR^{6a}R^{6b})_p$C(O)NR^{14}—, wherein $R^{6a}$, $R^{6b}$, $R^{14}$, and p are each as defined herein. In certain embodiments, L is —$(CR^{6a}R^{6b})_p$NR^{14}C(O)—, wherein $R^{6a}$, $R^{6b}$, $R^{14}$, and p are each as defined herein. In certain embodiments, L is —$(CR^{6a}R^{6b})_p$C(=NR^{14})NR^{15}—, wherein $R^{6a}$, $R^{6b}$, $R^{14}$, $R^{15}$, and p are each as defined herein. In certain embodiments, L is —$(CR^{6a}R^{6b})_p$NR^{15}C(=NR^{14})—, wherein $R^{6a}$, $R^{6b}$, $R^{14}$, $R^{15}$, and p are each as defined herein. In certain embodiments, L is —$(CR^{6a}R^{6b})_p$O—, wherein $R^{6a}$, $R^{6b}$, and p are each as defined herein. In certain embodiments, L is —CH$_2$O— or —CH(Ph)O—. In certain embodiments, L is —$(CR^{6a}R^{6b})_p$OC(O)O—, wherein $R^{6a}$, $R^{6b}$, and p are each as defined herein. In certain embodiments, L is —OP(O)(OR$^{14}$)—, wherein $R^{6a}$, $R^{6b}$, $R^{14}$, and p are each as defined herein. In certain embodiments, L is —NR$^{14}$—, wherein $R^{6a}$, $R^{6b}$, $R^{14}$, and p are each as defined herein. In certain embodiments, L is —$(CR^{6a}R^{6b})_p$NR^{14}C(O)NR^{15}—, wherein $R^{6a}$, $R^{6b}$, $R^{14}$, $R^{15}$, and p are each as defined herein. In certain embodiments, L is —$(CR^{6a}R^{6b})_p$NR^{14}C(=NR^{15})NR^{16}—, wherein $R^{6a}$, $R^{6b}$, $R^{14}$, $R^{15}$, $R^{16}$, and p are each as defined herein. In certain embodiments, L is —$(CR^{6a}R^{6b})_p$NR^{14}S(O)NR^{15}—, wherein $R^{6a}$, $R^{6b}$, $R^{14}$, $R^{15}$, and p are each as defined herein. In certain embodiments, L is —$(CR^{6a}R^{6b})_p$NR^{14}S(O)$_2$NR^{15}—, wherein $R^{6a}$, $R^{6b}$, $R^{14}$, $R^{15}$, and p are each as defined herein. In certain embodiments, L is —$(CR^{6a}R^{6b})_p$S—, wherein $R^{6a}$, $R^{6b}$, and p are each as defined herein. In certain embodiments, L is —$(CR^{6a}R^{6b})_p$S(O)—, wherein $R^{6a}$, $R^{6b}$, and p are each as defined herein. In certain embodiments, L is —$(CR^{6a}R^{6b})_p$S(O)$_2$—, wherein $R^{6a}$, $R^{6b}$, and p are each as defined herein. In certain embodiments, L is —$(CR^{6a}R^{6b})_p$S(O)NR^{14}—, wherein $R^{6a}R^{6b}$, $R^{14}$, and p are each as defined herein. In certain embodiments, L is —$(CR^{6a}R^{6b})_p$NR^{14}S(O)—, wherein $R^{6a}$, $R^{6b}$, $R^{14}$, and p are each as defined herein. In certain embodiments, L is —$(CR^{6a}R^{6b})_p$S(O)$_2$NR^{14}—, wherein $R^{6a}$, $R^{6b}$, $R^{14}$, and p are each as defined herein. In certain embodiments, L is —$(CR^{6a}R^{6b})_p$NR^{14}S(O)$_2$—, wherein $R^{6a}$, $R^{6b}$, $R^{14}$, k, and p are each as defined herein. In certain embodiments, L is —$(CR^{6a}R^{6b})_p$P(O)(OR$^{14}$)—, wherein $R^{6a}$, $R^{6b}$, $R^{14}$, and p are each as defined herein.

In certain embodiments, $R^{6a}$ is hydrogen. In certain embodiments, $R^{6a}$ is halo. In certain embodiments, $R^{6a}$ is fluoro. In certain embodiments, $R^{6b}$ is hydrogen. In certain embodiments. $R^{6b}$ is halo. In certain embodiments, $R^{6b}$ is fluoro. In certain embodiments, $R^{6a}$ and $R^{6b}$ are hydrogen. In certain embodiments, $R^{6a}$ and $R^{6b}$ are halo. In certain embodiments, $R^{6a}$ and $R^{6b}$ are fluoro.

In certain embodiments, L is —$(CH_2)_p$—, wherein p is as defined herein. In certain embodiments, —CH$_2$—. L is In certain embodiments, L is —$(CH_2)_{p-1}$CF$_2$— or —CF$_2$$(CH_2)_{p-1}$—, wherein p is as defined herein. In certain embodiments, L is —CF$_2$—. In certain embodiments, L is —$(CH_2)_p$O—, wherein p is as defined herein. In certain embodiments, L is —$(CH_2)_p$C(O)—, wherein p is as defined herein. In certain embodiments, L is —$(CH_2)_p$C(O)O—, wherein p is as defined herein. In certain embodiments, L is —$(CH_2)_p$OC(O)—, wherein p is as defined herein. In certain embodiments, L is —$(CH_2)_p$C(O)NR$^{14}$—, wherein $R^{14}$ and p is as defined herein. In certain embodiments, L is —$(CH_2)_p$NR$^{14}$C(O)—, wherein $R^{14}$ and p is as defined herein. In certain embodiments, L is —$(CH_2)_p$NR$^{14}$C(O)NR$^{15}$—, wherein $R^{14}$, $R^{15}$, and p are as defined herein.

In certain embodiments, p is 1. In certain embodiments, p is 2. In certain embodiments, p is 3.

In certain embodiments, -L-R$^6$ is —O—N═CR$^{6c}$R$^{6d}$, wherein R$^{6c}$ and R$^{6d}$ are each as defined herein.

In certain embodiments, $R^{6c}$ is hydrogen. In certain embodiments, $R^{6c}$ is $C_{1-6}$ alkyl, optionally substituted with one or more substituents as described herein. In certain embodiments, $R^{6c}$ is methyl, ethyl, propyl, isopropyl, or isobutyl, optionally substituted with one or more substituents as described herein. In certain embodiments, $R^{6c}$ is methyl, ethyl, propyl, isopropyl, isobutyl, or methoxymethyl. In certain embodiments, $R^{6c}$ is $C_{2-6}$ alkenyl, optionally substituted with one or more substituents as described herein. In certain embodiments, $R^{6c}$ is $C_{2-6}$ alkynyl, optionally substituted with one or more substituents as described herein. In certain embodiments, $R^{6c}$ is $C_{3-7}$ cycloalkyl, optionally substituted with one or more substituents as described herein. In certain embodiments, $R^{6c}$ is cyclopentyl or cyclohexyl. In certain embodiments, $R^{6c}$ is $C_{6-14}$ aryl, optionally substituted with one or more substituents as described herein. In certain embodiments, $R^{6c}$ is phenyl. In certain embodiments, $R^{6c}$ is $C_{7-15}$ aralkyl, optionally substituted with one or more substituents as described herein. In certain embodiments. $R^{6c}$ is heteroaryl, optionally substituted with one or more substituents as described herein. In certain embodiments, $R^{6c}$ is heterocyclyl, optionally substituted with one or more substituents as described herein.

In certain embodiments, $R^{6d}$ is hydrogen. In certain embodiments, $R^{6d}$ is $C_{1-6}$ alkyl, optionally substituted with one or more substituents as described herein. In certain embodiments, $R^{6d}$ is methyl, ethyl, propyl, isopropyl, or isobutyl, optionally substituted with one or more substituents as described herein. In certain embodiments, $R^{6d}$ is methyl, ethyl, propyl, isopropyl, isobutyl, or methoxymethyl. In certain embodiments, $R^{6d}$ is $C_{2-6}$ alkenyl, optionally substituted with one or more substituents as described herein. In certain embodiments, $R^{6d}$ is $C_{2-6}$ alkynyl, optionally substituted with one or more substituents as described herein. In certain embodiments, $R^{6d}$ is $C_{3-7}$ cycloalkyl, optionally substituted with one or more substituents as described herein. In certain embodiments, $R^{6d}$ is cyclopentyl or cyclohexyl. In certain embodiments, $R^{6d}$ is $C_{6-14}$ aryl, optionally substituted with one or more substituents as described herein. In certain embodiments, $R^{6d}$ is phenyl or naphthyl, each optionally substituted with one or more substituents as described herein. In certain embodiments, $R^{6d}$ is phenyl, 2-fluorophenyl, 3-fluorophenyl, 4-fluorophenyl, 2-phenylphenyl, 3-phenylphenyl, 4-phenylphenyl, 2-(thien-2-yl)phenyl, 2-(thien-2-yl)-5-methoxy-phenyl, 2-(1H-imidazol-1-yl)phenyl, 2-(isoxazol-5-yl)-5-methoxy-phenyl, 2-(thiazol-2-yl)phenyl, 2-(thiazol-2-yl)-5-methoxy-phenyl, 2-(pyrazol-1-yl)phenyl, 2-(1,2,4-1H-triazol-1-yl)phenyl, 2-methoxyphenyl, 3-methoxyphenyl, 4-methoxyphenyl, 1-naphthyl, or 2-naphthyl. In certain embodiments, $R^{6d}$ is $C_{7-15}$ aralkyl, optionally substituted with one or more substituents as described herein. In certain embodiments, $R^{6d}$ is heteroaryl, optionally substituted with one or more substituents as described herein. In certain embodiments, $R^{6d}$ is thien-2-yl, pyridin-2-yl, pyridin-3-yl, pyridin-4-yl, or quinolin-4-yl. In certain embodiments, $R^{6d}$ is heterocyclyl, optionally substituted with one or more substituents as described herein.

In certain embodiments, $R^{6c}$ is hydrogen; and $R^{6d}$ is 2-fluorophenyl, 3-fluorophenyl, 4-fluorophenyl, 2-phenylphenyl, 3-phenylphenyl, 4-phenylphenyl, 2-(thien-2-yl)phenyl, 2-(thien-2-yl)-5-methoxy-phenyl, 2-(1H-imidazol-1-yl)phenyl, 2-(isoxazol-5-yl)-5-methoxy-phenyl, 2-(thiazol-2-yl)phenyl, 2-(thiazol-2-yl)-5-methoxy-phenyl, 2-(pyrazol-1-yl)phenyl, 2-(1,2,4-1H-triazol-1-yl)phenyl, 2-methoxyphenyl, 3-methoxyphenyl, 4-methoxyphenyl, 1-naphthyl, 2-naphthyl, thien-2-yl, pyridin-2-yl, pyridin-3-yl, pyridin-4-yl, or quinolin-4-yl. In certain embodiments, $R^{6c}$ is hydrogen, methyl, ethyl, propyl, isopropyl, isobutyl, methoxymethyl, or phenyl; and $R^{6d}$ is phenyl. In certain embodiments, $R^{6c}$ is phenyl; and $R^{6d}$ is thien-2-yl. In certain embodiments, $R^{6c}$ is ethyl; and $R^{6c}$ is 2-phenyl-phenyl.

In certain embodiments, $R^{6c}$ and $R^{6d}$ together with the C atom to which they are attached form $C_{3-15}$ cycloalkylidene, $C_{6-14}$ arylidene, heteroarylidene, or heterocyclylidene, each optionally substituted with one or more substituents as described herein.

In certain embodiments, $R^{6c}$ and $R^{6d}$ together with the C atom to which they are attached form 9H-fluoren-9-ylidene, 9H-xanth-9-ylidene, anthracen-9(10H)-one-10-ylidene, 9,10-dihydroacridin-9-ylidene, 1,8-diaza-9H-fluoren-9-ylidene, 4,5-diaza-9H-fluoren-9-ylidene, 10,11-dihydro-5H-bibenzo[1,2-d]cyclohept-5-ylidene, 2,3-dihydro-1H-inden-1-ylidene, 1,2,3,4-tetrahydronaphth-1-ylidene, 5,6,7,8-tetrahydroquinolin-5-ylidene, 5,6,7,8-tetrahydroquinolin-8-ylidene, chroman-4-ylidene, or thiochroman-4-ylidene, each optionally substituted with one or more substituents as described herein. In certain embodiments, $R^{6c}$ and $R^{6d}$ together with the C atom to which they are attached form 9H-fluoren-9-ylidene, 2,7-difluoro-9H-fluoren-9-ylidene, 2-(allyloxy)-9H-fluoren-9-ylidene, 9H-xanth-9-ylidene, anthracen-9(10H)-one-10-ylidene, 10-methyl-9,10-dihydroacridin-9-ylidene, 1,8-diaza-9H-fluoren-9-ylidene, 4,5-diaza-9H-fluoren-9-ylidene, 10,11-dihydro-5H-bibenzo[1,2-d]cyclohept-5-ylidene, 2,3-dihydro-1H-inden-1-ylidene, 6-methoxy-1,2,3,4-tetrahydronaphth-1-ylidene, 7-methoxy-1,2,3,4-tetrahydronaphth-1-ylidene, 6,7-dimethoxy-1,2,3,4-tetrahydronaphth-1-ylidene, 7-(thien-2-yl)-1,2,3,4-tetrahydronaphth-1-ylidene, 5,6,7,8-tetrahydroquinolin-5-ylidene, 5,6,7,8-tetrahydroquinolin-8-ylidene, 6-fluoro-chroman-4-ylidene, 2-phenyl-chroman-4-ylidene, 3-phenyl-chroman-4-ylidene, 6-methoxy-chroman-4-ylidene, 2,2-dimethyl-6,7-dimethoxy-chroman-4-ylidene, or thiochroman-4-ylidene. In certain embodiments, $R^6$ is 9H-fluoren-9-ylidene. Further examples of ylidenes and their synthesis can be found, e.g., in U.S. Pat. Appl. Publ. Nos. 2009/0156800 and 20090175822; and International Pat. Appl. Publ. Nos. WO 2009/053828, WO 2009/073713, and WO 2009/073780; the disclosure of each of which is incorporated herein by reference in its entirety.

In certain embodiments, -L-$R^6$ is 5-(4-methoxyphenyl)-2H-tetrazol-2-yl. In certain embodiments, -L-$R^6$ is 9H-fluoren-9-ylideneaminooxy. In certain embodiments, -L-$R^6$ is (S)-1-(5-fluoropyridin-2-yl)ethylaminocarbonyloxy. In certain embodiments, -L-$R^6$ is 3-(thien-2-yl)-quinoxalin-2-yloxy. In certain embodiments, -L-$R^6$ is 2-(pyridin-2-yl)thieno[3,2-d]pyrimidin-4-yloxy.

In certain embodiments, $Q^1$ is —O—. In certain embodiments, $Q^1$ is —N($R^{17}$)—, wherein $R^{17}$ is as defined herein. In certain embodiments, $Q^1$ is —N(CH$_3$)—. In certain embodiments, $Q^1$ is —C($R^{18}R^{19}$)—, wherein $R^{18}$ and $R^{19}$ are each as defined herein. In certain embodiments, $Q^1$ is —CH$_2$—. In certain embodiments, $Q^1$ is —CR$^{17}$(NR$^{18}R^{19}$)—, wherein $R^{17}$, $R^{18}$, and $R^{19}$ are each as defined herein.

In certain embodiments, $R^{17}$ is hydrogen. In certain embodiments, $R^{17}$ is $C_{1-6}$ alkyl, optionally substituted with one or more substituents as described herein. In certain embodiments, $R^{17}$ is $C_{2-6}$ alkenyl, optionally substituted with one or more substituents as described herein. In certain embodiments, $R^{17}$ is $C_{2-6}$ alkynyl, optionally substituted with one or more substituents as described herein. In certain embodiments, $R^{17}$ is $C_{3-7}$ cycloalkyl, optionally substituted with one or more substituents as described herein. In certain embodiments, $R^{17}$ is $C_{6-14}$ aryl, optionally substituted with one or more substituents as described herein. In certain embodiments, $R^{17}$ is $C_{7-15}$ aralkyl, optionally substituted with one or more substituents as described herein. In certain embodiments, $R^{17}$ is heteroaryl, optionally substituted with one or more substituents as described herein. In certain embodiments, $R^{17}$ is heterocyclyl, optionally substituted with one or more substituents as described herein. In certain embodiments, $R^{17}$ is methyl.

In certain embodiments, $R^{18}$ is hydrogen. In certain embodiments, $R^{18}$ is $C_{1-6}$ alkyl, optionally substituted with one or more substituents as described herein. In certain embodiments, $R^{18}$ is $C_{2-6}$ alkenyl, optionally substituted with one or more substituents as described herein. In certain embodiments, $R^{18}$ is $C_{2-6}$ alkynyl, optionally substituted with one or more substituents as described herein. In certain embodiments, $R^{18}$ is $C_{3-7}$ cycloalkyl, optionally substituted with one or more substituents as described herein. In certain embodiments, $R^{18}$ is $C_{6-14}$ aryl, optionally substituted with one or more substituents as described herein. In certain embodiments, $R^{18}$ is $C_{7-15}$ aralkyl, optionally substituted with one or more substituents as described herein. In certain embodiments, $R^{18}$ is heteroaryl, optionally substituted with one or more substituents as described herein. In certain embodiments, $R^{18}$ is heterocyclyl, optionally substituted with one or more substituents as described herein. In certain embodiments, $R^{18}$ is methyl.

In certain embodiments, $R^{19}$ is hydrogen. In certain embodiments, $R^{19}$ is $C_{1-6}$ alkyl, optionally substituted with one or more substituents as described herein. In certain embodiments. $R^{19}$ is $C_{2-6}$ alkenyl, optionally substituted with one or more substituents as described herein. In certain embodiments, $R^{19}$ is $C_{2-6}$ alkynyl, optionally substituted with one or more substituents as described herein. In certain embodiments, $R^{19}$ is $C_{3-7}$ cycloalkyl, optionally substituted with one or more substituents as described herein. In certain embodiments, $R^{19}$ is $C_{6-14}$ aryl, optionally substituted with one or more substituents as described herein. In certain embodiments, $R^{19}$ is $C_{7-15}$ aralkyl, optionally substituted with one or more substituents as described herein. In certain embodiments, $R^{19}$ is heteroaryl, optionally substituted with one or more substituents as described herein. In certain embodiments, $R^{19}$ is heterocyclyl, optionally substituted with one or more substituents as described herein. In certain embodiments, $R^{19}$ is methyl. In certain embodiments, $R^{19}$ is —C(O)$R^{20}$, wherein $R^{20}$ is as defined herein. In certain embodiments, $R^{19}$ is —C(O)O$R^{20}$, wherein $R^{20}$ is as defined herein. In certain embodiments, $R^{19}$ is —C(O)N$R^{21}R^{22}$, wherein $R^{21}$ and $R^{22}$ are each as defined herein. In certain embodiments, $R^{19}$ is or —C(=N$R^{20}$)N$R^{21}R^{22}$, wherein $R^{20}$, $R^{21}$, and $R^{22}$ are each as defined herein.

In certain embodiments, $R^{18}$ and $R^{19}$ together with the C atom to which they are attached form cycloalkyl, optionally substituted with one or more substituents as described herein. In certain embodiments, $R^{18}$ and $R^{19}$ together with the N atom to which they are attached form heterocyclyl, optionally substituted with one or more substituents as described herein.

In certain embodiments, $R^{20}$ is hydrogen. In certain embodiments, $R^{20}$ is $C_{1-6}$ alkyl, optionally substituted with one or more substituents as described herein. In certain embodiments, $R^{20}$ is $C_{2-6}$ alkenyl, optionally substituted with one or more substituents as described herein. In certain embodiments, $R^{20}$ is $C_{2-6}$ alkynyl, optionally substituted with one or more substituents as described herein. In certain embodiments, $R^{20}$ is $C_{3-7}$ cycloalkyl, optionally substituted with one or more substituents as described herein. In certain embodiments, $R^{20}$ is $C_{6-14}$ aryl, optionally substituted with one or more substituents as described herein. In certain embodiments, $R^{20}$ is $C_{7-15}$ aralkyl, optionally substituted with one or more substituents as described herein. In certain embodiments, $R^{20}$ is heteroaryl, optionally substituted with one or more substituents as described herein. In certain embodiments, $R^{20}$ is heterocyclyl, optionally substituted with one or more substituents as described herein. In certain embodiments, $R^{20}$ is t-butyl. In certain embodiments, $R^{20}$ is benzyl.

In certain embodiments, $R^{21}$ is hydrogen. In certain embodiments, $R^{21}$ is $C_{1-6}$ alkyl, optionally substituted with one or more substituents as described herein. In certain embodiments, $R^{21}$ is $C_{2-6}$ alkenyl, optionally substituted with one or more substituents as described herein. In certain embodiments, $R^{21}$ is $C_{2-6}$ alkynyl, optionally substituted with one or more substituents as described herein. In certain embodiments, $R^{21}$ is $C_{3-7}$ cycloalkyl, optionally substituted with one or more substituents as described herein. In certain embodiments, $R^{21}$ is $C_{6-14}$ aryl, optionally substituted with one or more substituents as described herein. In certain embodiments, $R^{21}$ is $C_{7-15}$ aralkyl, optionally substituted with one or more substituents as described herein. In certain embodiments, $R^{21}$ is heteroaryl, optionally substituted with one or more substituents as described herein. In certain embodiments, $R^{21}$ is heterocyclyl, optionally substituted with one or more substituents as described herein.

In certain embodiments, $R^{22}$ is hydrogen. In certain embodiments, $R^{22}$ is $C_{1-6}$ alkyl, optionally substituted with one or more substituents as described herein. In certain embodiments, $R^{22}$ is $C_{2-6}$ alkenyl, optionally substituted with one or more substituents as described herein. In certain embodiments, $R^{22}$ is $C_{2-6}$ alkynyl, optionally substituted with one or more substituents as described herein. In certain embodiments, $R^{22}$ is $C_{3-7}$ cycloalkyl, optionally substituted with one or more substituents as described herein. In certain embodiments, $R^{22}$ is $C_{6-14}$ aryl, optionally substituted with one or more substituents as described herein. In certain embodiments, $R^{22}$ is $C_{7-15}$ aralkyl, optionally substituted with one or more substituents as described herein. In certain embodiments, $R^{22}$ is heteroaryl, optionally substituted with one or more substituents as described herein. In certain embodiments, $R^{22}$ is heterocyclyl, optionally substituted with one or more substituents as described herein.

In certain embodiments, $R^{21}$ and $R^{22}$ together with the N atom to which they are attached form heterocyclyl, optionally substituted with one or more substituents as described herein.

In certain embodiments, $R^5$ is —OH. In certain embodiments, $R^5$ is —N$R^8R^9$, wherein $R^8$ and $R^9$ are each as defined herein. In certain embodiments, $R^5$ is —NHS(O)$_2R^8$, wherein $R^8$ is as defined herein. In certain embodiments, $R^5$ is —NHS(O)$_2$N$R^8R^9$, wherein $R^8$ and $R^9$ are each as defined herein. In certain embodiments, $R^5$ is —NHC(O)$R^8$, wherein $R^8$ is as defined herein. In certain embodiments, $R^5$ is —NHC(O)N$R^8R^9$, wherein $R^8$ and $R^9$ are each as defined herein. In certain embodiments, $R^5$ is —C(O)$R^8$, wherein $R^8$ is as defined herein. In certain embodiments, $R^5$ is or —C(O)N$R^8R^9$; wherein $R^8$ and $R^9$ are each as defined herein.

In certain embodiments, $R^8$ is hydrogen. In certain embodiments, $R^8$ is $C_{1-6}$ alkyl, optionally substituted with one or more substituents as described herein. In certain embodiments, $R^8$ is methyl. In certain embodiments, $R^8$ is $C_{2-6}$ alkenyl, optionally substituted with one or more substituents as described herein. In certain embodiments, $R^8$ is $C_{2-6}$ alkynyl, optionally substituted with one or more substituents as described herein. In certain embodiments, $R^8$ is $C_{3-7}$ cycloalkyl, optionally substituted with one or more substituents as described herein. In certain embodiments, $R^8$ is cyclopropyl, 1-methylcyclopropyl, 1-ethynylcyclopropyl, 1-[2-(2-methoxy-ethoxy)-ethoxymethyl]-cyclopropyl, cyclobutyl, cyclopentyl, or cyclohexyl. In certain embodiments, $R^8$ is $C_{6-14}$ aryl, optionally substituted with one or more substituents as described herein. In certain embodiments, $R^8$ is $C_{7-15}$ aralkyl, optionally substituted with one or more substituents as described herein. In certain embodiments, $R^8$ is heteroaryl, optionally substituted with one or more substituents as described herein. In certain embodiments, $R^8$ is heterocyclyl, optionally substituted with one or more substituents as described herein. In certain embodiments, $R^8$ is $C_{1-6}$ alkyl-$C_{3-7}$ cycloalkylene, optionally substituted with one or more substituents as described herein. In certain embodiments, $R^8$ is —CH$_2$N$R^{8a}R^{8b}$, wherein $R^{8a}$ and $R^{8b}$ are each as defined herein. In certain embodiments, $R^8$ is —CH$R^{8c}$CH$R^{8d}$N$R^{8a}R^{8b}$, wherein $R^{8a}$, $R^{8b}$, $R^{8c}$, and $R^{8d}$ are each as defined herein. In certain embodiments, $R^8$ is —CH$_2$C$R^{8c}R^{8d}$N$R^{8a}R^{8b}$, wherein $R^{8a}$, $R^{8b}$, $R^{8c}$, and $R^{8d}$ are each as defined herein.

In certain embodiments, $R^8$ has the structure of

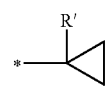

wherein R' is hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, halogen, heteroaryl, or heterocyclyl, each optionally substituted with one or more substituents as described herein.

In certain embodiments, $R^5$ has the structure of

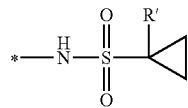

wherein R' is as defined herein.

In one embodiment, R' is $C_{1-6}$ alkyl. In another embodiment, R' is hydrogen. In yet another embodiment, R' is methyl. In yet another embodiment, R' is $C_{2-6}$ alkynyl. In still another embodiment, R' is ethynyl.

In certain embodiments, R' is hydrogen. In certain embodiments, R' is $C_{1-6}$ alkyl, optionally substituted with one or more substituents as described herein. In certain embodiments, R' is $C_{2-6}$ alkenyl, optionally substituted with one or more substituents as described herein. In certain embodiments, R' is $C_{2-6}$ alkynyl, optionally substituted with one or more substituents as described herein. In certain embodiments, R' is $C_{3-7}$ cycloalkyl, optionally substituted with one or more substituents as described herein. In certain embodiments, R' is $C_{6-14}$ aryl, optionally substituted with one or more substituents as described herein. In certain embodiments, R' is $C_{7-15}$ aralkyl, optionally substituted with one or more substituents as described herein. In certain embodiments, R' is heteroaryl, optionally substituted with one or more substituents as described herein. In certain embodiments, R' is heterocyclyl, optionally substituted with one or more substituents as described herein. In certain embodiments, R' is hydrogen, methyl, ethynyl, or 2-(2-methoxy-ethoxy)-ethoxymethyl.

In certain embodiments, $R^{8a}$ is hydrogen. In certain embodiments, $R^{8a}$ is $C_{1-6}$ alkyl, optionally substituted with one or more substituents as described herein. In certain embodiments, $R^{8a}$ is methyl. In certain embodiments, $R^{8a}$ is $C_{2-6}$ alkenyl, optionally substituted with one or more substituents as described herein. In certain embodiments, $R^{8a}$ is $C_{2-6}$ alkynyl, optionally substituted with one or more substituents as described herein. In certain embodiments, $R^{8a}$ is $C_{3-7}$ cycloalkyl, optionally substituted with one or more substituents as described herein. In certain embodiments, $R^{8a}$ is $C_{6-14}$ aryl, optionally substituted with one or more substituents as described herein. In certain embodiments, $R^{8a}$ is $C_{7-15}$ aralkyl, optionally substituted with one or more substituents as described herein. In certain embodiments, $R^{8a}$ is heteroaryl, optionally substituted with one or more substituents as described herein. In certain embodiments, $R^{8a}$ is heterocyclyl, optionally substituted with one or more substituents as described herein.

In certain embodiments, $R^{8b}$ is hydrogen. In certain embodiments, $R^{8b}$ is $C_{1-6}$ alkyl, optionally substituted with one or more substituents as described herein. In certain embodiments, $R^{8b}$ is methyl, ethyl, or isopropyl. In certain embodiments, $R^{8b}$ is $C_{2-6}$ alkenyl, optionally substituted with one or more substituents as described herein. In certain embodiments, $R^{8b}$ is $C_{2-6}$ alkynyl, optionally substituted with one or more substituents as described herein. In certain embodiments, $R^{8b}$ is $C_{3-7}$ cycloalkyl, optionally substituted with one or more substituents as described herein. In certain embodiments, $R^{8b}$ is $C_{6-14}$ aryl, optionally substituted with one or more substituents as described herein. In certain embodiments, $R^{8b}$ is phenyl, optionally substituted with one or more substituents as described herein. In certain embodiments, $R^{8b}$ is $C_{7-15}$ aralkyl, each optionally substituted with one or more substituents as described herein. In certain embodiments, $R^{8b}$ is benzyl. In certain embodiments, $R^{8b}$ is —C(O)$R^{11}$, wherein $R^{11}$ is as defined herein. In certain embodiments, $R^{8b}$ is —C(O)$R^{11}$, and $R^{11}$ is $C_{1-6}$ alkyl, optionally substituted with one or more substituents as described herein. In certain embodiments, $R^{8b}$ is acetyl. In certain embodiments, $R^{8b}$ is —C(O)O$R^{11}$, wherein $R^{11}$ is as defined herein. In certain embodiments, $R^{8b}$ is —C(O)O$R^{11}$, and $R^{11}$ is $C_{1-6}$ alkyl, optionally substituted with one or more substituents as described herein. In certain embodiments, $R^{8b}$ is —C(O)O-t-butyl (Boc). In certain embodiments, $R^{8b}$ is —C(O)N$R^{11}R^{12}$, wherein $R^{11}$ and $R^{12}$ are each as defined herein. In certain embodiments, $R^{8b}$ is —C(=N$R^{13}$)N$R^{11}R^{12}$; wherein $R^{11}$, $R^{12}$, and $R^{13}$ are each as defined herein. In certain embodiments, $R^{8b}$ is —S(O)$R^{11}$, wherein $R^{11}$ is as defined herein. In certain embodiments, $R^{8b}$ is —S(O)$_2R^{11}$, wherein $R^{11}$ is as defined herein. In certain embodiments, $R^{8b}$ is —S(O)N$R^{11}R^{12}$, wherein $R^{11}$ and $R^{12}$ are each as defined herein. In certain embodiments, $R^{8b}$ is —S(O)$_2$N$R^{11}R^{12}$, wherein $R^{11}$ and $R^{12}$ are each as defined herein.

In certain embodiments, $R^{11}$ is hydrogen. In certain embodiments, $R^{11}$ is $C_{1-6}$ alkyl, optionally substituted with one or more substituents as described herein. In certain embodiments, $R^{11}$ is methyl or (e.g., n-butyl, isobutyl, sec-butyl, or tert-butyl). In certain embodiments, $R^{11}$ is methyl or t-butyl. In certain embodiments, $R^{11}$ is $C_{2-6}$ alkenyl, optionally substituted with one or more substituents as described herein. In certain embodiments, $R^{11}$ is $C_{2-6}$ alkynyl, optionally substituted with one or more substituents as described herein. In certain embodiments, $R^{11}$ is $C_{3-7}$ cycloalkyl, optionally substituted with one or more substituents as described herein. In certain embodiments, $R^{11}$ is $C_{6-14}$ aryl, optionally substituted with one or more substituents as described herein. In certain embodiments, $R^{11}$ is $C_{7-15}$ aralkyl, optionally substituted with one or more substituents as described herein. In certain embodiments, $R^{11}$ is benzyl. In certain embodiments, $R^{11}$ is heteroaryl, optionally substituted with one or more substituents as described herein. In certain embodiments, $R^{11}$ is heterocyclyl, optionally substituted with one or more substituents as described herein.

In certain embodiments, $R^{12}$ is hydrogen. In certain embodiments, $R^{12}$ is $C_{1-6}$ alkyl, optionally substituted with one or more substituents as described herein. In certain embodiments, $R^{12}$ is $C_{2-6}$ alkenyl, optionally substituted with one or more substituents as described herein. In certain embodiments, $R^{12}$ is $C_{2-6}$ alkynyl, optionally substituted with one or more substituents as described herein. In certain embodiments, $R^{12}$ is $C_{3-7}$ cycloalkyl, optionally substituted with one or more substituents as described herein. In certain embodiments, $R^{12}$ is $C_{6-14}$ aryl, optionally substituted with one or more substituents as described herein. In certain embodiments, $R^{12}$ is $C_{7-15}$ aralkyl, optionally substituted with one or more substituents as described herein. In certain embodiments, $R^{12}$ is heteroaryl, optionally substituted with one or more substituents as described herein. In certain embodiments, $R^{12}$ is heterocyclyl, optionally substituted with one or more substituents as described herein.

In certain embodiments, $R^{11}$ and $R^{12}$ together with the N atom to which they are attached form heterocyclyl, optionally substituted with one or more substituents as described herein.

In certain embodiments, $R^{13}$ is hydrogen. In certain embodiments, $R^{13}$ is $C_{1-6}$ alkyl, optionally substituted with one or more substituents as described herein. In certain embodiments, $R^{13}$ is $C_{2-6}$ alkenyl, optionally substituted with one or more substituents as described herein. In certain embodiments, $R^{13}$ is $C_{2-6}$ alkynyl, optionally substituted with one or more substituents as described herein. In certain embodiments, $R^{13}$ is $C_{3-7}$ cycloalkyl, optionally substituted with one or more substituents as described herein. In certain embodiments, $R^{13}$ is $C_{6-14}$ aryl, optionally substituted with one or more substituents as described herein. In certain embodiments, $R^{13}$ is $C_{7-15}$ aralkyl, optionally substituted with one or more substituents as described herein. In certain embodiments, $R^{13}$ is heteroaryl, optionally substituted with one or more substituents as described herein. In certain embodiments, $R^{13}$ is heterocyclyl, optionally substituted with one or more substituents as described herein.

In certain embodiments, $R^{8c}$ is hydrogen. In certain embodiments, $R^{8c}$ is $C_{1-6}$ alkyl, optionally substituted with one or more substituents as described herein. In certain embodiments, $R^{8c}$ is methyl. In certain embodiments, $R^{8c}$ is $C_{2-6}$ alkenyl, optionally substituted with one or more substituents as described herein. In certain embodiments, $R^{8c}$ is alkynyl, optionally substituted with one or more substituents as described herein. In certain embodiments, $R^{8c}$ is $C_{3-7}$ cycloalkyl, optionally substituted with one or more substituents as described herein. In certain embodiments, $R^{8c}$ is $C_{6-14}$ aryl, optionally substituted with one or more substituents as described herein. In certain embodiments, $R^{8c}$ is $C_{7-15}$ aralkyl, optionally substituted with one or more substituents as described herein. In certain embodiments, $R^{8c}$ is heteroaryl, optionally substituted with one or more substituents as described herein. In certain embodiments, $R^{8c}$ is heterocyclyl, optionally substituted with one or more substituents as described herein.

In certain embodiments, $R^{8d}$ is hydrogen. In certain embodiments, $R^{8d}$ is $C_{1-6}$ alkyl, optionally substituted with one or more substituents as described herein. In certain embodiments, $R^{8d}$ is methyl. In certain embodiments, $R^{8d}$ is $C_{2-6}$ alkenyl, optionally substituted with one or more substituents as described herein. In certain embodiments, $R^{8d}$ is $C_{2-6}$ alkynyl, optionally substituted with one or more substituents as described herein. In certain embodiments, $R^{8d}$ is $C_{3-7}$ cycloalkyl, optionally substituted with one or more substituents as described herein. In certain embodiments, $R^{8d}$ is $C_{6-14}$ aryl, optionally substituted with one or more substituents as described herein. In certain embodiments, $R^{8d}$ is $C_{7-15}$ aralkyl, optionally substituted with one or more substituents as described herein. In certain embodiments, $R^{8d}$ is heteroaryl, optionally substituted with one or more substituents as described herein. In certain embodiments, $R^{8d}$ is heterocyclyl, optionally substituted with one or more substituents as described herein.

In certain embodiments, $R^{9}$ is hydrogen. In certain embodiments, $R^{9}$ is $C_{1-6}$ alkyl, optionally substituted with one or more substituents as described herein. In certain embodiments, $R^{9}$ is $C_{2-6}$ alkenyl, optionally substituted with one or more substituents as described herein. In certain embodiments, $R^{9}$ is $C_{2-6}$ alkynyl, optionally substituted with one or more substituents as described herein. In certain embodiments, $R^{9}$ is $C_{3-7}$ cycloalkyl, optionally substituted with one or more substituents as described herein. In certain embodiments, $R^{9}$ is $C_{6-14}$ aryl, optionally substituted with one or more substituents as described herein. In certain embodiments, $R^{9}$ is $C_{7-15}$ aralkyl, optionally substituted with one or more substituents as described herein. In certain embodiments, $R^{9}$ is heteroaryl, optionally substituted with one or more substituents as described herein. In certain embodiments, $R^{9}$ is heterocyclyl, optionally substituted with one or more substituents as described herein.

In certain embodiments, $R^{8}$ and $R^{9}$ together with the N atom to which they are attached form heterocyclyl, optionally substituted with one or more substituents as described herein.

In certain embodiments, Y is a bond. In certain embodiments, Y is —O—. In certain embodiments, Y is —S—. In certain embodiments, Y is —N($R^{Y}$)—, wherein $R^{Y}$ is as defined herein.

In certain embodiments, $R^{Y}$ is hydrogen. In certain embodiments, $R^{Y}$ is $C_{1-6}$ alkyl, optionally substituted with one or more substituents as described herein. In certain embodiments, $R^{Y}$ is $C_{2-6}$ alkenyl, optionally substituted with one or more substituents as described herein. In certain embodiments, $R^{Y}$ is $C_{2-6}$ alkynyl, optionally substituted with one or more substituents as described herein. In certain embodiments, $R^{Y}$ is $C_{3-7}$ cycloalkyl, optionally substituted with one or more substituents as described herein. In certain embodiments, $R^{Y}$ is $C_{6-14}$ aryl, optionally substituted with one or more substituents as described herein. In certain embodiments, $R^{Y}$ is $C_{7-15}$ aralkyl, optionally substituted with one or more substituents as described herein. In certain embodiments, $R^{Y}$ is —C(O)$R^{Ya}$, wherein $R^{Ya}$ is as defined herein. In certain embodiments, $R^{Y}$ is —C(O)O$R^{Ya}$, wherein $R^{Ya}$ is as defined herein. In certain embodiments, $R^{Y}$ is —C(O)N$R^{Yb}R^{Yc}$, wherein $R^{Yb}$ and $R^{Yc}$ are each as defined herein. In certain embodiments, $R^{Y}$ is —S(O)$_2$N$R^{Yb}R^{Yc}$, wherein $R^{Yb}$ and $R^{Yc}$ are each as defined herein. In certain embodiments, $R^{Y}$ is —S(O)$_2R^{Ya}$, wherein $R^{Ya}$ is as defined herein.

In certain embodiments, $R^{Ya}$ is hydrogen. In certain embodiments, $R^{Ya}$ is $C_{1-6}$ alkyl, optionally substituted with one or more substituents as described herein. In certain embodiments, $R^{Ya}$ is $C_{2-6}$ alkenyl, optionally substituted with one or more substituents as described herein. In certain embodiments, $R^{Ya}$ is $C_{2-6}$ alkynyl, optionally substituted with one or more substituents as described herein. In certain embodiments, $R^{Ya}$ is $C_{3-7}$ cycloalkyl, optionally substituted with one or more substituents as described herein. In certain embodiments, $R^{Ya}$ is $C_{6-14}$ aryl, optionally substituted with one or more substituents as described herein. In certain embodiments, $R^{Ya}$ is $C_{7-15}$ aralkyl, optionally substituted with one or more substituents as described herein. In certain embodiments, $R^{Ya}$ is heteroaryl, optionally substituted with one or more substituents as described herein. In certain embodiments, $R^{Ya}$ is heterocyclyl, optionally substituted with one or more substituents as described herein.

In certain embodiments, $R^{Yb}$ is hydrogen. In certain embodiments, $R^{Yb}$ is $C_{1-6}$ alkyl, optionally substituted with one or more substituents as described herein. In certain embodiments, $R^{Yb}$ is $C_{2-6}$ alkenyl, optionally substituted with one or more substituents as described herein. In certain embodiments, $R^{Yb}$ is $C_{2-6}$ alkynyl, optionally substituted with one or more substituents as described herein. In certain embodiments, $R^{Yb}$ is $C_{3-7}$ cycloalkyl, optionally substituted with one or more substituents as described herein. In certain embodiments, $R^{Yb}$ is $C_{6-14}$ aryl, optionally substituted with one or more substituents as described herein. In certain embodiments, $R^{Yb}$ is $C_{7-15}$ aralkyl, optionally substituted with one or more substituents as described herein. In certain embodiments, $R^{Yb}$ is heteroaryl, optionally substituted with one or more substituents as described herein. In certain embodiments, $R^{Yb}$ is heterocyclyl, optionally substituted with one or more substituents as described herein.

In certain embodiments, $R^{Yc}$ is hydrogen. In certain embodiments, $R^{Yc}$ is $C_{1-6}$ alkyl, optionally substituted with one or more substituents as described herein. In certain embodiments, $R^{Yc}$ is $C_{2-6}$ alkenyl, optionally substituted with one or more substituents as described herein. In certain embodiments, $R^{Yc}$ is $C_{2-6}$ alkynyl, optionally substituted with one or more substituents as described herein. In certain embodiments, $R^{Yc}$ is $C_{3-7}$ cycloalkyl, optionally substituted with one or more substituents as described herein. In certain embodiments, $R^{Yc}$ is $C_{6-14}$ aryl, optionally substituted with one or more substituents as described herein. In certain embodiments, $R^{Yc}$ is $C_{7-15}$ aralkyl, optionally substituted with one or more substituents as described herein. In certain embodiments, $R^{Yc}$ is heteroaryl, optionally substituted with one or more substituents as described herein. In certain embodiments, $R^{Yc}$ is heterocyclyl, optionally substituted with one or more substituents as described herein.

In certain embodiments, m is 0. In certain embodiments, m is 1.

In certain embodiments, n is 1. In certain embodiments, m is 2.

In certain embodiments, the sum of m and n is 2. In certain embodiments, the sum of m and n is 3.

In certain embodiments, q is 0. In certain embodiments, q is 1. In certain embodiments, q is 2. In certain embodiments, q is 3. In certain embodiments, q is 4.

In certain embodiments, r is 0. In certain embodiments, r is 1. In certain embodiments, r is 2. In certain embodiments, r is 3. In certain embodiments, r is 4.

In certain embodiments, U is N. In certain embodiments, U is CH. In certain embodiments, V is N. In certain embodiments, V is CH. In certain embodiments, one of U and V is N. In certain embodiments, U is CH and V is N. In certain embodiments, U is N and V is CH.

In certain embodiments, Z is $CR^{3'}$, wherein $R^{3'}$ is as defined herein. In certain embodiments, Z is CH. In certain embodiments, Z is N.

In one embodiment, the compound provided herein is

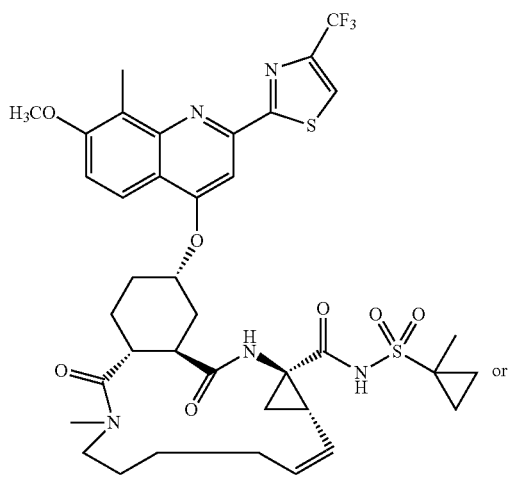

51

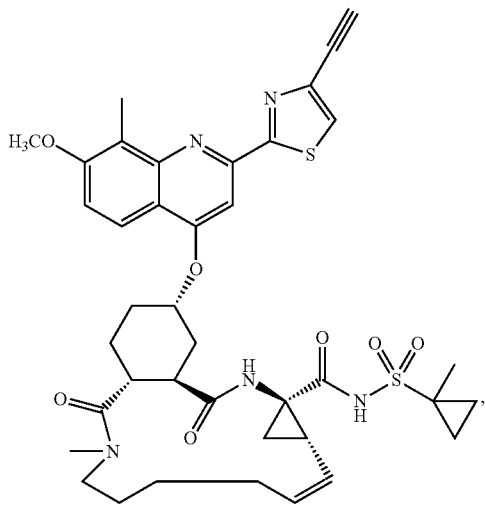

52 or a single enantiomer, a racemic mixture, a mixture of diastereomers, or an isotopic variant thereof; or a pharmaceutically acceptable salt, solvate, or prodrug thereof; or a pharmaceutically acceptable salt, solvate, or prodrug thereof.

The compounds provided herein are intended to encompass all possible stereoisomers, unless a particular stereochemistry is specified. Where the compound provided herein contains an alkenyl or alkenylene group, the compound may exist as one or a mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

For example, the heterocyclic moiety that is fused with the macrocyclic ring in the compounds provided herein, including the compounds of Formulae Ia, Ib, IIa, IIb, IIIa, IIIb, IVa, IVb, Va, Vb, VIa, VIb, VIIa, VIIb, VIIIa, VIIIb, IXa, IXb, Xa, Xb, XIa, XIb, XIIa, XIIb, XIIIa, XIIIb, XIVa, XIVb, XVa, XVb, XVIa, XVIb, XIIa, XIIb, XIIIa, XIIIb, XIVa, and XIVb, contain three chiral centers as indicated by star symbols. As result, the heterocyclic moiety may exist in eight different stereoisomeric forms as shown below.

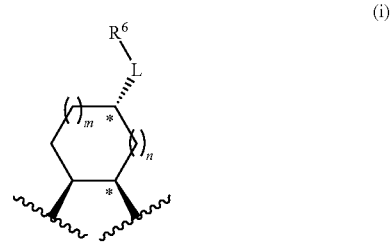

(i)

(ii)
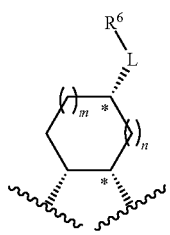

(iii)
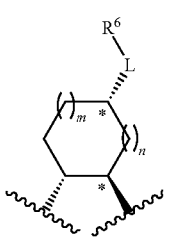

(iv)
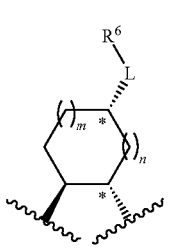

(v)
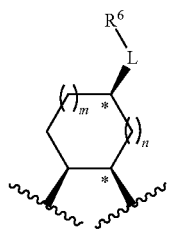

(vi)
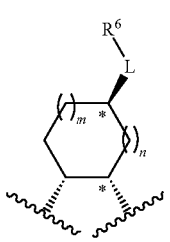

(vii)
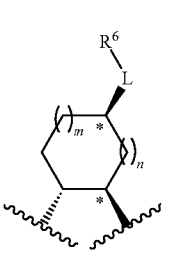

(viii)
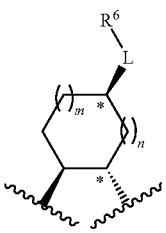

The heterocyclic moiety of a particular configuration can readily be introduced by selecting a chiral starting material that will yield the desired chirality.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt. See, Berge et al., *J. Pharm. Sci.* 1977, 66, 1-19; and *Handbook of Pharmaceutical Salts, Properties, and Use*; Stahl and Wermuth, Ed.; Wiley-VCH and VHCA: Zurich, Switzerland, 2002.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, Harper, *Progress in Drug Research* 1962, 4, 221-294; Morozowich et al. in *Design of Biopharmaceutical Properties through Prodrugs and Analogs*; Roche Ed., APHA Acad. Pharm. Sci.: 1977; Gangwar et al., *Des. Biopharm. Prop. Prodrugs Analogs,* 1977, 409-421; Bundgaard, *Arch. Pharm. Chem.* 1979, 86, 1-39; Farquhar et al., *J. Pharm. Sci.* 1983, 72, 324-325; Wernuth in *Drug Design: Fact or Fantasy*; Jolles et al. Eds.; Academic Press: London, 1984; pp 47-72; *Design of Prodrugs*; Bundgaard et al. Eds.; Elsevier: 1985; Fleisher et al., *Methods Enzymol.* 1985, 112, 360-381; Stella et al., *Drugs* 1985, 29, 455-473; *Bioreversible Carriers in Drug in Drug Design, Theory and Application*; Roche Ed.; APHA Acad. Pharm. Sci.: 1987; Bundgaard, *Controlled Drug Delivery* 1987, 17, 179-96; Waller et al., *Br. J. Clin. Pharmac.* 1989, 28, 497-507; Balant et al., *Eur. J. Drug Metab. Pharmacokinet.* 1990, 15, 143-53; Freeman et al., *J. Chem. Soc., Chem. Commun.* 1991, 875-877; Bundgaard, *Adv. Drug Delivery Rev.* 1992, 8, 1-38; Nathwani and Wood, *Drugs* 1993, 45, 866-94; Friis and Bundgaard, *Eur. J. Pharm. Sci.* 1996, 4, 49-59; Fleisher et al., *Adv. Drug Delivery Rev.* 1996, 19, 115-130; Sinhababu and Thakker, *Adv. Drug Delivery Rev.* 1996, 19, 241-273; Taylor, *Adv. Drug Delivery Rev.* 1996, 19, 131-148; Gaignault et al., *Pract. Med. Chem.* 1996, 671-696; Browne, *Clin. Neuropharmacol.* 1997, 20, 1-12; Valentino and Borchardt, *Drug Discovery Today* 1997, 2, 148-155; Pauletti et al., *Adv. Drug. Delivery Rev.* 1997, 27, 235-256; Mizen et al., *Pharm. Biotech.* 1998, 11, 345-365; Wiebe and Knaus, *Adv. Drug Delivery Rev.* 1999, 39, 63-80; Tan et al., *Adv. Drug Delivery Rev.* 1999, 39, 117-151; Balimane and Sinko, *Adv. Drug Delivery Rev.* 1999, 39, 183-209; Wang et al., *Curr. Pharm. Design* 1999, 5, 265-287; Han et al., *AAPS Pharm sci.* 2000, 2, 1-11; Asgharnejad in *Transport Processes in Pharmaceutical Systems*; Amidon et al., Eds.; Marcell Dekker: 2000; pp 185-218; Sinha et al., *Pharm. Res.* 2001, 18, 557-564; Anand et al., *Expert Opin. Biol. Ther.* 2002, 2, 607-620; Rao, *Resonate* 2003, 19-27; Sloan et al., *Med. Res. Rev.* 2003, 23, 763-793; Patterson et al., *Curr. Pharm. Des.* 2003, 9, 2131-2154; Hu, *IDrugs* 2004, 7, 736-742; Robinson et al., *Proc. Natl. Acad. Sci. U.S.A.* 2004, 101, 14527-14532; Erion et al., *J. Pharmacol. Exp. Ther.* 2005, 312, 554-560; Fang et al., *Curr. Drug Discov. Technol.* 2006, 3, 211-224; Stanczak et al., *Pharmacol. Rep.* 2006, 58, 599-613; Sloan et al., *Pharm. Res.* 2006, 23, 2729-2747; Stella et al., *Adv. Drug Deliv. Rev.* 2007, 59, 677-694; Gomes et al., *Molecules* 2007, 12, 2484-2506; Krafz et al., *Chem Med Chem* 2008, 3, 20-53; Rautio et al., *AAPS J.* 2008, 10, 92-102; Rautio et al., *Nat. Rev. Drug. Discov.* 2008, 7, 255-270; Pavan et al., *Molecules,* 2008, 13, 1035-1065; Sandros et al., *Molecules* 2008, 13, 1156-1178; Singh et al., *Curr. Med. Chem.* 2008, 15, 1802-1826; Onishi et al., *Molecules,* 2008, 13, 2136-2155; Huttunen et al., *Curr. Med. Chem.* 2008, 15, 2346-2365; and Serafin et al., *Mini Rev. Med. Chem.* 2009, 9, 481-497.

Methods of Synthesis

The compound provided herein can be prepared, isolated, or obtained by any method known to one of skill in the art. For an example, a compound of Formula I can be prepared as shown in Scheme 1.

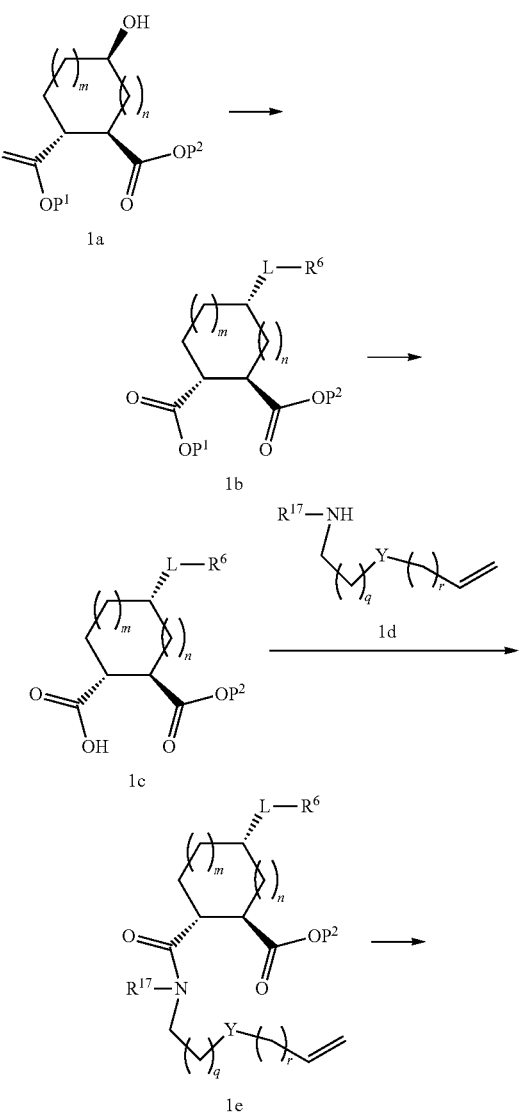

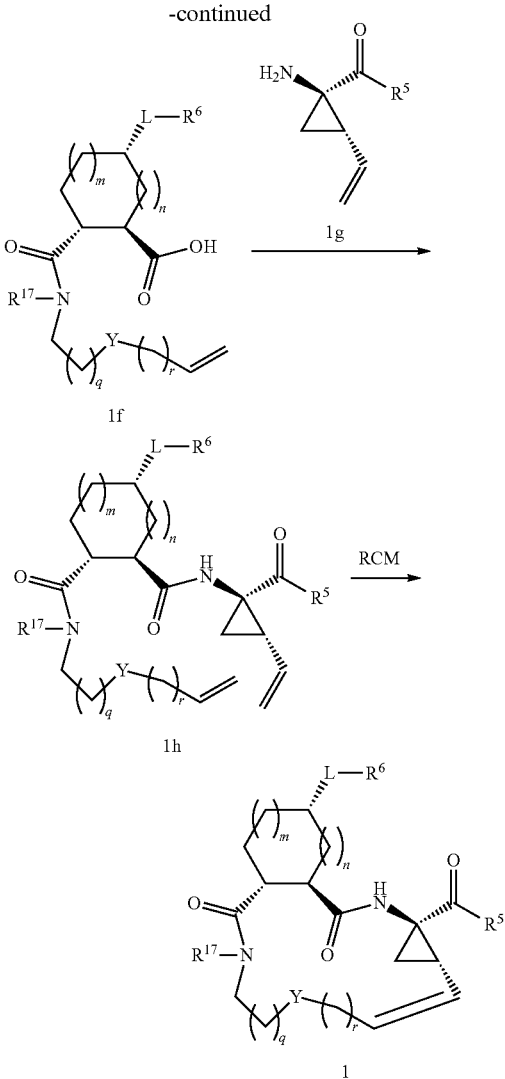

A variety of $R^6$-L groups can be introduced at the hydroxyl position compound 1a using various chemistries, such as coupling reactions to form ester, carbonate, or carbamate with the hydroxyl group, or nucleophilic substitution reactions to form ether, amine, or thioether. A nucleophilic substitution reaction to form an ether linkage is illustrated in Scheme 1. Compound 1a with a desired stereochemistry reacts with $R^6$-L-V, where V is hydrogen or a metal ion or complex, with inversion of the stereochemistry at the position of the hydroxyl group to produce compound 1b. In the case of L is heteroatom, the reaction may be run under the Mitsunobu condition where V is hydrogen. Where L is a carbon atom moiety, the hydroxyl in compound 1a may be derivatized as a leaving group and reacted with $R^6$-L-V, where V is a metal ion or complex. The carboxyl protecting group $P^1$ is then selectively removed to produce a free acid 1c, which is coupled with compound 1d in the presence of a coupling reagent to form compound 1e. The carboxyl protecting group $P^2$ is removed to form a free acid 1f, which is coupled with compound 1g in the presence of a coupling reagent to compound 1h. Compound 1h is cyclized in the presence of a metathesis catalyst to form macrocyclic compound 1. Suitable examples of metathesis catalysts can also be found, e.g., in U.S. Pat. Provisional Pat. Appl. Ser. Nos. 61/149,662, filed Feb. 3, 2009; and 61/231,408, filed Aug. 5, 2009; the disclosure of each of which is incorporated herein by reference in its entirety.

The starting materials used in the synthesis of the compounds provided herein are either commercially available or can be readily prepared. Suitable examples of $R^6$ groups can be found, e.g., in International Pat. Appl. Publ. Nos. WO 2009/014730 and WO 2009/082697; U.S. patent application Ser. No. 12/365,127, filed Feb. 3, 2009; and U.S. Provisional Pat. Appl. Ser. Nos. 61/167,847, filed Apr. 8, 2009, and 61/231,600, filed Aug. 5, 2009; the disclosure of each of which is incorporated herein by reference in its entirety.

Pharmaceutical Compositions

Provided herein are pharmaceutical compositions comprising a compound provided herein, e.g., a compound of Formula Ia or Ib, as an active ingredient, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug; in combination with a pharmaceutically acceptable vehicle, carrier, diluent, or excipient, or a mixture thereof.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage founts comprise an active ingredient, microcrystalline cellulose, pre-gelatinized starch, and magnesium stearate.

The compound provided herein may be administered alone, or in combination with one or more other compounds provided herein. The pharmaceutical compositions that comprise a compound provided herein, e.g., a compound of Formula Ia or Ib, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd ed.; Rathbone et al., Eds.; Marcel Dekker, Inc.: New York, N.Y., 2008).

In one embodiment, the pharmaceutical compositions are provided in a dosage form for oral administration, which comprise a compound provided herein, e.g., a compound of Formula Ia or Ib, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more pharmaceutically acceptable excipients or carriers.

In another embodiment, the pharmaceutical compositions are provided in a dosage form for parenteral administration, which comprise a compound provided herein, e.g., a compound of Formula Ia or Ib, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more pharmaceutically acceptable excipients or carriers.

In yet another embodiment, the pharmaceutical compositions are provided in a dosage form for topical administration, which comprise a compound provided herein, e.g., a compound of Formula Ia or Ib, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfate and sodium metabisulfite. Suitable vehicles include, but are not limited to, cocoa butter (theobroma oil), glycerin-gelatin, carbowax (polyoxyethylene glycol), spermaceti, paraffin, white and yellow wax, appropriate mixtures of mono-, di- and triglycerides of fatty acids, hydrogels (such as polyvinyl alcohol and hydroxyethyl methacrylate), and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology,* 2nd ed.; Rathbone et al., Eds.; Marcel Dekker A G: 2005; Maroni et al., *Expert. Opin. Drug Deliv.* 2005, 2, 855-871; Shi et al., *Expert Opin. Drug Deliv.* 2005, 2, 1039-1058; *Polymers in Drug Delivery*; Ijeoma et al., Eds.; CRC Press LLC: Boca Raton, Fla., 2006; Badawy et al., *J. Pharm. Sci.* 2007, 9, 948-959; *Modified-Release Drug Delivery Technology*, supra; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deliv.* 2008, 5, 282-289; Gallardo et al., *Pharm. Dev. Technol.* 2008, 13, 413-423; Chrzanowski, *AAPS Pharm Sci Tech.* 2008, 9, 635-638; Chrzanowski, *AAPS Pharm Sci Tech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80.

1. Matrix Controlled Release Devices

The pharmaceutical compositions provided herein in a modified release dosage form can be fabricated using a matrix controlled release device known to those skilled in the art. See, Takada et al. in *Encyclopedia of Controlled Drug Delivery*; Mathiowitz Ed.; Wiley: 1999; Vol 2.

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma. Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage foam can further comprise additional conventional excipients or carriers as described herein to promote performance or processing of the formulation.

The osmotic controlled-release dosage forms can be prepared according to conventional methods and techniques known to those skilled in the art. See, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; and Verma et al., *J. Controlled Release* 2002, 79, 7-27.

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and International Pat. Appl. Publ. No. WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxyl-ethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Ghebre-Sellassie Ed.; Marcel Dekker: 1994; and *Pharmaceutical Pelletization Technology*; Ghebre-Sellassie Ed.; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 5,709,874; 5,759,542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

Methods of Use

In one embodiment, provided herein are methods for treating or preventing a hepatitis C viral infection in a subject, which comprises administering to a subject a therapeutically effective amount of a compound provided herein, e.g., a compound of Formula Ia or Ib, including a single enantiomer, a racemic mixture, a mixture of diastereomers, or an isotopic variant thereof; or a pharmaceutically acceptable salt, solvate, or prodrug thereof. In one embodiment, the subject is a mammal. In another embodiment, the subject is a human.

As used herein, the term "hepatitis C virus" or "HCV" refers to a viral species or a genetic variation thereof, a pathogenic strain of which causes hepatitis C. Examples of HCV include, but are not limited to, HCV genotypes 1, 2, 3, 4, and 5, and subtype 1a, 1b, 1c, 2a, 2b, 2c, 3a, and 3b.

In one embodiment, the hepatitis C viral infection is caused by HCV genotype 1. In certain embodiments, the hepatitis C viral infection is caused by HCV subtype 1a. In certain embodiments, the hepatitis C viral infection is caused by HCV subtype 1b. In certain embodiments, the hepatitis C viral infection is caused by HCV subtype 1c. In another embodiment, the hepatitis C viral infection is caused by HCV genotype 2. In certain embodiments, the hepatitis C viral infection is caused by HCV subtype 2a. In certain embodiments, the hepatitis C viral infection is caused by HCV subtype 2b. In certain embodiments, the hepatitis C viral infection is caused by HCV subtype 2c. In yet another embodiment, the hepatitis C viral infection is caused by HCV genotype 3. In certain embodiments, the hepatitis C viral infection is caused by HCV subtype 3a. In certain embodiments, the hepatitis C viral infection is caused by HCV subtype 3b. In yet another embodiment, the hepatitis C viral infection is caused by HCV genotype 4. In yet another embodiment, the hepatitis C viral infection is caused by HCV genotype 5. In yet another embodiment, the hepatitis C viral infection is caused by HCV genotype 6.

In another embodiment, provided herein is a method for inhibiting replication of a virus in a host, which comprises contacting the host with a therapeutically effective amount of a compound provided herein, e.g., a compound of Formula Ia or Ib, including a single enantiomer, a racemic mixture, a mixture of diastereomers, or an isotopic variant thereof; or a pharmaceutically acceptable salt, solvate, or prodrug thereof. In one embodiment, the host is a cell. In another embodiment, the host is a human cell. In yet another embodiment, the host is a mammal. In still another embodiment, the host is human.

In one embodiment, the virus is a hepatitis C virus. In another embodiment, the virus is HCV genotype 1. In certain embodiments, the virus is HCV subtype 1a. In yet certain embodiments, the virus is HCV subtype 1b. In certain embodiments, the virus is HCV subtype 1c. In another embodiment, the virus is HCV genotype 2. In certain embodiments, the virus is HCV subtype 2a. In certain embodiments, the virus is HCV subtype 2b. In certain embodiments, the virus is HCV subtype 2c. In yet another embodiment, the virus is HCV genotype 3. In certain embodiments, the virus is HCV subtype 3a. In certain embodiments, the virus is HCV subtype 3b. In yet another embodiment, the virus is HCV genotype 4. In yet another embodiment, the virus is HCV genotype 5. In yet another embodiment, the virus is HCV genotype 6.

In certain embodiments, administration of a therapeutically effective amount of a compound provided herein (e.g., a compound of Formula Ia or Ib, including a single enantiomer, a racemic mixture, a mixture of diastereomers, or an isotopic variant thereof; or a pharmaceutically acceptable salt, solvate, or prodrug thereof) results in a 10%, 20%, 30%, 40%, 50%, 60%, 70%, 80%, 90%, 95%, 99% or more reduction in the replication of the virus relative to a subject without administration of the compound, as determined at 1 day, 2 days, 3 days, 4 days, 5 days, 10 days, 15 days, or 30 days after the administration by a method known in the art, e.g., determination of viral titer.

In certain embodiments, administration of a therapeutically effective amount of a compound provided herein (e.g., a compound of Formula Ia or Ib, including a single enantiomer, a racemic mixture, a mixture of diastereomers, or an isotopic variant thereof; or a pharmaceutically acceptable salt, solvate, or prodrug thereof) results in a 1, 2, 3, 4, 5, 10, 15, 20, 25, 50, 75, 100-fold or more reduction in the replication of the virus relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound provided herein (e.g., a compound of Formula Ia or Ib, including a single enantiomer, a racemic mixture, a mixture of diastereomers, or an isotopic variant thereof; or a pharmaceutically acceptable salt, solvate, or prodrug thereof) results in a 10%, 20%, 30%, 40%, 50%, 60%, 70%, 80%, 90%, 95%, 99% or more reduction in the viral titer relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound provided herein (e.g., a compound of Formula Ia or Ib, including a single enantiomer, a racemic mixture, a mixture of diastereomers, or an isotopic variant thereof; or a pharmaceutically acceptable salt, solvate, or prodrug thereof) results in a 1, 2, 3, 4, 5, 10, 15, 20, 25, 50, 75, 100 or more fold reduction in the viral titer relative to a subject without administration of the compound, as determined at 1 day, 2 days, 3 days, 4 days, 5 days, 10 days, 15 days, or 30 days after the administration by a method known in the art.

In yet another embodiment, provided herein is a method for inhibiting the replication of an HCV virus, which comprises contacting the virus with a therapeutically effective amount of a compound provided herein, e.g., a compound of Formula Ia or Ib, including a single enantiomer, a racemic mixture, a mixture of diastereomers, or an isotopic variant thereof; or a pharmaceutically acceptable salt, solvate, or prodrug thereof.

In one embodiment, the HCV is genotype 1. In certain embodiments, the HCV is subtype 1a. In certain embodiments, the HCV is subtype 1b. In certain embodiments, the HCV is subtype 1c. In another embodiment, the HCV is genotype 2. In certain embodiments, the HCV is subtype 2a. In certain embodiments, the HCV is subtype 2b. In certain embodiments, the HCV is subtype 2c. In yet another embodiment, the HCV is genotype 3. In certain embodiments, the HCV is subtype 3a. In certain embodiments, the HCV is subtype 3b. In yet another embodiment, the HCV is genotype 4. In yet another embodiment, the HCV is genotype 5. In yet another embodiment, the HCV is genotype 6.

In certain embodiments, the contacting of the virus with a therapeutically effective amount of a compound provided herein (e.g., a compound of Formula Ia or Ib, including a single enantiomer, a racemic mixture, a mixture of diastereomers, or an isotopic variant thereof; or a pharmaceutically acceptable salt, solvate, or prodrug thereof) results in a 10%, 20%, 30%, 40%, 50%, 60%, 70%, 80%, 90%, 95%, 99% or more reduction in the virus titer relative to the virus without such contact, as determined at 1 day, 2 days, 3 days, 4 days, 5 days, 10 days, 15 days, or 30 days after the initial contact, by a method known in the art.

In certain embodiments, the contacting of the virus with a therapeutically effective amount of a compound provided herein (e.g., a compound of Formula Ia or Ib, including a single enantiomer, a racemic mixture, a mixture of diastereomers, or an isotopic variant thereof; or a pharmaceutically acceptable salt, solvate, or prodrug thereof) results in a 1, 2, 3, 4, 5, 10, 15, 20, 25, 50, 75, 100 or more fold reduction in the viral titer relative to the virus without such contact, as determined at 1 day, 2 days, 3 days, 4 days, 5 days, 10 days, 15 days, or 30 days after the initial contact, by a method known in the art.

In yet another embodiment, provided herein is a method for treating, preventing, or ameliorating one or more symptoms of a liver disease or disorder associated with an HCV infection, comprising administering to a subject a therapeutically effective amount of the compound provided herein, e.g., a compound of Formula Ia or Ib, including a single enantiomer, a racemic mixture, a mixture of diastereomers, or an isotopic variant thereof; or a pharmaceutically acceptable salt, solvate, or prodrug thereof. Non-limiting examples of diseases associated with HCV infection include chronic hepatitis, cirrhosis, hepatocarcinoma, or extra hepatic manifestation.

In one embodiment, the HCV infection is caused by HCV genotype 1. In certain embodiments, the HCV infection is caused by HCV subtype 1a. In certain embodiments, the HCV infection is caused by HCV subtype 1b. In certain embodiments, the HCV infection is caused by HCV subtype 1c. In another embodiment, the HCV infection is caused by HCV genotype 2. In certain embodiments, the HCV infection is caused by HCV subtype 2a. In certain embodiments, the HCV infection is caused by HCV subtype 2b. In certain embodiments, the HCV infection is caused by HCV subtype 2c. In yet another embodiment, the HCV infection is caused by HCV genotype 3. In certain embodiments, the HCV infection is caused by HCV subtype 3a. In certain embodiments, the HCV infection is caused by HCV subtype 3b. In yet another embodiment, the HCV infection is caused by HCV genotype 4. In yet another embodiment, the HCV infection is caused by HCV genotype 5. In yet another embodiment, the HCV infection is caused by HCV genotype 6.

In still another embodiment, provided herein is a method for inhibiting the activity of a serine protease, which comprises contacting the serine protease with an effective amount of a compound provided herein, e.g., a compound of Formula Ia or Ib, including a single enantiomer, a racemic mixture, a mixture of diastereomers, or an isotopic variant thereof; or a pharmaceutically acceptable salt, solvate, or prodrug thereof. In one embodiment, the serine protease is hepatitis C NS3 protease. In another embodiment, the serine protease is HCV protease. In yet another embodiment, the serine protease is HCV NS3/4protease.

In one embodiment, the HCV protease is genotype 1 NS3/4A protease. In certain embodiments, the HCV protease is subtype 1a NS3/4A protease. In certain embodiments, the HCV protease is subtype 1b NS3/4A protease. In certain embodiments, the HCV protease is subtype 1c NS3/4A protease. In another embodiment, the HCV protease is genotype 2 NS3/4A protease. In certain embodiments, the HCV protease is subtype 2a NS3/4A protease. In certain embodiments, the HCV protease is subtype 2b NS3/4A protease. In certain embodiments, the HCV protease is subtype 2c NS3/4A protease. In yet another embodiment, the HCV protease is genotype 3 NS3/4A protease. In certain embodiments, the HCV protease is subtype 3a NS3/4A protease. In yet another embodiment, the HCV protease is genotype 3 NS3/4A protease. In yet another embodiment, the HCV protease is genotype 5 NS3/4A protease. In yet another embodiment, the HCV protease is genotype 6 NS3/4A protease.

Depending on the condition, disorder, or disease, to be treated and the subject's condition, a compound provided herein may be administered by oral, parenteral (e.g., intramuscular, intraperitoneal, intravenous, intracerebroventricular (ICV), intracisternal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1,000 milligram, from about 0.1 to about 500 milligrams, or from 0.5 about to about 100 milligram active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

Combination Therapy

The compounds provided herein may also be combined or used in combination with other therapeutic agents useful in the treatment and/or prevention of an HCV infection.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of a compound provided herein and another therapy (e.g., a prophylactic or therapeutic agent) which has been or is currently being used to prevent, treat, or manage a condition, disorder, or disease, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a condition, disorder, or disease. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, treatment, or management of a condition, disorder, or disease). In addition, a synergistic effect can result in improved efficacy of agents in the prevention, treatment, or management of a condition, disorder, or disease. Finally, a synergistic effect of a combination of therapies (e.g., a combination of prophylactic or therapeutic agents) may avoid or reduce adverse or unwanted side effects associated with the use of either therapy alone.

The compound provided herein can be administered in combination or alternation with another therapeutic agent, such as an anti-HCV agent. In combination therapy, effective dosages of two or more agents are administered together, whereas in alternation or sequential-step therapy, an effective dosage of each agent is administered serially or sequentially. The dosages given will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

It has been recognized that drug-resistant variants of HCV can emerge after prolonged treatment with an antiviral agent. Drug resistance most typically occurs due to the mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameters of the drug can be altered by such combination or alternation therapy. In general, combination therapy is typically preferred over alternation therapy because it induces multiple simultaneous stresses on the virus.

In certain embodiments, the pharmaceutical compositions provided herein further comprise a second antiviral agent as described herein. In certain embodiments, the compound provided herein is combined with one or more agents selected from the group consisting of an interferon, ribavirin, amantadine, an interleukin, a NS3 protease inhibitor, a cysteine protease inhibitor, a phenanthrenequinone, a thiazolidine, a benzanilide, a helicase inhibitor, a polymerase inhibitor, a nucleotide analogue, a gliotoxin, a cerulenin, an antisense phosphorothioate oligodeoxynucleotide, an inhibitor of IRES-dependent translation, and a ribozyme. In one embodiment, the second antiviral agent is an interferon. In another embodiment, the interferon is selected from the group consisting of pegylated interferon alpha 2a, interferon alfacon-1, natural interferon, ALBUFERON®, interferon beta-1a, omega interferon, interferon alpha, interferon gamma, interferon tau, interferon delta, and interferon gamma-1b.

In certain embodiments, the compound provided herein is combined with a HCV protease inhibitor, including, but not limited to, Medivir HCV protease inhibitor (Medivir/Tibotec); ITMN-191 (InterMune); SCH 503034 (Schering); VX950 (Vertex); substrate-based NS3 protease inhibitors as disclosed in DE 19914474, WO 98/17679, WO 98/22496, WO 99/07734, and Attwood et al., *Antiviral Chemistry and Chemotherapy* 1999, 10, 259-273; non-substrate-based NS3 protease inhibitors, including 2,4,6-trihydroxy-3-nitro-benzamide derivatives (Sudo et al., *Biochem. Biophys. Res. Commun.* 1997, 238, 643-647), a phenanthrenequinone (Chu et al., *Tetrahedron Letters* 1996, 37, 7229-7232), RD3-4082, RD3-4078, SCH 68631, and SCH 351633 (Chu et al., *Bioorganic and Medicinal Chemistry Letters* 1999, 9, 1949-1952); and Eglin C, a potent serine protease inhibitor (Qasim et al., *Biochemistry* 1997, 36, 1598-1607).

Other suitable protease inhibitors for the treatment of HCV include those disclosed in, for example, U.S. Pat. No. 6,004, 933, which discloses a class of cysteine protease inhibitors of HCV endopeptidase 2.

Additional hepatitis C virus NS3 protease inhibitors include those disclosed in, for example, Llinás-Brunet et al., *Bioorg. Med. Chem. Lett.* 1998, 8, 1713-1718; Steinkühler et al., *Biochemistry* 1998, 37, 8899-8905; U.S. Pat. Nos. 5,538, 865; 5,990,276; 6,143,715; 6,265,380; 6,323,180; 6,329,379; 6,410,531; 6,420,380; 6,534,523; 6,608,027; 6,642,204; 6,653,295; 6,727,366; 6,838,475; 6,846,802; 6,867,185; 6,869,964; 6,872,805; 6,878,722; 6,908,901; 6,911,428;

6,995,174; 7,012,066; 7,041,698; 7,091,184; 7,169,760; 7,176,208; 7,208,600; and 7,491,794; U.S. Pat. Appl. Publ. Nos. 2002/0016294, 2002/0016442; 2002/0032175; 2002/0037998; 2004/0229777; 2005/0090450; 2005/0153877; 2005/176648; 2006/0046956; 2007/0021330; 2007/0021351; 2007/0049536; 2007/0054842; 2007/0060510; 2007/0060565; 2007/0072809; 2007/0078081; 2007/0078122; 2007/0093414; 2007/0093430; 2007/0099825; 2007/0099929; 2007/0105781, 2008/0152622, 2009/0035271, 2009/0035272, 2009/0111969, 2009/0111982, 2009/0123425, 2009/0130059, 2009/148407, 2009/0156800, 2009/0169510, 2009/0175822, and 2009/0180981; and International Pat. Appl. Publ. Nos. WO 98/17679; WO 98/22496; WO 99/07734; WO 00/09543; WO 00/59929; WO 02/08187; WO 02/08251; WO 02/08256; WO 02/08198; WO 02/48116; WO 02/48157; WO 02/48172; WO 02/60926; WO 03/53349; WO 03/64416; WO 03/64455; WO 03/64456; WO 03/66103; WO 03/99274; WO 03/99316; WO 2004/032827; WO 2004/043339; WO 2005/037214; WO 2005/037860; WO 2006/000085; WO 2006/119061; WO 2006/122188; WO 2007/001406; WO 2007/014925; WO 2007/014926; WO 2007/015824, WO 2007/056120, WO 2008/019289, WO 2008/021960, WO 2008/022006, WO 2009/053828, WO 2009/058856, WO 2009/073713, WO 2009/073780, WO 2009/080542, WO 2009/082701, WO 2009/082697, WO 2009/085978, and WO 2008/086161; the disclosure of each of which is incorporated herein by reference in its entirety.

Other protease inhibitors include thiazolidine derivatives, such as RD-1-6250, RD4 6205, and RD4 6193, which show relevant inhibition in a reverse-phase HPLC assay with an NS3/4A fusion protein and NS5A/5B substrate (Sudo et al., *Antiviral Research* 1996, 32, 9-18); and thiazolidines and benzanilides identified in Kakiuchi et al., *FEBS Lett.* 1998, 421, 217-220; and Takeshita et al., *Analytical Biochemistry* 1997, 247, 242-246.

Suitable helicase inhibitors include, but are not limited to, those disclosed in U.S. Pat. No. 5,633,358; and International Pat. Appl. Publ. No. WO 97/36554.

Suitable nucleotide polymerase inhibitors include, but are not limited to, gliotoxin (Ferrari et al., *Journal of Virology* 1999, 73, 1649-1654) and cerulenin (Lohmann et al., *Virology* 1998, 249, 108-118).

Suitable interfering RNA (iRNA) based antivirals include, but are not limited to, short interfering RNA (siRNA) based antivirals, such as Sirna-034 and those described in International Pat. Appl. Publ. Nos. WO/03/070750 and WO 2005/012525, and U.S. Pat. Appl. Publ. No. 2004/0209831.

Suitable antisense phosphorothioate oligodeoxynucleotides (S-ODN) complementary to sequence stretches in the 5' non-coding region (NCR) of HCV virus include, but are not limited to those described in Alt et al., *Hepatology* 1995, 22, 707-717, and nucleotides 326-348 comprising the 3' end of the NCR and nucleotides 371-388 located in the core coding region of HCV RNA (Alt et al., *Archives of Virology* 1997, 142, 589-599; and Galderisi et al., *Journal of Cellular Physiology* 1999, 181, 251-257);

Suitable inhibitors of IRES-dependent translation include, but are not limited to, those described in Japanese Pat. Appl. Publ. Nos.: JP 08268890 and JP 10101591.

Suitable ribozymes include those disclosed in, for example, U.S. Pat. Nos. 6,043,077; 5,869,253; and 5,610,054.

Suitable nucleoside analogs include, but are not limited to, the compounds described in U.S. Pat. Nos. 6,660,721; 6,777,395; 6,784,166; 6,846,810; 6,927,291; 7,094,770; 7,105,499; 7,125,855; and 7,202,224; U.S. Pat. Appl. Publ. Nos. 2004/0121980; 2005/0009737; 2005/0038240; and 2006/0040890; and International Pat. Appl. Publ. Nos: WO 99/43691; WO 01/32153; WO 01/60315; WO 01/79246; WO 01/90121, WO 01/92282, WO 02/18404; WO 02/32920, WO 02/48165. WO 02/057425; WO 02/057287; WO 2004/002422, WO 2004/002999, and WO 2004/003000.

Other miscellaneous compounds that can be used as second agents include, for example, 1-amino-alkylcyclohexanes (U.S. Pat. No. 6,034,134), alkyl lipids (U.S. Pat. No. 5,922,757), vitamin E and other antioxidants (U.S. Pat. No. 5,922,757), squalene, amantadine, bile acids (U.S. Pat. No. 5,846,964), N-(phosphonacetyl)-L-aspartic acid (U.S. Pat. No. 5,830,905), benzenedicarboxamides (U.S. Pat. No. 5,633,388), polyadenylic acid derivatives (U.S. Pat. No. 5,496,546), 2',3'-dideoxyinosine (U.S. Pat. No. 5,026,687), benzimidazoles (U.S. Pat. No. 5,891,874), plant extracts (U.S. Pat. Nos. 5,725,859; 5,837,257; and 6,056,961), and piperidines (U.S. Pat. No. 5,830,905).

In certain embodiments, one or more compounds provided herein are administered in combination or alternation with an anti-hepatitis C virus interferon, including, but not limited to, INTRON® A (interferon alfa-2b), PEGASYS® (Peginterferon alfa-2a) ROFERON® A (recombinant interferon alfa-2a), INFERGEN® (interferon alfacon-1), and PEG-INTRON® (pegylated interferon alfa-2b). In one embodiment, the anti-hepatitis C virus interferon is INFERGEN®, IL-29 (PEG-Interferon lambda), R7025 (Mazy-alpha), BELEROFON®, oral interferon alpha, BLX-883 (LOCTERON®), omega interferon, MULTIFERON®, medusa interferon, ALBUFERON®, or REBIF®.

In certain embodiments, one or more compounds provided herein are administered in combination or alternation with an anti-hepatitis C virus polymerase inhibitor, such as ribavirin, viramidine, NM 283 (valopicitabine), PSI-6130, R1626, HCV-796, and R7128.

In certain embodiments, the one or more compounds provided herein are administered in combination with ribavirin and an anti-hepatitis C virus interferon, such as INTRON® A (interferon alfa-2b), PEGASYS® (Peginterferon alfa-2a), ROFERON® A (recombinant interferon alfa-2a), INFERGEN® (interferon alfacon-1), and PEG-INTRON® (pegylated interferon alfa-2b), In certain embodiments, one or more compounds provided herein are administered in combination or alternation with an anti-hepatitis C virus protease inhibitor, such as ITMN-191, SCH 503034, VX950 (telaprevir), and Medivir HCV protease inhibitor.

In certain embodiments, one or more compounds provided herein are administered in combination or alternation with an anti-hepatitis C virus vaccine, including, but not limited to, TG4040, PEVIPRO™, CGI-5005, HCV/MF59, GV1001, IC41, and INNO0101 (E1).

In certain embodiments, one or more compounds provided herein are administered in combination or alternation with an anti-hepatitis C virus monoclonal antibody, such as AB68 and XTL-6865 (formerly HepX-C); or an anti-hepatitis C virus polyclonal antibody, such as cicavir.

In certain embodiments, one or more compounds provided herein are administered in combination or alternation with an anti-hepatitis C virus immunomodulator, such as ZADAXIN® (thymalfasin), NOV-205, and oglufanide.

In certain embodiments, one or more compounds provided herein are administered in combination or alternation with NEXAVAR®, doxorubicin, PI-88, amantadine, JBK-122, VGX-410C, MX-3253 (celgosivir), SUVUS® (BIVN-401 or virostat), PF-03491390 (formerly IDN-6556), G126270, UT-231B, DEBIO-025, EMZ702, ACH-0137171, MitoQ, ANA975, AVI-4065, bavituximab (tarvacin), ALINIA® (nitrazoxanide), and PYN17.

The compounds provided herein can also be administered in combination with other classes of compounds, including, but not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer, a racemic mixture, a mixture of diastereomers, or an isotopic variant thereof; or a pharmaceutically acceptable salt, solvate, or prodrug thereof.

In certain embodiments, the kit includes a container comprising a dosage form of the compound provided herein, including a single enantiomer, a racemic mixture, a mixture of diastereomers, or an isotopic variant thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); L, (liter); mM (millimolar); μM (micromolar); Hz (Hertz); MHz (megahertz); mmol (millimoles); eq. (equivalent); hr or hrs (hours); min (minutes); MS (mass spectrometry); NMR (nuclear magnetic resonance); ESI (electrospray ionization); ACN, (acetonitrile); CDCl$_3$ (deuterated chloroform); DCM (dichloromethane); DMF (N,N-dimethylformamide); DMSO (dimethylsulfoxide); DMSO-d$_6$ (deuterated dimethylsulfoxide); EtOAc (ethyl acetate); EtOH (ethanol); MeOH (methanol); THF (tetrahydrofuran); DIPEA (N,N-diisopropylethylamine); TEA (triethylamine); DSU (1,8-diazabicyclo[5.4.0]undec-7-ene); CDI (carbonyldiimidazole); EDCI or EDC (N'-ethyl-N-(3-dimethylaminopropyl)-carbodiimide); P$_2$O$_5$, (phosphorus pentoxide); TBTU (O-(benzotriazol-1-yl)-N,N,N',N'-tetramethyluronium tetrafluoroborate); Me (methyl); Et (ethyl); iPr, (isopropyl); tBu (tert-butyl); Boc (tert-butoxylcarbony); Bn (benzyl); TsOH (tosylic acid); TsO (tosylate); DEAD (diethylazodicarboxylate), DIAD (diisopropylazodicarboxylate); PPh$_3$ (triphenylphosphine); AcCl (acetyl chloride); TFA (trifluoroacetic acid); Cbz (benzylcarbomate); Fmoc (9-fluorenylmethyl carbomate); tBuOK (potassium tert-butoxide) and Zhan IB catalyst ((1,3-dimesityl-imidazolidin-2-yl)(5-(N,N-dimethylsulfamoyl)-2-isopropoxybenzylidene)-ruthenium(V) chloride).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies herein are intended to exemplify the applicable chemistry through the use of specific examples and are not indicative of the scope of the disclosure.

Example 1

HCV Protease Assay

General Procedure:

Measurement of the inhibitory effect of compounds on HCV protease activity was performed with the SensoLyte™ 620 HCV Protease Assay kit from AnaSpec, Inc. (San Jose, Calif.) under conditions described by the supplier using 1.2 nM HCV NS3-NS4A protease, which was obtained according to Taremi et al. (*Protein Science*, 1998, 7, 2143-2149). The compounds were tested at a variety of concentrations in assay buffer containing a final DMSO concentration of 5%. Reactions were allowed to proceed for 60 min at room temperature and fluorescence measurements were recorded with a Tecan Infinity Spectrofluorimeter. The IC$_{50}$ values were determined from the percent inhibition versus concentration data using a sigmoidal non-linear regression analysis based on four parameters with Tecan Magellan software.

HCV Replicon Assay

General Procedure:

Huh-7 cells containing HCV Con1 subgenomic replicon (GS4.1 cells) were grown in Dulbecco's Modified Eagle Medium (DMEM) supplemented with 10% fetal bovine serum (FBS), 2 mM L-glutamine, 110 mg/L sodium pyruvate, 1× non-essential amino acids, 100 U/mL penicillin-streptomycin, and 0.5 mg/mL G418 (Invitrogen). For dose-response testing, the cells were seeded in 96-well plates at 7.5×10$^3$ cells/well in a volume of 50 μL, and incubated at 37° C./5% CO$_2$. Three hours after plating, 50 μL of ten 2-fold serial dilutions of compounds (highest concentration, 75 μM) were added, and cell cultures were incubated at 37° C./5% CO$_2$ in the presence of 0.5% DMSO. Alternatively, compounds were tested at a single concentration of 15 μM. In all cases, Huh-7 cells lacking the HCV replicon served as negative control. The cells were incubated in the presence of compounds for 72 hr after which they were monitored for expression of the NS4A protein by enzyme-linked immunosorbent assay (ELISA). For this, the plates were then fixed for 1 min with acetone/methanol (1:1, v/v), washed twice with phosphate-buffered saline (PBS), 0.1% Tween 20, blocked for 1 hr at room temperature with TNE buffer containing 10% FBS and then incubated for 2 hr at 37° C. with the anti-NS4A mouse monoclonal antibody A-236 (ViroGen) diluted in the same buffer. After washing three times with PBS, 0.1% Tween 20, the cells were incubated 1 hr at 37° C. with anti-mouse immunoglobulin G-peroxidase conjugate in TNE, 10% FBS. After washing as described above, the reaction was developed with O-phenylenediamine (Zymed). The reaction was stopped after 30 min with 2 N H$_2$SO$_4$, and absorbance was read at 492 nm using Sunrise Tecan spectrophotometer. EC$_{50}$ values were determined from the % inhibition versus concentration data using a sigmoidal non-linear regression analysis based on four parameters with Tecan Magellan software. When screening at a single concentration, the results were expressed as % inhibition at 15 μM.

For cytotoxicity evaluation, GS4.1 cells were treated with compounds as described above and cellular viability was monitored using the Cell Titer 96 AQ$_{ueous}$ One Solution Cell Proliferation Assay (Promega). CC$_{50}$ values were determined from the % cytotoxicity versus concentration data with Tecan Magellan software as described above.

The biological results are summarized in Table 1, wherein A represents a value smaller than 1 μM, and B represents a value between 1 µM to 10 µM, C represents a value between 10 µM to 75 µM and D represents a value greater than 75 µM.

TABLE 1

| Compound | IC$_{50}$ (µM) | EC$_{50}$ (µM) | CC$_{50}$ (µM) |
|---|---|---|---|
| 51 | A | A | C |

Example 2

HCV Protease Assay

General Procedure:

Measurement of the inhibitory effect of compounds on HCV protease activity was performed using the HiLyte Fluor™ TR/QXL™ 610 FRET peptide from AnaSpec, Inc. (San Jose, Calif.) under conditions developed in-house using 2-3 nM HCV NS3-NS4A protease, which was produced according to the method of Taremi et al. (*Protein Science*, 1998, 7, 2143-2149). The compounds were tested at a variety of concentrations in assay buffer containing a final DMSO concentration of 5%. Reactions were allowed to proceed for 60 min at 30° C. and fluorescence measurements were recorded with a PerkinElmer Victor³ V 1420 Multilabel Counter. The IC$_{50}$ values were determined from the percent inhibition versus concentration data using a sigmoidal non-linear regression analysis based on four parameters with XLfit 4.1 software.

Luciferase Replicon Assay

General Procedure:

The HCV luciferase replicon assay measures the ability of a test compound to inhibit HCV replication in cell culture after 3 days of treatment in a human hepatoma cell line (Huh-7) bearing a HCV replicon containing a luciferase-neomycin phosphotransferase fusion gene. The inhibition of HCV replication was measured by quantification of luciferase protein expression. Briefly, Huh-7 cells containing either the HCV genotype 1a H77 strain or genotype 1b Con1 strain subgenomic luciferase replicon (H1a-luc or Z1uc, respectively) were grown in DMEM containing glucose, L-glutamine and sodium pyruvate, 10% fetal bovine serum (FBS), 100 IU/mL penicillin, 100 µg/mL streptomycin, 2 mM GlutaMAX, non-essential amino acids and 0.25 (H1a-luc) or 0.5 (Z1uc) mg/mL G418. GlutaMAX was obtained from Invitrogen. Corp.; all other media reagents were obtained from Mediatech, Inc. For dose-response testing, the cells were seeded in 96-well plates at 1×10⁴ (H1a-luc) or 7.5×10³ (Z1uc) cells/well in a volume of 50 µL, and incubated at 37° C./5% CO$_2$. Three hours after plating, 50 µL of ten 5-fold serial dilutions of compound were added, and cell cultures were incubated at 37° C./5% CO$_2$ for 72 hours. In all cases, Huh-7 cells lacking the HCV replicon served as negative control. To assess luciferase expression, the media/compound was removed from the plates and ONE-glo Luciferase assay reagent (Promega) was added to each well. The assay plates were shaken for 3 minutes at room temperature and luciferase activity for each well was measured with a 1 sec read time on the Victor³V multilabel counter using a 700 nm cut-off filter (Perkin Elmer). EC$_{50}$ values were calculated from dose response curves from the resulting best-fit equations determined by Microsoft Excel and XLfit 4.1 software.

For cytotoxicity evaluation, H1a-luc or Z1uc cells were treated with compounds as described above and cellular viability was monitored using the Cell Titer 96 AQueous One Solution Cell Proliferation Assay (Promega). Plates were then read at 490 nm in a Victor³V 1420 multilabel counter (Perkin Elmer) and CC$_{50}$ concentrations were determined using Microsoft Excel and XLfit 4.1 software.

The table below presents data for compounds 51 and 52 A represents a value smaller than 1 µM, and B represents a value between 1 µM to 10 µM, C represents a value between 10 µM to 75 µM and D represents a value greater than 75 µM.

TABLE 2

| Cmpd | IC$_{50}$ Against HS3/4A | | | | | EC$_{50}$ Against Replicon | | CC$_{50}$ | EC$_{50}$ JFH-1 Virus |
|---|---|---|---|---|---|---|---|---|---|
| | 1a | 1b | 2a | 3a | 4a | 1a | 1b | | |
| 51 | A | A | A | A | A | A | A | C | A |
| 52 | | | | | | A | A | D | A |

Example 3

Genotype 2a Infectious Virus Assay

General Procedure:

The genotype 2a infectious virus assay measures the ability of a test compound to inhibit HCV replication in cell culture after 5 days of treatment at the time of HCV genotype 2a virus infection of a permissive human hepatoma cell line (HPC cells). The inhibition of HCV replication was measured by quantification of HCV core protein expression by an enzyme-linked immunosorbent assay (ELISA). Briefly, HPC cells were grown in DMEM containing glucose, L-glutamine and sodium pyruvate, 10% FBS, 100 IU/mL penicillin, 100 µg/mL streptomycin, 2 mM GlutaMAX, and non-essential amino acids. GlutaMAX was obtained from Invitrogen, Corp.; all other media reagents were obtained from Mediatech, Inc. For dose-response testing, ninety-six-well plates were seeded with HPC cells at a density of 2.5×10³ cells/well in a volume of 50 µL, and incubated at 37° C./5% CO$_2$. Three hours after plating, 50 µL of ten 5-fold serial dilutions of compound and 100 µL of genotype 2a virus were added, and cell cultures were incubated at 37° C./5% CO$_2$. In all cases, mock infected HPC cells served as negative control. At 16 hours post treatment and infection, the virus inoculum was removed by aspiration. The cultures were treated at the same final concentrations of drug diluted in media and incubated for 4 additional days at 37° C./5% CO$_2$. Subsequently, the core ELISA was performed as follows. The plates were fixed for 90 seconds with acetone/methanol (1:1, v/v), washed three times with KPL wash solution (KPL, Inc.), blocked for 1 hr at room temperature with THE buffer containing 10% FBS and then incubated for 2 hr at 37° C. with the anti-HCV core mouse monoclonal antibody (Thermo Scientific) diluted in the same buffer. After washing three times with KPL wash solution, the cells were incubated for 1 hr at 37° C. with an anti-mouse immunoglobulin G-peroxidase conjugate in THE/10% FBS. After washing as described above, the reaction was developed with O-phenylenediamine (Invitrogen). The reaction was stopped after 30 min with 2 N H$_2$SO$_4$, and absorbance was read at 490 nm in a Victor³V 1420 multilabel counter (Perkin Elmer) and EC$_{50}$ concentrations were determined using Microsoft Excel and XLfit 4.1 software.

For cytotoxicity evaluation, HPC cells were treated with compounds as described above in the absence of the genotype 2a virus and cellular viability was monitored using the Cell Titer 96 AQueous One Solution Cell Proliferation Assay (Promega). Plates were then read at 490 nm in a Victor³V 1420 multilabel counter (Perkin Elmer) and $CC_{50}$ concentrations were determined using Microsoft Excel and XLfit 4.1 software.

Example 4

In Vitro CYP450 Inhibition Screen for Compound 51 and Compound 52

CYP1A2 (BD Bioscience Cat #459500), CYP2B6 (BD Bioscience cat #459220), and CYP3A4 (BD Bioscience Cat #459100) inhibition fluorogenic assays were performed according to the manufacturer's protocol. Test articles were prepared as 10 mM stock solutions in DMSO.

CYP2C8, 2C9, 2C19 and 2D6 (BD Bioscience) inhibition luminogenic assay was performed as per the protocol provided by Promega (P450-Glo™ Assay Technical Bulletin #TB325, P450-Glo™ Screening Systems Technical Bulletin #TB340). Test articles were prepared as 10 mM stock solutions in DMSO.

Data represent the average of two independent experiments. A represents inhibition of 5 to 10%. B represents inhibition of >10% to 20%. C represents inhibition of >20% to 30%. D represents inhibition of >30% to 40%. I represents an $IC_{50}$ of 5 to 9 µM. II represents an $IC_{50}$ of >9 to 15 µM. III represents an $IC_{50}$ of >15 to 20 µM. IV represents an $IC_{50}$ of >20 to 25 µM.

TABLE 3

| CYP450 | Probe Substrate | $IC_{50}$ (µM) or % Inhibition at 20 µM | |
|---|---|---|---|
| | | Compound 51 | Compound 52 |
| 1A2 | 3-Cyano-7-Ethoxy-coumarin | No Inhibition | No Inhibition |
| 2B6 | 7-Ethoxy-4-trifluoro-methylcoumarin | No Inhibition | D |
| 2C8 | Luciferin-ME | B | No Inhibition |
| 2C9 | Luciferin-H | C | C |
| 2C19 | Luciferin-H EGE | II | II |
| 2D6 | Luciferin-ME EGE | C | A |
| 3A4 | 7-Benzyloxy-trifluoro-methylcoumarin | IV | III |

Example 5

Luciferase Replicon Transient Transfection Assay

General Procedure:

The luciferase replicon transient transfection assay measures the ability of a test compound to inhibit the replication of a transiently-transfected HCV luciferase-bearing wild-type or mutant replicon in cured human hepatoma cells (cured GS4.1). The mutant replicons bear a specific single-site mutation in NS3 that is known to confer resistance to protease inhibitors currently in development. The inhibition of HCV replication was measured by quantification of luciferase protein expression. This assay has been validated using a panel of replicons bearing known protease inhibitor resistance mutations and their respective reference compounds. Briefly, sub-confluent cured GS4.1 cells in OptiBuffer (ThermoElectron Corp.) were electroporated with 40 µg of wild-type or mutant luciferase-bearing HCV replicon RNA. The cells were then seeded in 96-well opaque white plates at $2.4 \times 10^4$ cells/well in 150 µL/well and incubated for 4 hours at 37° C./5% $CO_2$. Ten 1:5 dilutions of each compound were made in Huh-7 media (DMEM containing glucose, L-glutamine and sodium pyruvate, 10% fetal bovine serum, 100 IU/mL penicillin, 100 µg/mL streptomycin, 2 mM GlutaMAX, and 1×MEM non-essential amino acids [Mediatech, Inc. and Invitrogen Corp.]) at concentrations that were 4× higher than the final concentrations to be tested and 50 µL/well was added to the transfected cells. Untreated, mock-transfected cells served as a negative control of luciferase expression. The plates were incubated at 37° C./5% $CO_2$ for 4 days whereupon the media was removed and 50 µL of ONE-glo luciferase substrate (Promega) was added to each well. The plates were agitated on a rotating platform at room temperature for 3 minutes and read in a Victor³V microplate reader (Perkin-Elmer) using a 700 nm cut-off filter with a 1 second read time. $EC_{50}$ values were calculated from dose response curves from the resulting best-fit equations determined by Microsoft Excel and XLfit 4.1 software.

The table below presents data for compound 51. A represents an EC50 (nM) of 0.1 to 0.35. B represents an EC50 (nM) of >0.35 to 1.1. C represents an EC50 (nM) of 1.1> to 5. D represents an EC50 (nM) of >5 to 15. E represents an EC50 (nM) of >15 to 25. F represents an EC50 (nM) of >25 to 40. G represents an EC50 (nM) of >40 to 2000. H represents an EC50 (nM) of >2000 to 2750.

TABLE 4

| Replicon | EC50(nm) | Fold Change |
|---|---|---|
| Wild Type | B | 1 |
| R155K | D | 10-20 |
| A156S | A | 0.2 to 0.6 |
| A156T | F | 20-95 |
| D168V | H | 1000-3000 |

Example 6

Generation of Recombinant JFH-1 Virus Stocks

The recombinant JFH-1 HCV virus used in the HCV in vitro infection assay was generated by transfection of HPC cells with JFH-1 RNA produced by in vitro transcription. The JFH-1 DNA template was derived synthetically using sequence information derived from NCBI Accession #AB047639 (Wakita, et al., Nat. Med. 2005, 11:791-796). Source: DNA2.0, Menlo Park, Calif.

The cDNA for the JFH-1 HCV clone was synthesized by DNA2.0 and contains a T7 promoter to drive the transcription of the JFH-1 genomic RNA. This plasmid was amplified using the Hi-Speed Plasmid Midi kit (Qiagen) according to the manufacturer's instructions.

Thirty micrograms of purified DNA was digested overnight at 37° C. with 300 U XbaI. The digested DNA served as a template for the in vitro transcription of the JFH-1 genomic RNA using the MEGAScript T7 kit (Ambion) as instructed by the manufacturer. The JFH-1 RNA product was resuspended to 1 µg/µL in RNA storage solution (Ambion). The quality of the JFH-1 RNA was verified by agarose gel electrophoresis (1.2% E-gel) prior to electroporation.

Complete growth media for Huh-7 and HPC cells (Huh-7 media) was prepared as follows: DMEM (containing glucose, L-glutamine and sodium pyruvate), 10% FBS, 100 IU/mL penicillin, 100 µg/mL streptomycin, 2 mM GlutaMAX, 1%

MEM non-essential amino acids. Subconfluent HPC cells were treated with trypsin-EDTA, collected with Huh-7 media, and centrifuged at 1,500 rpm for 5 mM at 4° C. in an Allegra 6R centrifuge (Beckman Coulter) in a 50 mL conical tube. The cells were then rinsed twice by resuspending the cells in 50 mL of PBS and centrifuging at 1,500 rpm for 5 mM at 4° C.

JFH-1 RNA was electroporated into HPC cells using a Thermo Scientific Hybaid OptiBuffer kit (containing buffer A, solution B and compounds C and D). After washing, the HPC cells were resuspended in OptiBuffer buffer A at $1 \times 10^7$ cells/mL, and 400 µL ($4 \times 10^6$ cells) was transferred to a 1.5 mL RNase-free microfuge tube and gently centrifuged at 2,000 rpm in a Microfuge 18 (Beckman Coulter) centrifuge at room temperature for 5 minutes. During this centrifugation step, the electroporation medium was prepared by mixing 2.5 mL of OptiBuffer solution B with 1 vial of OptiBuffer compound C (5.5 mg of ATP), 1 vial of OptiBuffer compound D (7.7 mg of glutathione) and 2.5 mL of autoclaved water. After aspirating the supernatant, the cell pellet was resuspended in 400 µL of electroporation medium. JFH-1 RNA (8 µg) was added to the resuspended cells, whereupon they were transferred to a 0.4 cm cuvette and electroporated in a Bio-Rad GenePulser XCell electroporation module with a single pulse at 960 µf, 270 V and maximum resistance. A mock transfection, without RNA, was electroporated as a negative control. Growth media (600 µL) was immediately added to the cuvette. Cells were then transferred into a 15 mL conical tube containing 3.4 mL of Huh-7 media. Approximately $1.2 \times 10^5$ cells were seeded into each well of a Corning Costar 6-well plate and incubated at 37° C. with 5% $CO_2$.

When confluent, the transfected HPC cells were trypsinized and split 1:5 into new 6-well plates. At day 5 and 14 post transfection, conditioned media was collected from the cultures, cell debris was removed by centrifugation at 2,000 rpm for 10 min in a table-top centrifuge (Beckman Coulter Allegra 6R with GH3.8 rotor) and media was filtered through a 0.2 µm syringe-top filter. The transfected cells were also fixed for immunohistochemistry and lysed for immunoblotting analysis.

The recombinant JFH-1 HCV virus was amplified in a manner described by (Zhong, et al., *Proc. Nat. Acad. Sci. USA.* 2005, 102:9294-9299). HPC cells were split to 10% confluency in 225 cm² flasks and infected with 1 mL of the transfected cell culture media (described above) at 5 hrs post seeding. At 5 days post infection (p.i.), the cultures were split 1:2 into new 225 cm² flasks. One half the initial culture media was carried over into the split cultures to facilitate virus amplification. At 10 day p.i., conditioned media was collected from the 225 cm² flasks, centrifuged at 2,000 rpm for 10 min in a table-top centrifuge and filtered through a MF75 sterilization filter (0.45 µm) bottle-top unit. Two milliliter aliquots of this virus stock were stored at −80° C. for future use.

Example 7

HCV In Vitro Infection Core ELISA Assay

The HCV in vitro infection core ELISA assay measures the ability of a test compound to inhibit replication of an infectious HCV (strain JFH-1; genotype 2a) in cell culture. Recently, an in vitro infection model identified by Wakita et al. (*Nat. Med.* 2005, 11:791-796) was found to replicate in retinoic acid-inducible gene I (RIG-I)-deficient or cluster of differentiation (CD)-81-positive Huh-7 hepatoma cell lines. We have developed this model for determining the efficacy of antiviral compounds against an infectious virus in vitro using HCV producing cells (HPC), a proprietary Huh-7-derived cell sublineage capable of propagating the JFH-1 HCV virus. The readout of the assay is quantification of HCV core protein by ELISA 5 days post infection with JFH-1 virus and treatment with a test compound.

Ninety-six-well Corning Costar plates were seeded with HPC cells at a density of $3.0 \times 10^3$ cells per well in 50 µL of Huh-7 media. Compound stock solutions were made up freshly in Huh-7 media (DMEM (containing glucose, L-glutamine and sodium pyruvate), 10% FBS, 100 IU/mL penicillin, 100 µg/mL streptomycin, 2 mM GlutaMAX, 1% MEM non-essential amino acids) as 2× stock. Seven additional 3-fold drug dilutions were prepared from the 2× stocks in Huh-7 media. At least 4 hours after HPC cells were seeded, the media in the 96-well culture plates was aspirated and 50 µL of each drug dilution and 50 µL of JFH-1 HCV was added to each well.

At 16 hrs post treatment and infection, the virus inoculum was removed by aspiration. The cultures were treated at the same final concentrations of drug diluted to 1× in Huh-7 media to a final volume of 200 µL. Cells were incubated in the presence of drug for 4 additional days at 37° C./5% $CO_2$.

Media was removed from the plates by aspiration. Cells were fixed with 250 µL, 1:1 acetone:methanol for 90 seconds, washed once in PBS and then three times with 1×KPL wash solution. The assay plates were then blocked with 150 µL/well 10% FBS-TNE (50 mM Tris-HCl (pH 7.5; Sigma), 100 mM NaCl, 1 mM EDTA with 10% FBS) for 1 hr at room temperature. Cells were washed three times with 1×KPL wash solution and incubated with 100 µL/well anti-hepatitis C core mAb (1 mg/mL stock diluted 1:500 in 10% FBS-TNE) for 2 hours at 37° C. Cells were washed three times with 1×KPL wash solution and incubated with 100 µL/well HRP-goat anti-mouse antibody (diluted 1:2,500 in 10% PBS-TNE) for 1 hr at 37° C.

OPD solution was prepared using 1 OPD tablet+12 mL citrate/phosphate buffer (16 mM citric acid, 27 mM $Na_2HPO_4$) plus 5 µL 30% $H_2O_2$ per plate. Cells were washed three times with 1×KPL wash solution and developed with 100 µL/well OPD solution for 30 minutes in the dark at room temperature. The reaction was stopped with 100 µL/well of 2N $H_2SO_4$, and absorbance measured at $A_{490}$ nm in a Victor³ V 1420 multilabel counter (Perkin Elmer). The $EC_{50}$ values for each compound were calculated from dose response curves from the resulting best-fit equations determined by Microsoft Excel and XLfit 4.1 software. The negative control for inhibition of virus replication was untreated HPC cells infected with the JFH-1 HCV virus strain. The negative ELISA control was untreated, uninfected HPC cells. The positive ELISA control was untreated HPC cells infected the JFH-1 HCV virus strain.

Example 8

MTS Cytotoxicity Assay

The cytotoxicity assay measures the viability of cells after treatment with a test compound for 5 days. The assay readout is the bioreduction of the yellow MTS tetrazolium compound to a purple formazan product. This conversion is mediated by NADPH or NADH and is directly proportional to the number of live cells in a culture.

Ninety-six-well Corning Costar plates were seeded with HPC cells at a density of $3.0 \times 10^3$ cells per well in 50 µL of Huh-7 media. Compound stock solutions were made up freshly in Huh-7 media as 2× stocks. Seven additional 3-fold drug dilutions were prepared from the 2× stocks in Huh-7 media for a total of 8 dilutions.

At least 4 hours after HPC cells were seeded, 50 μL of each drug dilution was added to the cultures. At 16 hrs post treatment, the existing media was removed by aspiration. Cultures were treated at the same final concentrations of drug diluted to 1× in Huh-7 medium to a final volume of 100 μL. Cells were incubated for 4 additional days at 37° C./5% $CO_2$ in the presence of drug.

After 5 days of treatment, the CellTiter 96® Aqueous One Solution cell proliferation assay was performed by adding 20 μL of MTS solution to each well. The plates were then incubated at 37° C./5% $CO_2$ for 3 hours. Plates were read at $A_{490}$ nm in a Victor³ V 1420 multilabel counter (Perkin Elmer) and $CC_{50}$ concentrations were determined using Microsoft Excel and XLfit 4.1 software. The positive control for cell death: culture wells containing only Huh-7 medium. The negative control for cell death: culture wells containing untreated, uninfected HPC cells.

Example 9

HCV In Vitro Infection Western Blotting Assay

This assay measures the ability of a test compound to inhibit replication of the JFH-1 HCV strain in cell culture. The readout of the assay is the quantification of HCV NS3 or core protein by western blotting 5 days post infection with JFH-1 virus and drug treatment. Negative controls: untreated, uninfected HPC cells. Positive controls: untreated HPC cells infected the JFH-1 HCV virus strain.

Twenty-four-well Corning Costar plates were seeded with HPC cells at a density of 1.5×10⁴ cells per well in 0.8 mL of Huh-7 media (DMEM (containing glucose, L-glutamine and sodium pyruvate), 10% FBS, 100 IU/mL penicillin, 100 μg/mL streptomycin, 2 mM GlutaMAX, 1% MEM non-essential amino acids). Compound stock solutions were made up freshly in Huh-7 media as 10× stocks. Four additional 5-fold drug dilutions were prepared from the 10× stocks in Huh-7 media for a total of 5 dilutions.

At least 3 hrs after HPC cells were seeded, 100 μL of each drug dilution and 100 μL of JFH-1 HCV was added to each well. At 16 hrs post treatment and infection, the virus inoculum was removed by aspiration. The cultures were treated at the same final concentrations of drug diluted to 1× in Huh-7 media to a final volume of 1 mL. Cells were incubated in the presence of drug for 4 additional days at 37° C./5% $CO_2$.

Media was removed from the plates by aspiration and the cells washed with 1 mL of PBS. After removing the PBS, 100 μL/well of SDS sample buffer (50 mM Tris-HCl, pH7.5, 2% ultrapure SDS, 10% glycerol, 0.01% bromophenol blue, 0.1 M DTT) was added. The samples were collected into RNase-free microfuge tubes, incubated at 95° C. for 5-10 minutes and centrifuged at maximum speed for 2 min in an Eppendorf 5415D centrifuge.

To prepare the Western Blot, fifteen microliters of each sample was loaded into each lane of a 4-20% Tris-glycine polyacrylamide gel in an XCell II Blot Module (Invitrogen); 6 μL of the SeeBluePlus2 prestained protein standard was also loaded into one lane. Each gel was run at 125 V for 1.5 hrs in Novex SDS (1× Tris/glycine/SDS) running buffer (Invitrogen). Each gel was transferred onto an iBlot nitrocellulose membrane using the iBlot apparatus (Invitrogen) according to the manufacturer's protocol. The membrane was rinsed in PBST (Sigma) and then blocked with 6 mL of blocking buffer (5% (w/v) nonfat milk in PBST solution) at room temperature for 1 hour with rocking. Each blot was incubated in 6 mL of blocking buffer containing HCV NS3 murine mAb (1:500; ViroGen Corp.) and anti-GAPDH murine IgG Ab (1:1,000,000; Calbiotech) or anti-core mAb (1:500; Affinity BioReagents) overnight at 4° C. with rocking. After 3 ten minute washes in PBST at room temperature with rocking each blot was incubated with 6 mL of blocking buffer (5% (w/v) nonfat milk in PBST solution) containing HRP conjugated donkey anti-mouse Ab (1:5,000) for 1 hour at room temperature with rocking. Each blot was washed as described above and then exposed to 5 mL of substrate from the Super-Signal West Dura substrate kit (Pierce) according to the manufacturer's protocol. The blots were then exposed using the Florochem 5,500 imager (Alpha Innotech).

Virus replication was quantified by determining the band densities of NS3 and core proteins using ImageQuant 5.2 software. Background (the density determined within the NS3 or core region with mock-transfected cells) was subtracted from NS3, core, and GAPDH band densities. Each corrected NS3 or core value was then normalized to the corresponding corrected GAPDH value for the same sample. The $EC_{50}$ value, which is the concentration of a test compound that reduced NS3 or core protein production by 50%, was determined for each compound using Microsoft Excel and XLfit 4.1 software. Each $EC_{50}$ value determination was performed in duplicate.

Example 10

Preparation of N-methyl-ω-alkenyl-1-amine tosylate salts 31

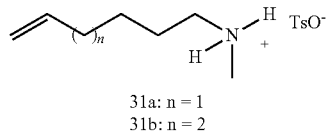

31a: n = 1
31b: n = 2
31c: n = 3

The syntheses of N-methyl-ω-alkenyl-1-amine tosylate salts 31 are shown in Scheme 2.

Step A:

Preparation of 2,2,2-trifluoro-N-(hex-5-enyl)-N-methylacetamide 31A. Sodium hydride (60% dispersion in mineral oil, 31.5 g, 1.28 eq.) was slowly added under nitrogen atmosphere to a solution of N-methyl-2,2,2-trifluoroacetamide (100 g, 1.28 eq.) in DMF (500 mL) at 0° C. The reaction mixture was stirred for 90 min at 0° C., and then 6-bromo-1-hexene (100 g, 1 eq.) was added dropwise over 45 min. The reaction mixture was allowed to warm up to room temperature, and stirred for 3 days at room temperature. The reaction mixture was then poured into water and extracted tree time with EtOAc. The combined organics layers were dried over anhydrous sodium sulphate and concentrated under reduced pressure. The residue was purified by flash chromatography on silica gel to produce compound 31A as colorless oil in 56% yield. ¹H NMR (DMSO-$d_6$, 400 MHz) δ 1.27-1.38 (m, 2H), 1.48-1.60 (m, 2H), 2.00-2.06 (m, 2H), 2.93-3.07 (2m, 3H), 3.35-3.40 (m, 2H), 4.92-5.04 (m, 2H), 5.73-5.83 (m, 1H).

Scheme 2

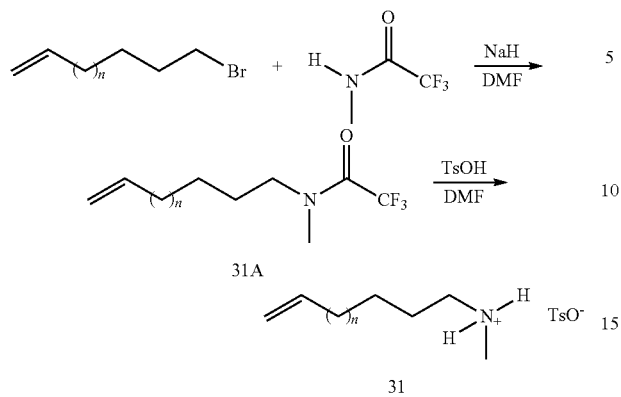

Step B:

N-Methylhex-5-en-1-amine tosylate salt 31a. At room temperature, compound 31A (71.88 g, 1 eq.) and p-toluene sulfonic acid (74.4 g, 1.2 eq.) were dissolved in MeOH (640 mL). The reaction mixture was refluxed for 7 days. The solvent was then removed under vacuum, and the residue was recrystallized in acetone. The product was isolated by filtration, dried over $P_2O_5$ to give compound 31a as a white powder in 76% yield. $^1$H NMR (CDCl$_3$, 400 MHz): δ 1.38 (q, J=7.76 Hz, 2H), 1.71 (q, J=7.76 Hz, 2H), 1.99 (q, J=6.98 Hz, 2H), 2.38 (s, 3H), 2.70 (t, J=5.17 Hz, 3H), 2.87-2.93 (m, 2H), 4.92-4.99 (m, 2H), 5.67-5.73 (m, 1H), 7.20 (d, J=7.76 Hz, 2H), 7.75 (d, J=7.76 Hz, 2H), 8.62 (br s, 2H).

N-Methylhept-5-en-1-amine tosylate salt 31b was synthesized from 7-bromo-heptene, according to the procedure as described for compound 31a, as a white solid in quantitative yield. $^1$H NMR (CDCl$_3$, 400 MHz) δ 1.38 (q, J=7.76 Hz, 2H), 1.71 (q, J=7.76 Hz, 2H), 1.80 (q, J=6.98 Hz, 2H), 1.99 (q, J=6.98 Hz, 2H), 2.38 (s, 3H), 2.70 (t, J=5.17 Hz, 3H), 2.87-2.93 (m, 2H), 4.92-4.99 (m, 2H), 5.67-5.73 (m, 1H), 7.20 (d, J=7.76 Hz, 2H), 7.75 (d, J=7.76 Hz, 2H), 8.62 (br s, 2H).

N-Methyloct-5-en-1-amine tosylate salt 31c was synthesized from 7-bromo-octene, according to the procedure as described for compound 31a, as a white powder in quantitative yield. $^1$H NMR (CDCl$_3$, 400 MHz) δ 1.38 (q, J=7.76 Hz, 2H), 1.71 (q, J=7.76 Hz, 2H), 1.80 (q, J=6.98 Hz, 2H), 1.90 (q, J=6.9 Hz, 2H), 1.99 (q, J=6.98 Hz, 2H), 2.38 (s, 3H), 2.70 (t, J=5.17 Hz, 3H), 2.87-2.93 (m, 2H), 4.92-4.99 (m, 2H), 5.67-5.73 (m, 1H), 7.20 (d, J=7.76 Hz, 2H), 7.75 (d, J=7.76 Hz, 2H), 8.62 (brs, 2H).

Example 11

Preparation of Compounds 32

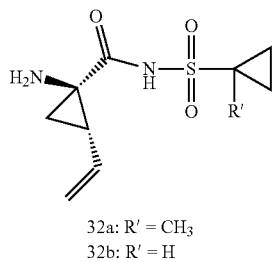

32a: R' = CH$_3$
32b: R' = H

Compounds 32 were synthesized according to Scheme 3.

Scheme 3

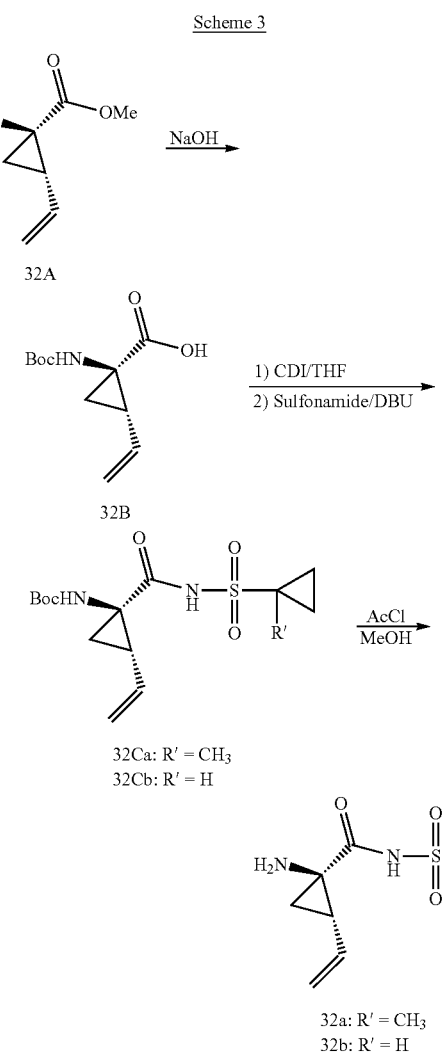

32Ca: R' = CH$_3$
32Cb: R' = H

32a: R' = CH$_3$
32b: R' = H

Step A:

Preparation of N-Boc-(1R,2S)-1-amino-2-vinylcyclopropane carboxylic acid 32B. To a solution of N-Boc-(1R,2S)-ethyl 1-amino-2-vinylcyclopropane-carboxylate tosylate salt 32A (4.32 g, 1 eq.), which was synthesized according to the procedure as described in J. Org. Chem. 2006, 71, 8864-8875, in anhydrous THF (30 mL) was added a solution of NaOH (1.02 g, 1.5 eq.) in H$_2$O. The reaction mixture was stirred at room temperature for 48 hrs. One more equivalent of NaOH was added and the mixture was heated at 50° C. for 24 hrs. Solvent was removed under reduced pressure. Aqueous layer was acidified with 1N HCl and extracted with DCM. Organics were washed with water and brine, dried over Na$_2$SO$_4$, filtered, and concentrated under reduced pressure to yield compound 32B as a white powder in 98% yield. $^1$H NMR (CDCl$_3$, 400 MHz) δ (ppm) 1.36 (s, 9H), 1.47 (brs, 1H), 1.75 (brs, 1H), 2.09-2.15 (q, J=8.82 Hz, 1H), 5.07 (d, J=10.08 Hz, 1H), 5.24 (d, J=16.8 Hz, 1H), 5.65-5.72 (m, 1H).

Step B:

Preparation of (1-methyl-cyclopropanesulfonaminocarbonyl-2-vinyl-cyclopropyl)-carbamic acid tert-butyl ester 32Ca. Carbonyldiimidazole (1.75 g, 1.3 eq.) was added to a solution of compound 32B (1.89 g, 1 eq.) in anhydrous THF (20 mL) at room temperature. The reaction mixture was refluxed for 2 hrs and allowed to cooled down to room temperature. Methyl cyclopropyl sulfonamide (1.68 g, 1.5 eq.) and DBU (1.68 g, 1.5 eq.) were then added at 0° C. and the mixture was stirred at room temperature for 16 hrs. Solvent was removed in vacuo and the residue was dissolved in EtOAc, washed sequentially with 1N HCl and brine, dried over $Na_2SO_4$, filtered, and concentrated under reduced pressure to yield compound 32Ca as a white powder in 65% yield. $^1$H NMR ($CDCl_3$, 400 MHz) δ (ppm) 1.01-1.05 (m. 2H), 1.25-1.28 (m, 2H), 1.35-1.40 (m, 2H), 1.45 (s, 9H), 1.50 (s, 3H), 1.77-1.80 (m, 1H), 4.90 (d, J=10.60 Hz, 1H). 5.04 (d, J=17.32 Hz, 1H), 5.42 (m, 1H).

1-Cyclopropanesulfonaminocarbonyl-2-vinyl-cyclopropyl)-carbamic acid tert-butyl ester 32Cb was synthesized from compound 32B and cyclopropyl sulfonamide as a white solid in 97% yield, according to the procedure as described for compound 32Ca. $^1$H NMR ($CDCl_3$, 400 MHz) δ (ppm) 1.01-1.11 (m, 2H), 1.25-1.32 (m, 2H), 1.39-1.43 (m, 2H), 1.48 (s, 9H), 1.89-1.93 (m, 1H), 5.16 (d, J=10.72 Hz, 1H), 5.30 (d, J=17.38 Hz, 1H), 5.60 (m, 1H).

Step C:

Preparation of 1-methyl-cyclorpopanesulfonicacid (1-amino-2-vinylcyclopropanecarbonyl)-amide 32a. To a stirred solution of compound 32Ca (1.87 g, 1 eq.) in MeOH (5 mL) at room temperature was added acetyl chloride (0.35 mL, 3 eq.). The reaction mixture was then heated at 50° C. for 3 hrs, and concentrated under reduced pressure to yield compound 32a as a white powder in 90% yield. $^1$H NMR (DMSO, 400 MHz) δ (ppm) 1.04-1.08 (m, 2H), 1.20-1.23 (m, 2H), 1.41-1.44 (m, 2H), 1.45 (s, 3H), 2.02 (brs, 2H), 2.78 (m, 1H), 5.25 (d, J=10.60 Hz, 1H), 5.35 (d, J=17.30 Hz, 1H), 5.52-5.56 (m, 1H), 8.10 (brs 1H).

1-Cyclorpopanesulfonicacid (1-amino-2-vinylcyclopropane-carbonyl)-amide 32b was synthesized from compound 32Cb, according to the procedure as described for compound 32a, as a white solid in 97% yield. $^1$H NMR ($CDCl_3$, 400 MHz) δ (ppm) 1.04-1.07 (m, 2H), 1.25-1.29 (m, 2H), 1.41-1.44 (m, 2H), 2.02 (brs, 2H), 2.78 (m, 1H), 3.00 (m, 1H), 5.29 (d, J=10.64 Hz, 1H), 5.40 (d, J=17.35 Hz, 1H), 5.62-5.68 (m, 1H), 8.73 (brs 1H).

Example 12

Preparation of Substituted Quinolines 203

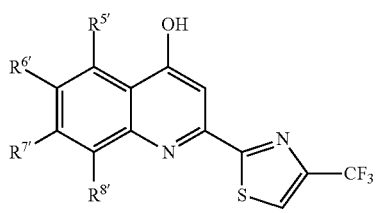

203a: $R^{5'}$ = H, $R^{6'}$ = H, $R^{7'}$ = $OCH_3$, $R^{8'}$ = H
203b: $R^{5'}$ = H, $R^{6'}$ = H, $R^{7'}$ = $OCH_3$, $R^{8'}$ = $CH_3$
203c: $R^{5'}$ = H, $R^{6'}$ = H, $R^{7'}$ = $OCH_3$, $R^{8'}$ = F
203d: $R^{5'}$ = H, $R^{6'}$ = H, $R^{7'}$ = $OCH_3$, $R^{8'}$ = Cl
203e: $R^{5'}$ = $OCH_3$, $R^{6'}$ = H, $R^{7'}$ = $OCH_3$, $R^{8'}$ = H
203f: $R^{5'}$ = H, $R^{6'}$ = $OCH_3$, $R^{7'}$ = H, $R^{8'}$ = $CH_3$
203g: $R^{5'}$ = H, $R^{6'}$ = $OCH_3$, $R^{7'}$ = Cl, $R^{8'}$ = H
203h: $R^{5'}$ = H, $R^{6'}$ = H, $R^{7'}$ = $OCH_3$, $R^{8'}$ = Br

The syntheses of substituted quinolines 203 are illustrated with compounds 203b and 203d, as shown in Scheme 4. The same procedures are also applicable to compounds 203a, 203c, and 203e to 203h. The substituents $R^{5'}$, $R^{6'}$, $R^{7'}$, and $R^{8'}$ in intermediates 201 and 202 in Scheme 4 are each as defined in compounds 203.

Scheme 4

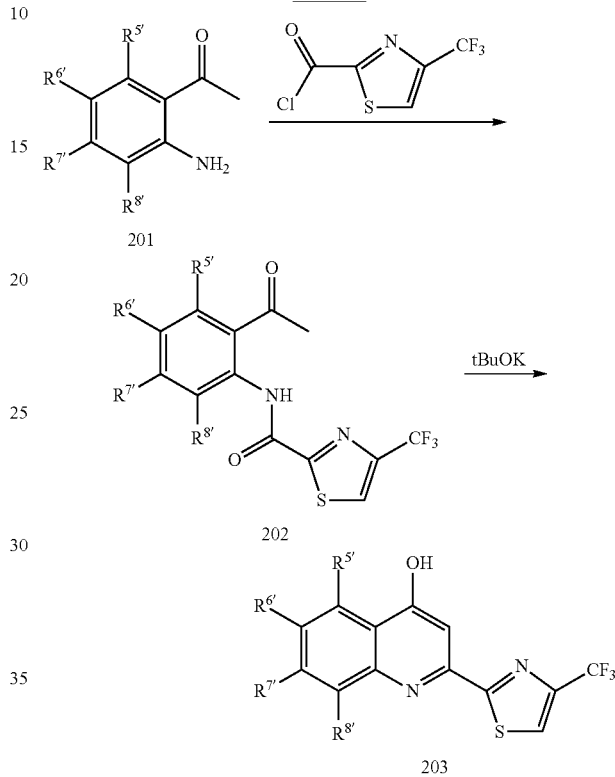

Step A:

Preparation of 4-trifluoromethyl-4H-thiazole-2-carboxylic acid-(6-acetyl-3-methoxy-2-methyl-phenyl)-amide 202b. To a stirred solution of 4-(trifluoromethyl)-1,3-thiazole-2-carboxylic acid (3.5 g, 1 eq.) in DCM (35 mL) at 0° C. under nitrogen was added anhydrous DMF (few drops) and oxalyl chloride (3.14 mL, 2 eq.). At the end of the gas evolution, the reaction mixture was allowed to warm up to room temperature. The mixture was stirred at room temperature for 2 hrs and was evaporated. Dioxane (70 mL) was added under nitrogen followed by a solution of 1-(2-amino-4-methoxy-3-methyl-phenyl)-ethanone 9 (3.18 g, 1 eq.) in dioxane (15 mL). The reaction mixture was stirred at room temperature for 16 hrs. The reaction mixture was washed with saturated $NaHCO_3$. Organics were dried over $Na_2SO_4$, filtered, and concentrated under reduced pressure. The crude material was triturated in $Et_2O$ to yield compound 202b as a white solid in 86% yield. $^1$H NMR ($CDCl_3$, 400 MHz) δ (ppm) 2.15 (s, 3H), 2.58 (s, 3H), 3.94 (s, 3H), 6.82 (d, J=8.55 Hz, 1H), 7.78 (d, J=8.55 Hz, 1H), 8.01 (s, 1H), 11.25 (s, 1H).

N-(6-Acetyl-2-chloro-3-methoxyphenyl)-4-trifluoromethylthiazole-2-carboxamide 202d was synthesized from 4-(trifluoromethyl)-1,3-thiazole-2-carboxylic acid and 1-(2-amino-3-chloro-4-methoxyphenyl)-ethanone as a beige solid in 65% yield, following the procedure as described for compound 202b.

Step B: Preparation of 7-methoxy-8-methyl-2-(4-trifluoromethyl-thiazol-2-yl)-quinolin-4-ol 203b. To a solution of compound 202b (70 g, 1 eq.) in tBuOH (1.2 L) was added potassium t-butoxide (46 g, 2.1 eq.) under nitrogen. The mixture was heated to 70° C. for 16 hrs. The reaction mixture was concentrated under reduced pressure and then acidified to pH 5. The precipitate was filtered, washed with water, and triturated in a diisopropylether/pentane mixture to yield compound 203b as a beige solid in 89% yield. $^1$H NMR (CDCl$_3$, 400 MHz) δ (ppm) 2.43 (s, 3H), 3.98 (s, 3H), 6.76 (d, J=1.76 Hz, 1H), 7.04 (d, J=9.10 Hz, 1H), 7.96 (s, 1H), 8.24 (d, J=9.10 Hz, 1H), 9.31 (brs, 1H).

8-Chloro-7-methoxy-2-(4-trifluoromethyl-thiazol-2-yl)-quinolin-4-ol 203d was synthesized from compound 202d as a yellow powder in 70% yield, following the procedure as described for compound 203b. MS (ESI, EI$^+$): m/z=361 (MH$^+$).

Example 13

Preparation of Compound 51

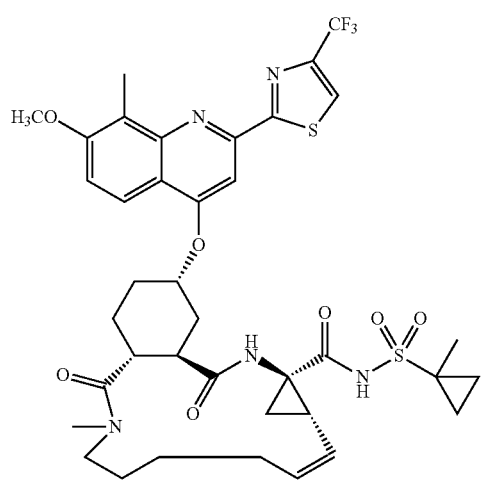
51

Compound 51 was synthesized according to Scheme 5.

Step A:

Preparation of (1R,2R) 1-methyl-cis-1,2,3,6-tetrahydrophtalate 34a. To a suspension of tBuOK (9.66 g, 1.5 eq.) in anhydrous THF (50 mL) was added slowly a solution of (1S,2R)-1-methyl-cis-1,2,3,6-tetrahydrophtalate (10.57 g, 1 eq.) in anhydrous THF (125 mL) under nitrogen at 0° C. The solution was stirred at room temperature for 2 hrs. The reaction mixture was concentrated under reduced pressure. The mixture was acidified to pH 1 with 2 N HCl and extracted with Et$_2$O (3×100 mL). The combined organic layers were dried over anhydrous sodium sulphate, filtered, and concentrated under reduced pressure. The crude compound was used directly in the next step without further purification. $^1$H NMR (CDCl$_3$, 400 MHz) δ2.22 (m, 2H), 2.46 (m, 2H), 2.86-2.88 (m, 2H), 3.71 (s, 3H). 5.68-5.72 (m, 2H) 8.88 (brs, 1H).

Step B:

Preparation of (1R,2R,4R,5S)-4-iodo-7-oxo-6-oxa-bicyclo[3.2.1]-octane-2-carboxylic acid methyl ester 34b. To a stirred solution of compound 34a (8.34 g, 1 eq.) in DCM (110 mL) were added I$_2$ (34.2 g, 3 eq.), KI (44.9 g, 6 eq.), NaHCO$_3$ (11.3 g, 3 eq.), and distilled H$_2$O (170 mL). The reaction mixture was stirred in darkness for 2 days. Saturated Na$_2$S$_2$O$_3$ aqueous solution (500 mL) was added and the mixture was extracted with DCM (2×500 mL). Organics were washed sequentially with H$_2$O (500 mL) and brine (500 mL), dried over MgSO$_4$, filtered, concentrated under reduced pressure, and purified by chromatography on silica gel (petroleum ether/EtOAc) to yield compound 34b as a yellow Scheme 5

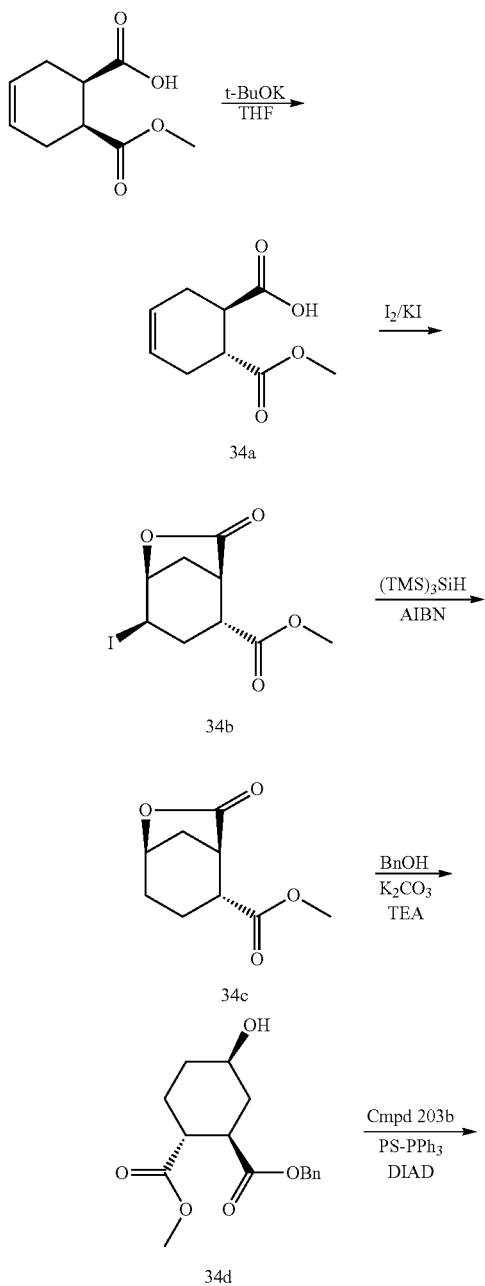

109
-continued
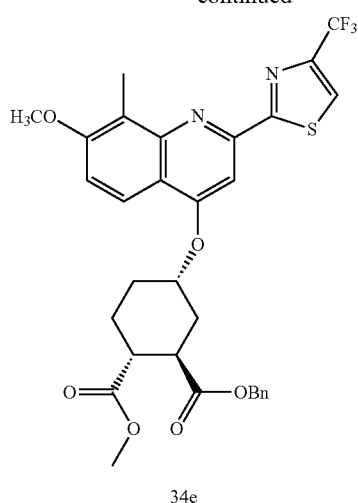
34e
→ LiOH
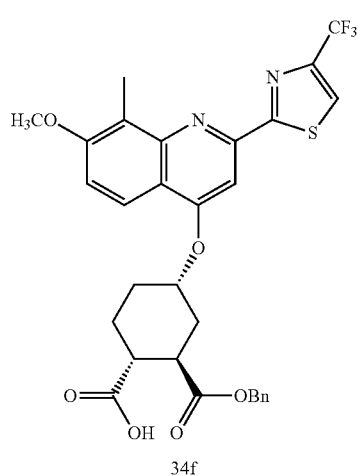
34f
→ Cmpd 31a
TBTU
DIPEA
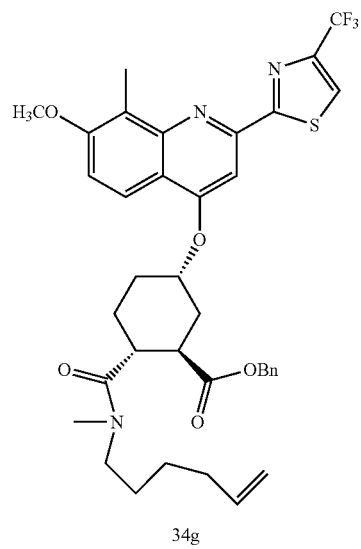
34g
→ LiOH
110
-continued
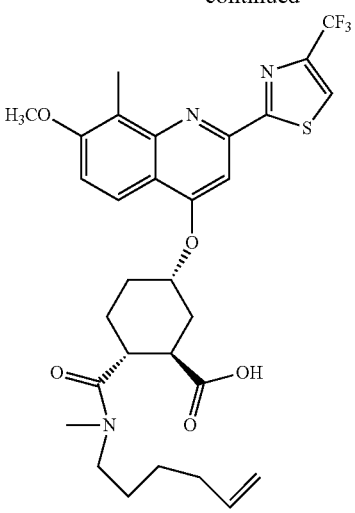
34h
→ Cmpd 32a
TBTU
DIPEA
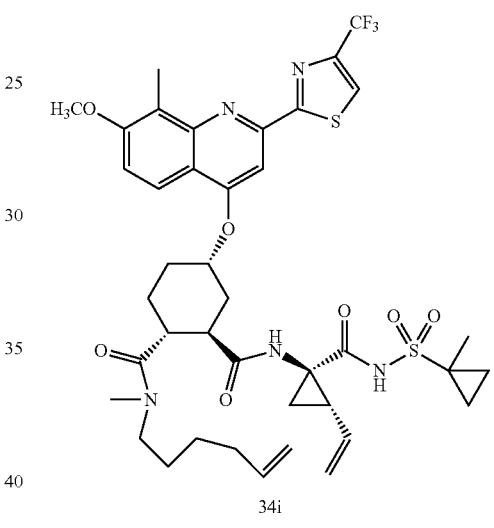
34i
→ Zhan 1B
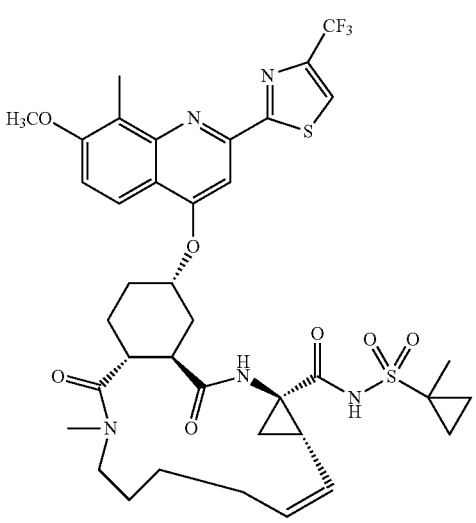
51
brown oil in 52% yield. $^1$H NMR (CDCl$_3$, 400 MHz) δ 1.68-1.73 (m, 4H), 2.82-2.85 (m, 2H), 3.60 (s, 3H).

Step C:

Preparation of (1R,2R,5R)-7-oxo-6-oxa-bicyclo[3,2,1]octane-2-carboxylic acid methyl ester 34c. To a solution of compound 34b (1.24 g, 1.0 eq.) in toluene (12 mL) was added tris(trimethylsilyl)silane (1.48 mL, 1.2 eq.) with stirring, followed addition of 1,1'-azobis(cyclohexanecarbonitrile) (AIBN) (98 mg, 0.1 eq.). The reaction mixture was stirred at 90° C. for 1.5 hrs. The solution was cooled down to room temperature, quenched with 5% citric acid solution, and extracted with EtOAc (50 mL). Organics were washed sequentially with $H_2O$ (30 mL), saturated $NaHCO_3$ aqueous solution (30 mL), and brine (30 mL), and concentrated under reduced pressure to yield a colourless oil. Crude material was purified by chromatography on silica gel (petroleum ether/EtOAc) to yield compound 34c as white crystals in 71% yield. $^1$H NMR ($CDCl_3$, 400 MHz) δ 1.68-1.73 (m, 4H), 2.05-2.18 (m, 2H), 2.82-2.85 (m, 2H), 3.60 (s, 3H), 4.71 (m, 1H).

Step D:

Preparation of (1R,2R,4R)-4-hydroxy-cyclohexane-1,2-dicarboxylic acid 2-benzyl ester 1-methyl ester 34d. To a stirred solution of compound 34c (1.85 g, 1 eq.), in dry DMF (10 mL) were added benzyl alcohol (1.25 mL, 1.2 eq.) and $K_2CO_3$ (2.8 g, 2 eq.). The reaction mixture was stirred for 16 hrs under nitrogen. Water was then added and the reaction was extracted with TBDME. The combined organic layers were washed with brine, dried over $MgSO_4$, concentrated under reduced pressure, and purified by chromatography on silica gel (DCM/MeOH) to yield compound 34d as beige solid in 70% yield.

Step E:

Preparation of (1R,2R,4R)-4-[7-methoxy-8-methyl-2-(4-trifluoromethyl-thiazol-2-yl)-quinolin-4-yloxy]-cyclohexane-1,2-dicarboxylic acid 2-benzyl ester-1-methyl ester 34e. To a stirred solution of compound 34d (2.18 g, 1.2 eq.), compound 203b (1.58 mg, 1 eq.), and $PPh_3$-PS (polystyrene supported triphenylphosphine) (3.34 g, 2 eq.) in THF (50 mL) was added DIAD (2.1 mL, 2 eq.) under nitrogen. The reaction mixture was stirred at room temperature for 16 hrs. The mixture was filtered, and the filtrated was concentrated in vacuo and purified by chromatography on silica gel (DCM/MeOH) to yield compound 34e as a beige solid in 65% yield. MS (ESI, EI$^+$): m/z=617 (MH$^+$).

Step F:

Preparation of (1R,2R,4R)-4-[7-methoxy-8-methyl-2-(4-trifluoromethyl-thiazol-2-yl)-quinolin-4-yloxy]-cyclohexane-1,2-dicarboxylic acid 2-benzyl ester 34f. A solution of compound 34e (293 mg, 1 eq.) and LiOH (49 mg, 4 eq) in $H_2O$ (5 mL) and THF (5 mL) was stirred at room temperature for 4 hrs. The reaction mixture was acidified with 1N HCl to pH 2 and then extracted with DCM. Organics were concentrated under reduced pressure and purified by chromatography on silica gel (DCM/MeOH) to yield compound 34f as beige solid in 80% yield. MS (ESI, EI$^+$): m/z=601 (MH$^+$).

Step G:

Preparation of (1R,2R,4R)-2-(hex-5-enyl-methyl-carbamoyl)-5-[7-methoxy-8-methyl-2-(4-trifluoromethyl-thiazol-2-yl)quinolin-4-yloxy]-cyclohexane carboxylic acid benzyl ester 34g. To a cold solution of compound 34f (1.1 g, 1 eq.), O-(benzotriazol-1-yl)-N,N,N',N'-tetramethyluronium tetrafluoroborate (TBTU) (595 mg, 1 eq.), and compound 31a (528 mg, 1 eq.) in DMF (50 mL) was added diisopropyl ethyl amine (DIPEA) (650 μL, 2 eq) dropwise under nitrogen at 0° C. The reaction mixture was stirred overnight at room temperature, then quenched with water, and extracted with diethyl ether. The organic layer was washed with brine, and then dried on magnesium sulphate. The solvent was removed under reduced pressure and the residue was purified by chromatography on silica gel to yield compound 34g as a beige solid in 20% yield. MS (ESI, EI$^+$): m/z=697(MH$^+$).

Step H:

Preparation of (1R,2R,4R)-2-(hex-5-enyl-methyl-carbamoyl)-5-[7-methoxy-8-methyl-2-(4-trifluoromethyl-thiazol-2-yl)quinolin-4-yloxy]-cyclohexane carboxylic acid 34h. Compound 34h was synthesized from compound 34g as described for compound 34f as an off-white solid in 85% yield. MS (ESI, EI$^+$): m/z=606 (MH$^+$).

Step I:

Preparation of (1R,2R,4R)-4-[7-methoxy-8-methyl-2-(4-trifluoromethyl-thiazol-2-yl)quinolin-4-yloxy]-cyclohexane 1,2-dicarboxylic acid 1-(hex-5-enyl-methyl amide) 2-{[1-(1-methylcyclopropanesulfonamino carbonyl)-2-(S)-vinyl (R) cyclopropyl]-amide} 34i. Compound 34i was synthesized from compound 34h and compound 32a as described for compound 34h as a beige solid in 30% yield. MS (ESI, EI$^+$): m/z=832 (MH$^+$).

Step J:

Preparation of (1R,4R,6R,18S)-1-methylcyclopropanesulfonic acid {[18-[7-methoxy-8-methyl-2-(4-trifluoromethyl-thiazol-2-yl)quinolin-4-yloxy]-13-methyl-2,14-dioxo-3,13-diaza-tricyclo[13.4.0.0]-nonadec-7-ene-4-carbonyl}-amide 51. To a solution of compound 34i (16 mg, 1 eq.) in dichloroethane (20 mL), which was degassed for 45 min by bubbling nitrogen, the Zhan IB catalyst ((1,3-dimesitylimidazolidin-2-yl)(5-(N,N-dimethylsulfamoyl)-2-isopropoxybenzylidene)ruthenium(V) chloride) (8 mol. %, 1.03 mg) was added. The reaction mixture was flushed with nitrogen for 15 min and then refluxed for 1 hr. The reaction mixture was cooled down to room temperature, poured onto a silica pad, and eluted with DCM. The crude material was purified by chromatography on silica gel (DCM/MeOH) to yield compound 51 as a beige solid in 80% yield. MS (ESI, EI$^+$): m/z=804 (MH$^+$).

Example 14

Preparation of 7-methoxy-8-methyl-2-[(4-trifluoromethyl-thiazole-2-yl)-quinazolin-4-ol 206

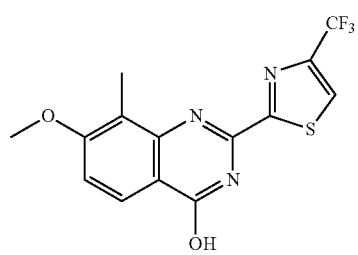

7-Methoxy-8-methyl-2-[(4-trifluoromethyl-thiazole-2-yl)-quinazolin-4-ol 206 was synthesized according to Scheme 6.

Scheme 6

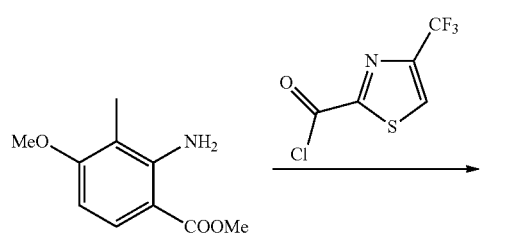

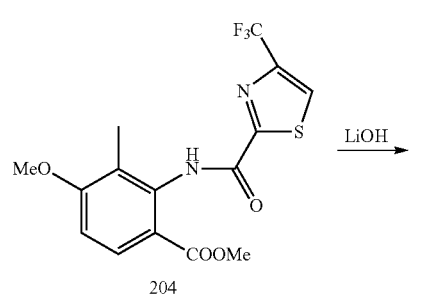

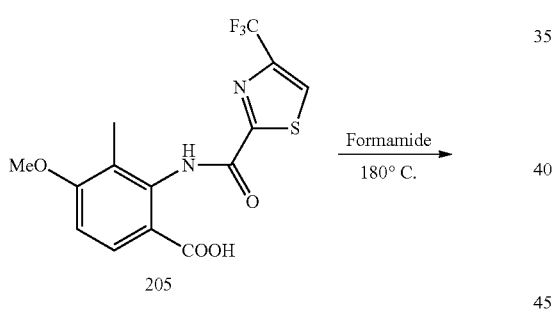

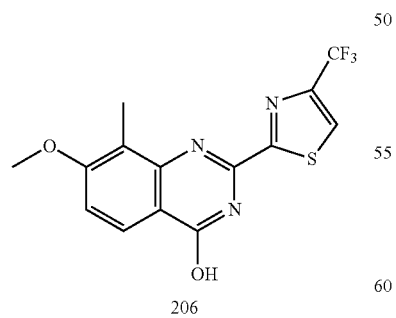

Step A:
Preparation of 4-methoxy-3-methyl-2-[(4-trifluoromethyl-thiazole-2-carbonyl)-amino]-benzoic acid methyl ester 204. Under nitrogen atmosphere, a solution of methyl anthranilate (2 g, 1 eq.) in 1,4-dioxane (30 mL) was added at 0° C. to a solution of 4-trifluoromethyl-thiazole-2-carbonyl chloride (4.36 g, 2 eq.) in 1,4-dioxane (65 mL). The reaction mixture was stirred at room temperature for 16 hrs. The solvent was removed under reduced pressure and the residue was purified by chromatography on silica gel (DCM/MeOH) to yield compound 204 as a white solid in 81% yield. $^1$H NMR (CDCl$_3$, 400 MHz) δ (ppm) 1.51 (s, 3H), 3.80 (s, 3H), 3.85 (s, 3H), 6.75 (d, J=8.75 Hz, 1H), 7.87 (d, J=8.75 Hz, 1H), 7.95 (s, 1H), 10.48 (s, 1H).

Step B:
Preparation of 4-methoxy-3-methyl-2-[(4-trifluoromethyl-thiazole-2-carbonyl)-amino]-benzoic acid 205. LiOH (240 mg, 1.2 eq.) was added to a mixture of compound 204 (3 g, 1 eq.) in EtOH/H$_2$O (20 mL/20 mL) at room temperature. The reaction mixture was stirred at 60° C. for 3 hrs and was allowed to cooled down to room temperature. A 5% aqueous solution of citric acid was added and the mixture was extracted with EtOAc. Organic phase was dried over MgSO$_4$, filtered, and concentrated under reduced pressure to yield compound 205 as a white solid in 88% yield. $^1$H NMR (CDCl$_3$, 400 MHz) δ (ppm) 1.51 (s, 3H), 3.85 (s, 3H), 6.75 (d, J=8.75 Hz, 1H), 7.87 (d, J=8.75 Hz, 1H), 7.95 (s, 1H), 10.48 (s, 1H).

Step C:
Preparation of 7-methoxy-8-methyl-2-[(4-trifluoromethyl-thiazole-2-yl)-quinazolin-4-ol 206. Compound 205 (2.5 g, 1 eq.) was refluxed in formamide (20 mL) at 160° C. for 5 hrs. Water was then added and the reaction mixture was extracted with EtOAc. Organics were dried over Na$_2$SO$_4$, filtered, concentrated under reduced pressure, and purified by silica gel chromatography (DCM) to yield compound 206 as a brown solid in 92% yield. $^1$H NMR (CDCl$_3$, 400 MHz) δ (ppm) 2.46 (s, 3H), 3.92 (s, 3H), 7.07 (d, J=9.28 Hz, 1H), 7.92 (s, 1H), 8.15 (d, J=9.28 Hz, 1H), 9.87 (s, 1H).

Example 15

Preparation of Substituted Quinolines 209

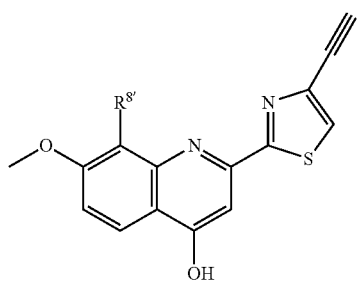

209a: R$^{8'}$ = Cl
209b: R$^{8'}$ = CH$_3$

Substituted quinolines 209 were synthesized according to Scheme 7.

Step A:
Preparation of N-(6-acetyl-2-chloro-3-methoxyphenyl)-4-bromothiazole-2-carboxamide 207a. Oxalyl chloride (6.77 g, 1.4 eq.) was added dropwise under nitrogen at 0° C. to a suspension of 4-bromothiazole-2-carboxylic acid (9.52 g, 1.2 eq.) in DCM (310 mL) and DMF (315 µL). The reaction mixture was stirred at 0° C. for 30 min and then at room temperature for additional 90 min. The solvent was then removed under reduced pressure to give acid chloride used directly in the next step without further purification. Under nitrogen, a solution of 6-acetyl-2-chloro-3-methoxy aniline (7.6 g, 1 eq.) in 1,4-dioxane (310 mL) was added at 0° C. to a solution of acid chloride in 1,4-dioxane. The reaction mixture was stirred at room temperature for 2.5 hrs and the solvent was removed under reduced pressure. The residue was triturated in ether and then in isopropylacetate to yield compound 207a in 14% yield. $^{1}$H NMR (CDCl$_{3}$, 400 MHz): δ (ppm) 2.59 (s, 3H), 4 (s, 3H), 6.91 (d, J=8.78 Hz, 1H), 7.54 (s, 1H), 7.72 (d, J=8.78 Hz, 1H), 10.28 (s, 1H).

Scheme 7

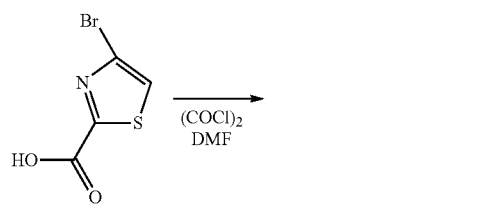

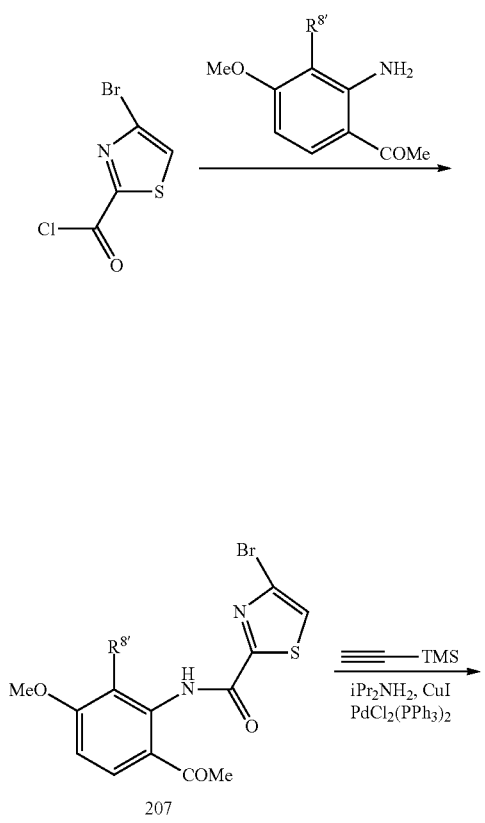

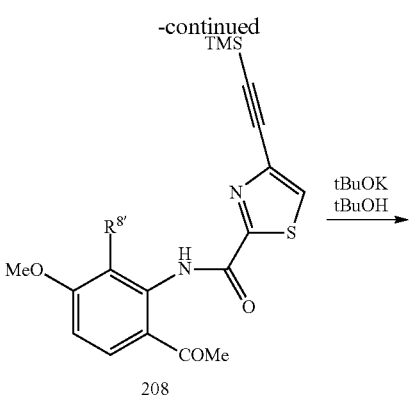

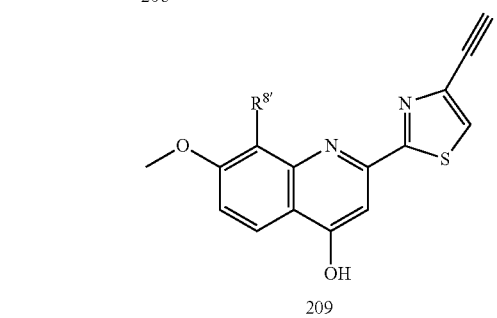

Step B:

Preparation of N-(6-acetyl-2-chloro-3-methoxyphenyl)-4-(2-trimethylsilyl)ethynyl)thiazole-2-carboxamide 208a. Compound 207a (3 g, 1 eq.), ethynyltrimethylsilane (1.6 mL, 1.5 eq.), diisopropylamine (12 mL), triphenylphosphine (0.081 g, 4%), copper(I) iodide (0.059 mg, 4%), Cl$_{2}$Pd (PPh$_{3}$)$_{2}$ (0.113 g, 2%) were mixed together and stirred at 90° C. overnight. After cooled down to room temperature, diisopropyl ether was added. The precipitate was collected by filtration, washed with diisopropyl ether and pentane. The solid was solubilized in dichloromethane and washed with water. The organic layer was dried over Na$_{2}$SO$_{4}$, filtered, and concentrated under diminished pressure to give compound 208a as a brown solid in 93% yield. $^{1}$H NMR (CDCl$_{3}$, 400 MHz) δ (ppm) 0.29 (s, 9H), 2.57 (s, 3H), 4 (s, 3H), 6.91 (d. J=8.91 Hz, 1H), (d, J=8.65 Hz, 1H), 7.73 (s, 1H): MS (ESI, EI$^{+}$): m/z=407 (MH$^{+}$).

Step C:

Preparation of 8-chloro-7-methoxy-2-(4-ethynylthiazol-2-yl)quinolin-4-ol 209a. To a solution of compound 208a (2.94 g, 1 eq.) in tert-butanol (15 mL) was added potassium tert-butoxide (1.7 g, 2.1 eq.) and the mixture was stirred at 90° C. for 2 hrs. Tert-butanol was evaporated in vacuo and water added before acidification to pH 5 by addition of 1N HCl. The product was extracted with dichloromethane. The organic layer was dried over Na$_{2}$SO$_{4}$, filtered, and concentrated under diminished pressure. The residue was triturated in diisopropyl ether and filtered off. The filtrate was purified by chromatography on silica gel column (methanol/dichloromethane) to yield compound 209a as an orange solid in 48% yield. $^{1}$H NMR (CDCl$_{3}$, 400 MHz) δ (ppm) 3.26 (s, 1H), 4.06 (s, 3H), 6.75 (s, 1H), 7.07 (d, J=9.15 Hz, 1H), 7.72 (s, 1H), 8.27 (d, J=9.15 Hz, 1H), 9.84 (brs, 1H); MS (ESI, EI$^{+}$): m/z=316.92 (MH$^{+}$).

Step D:

Preparation of 4-bromo-thiazole-2-carboxylic acid-(6-acetyl-3-methoxy-2-methyl-phenyl)-amide 207b. Bromothiazole (10 g, 1.3 eq.) was suspended in dichloromethane and cooled down to 0° C. Oxalyl chloride (8.1 mL, 2.6 eq.) was added slowly, and then DMF dropwise. The mixture was stirred at 0° C. for 30 min, and then at room temperature. After 2 hrs, the bubbling stopped. The reaction was complete as determinated by TLC analysis. The solvent was removed in vacuo to give a beige residue. This residue was suspended in dioxane and a solution of a derivatized aniline (6.62 g, 1 eq.) in dioxane was added into the acyl chloride solution. The reaction mixture was stirred at room temperature for 16 hrs. Water (100 mL) was added and the mixture was extracted with ethyl acetate. The organic layer was dried over $Na_2SO_4$, filtered, and concentrated under vacuo to give a beige residue. The residue was triturated in TBDME and the beige solid was recovered by filtration and dried in vacuo to give compound 207b in 74% yield. $^1$H NMR ($CDCl_3$, 400 MHz) δ (ppm) 2.14 (s, 3H), 2.59 (s, 3H), 3.94 (s, 3H), 6.81 (d, J=8.76 Hz, 1H), 7.51 (s. 1H), 7.78 (d, J=8.76 Hz, 1H), 11.20 (s, 1H).

Step E:

Preparation of 4-trimethylsilanylethynyl-thiazole-2-carboxylic acid-(6-acetyl-3-methoxy-2-methyl-phenyl)-amide 208b. To a suspension of compound 207b (10.12 g, 1 eq.) in diisopropylamine (40 mL) were added ethynyltrimethylsilane (5.7 mL, 1.5 eq.), triphenylphosphine (0.283 g, 0.04 eq.), copper iodide (0.206 g, 0.04 eq.), and $PdCl_2(PPh_3)_2$ (0.38 g, 0.02 eq.). The mixture was stirred under nitrogen and heated to 80° C. (external temperature). After 10 min, the solvent was refluxed, and the mixture solidified and turned brown grey. DIPA (20 mL) was added to solubilize the reaction mixture. After 2.5 hrs, the reaction was complete and the mixture cooled down to room temperature. Diisopropyl ether (20 mL) was added. A grey solid was recovered by filtration, dissolved in dichloromethane, and washed with water. The organic layer was dried over $Na_2SO_4$, filtered, and concentrated to give black solid. The residue was purified by chromatography on silica gel (dichloromethane) to give compound 208b as a beige solid in 84% yield. $^1$H NMR ($CDCl_3$, 400 MHz) δ (ppm) 0.29 (s, 9H), 2.13 (s, 3H), 2.58 (s, 3H), 3.93 (s, 3H), 6.81 (d, J=8.78 Hz, 1H), 7.69 (s, 1H), 7.76 (d, J=8.78 Hz, 1H), 11.05 (s, 1H).

Step F.

Preparation of 7-methoxy-8-methyl-2-(4-ethynyl-thiazol-2-yl)-quinolin-4-ol 209b. To a suspension of compound 208b (8.71 g, 1 eq.) in tert-butanol (240 mL) was added potassium tert-butoxide (5.32 g, 2.1 eq.). The heterogeneous mixture was stirred and heated to 80° C. The solvent was then evaporated and water was added to the resulting black residue. The pH of the mixture was brought to 6 with 1N HCl. The mixture was extracted with dichloromethane. The organic layer was dried over $Na_2SO_4$, filtered, and concentrated under vacuo. The solid was purified by chromatography on silica gel to give compound 209b as an orange solid in 52% yield. $^1$H NMR ($CDCl_3$, 400 MHz) δ (ppm) 2.45 (s, 3H), 3.25 (s, 1H), 3.99 (s, 3H), 6.89 (br s, 1H), 7.06 (d, J=9.09 Hz, 1H), 7.72 (s, 1H), 8.26 (d, J=9.09 Hz, 1H), 9.50 (br s, 1H); MS (ESI, EI$^+$): m/z=297 (MH$^+$).

Example 16

Preparation of 2-(4-isopropylthiazol-2-yl)-substituted quinolin-4-ols 218

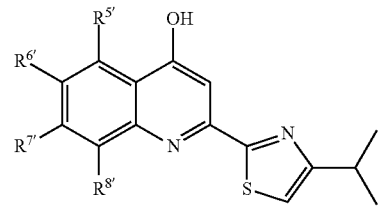

218a: $R^{5'}$ = H, $R^{6'}$ = H, $R^{7'}$ = $OCH_3$, $R^{8'}$ = H
218b: $R^{5'}$ = H, $R^{6'}$ = H, $R^{7'}$ = $OCH_3$, $R^{8'}$ = $CH_3$
218c: $R^{5'}$ = H, $R^{6'}$ = H, $R^{7'}$ = $OCH_3$, $R^{8'}$ = F
218d: $R^{5'}$ = H, $R^{6'}$ = H, $R^{7'}$ = $OCH_3$, $R^{8'}$ = Cl
218e: $R^{5'}$ = $OCH_3$, $R^{6'}$ = H, $R^{7'}$ = $OCH_3$, $R^{8'}$ = H
218f: $R^{5'}$ = H, $R^{6'}$ = $OCH_3$, $R^{7'}$ = H, $R^{8'}$ = $CH_3$
218g: $R^{5'}$ = H, $R^{6'}$ = $OCH_3$, $R^{7'}$ = Cl, $R^{8'}$ = H
218h: $R^{5'}$ = H, $R^{6'}$ = H, $R^{7'}$ = $OCH_3$, $R^{8'}$ = Br

The syntheses of compounds 218 are shown in Schemes 8 to 10, where $R^{5'}$, $R^{6'}$, $R^{7'}$, and $R^{8'}$ in compounds 201, 215 to 217, and 220 to 222 are each as defined in compounds 218.

Scheme 8

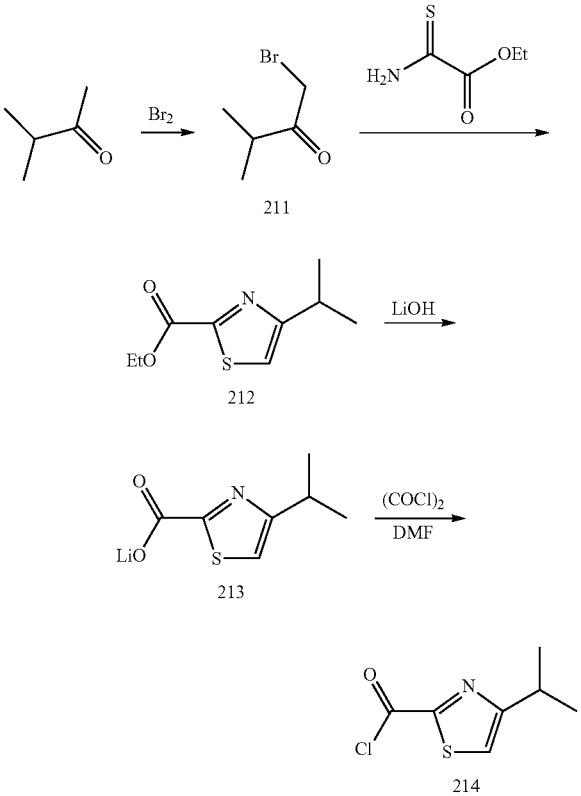

Method A:

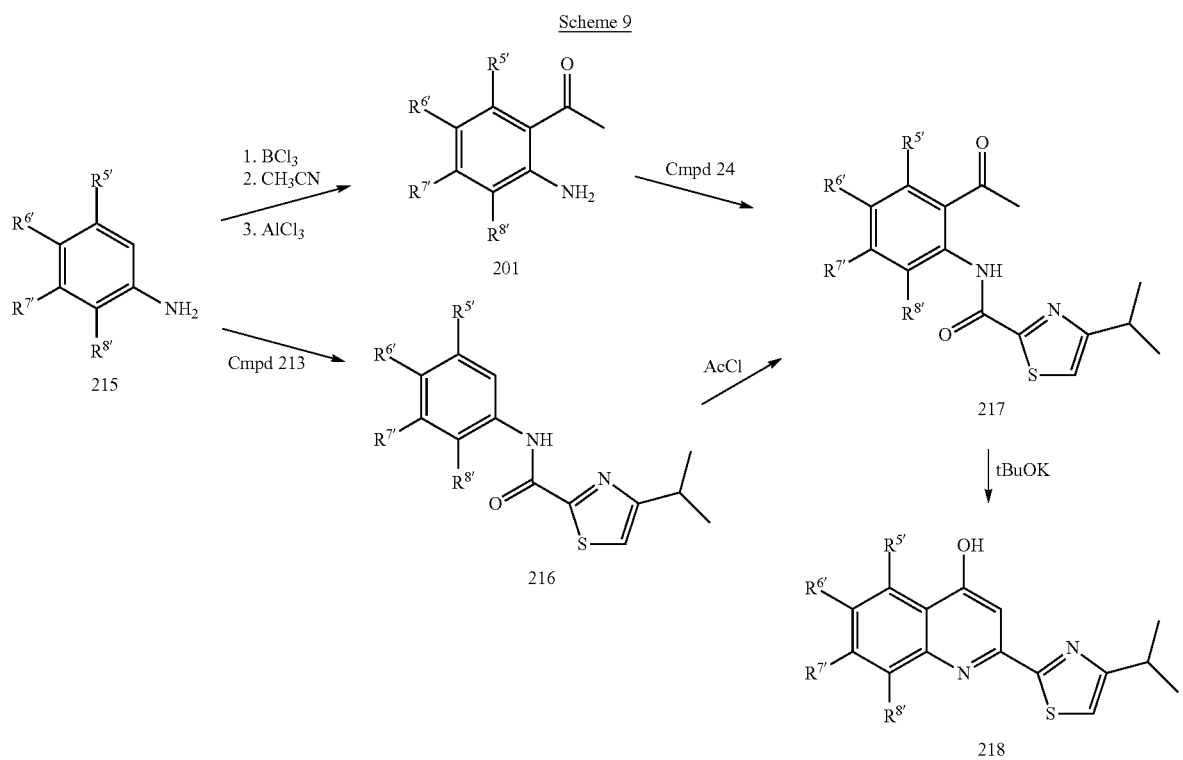

Scheme 9

Step A:

Preparation of 1-bromo-3-methylbutan-2-one 211. To a solution of 3-methyl-2-butanone (40.7 g, 1 eq.) in ethanol (391 mL) was added bromide (62.4 g, 0.83 eq.) under nitrogen at 0° C. over 30 min. The reaction mixture was stirred at 0° C. for 4 hrs, then quenched with 1M aqueous sodium metabisulfite (100 mL) and extracted with petroleum ether (750 mL). The organic layer was washed twice with water (100 mL), twice with a cold saturated aqueous bicarbonate, and then brine. The organic layer was dried over sodium sulfate and then concentrated under reduced pressure. The product was purified by distillation under vacuum to yield compound 211 as colourless oil in 42% yield. $^1$H NMR (CDCl$_3$, 400 MHz): δ (ppm) 1.17 (d, J=6.98 Hz, 6H), 2.99 (m, J=6.98 Hz, 1H), 3.99 (s, 2H).

Step B:

Preparation of ethyl 4-isopropylthiazole-2-carboxylate 212. A solution of compound 211 (3.5 g, 1.25 eq.) and ethylthioxamate (2.3 g, 1 eq.) in ethanol (40 mL) was heated to 80° C. for 6 hrs, and then cooled to 0° C. The reaction mixture was diluted with water and EtOAc, and then neutralized to pH 7 with NH$_3$ (28%). The aqueous layer was extracted with EtOAc. The combined organic layers were dried over sodium sulfate and then removed under reduced pressure. The residue was purified by chromatography on silica gel to yield compound 212 as yellow oil in quantitative yield. $^1$H NMR (DMSO-d$_6$, 400 MHz): δ (ppm) 1.25 (d, J=6.73 Hz, 6H), 1.31 (t, J=7.24 Hz, 3H), 3.11 (hep, J=6.73 Hz, 1H), 4.35 (q, J=7.24 Hz, 2H), 7.72 (s, 1H).

Step C:

Preparation of 4-isopropylthiazole-2-carboxylic acid, lithium salt 213. To a solution of compound 212 (26 g, 1 eq.) in a mixture of MeOH (78 mL) and THF (260 mL), lithium hydroxide (2.8 g, 0.9 eq.) was added. The reaction mixture was stirred at room temperature overnight. The solvents were then removed under reduced pressure. The residue was triturated with petroleum ether (500 mL), filtrated, washed with petroleum ether, and dried under vacuum to yield compound 213 as a beige solid in 56% yield. $^1$H NMR (DMSO-d$_6$, 400 MHz): δ (ppm) 1.21 (d, J=6.73 Hz, 6H), 2.95 (hep, J=6.73 Hz, 1H), 7.19 (s, 1H).

Step D:

Preparation of 4-isopropylthiazole-2-carbonyl chloride 214. Oxalyl chloride (2.9 g, 1.5 eq.) was added dropwise under nitrogen at 0° C. to a suspension of compound 213 (1.8 g, 1 eq.) in DCM (25 mL) and DMF (50 μL). The reaction mixture was stirred at 0° C. for 30 min and then at room temperature for additional 90 min. Lithium chloride salt was removed from the reaction mixture through filtration. The solvent was then removed under reduced pressure to give compound 214 as yellow oil in quantitative yield, which was stored under nitrogen and used directly in the next step without further purification.

Step E:

Preparation of 1-(2-amino-4-methoxyphenyl)ethanone 201a. Trichloroborane (1M, 82 mL, 1 eq.) in DCM was added dropwise to a solution of meta-anisidine 215a (10 g, 1 eq.) in toluene (56 mL) under nitrogen at 0-5° C. over 1 hr. After stirred for 10 min at 0° C., ACN (5.2 mL, 1.20 eq.) was added. After the reaction mixture was stirred for additional 1 hr at 0° C., aluminium(III) chloride (11.9 g, 1.1 eq.) was added at 0° C. The reaction mixture was stirred at 50° C. for 16 hrs. The reaction mixture was then cooled down to 0° C., and propan-2-ol (38 mL) was added over 10 min, followed by addition of water (110 mL) over 30 min. The reaction mixture was heated to 50° C. for 3 hrs. After cooling down to 0° C., aqueous solution of sodium hydroxide (25%) was added. The aqueous layer was extracted with toluene (100 mL). The combined organic layers were washed with NaOH (25%), brine, and dried over sodium sulfate. The solvent was removed to yield compound 201a as a yellow solid in 63% yield. $^1$H NMR (CDCl$_3$, 400 MHz): δ (ppm) 2.52 (s, 3H), 3.80 (s, 3H), 6.07 (d, J=2.43, 1H), 6.23 (dd, J=2.43 and 8.98 Hz, 1H), 6.43 (br s, 2H), 7.63 (d, J=8.98 Hz).

1-(2-Amino-3-methyl-4-methoxyphenyl)ethanone 201b was synthesized from 3-methoxy-2-methylaniline 215b as a yellow solid in 23% yield, according to the procedure as described for compound 215a. MS (ESI, EI$^+$): m/z=180 (MH$^+$).

1-(2-Amino-4-chloro-5-methoxy-phenyl)-ethanone 201g was synthesized from 3-chloro-4-methoxy-aniline 215g as a brown solid in 50% yield, according to the procedure as described for compound 215a. MS (ESI, EI$^+$): m/z=200 (MH$^+$).

Step F:

Preparation of N-(3,5-dimethoxy-phenyl)-4-isopropylthiazole-2-carboxamide 216e. To a stirred solution of compound 213 (1.38 g, 7.8 mmol) in DCM (50 mL) under nitrogen was added oxalyl chloride (1.16 g, 9.1 mmol). The reaction mixture was stirred at room temperature for 90 min. The solution was filtered under nitrogen and washed with DCM. The filtrate was concentrated under reduced pressure and the residue was dissolved in dioxane (20 mL). 3,5-Dimethoxyaniline (1 g, 6.5 mmol) in dioxane (9 mL) was added dropwise. The reaction mixture was stirred at room temperature for 90 min. Solvent was removed under reduced pressure and the crude material was purified by chromatography on silica gel (EtOAc/DCM) to yield compound 216e as a white solid in 90% yield. $^1$H NMR (CDCl$_3$, 400 MHz) δ (ppm) 1.35 (s, 3H), 1.37 (s, 3H), 3.14-3.17 (m, 1H), 3.82 (s, 6H). 6.30 (brs, 1H), 6.97 (d. J=2.30 Hz, 2H), 7.19 (s. 1H); MS (ESI, EI$^+$): m/z=307 (MH$^+$).

Step G:

Preparation of N-(2-acetyl-5-methoxyphenyl)-4-isopropylthiazole-2-carboxamide 217a. Under nitrogen, a solution of compound 201a (3 g, 1 eq.) in 1,4-dioxane (30 mL) was added at 0° C. to a solution of compound 214 (4.1 g, 1.2 eq.) in 1,4-dioxane. The reaction mixture was stirred at room temperature overnight. The solvent was removed under reduced pressure and the residue was purified by chromatography on silica gel to yield compound as a beige solid 217a in 75% yield. $^1$H NMR (CDCl$_3$, 400 MHz): δ (ppm) (ppm) 1.43 (d, J=6.98 Hz, 6H), 2.65 (s, 3H), 3.26 (hep, J=6.98 Hz, 1H), 3.92 (s, 3H), 6.69 (dd, J=2.59 and 8.80 Hz, 1H), 7.2 (d, J=0.84, 1H), 7.87 (d, J=8.9 Hz, 1H), 8.58 (d, J=2.59 Hz, 1H), 13.5 (br s, 1H); MS (ESI, EI$^+$): m/z=319 (MH$^+$).

N-(6-Acetyl-2-methyl-3-methoxyphenyl)-4-isopropylthiazole-2-carboxamide 217b was synthesized from compound 201b and compound 214 as a beige solid in 66% yield, according to the procedure as described for compound 217a. MS (ESI, EI$^+$): m/z=333 (MH$^+$).

N-(6-Acetyl-2-fluoro-3-methoxyphenyl)-4-isopropylthiazole-2-carboxamide 217c was synthesized from 1-(2-amino-3-fluoro-4-methoxyphenyl)ethanone and compound 214 as a beige solid in 84% yield, according to the procedure as described for compound 217a. MS (ESI, EI$^+$): m/z=337 (MH$^+$).

N-(6-Acetyl-2-chloro-3-methoxyphenyl)-4-isopropylthiazole-2-carboxamide 217d was synthesized from 1-(2-amino-3-chloro-4-methoxyphenyl)ethanone and compound 214 as a beige solid in 80% yield, according to the procedure as described for compound 217a. $^1$H NMR (CDCl$_3$, 400 MHz) δ (ppm) 1.47 (s, 3H), 1.48 (s, 3H), 2.57 (s, 3H), 3.34- 3.41 (quint, J=6.90 Hz, 1H), 3.98 (s, 3H), 6.86 (d, J=8.48 Hz, 1H), 7.64 (d, J=8.48 Hz, 1H), 8.07 (s, 1H); MS (ESI, EI$^+$): m/z=351 (MH$^-$); MS (ESI, EI$^+$): m/z=353 (MH$^+$).

N-(6-Acetyl-3-chloro-4-methoxyphenyl)-4-isopropylthiazole-2-carboxamide 217g was synthesized from compounds 201g and 214 as a beige solid in 69% yield, according to the procedure as described for compound 217a. MS (ESI, EI$^+$): m/z=354 (MH$^+$).

Step H:

Preparation of N-(2-acetyl-3,5-dimethoxy-phenyl)-4-isopropylthiazole-2-carboxamide 217e. To a suspension of Et$_2$AlCl (1.61 g, 12.04 mmol) in DCM at 0° C. was added acetyl chloride (630 mg, 8.02 mmol). The mixture was stirred at 0° C. for 30 min. Compound 216e (1.23 g, 4.01 mmol) was then added and the reaction mixture was stirred at 80° C. for 90 min. The reaction was poured in ice and DCM was added. The organic layers were separated, dried over Na$_2$SO$_4$, filtered, and concentrated under reduced pressure. The crude product was purified by chromatography on silica gel (EtOAc/DCM) to yield compound 217e as a white solid in 82% yield. $^1$H NMR (CDCl$_3$, 400 MHz) δ (ppm) 1.41 (s, 3H), 1.43 (s, 3H), 2.63 (s, 3H), 3.20-3.27 (m, 1H), 3.89 (s, 3H), 3.90 (s, 3H), 6.27 (d, J=2.30, 1H), 7.19 (s, 1H), 8.12 (d, J=2.30 Hz, 1H).

Step I:

Preparation of 2-(4-isopropylthiazol-2-yl)-7-methoxyquinolin-4-ol 218a. To a solution of compound 217a (4.312 g, 1 eq.) in tBuOH (60 mL) was added potassium t-butoxide (3.8 g, 2.5 eq.) under nitrogen. The mixture was stirred at 70° C. for 16 hrs, and then cooled down to 0° C. and quenched with MeOH (10 mL) and acetic acid (2.5 mL). The solvent was removed under reduced pressure and the residue was triturated in a mixture of MeOH/water, isolated by filtration, washed with ACN, and then petroleum ether to yield compound 218a as a yellow solid in 71% yield. $^1$H NMR (DMSO-d$_6$, 400 MHz): δ (ppm) 1.32 (d, J=6.98 Hz, 6H), 3.14 (m, 1H), 3.89 (s, 3H), 7.06 (br s, 1H), 7.50-7.66 (m, 3H), 8 (d, J=9.05 Hz, 1H), 11.62 (br s, 1H); MS (ESI, EI$^+$): m/z=301 (MH$^+$).

2-(4-Isopropylthiazol-2-yl)-7-methoxy-8-methylquinolin-4-ol 218b was synthesized from compound 217b as a yellow solid in 60% yield, according to the procedure as described for compound 218a. MS (ESI, EI$^+$): m/z=315 (MH$^+$).

2-(4-Isopropylthiazol-2-yl)-8-fluoro-7-methoxyquinolin-4-ol 218c was synthesized from compound 217c as a yellow solid in 90% yield, according to the procedure as described for compound 218a. MS (ESI, EI$^+$): m/z=319 (MH$^+$).

2-(4-Isopropylthiazol-2-yl)-5,7-dimethoxyquinolin-4-ol 218e was synthesized from compound 217e as a yellow solid in 60% yield, according to the procedures as described for compound 218a. $^1$H NMR (CDCl$_3$, 400 MHz) δ (ppm) 1.37 (s, 3H), 1.39 (s, 3H), 3.15-3.22 (m, 1H), 3.95 (s, 3H), 4.05 (s, 3H), 6.45 (s, 1H), 7.03 (s, 2H), 7.62 (brs, 1H), 9.55 (s, 1H); MS (ESI, EI$^+$): m/z=331(MH$^+$).

7-Chloro-2-(4-isopropylthiazol-2-yl)-6-methoxyquinolin-4-ol 218g was synthesized from compound 217g as a yellow solid in 70% yield, according to the procedures as described for compound 218a. MS (ESI, EI$^+$): m/z=335 (MH$^+$).

8-Bromo-7-methoxy-2-(4-isopropyl-thiazol-2-yl)-quinolin-4-ol 218h was synthesized according to the procedures as described for compounds 217a and 218a, and in WO 2007014919, the disclosure of which is incorporated herein by reference in its entirety. MS (ESI, EI$^+$): m/z=380 (MH$^+$).

Method B:

Step AA:

Preparation of 4-isopropyl-2-tributylstannanyl-thiazole 219. To a stirred solution of 4-isopropylthiazole (9 g, 71 mmol) in anhydrous THF (100 mL) at −78° C. was added nBuLi (40 mL, 99 mmol). The reaction was stirred for 1 hr and the temperature reached −40° C. The reaction mixture was cooled to −78° C. and tri-n-butyltinchloride (23 g, 71 mmol) was added. The reaction mixture was stirred at room temperature for 48 hrs. Water was added and solvent was evaporated under reduced pressure. The residue was partioned between water and EtOAc. Organics were dried over $Na_2SO_4$, filtered, and concentrated under reduced pressure to yield compound 219 as colorless oil in 55% yield. $^1$H NMR ($CDCl_3$, 400 MHz) δ (ppm) 0.88-1.62 (m, 27H), 1.40 (s, 3H), 1.42 (s, 3H), 3.17-3.24 (m, 1H).

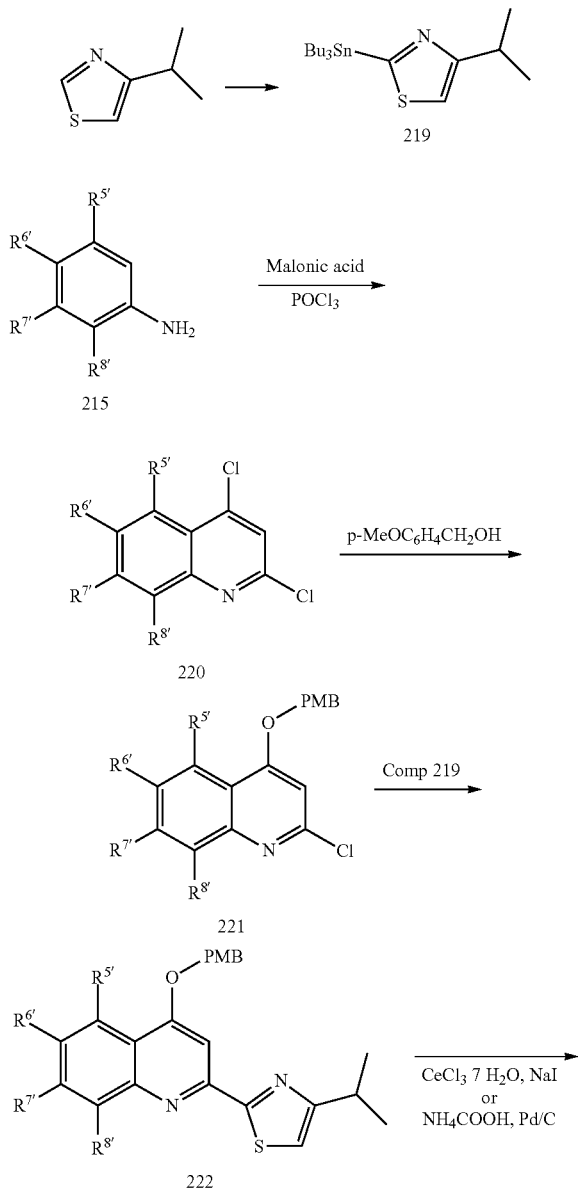

Scheme 10

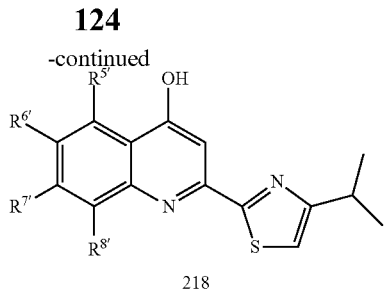

218

Step AB:

Preparation of 2,4,8-trichloro-7-methoxyquinoline 220d. A mixture of 2-chloro-3-methoxyaniline hydrochloride 215d (15 g, 1 eq.), malonic acid (12.06 g, 1.5 eq.), and phosphorus oxochloride (80 mL) was refluxed for 16 hrs. The reaction mixture was slowly poured into water and extracted with DCM. The organic layer was dried over $Na_2SO_4$, filtered, and concentrated under reduced pressure. The crude material was purified on silica pad, eluted with DCM, to yield compound 220d as a white solid in 74% yield.

$^1$H NMR ($CDCl_3$, 376 MHz) δ 4.10 (s, 3H), 7.43 (t, J=4.88 Hz, 2H), 8.12 (d, J=9.48 Hz, 1H).

2,4-Dichloro-8-methyl-7-methoxyquinoline 220b was synthesized from 2-methyl-3-methoxyaniline hydrochloride 215b and malonic acid as a white powder in 43% yield, following the procedure as described for compound 220d. $^1$H NMR ($CDCl_3$, 376 MHz) δ (ppm) 2.62 (s, 3H), 4.03 (s, 3H), 7.34 (s, 1H), 7.37 (d, J=9.02 Hz, 1H), 8.05 (d, J=9.02 Hz, 1H).

Step AC:

Preparation of 2,4-dichloro-6-methoxy-8-methyl-quinoline 220f. A mixture of 4-methoxy-2-methyl aniline 215f (5 g, 36.45 mmol), malonic acid (5.68 g, 54.67 mmol) in phosphorus oxide trichloride (36 mL) was refluxed for 16 hrs. The reaction mixture was then poured dropwise into cooled water (400 mL), extracted with ethyl acetate, washed with brine, dried over $Na_2SO_4$, filtered, concentrated under reduced pressure, and purified by chromatography on silica gel (DCM) to yield compound 220f as a beige solid in 43% yield. $^1$H NMR ($CDCl_3$, 400 MHz) δ (ppm) 2.72 (s, 3H), 3.95 (s, 3H), 7.27-7.28 (m, 2H), 7.47 (s, 1H).

Step AD:

Preparation of 2,8-dichloro-7-methoxy-4-(4-methoxy-benzyloxy)-quinoline 221d. NaH (60% in oil) (670 mg, 1.2 eq.) was added portionwise to a stirred solution of p-methoxybenzylalcohol (2.31 g, 1.2 eq.) and 15-crown-5 (3.32 mL, 1.2 eq.) in anhydrous DMF (10 mL). The mixture was stirred at room temperature for 30 min. Compound 220d (3.66 g, 1 eq.) in anhydrous DMF (25 mL) was then added and the reaction mixture was stirred at room temperature for 16 hrs. The reaction mixture was then poured into water (300 mL), extracted with EtOAC, dried over $Na_2SO_4$, filtered, and concentrated under reduced pressure. The crude material was purified by chromatography on silica gel (petroleum ether/DCM, 50/50) to give compound 221d as a yellow solid in 38% yield. $^1$H NMR ($CDCl_3$, 376 MHz) δ (ppm) 3.86 (s, 3H), 4.05 (s, 3H). 5.20 (s, 2H), 6.77 (s, 1H), 6.98 (d, J=8.53 Hz, 2H), 7.23 (d, J=9.41, 1H), 7.42 (d, J=8.53 Hz, 2H), 8.08 (d, J=9.41 Hz, 1H).

2-Chloro-8-methyl-7-methoxy-4-(4-methoxy-benzyloxy)-quinoline 221b was synthesized from compound 220b as a white powder in 50% yield, following the procedure as described for compound 221d. $^1$H NMR ($CDCl_3$, 376 MHz) δ (ppm) 2.60 (s, 3H), 3.85 (s, 314), 3.97 (s, 3H), 5.18 (s, 2H), 6.69 (s, 1H), 6.97 (d, J=8.57 Hz, 1H), 7.19 (d, J=8.57 Hz, 1H), 7.42 (d, J=8.57 Hz, 1H), 8.02 (d, J=8.57 Hz, 1H).

2-Chloro-6-methoxy-4-(4-methoxybenzyloxy)-8-methyl-quinoline 221f was synthesized from compound 220f as a white solid in 58% yield, following the procedure as described for compound 221d. $^1$H NMR (CDCl$_3$, 400 MHz) δ (ppm) 2.68 (s, 3H), 3.80 (s, 3H), 3.83 (s, 3H), 5.11 (s, 2H), 6.72 (s, 1H), 6.97 (d, J=9.03 Hz, 2H), 7.15 (dd, J=3.01 Hz and J=0.96 Hz, 1H), 7.20 (d, J=3.00 Hz, 1H), 7.40 (d, J=9.03 Hz, 2H).

Step AE:

Preparation of 2-(4-isopropyl-thiazol-2-yl)-6-methoxy-4-(4-methoxy-benzyloxy)-8-methyl-quinoline 222f. Compound 219 (100 mg, 0.29 mmol), compound 221f (242 mg, 0.35 mmol), and potassium carbonate (48 mg, 0.35 mmol) in degassed anhydrous DMF were stirred under microwave radiations at 80° C. for 1 hr. Solvent was removed under reduced pressure and the crude material was purified by chromatography on silica gel (Petroleum ether/DCM) to yield compound 222f as yellow powder in 63% yield. $^1$H NMR (CDCl$_3$, 400 MHz) δ 1.40 (s, 3H), 1.42 (s, 3H), 2.80 (s, 314), 3.17-3.24 (m, 1H), 3.85 (s, 3H), 3.89 (s, 3H), 5.31 (s, 2H), 6.99 (d, J=9.10 Hz, 2H), 7.00 (s, 1H), 7.21 (m, 1H), 7.31 (d, J=2.93 Hz, 1H), 7.49 (d, J=9.10 Hz, 214), 7.79 (s, 1H).

Step AF:

Preparation of 4-hydroxy-[2-(4-isopropyl-thiazol-2-yl)]-6-methoxy-8-methyl-quinoline 218f. Compound 222f (1.23 g, 2.82 mmol), cesium trichloride (1.58 g, 4.23 mmol), and sodium iodide (423 mg, 2.82 mmol) in ACN (26 mL) were stirred at 85° C. for 1 hr. The mixture was then filtered through celite and the solvent was evaporated. The brown solid obtained was suspended in water, pH was adjusted at 5 with 1N HCl. The mixture was extracted with DCM, dried over Na$_2$SO$_4$, filtered, concentrated under reduced pressure, and purified by chromatography on silica gel (petroleum ether/DCM) to yield compound 218f as a brown solid in 55% yield. $^1$H NMR (CDCl$_3$, 400 MHz) δ (ppm) 1.40 (d, J=6.91 Hz, 6H), 2.80 (s, 3H), 3.17-3.24 (m, 1H), 3.89 (s, 3H), 7.00 (s, 1H), 7.21 (m, 1H), 7.55 (s, 1H), 7.79 (s, 1H), 9.56 (brs, 1H).

Example 17

Preparation of Substituted Quinolines 236

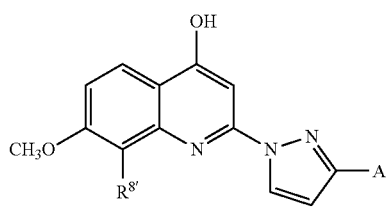

236a: R$^{8'}$ = Cl, A = CF$_3$
236b: R$^{8'}$ = CH$_3$, A = iPr
236c: R$^{8'}$ = CH$_3$, A = CF$_3$
236d: R$^{8'}$ = Cl, A = iPr

The syntheses of substituted quinolines 236 are illustrated in Schemes 11 and 12, where R$^{8'}$ and A in compound 234 and 235 are each as defined in compounds 236.

Method A:

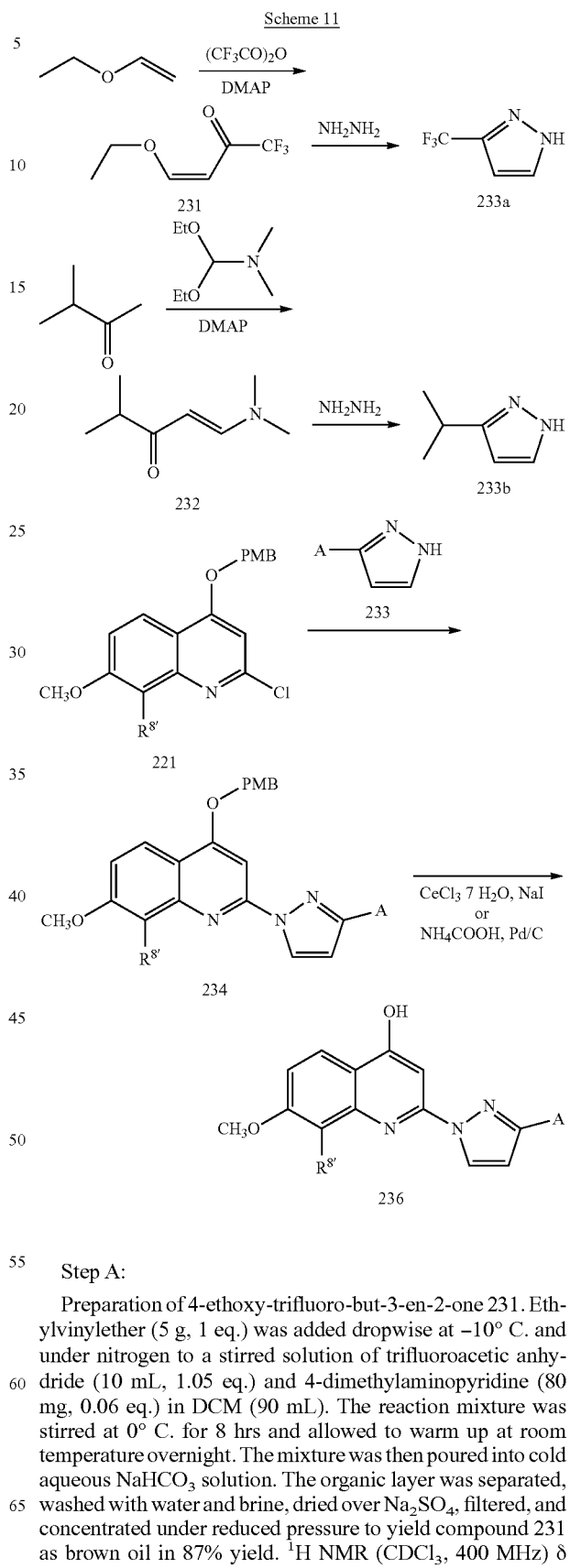

Step A:

Preparation of 4-ethoxy-trifluoro-but-3-en-2-one 231. Ethylvinylether (5 g, 1 eq.) was added dropwise at −10° C. and under nitrogen to a stirred solution of trifluoroacetic anhydride (10 mL, 1.05 eq.) and 4-dimethylaminopyridine (80 mg, 0.06 eq.) in DCM (90 mL). The reaction mixture was stirred at 0° C. for 8 hrs and allowed to warm up at room temperature overnight. The mixture was then poured into cold aqueous NaHCO$_3$ solution. The organic layer was separated, washed with water and brine, dried over Na$_2$SO$_4$, filtered, and concentrated under reduced pressure to yield compound 231 as brown oil in 87% yield. $^1$H NMR (CDCl$_3$, 400 MHz) δ

(ppm) 1.39-1.43 (t, J=7.04 Hz, 3H), 4.08-4.13 (q, J=7.04 Hz, 2H), 5.86 (d, J=12.40 Hz, 1H), 7.90 (d, J=12.40 Hz, 1H).

Step B:

Preparation of 3-trifluoromethyl-1H-pyrazole 233a. To a stirred solution of hydrazine monochloride (6.62 g, 1.6 eq.) in EtOH (300 mL) was added dropwise compound 231 (10.16 g, 1 eq.) in EtOH (200 mL). The reaction mixture was refluxed for 6 hrs and evaporated to dryness. Water and EtOAc were added to the residue. The organic layer was washed with water and brine, dried over $Na_2SO_4$, filtered, and concentrated under reduced pressure to yield compound 233a as a brown solid in 86% yield. $^1H$ NMR ($CDCl_3$, 376 MHz) δ (ppm) 6.66 (d, J=2.30 Hz, 1H), 7.72 (d, J=2.30 Hz, 1H); $^{19}F$ NMR ($CDCl_3$, MHz) δ (ppm) 61.41 (s, 3F).

Step C:

Preparation of 1-dimethylamino-4-methyl-pent-1-en-3-one 232. 3-Methylbutan-2-one (2.5 g, 1 eq.) and dimethylformamide diethylacetal (7.46 mL, 1.5 eq.) were heated at 100° C. for 4 days to give compound 232 as yellow viscous oil in 80% yield, which was used directly without further purification in the next step. $^1H$ NMR (DMSO-$d_6$, 400 MHz) δ (ppm) 0.94 (s, 3H), 0.95 (s, 3H), 2.52 (s, 1H), 2.74 (brs, 3H), 3.01 (brs, 3H), 4.96 (d, J=12.97 Hz, 1H), 7.45 (d, J=12.97 Hz, 1H).

Step D:

Preparation of 3-isopropyl-1H-pyrazole 233b. Compound 232 (6.6 g, 1 eq.) was added dropwise to a stirred solution of hydrazine monochloride (3.2 g, 1 eq.), sulfuric acid (1.13 mL), and $H_2O$ (6 mL). The mixture was stirred at 68° C. for 2 hrs. The mixture was then neutralized with 1N NaOH and extracted with diethyl ether. The organic layer was dried over $Na_2SO_4$, filtered, and concentrated under reduced pressure to yield compound 233b as a beige solid in 94% yield. $^1H$ NMR (DMSO-$d_6$, 400 MHz) δ (ppm) 1.17 (s, 3H), 1.19 (s, 3H), 2.87-2.93 (m, 1H). 5.99 (s, 1H), 7.40 (s, 1H), 1.39-1.43 (t, J=7.04 Hz, 3H). 4.08-4.13 (q, J=7.04 Hz, 2H), 5.86 (d, 1=12.40 Hz, 1H), 7.90 (d, J=12.40 Hz, 1H).

Step E:

Preparation of 8-chloro-7-methoxy-4-(4-methoxy-benzyloxy)-2-(3-trifluoromethyl-1H-pyrazol-1-yl)-quinoline 234a. To a stirred solution of compound 233a (821 mg, 1.1 eq.) in anhydrous DMF (20 mL) at 0° C. was added NaH (241 mg, 1.1 eq.) portionwise. After the reaction mixture was stirred for 1 hr at room temperature, compound 221d (2 g, 1 eq.) was added and the mixture was stirred at 90° C. for 16 hrs. After the reaction mixture was cooled to room temperature, EtOAc was added. The organic phase was washed with HCl (2.5 N), dried over $Na_2SO_4$, filtered, and concentrated under reduced pressure. The crude material was purified by chromatography on silica gel (petroleum ether/DCM, 50/50) to give compound 234a as a white solid in 51% yield. MS (ESI, EI$^+$): m/z=461.9 (MH$^-$).

7-Methoxy-4-(4-methoxy-benzyloxy)-8-methyl-2-(3-trifluoromethyl-1H-pyrazol-1-yl)-quinoline 234c was synthesized from compounds 221b and 233a, following the procedure as described for compound 234a, as a white solid in 19% yield. $^1H$ NMR ($CDCl_3$, 400 MHz) δ (ppm) 2.64 (s, 3H), 3.86 (s, 3H), 3.99 (s, 3H), 5.33 (s, 214), 6.75 (d, J=2.58 Hz, 1H), 6.98 (d, J=8.78 Hz, 2H), 7.20 (d, J=9.22 Hz, 1H), 7.48 (d, J=8.78 Hz, 2H), 7.57 (s, 1H), 8.07 (d, J=9.08 Hz, 1H), 8.88 (s, 1H).

Step F:

Preparation of 8-chloro-4-hydroxy-7-methoxy-2-(3-trifluoromethyl-1H-pyrazol-1-yl)-quinoline 236a. Compound 234a (800 mg, 1 eq.), $CeCl_3.7H_2O$ (965 mg, 1.5 eq.), and NaI (258 mg, 1 eq.) in ACN (10 mL) were stirred at 85° C. for 1 hr under microwave irradiation. Water was added and the mixture was acidified with 1N HCl to pH 5. The reaction mixture was extracted with diethyl ether. The organic layer was dried over $Na_2SO_4$, filtered, and concentrated under reduced pressure. The crude material was purified by chromatography on silica gel (MeOH/DCM) to give compound 236a as a beige solid in 96% yield. $^1H$ NMR (DMSO-$d_6$, 400 MHz) δ (ppm) 4.02 (s, 3H), 7.07 (s, 1H), 7.43 (s, 1H), 7.51 (d, J=9.11 Hz, 1H), 8.11 (d, J=9.11 Hz, 1H), 8.88 (s, 1H); MS (ESI, EI$^+$): m/z=343.9 (MH$^+$).

Step G:

Preparation of 4-hydroxy-7-methoxy-8-methyl-2-(3-isopropyl-pyrazol-1-yl)-quinoline 236b. A solution of compound 233b (350 mg, 1 eq.) and compound 221b (480 mg, 6 eq.) in N-methylpyrrolidone (5 mL) was heated at 200° C. for 30 min. After the reaction mixture was cooled to room temperature, water was added. The mixture was extracted with EtOAc, dried over $Na_2SO_4$, filtered, and concentrated under reduced pressure. The crude material was purified by chromatography on silica gel (EtOAc/DCM). Recrystallisation in diethylether gave compound 236b as a white solid in 49% yield. $^1H$ NMR ($CDCl_3$, 376 MHz) δ (ppm) 1.35 (s, 3H), 1.36 (s, 3H), 2.85 (s, 3H), 3.97 (s, 3H), 6.40 (d, J=2.65 Hz, 2H), 7.01 (d, J=9.00 Hz, 1H), 8.00 (brs, 1H), 8.23 (d, J=9.00 Hz, 1H), 9.81 (brs, 1H); MS (ESI, EI$^+$): m/z=298 (MH$^+$).

Step H:

Preparation of 4-hydroxy-7-methoxy-8-methyl-2-(3-trifluoromethyl-1H-pyrazol-1-yl)-quinoline 236c. A mixture of compound 234c (885 mg, 1.99 mmol), ammonium formate (629 mg, 9.98 mmol), and Pd/C (89 mg, 10% w) in EtOH (16 mL) was refluxed for 1 hr. The reaction was then filtered though celite and concentrated under reduced pressure. The residue was diluted with DCM and washed with water. Organics were dried over $Na_2SO_4$, filtered, concentrated under reduced pressure, and purified by chromatography on silica gel (petroleum ether/EtOAc) to yield compound 236c as a white solid in 93% yield. $^1H$ NMR (DMSO-$d_6$, 400 MHz) δ (ppm) 2.54 (s, 3H), 3.94 (s, 3H), 7.06 (d, J=2.48 Hz, 1H), 7.37-7.40 (m, 2H), 8.02 (d, J=9.18 Hz, 1H), 8.97 (s, 1H), 11.89 (s, 1H).

Step I:

Preparation of 8-chloro-4-hydroxy-7-methoxy-2-(3-isopropyl-1H-pyrazol-1-yl)-quinoline 236d. A mixture of compound 221a (500 mg, 1.37 mmol) and compound 233b (452 mg, 4.11 mmol) in N-methylpyrrolidone (2 mL) was stirred at 200° C. for 30 min under microwave radiation. After the reaction mixture was cooled to room temperature, water was added. The reaction mixture was then extracted with EtOAc, dried over $Na_2SO_4$, filtered, concentrated under reduced pressure, and purified by chromatography on silica gel (DCM/EtOAc) to yield compound 236d as a white solid in 35% yield. $^1H$ NMR (DMSO-$d_6$, 400 MHz) δ (ppm) 1.26 (s, 3H), 1.28 (s, 3H), 2.98-3.01 (m, 1H), 4.00 (s, 3H), 6.46 (m, 1H), 7.16 (d, 9.32 Hz, 1H), 7.89 (d, J=9.32 Hz, 1H), 8.05 (d, J=10.85 Hz, 1H), 8.60 (m, 1H), 10.69 (s, 1H).

Method B:

Step A:

Preparation of 4,8-dichloro-7-methoxy-2-(3-(trifluoromethyl)-1H-pyrazol-1-yl)quinoline 235a. A mixture of compound 220d (5 g, 19 mmol) and 3-trifluoromethyl)pyrazole 233a (7.76 g, 57 mmol) was heated at 120° C. for 4-6 hrs and the reaction was followed by LCMS and TLC. The reaction mixture was purified by silica gel column (mono and dipyrazole were separated) using DCM and heptane as mobile phase to yield compound 235a (3.5 g) in 51% yield.

Scheme 12

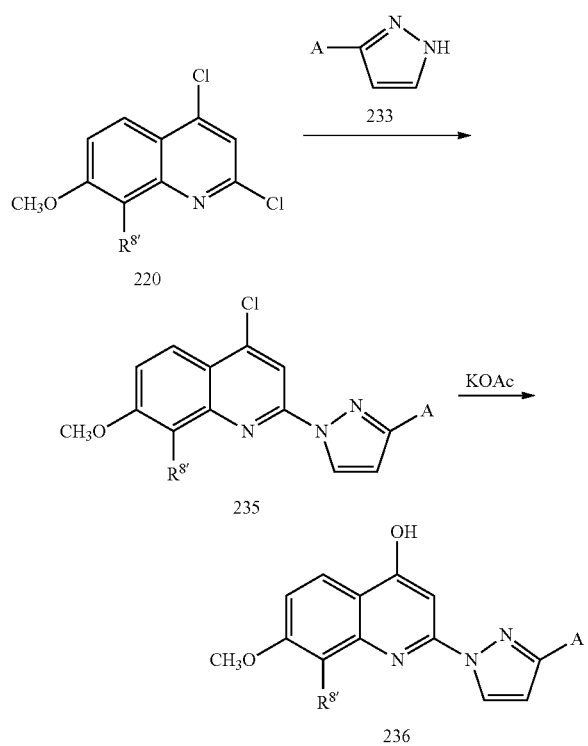

Step B:
Preparation of 8-chloro-7-methoxy-2-(3-(trifluoromethyl)-1H-pyrazol-1-yl)quinolin-4-ol 236a. To a solution of compound 235a (250 mg) in DMSO (2.5 mL) was added $CH_3COOK$ (3 eq.), water (2 eq.). The reaction mixture was heated to 140° C. for 4 hrs. After cooled to RT, water (1 mL) was added to the reaction mixture slowly under stirring. Solid was filtered and washed with water to yield compound 236a in >80% yield. In a separate reaction, when 5 eq. of $CH_3COOK$ was used, the reaction was completed in 1 hr.

Example 18

Preparation of Substituted Quinolines 242

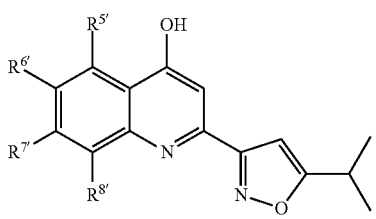

242a: $R^{5'} = H, R^{6'} = H, R^{7'} = OCH_3, R^{8'} = H$
242b: $R^{5'} = H, R^{6'} = H, R^{7'} = OCH_3, R^{8'} = CH_3$
242c: $R^{5'} = H, R^{6'} = H, R^{7'} = OCH_3, R^{8'} = F$
242d: $R^{5'} = H, R^{6'} = H, R^{7'} = OCH_3, R^{8'} = Cl$
242e: $R^{5'} = OCH_3, R^{6'} = H, R^{7'} = OCH_3, R^{8'} = H$
242f: $R^{5'} = H, R^{6'} = OCH_3, R^{7'} = H, R^{8'} = CH_3$
242g: $R^{5'} = H, R^{6'} = OCH_3, R^{7'} = Cl, R^{8'} = H$
242h: $R^{5'} = H, R^{6'} = H, R^{7'} = OCH_3, R^{8'} = Br$

The syntheses of substituted quinolines 242 are illustrated with compound 242d as shown in Scheme 13, where $R^{5'}$, $R^{6'}$, $R^{7'}$, and $R^{8'}$ in compounds 201 and 241 are each as defined in compounds 242. The same procedures are also applicable to other compounds 242.

Scheme 13

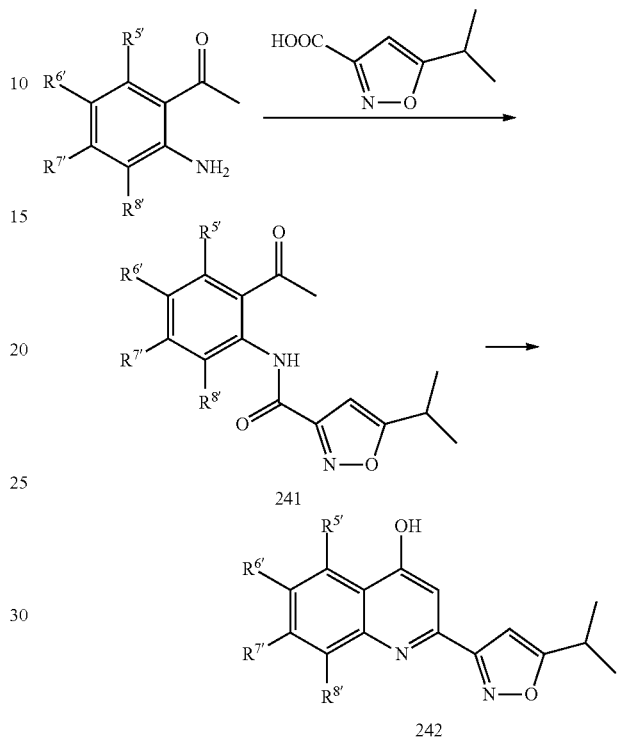

Step A:
Preparation of N-(6-acetyl-2-chloro-3-methoxyphenyl)-5-isopropylisoxazole-3-carboxamide 241d. To a stirred solution of 5-isopropylisoxazole-3-carboxylic acid (3.5 g, 22.6 mmol) in DCM (35 mL) was added anhydrous DMF (few drops) and oxalyl chloride (3.82 mL, 43.2 mmol) at 0° C. under nitrogen. At the end of the gas escape, the reaction mixture was allowed to warm up to room temperature. The mixture was stirred at room temperature for 2 hrs and was evaporated. Dioxane (70 mL) was added under nitrogen, followed by a solution of 1-(2-amino-3-chloro-4-methoxy-phenyl)-ethanone 201d (4.10 g, 20.6 mmol) in dioxane (15 mL). The reaction mixture was stirred at room temperature for 16 hrs. $NaHCO_3$ was then added. The mixture was extracted with EtOAc. Organics were dried over $Na_2SO_4$, filtered, and concentrated under reduced pressure. The crude material was triturated in $Et_2O$ to yield compound 241d as a brown solid in 60% yield. $^1H$ NMR ($CDCl_3$, 400 MHz) δ (ppm) 1.47 (s, 3H), 1.48 (s, 3H), 1.76 (brs, 1H), 2.57 (s, 3H), 3.34-3.40 (m, 1H), 3.98 (s, 3H), 6.86 (d, J=8.53 Hz, 1H), 7.64 (d, J=8.53 Hz, 1H), 8.07 (s, 1H).

Step B:
Preparation of 8-chloro-2(5-isopropyl-isoxazol-3-yl)-7-methoxy-quinolin-4-ol 242d was synthesized from compound 241d as a white solid in quantitative yield, following the procedure as described for compound 218a. $^1H$ NMR ($CDCl_3$, 400 MHz) δ (ppm) 1.39 (s, 3H), 1.41 (s, 3H), 3.17-3.31 (m, 1H), 4.06 (s, 3H), 6.36 (s, 1H), 6.59 (s, 1H), 7.06 (d, J=8.48 Hz, 1H), 8.28 (d, J=8.48 Hz, 1H), 9.42 (s, 1H).

Example 19

Preparation of Substituted Quinolines 244

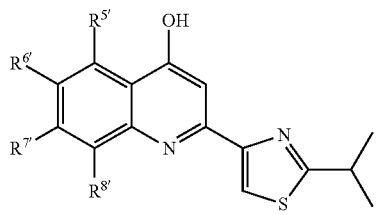

69a: $R^{5'}$ = H, $R^{6'}$ = H, $R^{7'}$ = OCH$_3$, $R^{8'}$ = H
69b: $R^{5'}$ = H, $R^{6'}$ = H, $R^{7'}$ = OCH$_3$, $R^{8'}$ = CH$_3$
69c: $R^{5'}$ = H, $R^{6'}$ = H, $R^{7'}$ = OCH$_3$, $R^{8'}$ = F
69d: $R^{5'}$ = H, $R^{6'}$ = H, $R^{7'}$ = OCH$_3$, $R^{8'}$ = Cl
69e: $R^{5'}$ = OCH$_3$, $R^{6'}$ = H, $R^{7'}$ = OCH$_3$, $R^{8'}$ = H
69f: $R^{5'}$ = H, $R^{6'}$ = OCH$_3$, $R^{7'}$ = H, $R^{8'}$ = CH$_3$
69g: $R^{5'}$ = H, $R^{6'}$ = OCH$_3$, $R^{7'}$ = Cl, $R^{8'}$ = H
69h: $R^{5'}$ = H, $R^{6'}$ = H, $R^{7'}$ = OCH$_3$, $R^{8'}$ = Br

The syntheses of substituted quinolines 244 are illustrated with compound 244d as shown in Scheme 14, where $R^{5'}$, $R^{6'}$, $R^{7'}$, and $R^{8'}$ in compounds 201 and 243 are each as defined in compounds 244. The same procedures are also applicable to other compounds 244.

Step A:

Preparation of N-(6-acetyl-2-chloro-3-methoxyphenyl)-2-isopropylthiazole-4-carboxamide 243d. To a stirred solution of 2-isopropyl-1,3-thiazol-4-carboxylic acid (3.5 g, 20.4 mmol) in DCM (35 mL) was added oxalyl chloride (3.46 mL, 40.9 mmol) with a few drop of anhydrous DMF at 0° C. At the end of gas escape, the mixture was allowed to warm up at room temperature and then stirred for 2 hrs. The reaction mixture was concentrated under reduced pressure and solubilized in dioxane (70 mL). A solution of 1-(2-amino-3-chloro-4-methoxy-phenyl)-ethanone 201d (3.71 g, 18.6 mmol) in dioxane (15 mL) was then slowly added. The mixture was stirred at room temperature for 16 hrs. NaHCO$_3$ was added. The mixture was extracted with EtOAc, dried over Na$_2$SO$_4$, filtered, and concentrated under reduced pressure. The crude material was triturated in diethyl ether to yield compound 243b in 60% yield. $^1$H NMR (CDCl$_3$, 400 MHz) δ (ppm) 1.47 (s, 3H), 1.48 (s, 3H), 2.57 (s, 3H), 3.34-3.41 (quint, J=6.90 Hz, 1H), 3.98 (s, 3H), 6.86 (d, J=8.48 Hz, 1H), 7.64 (d, 8.48 Hz, 1H), 8.07 (s, 1H); MS (ESI, EI$^+$): m/z=351 (MH$^-$).

Scheme 14

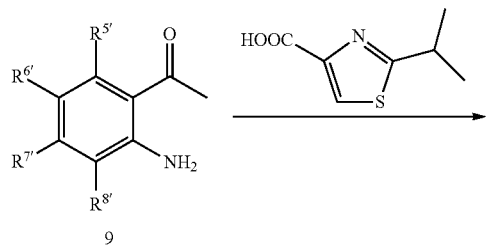

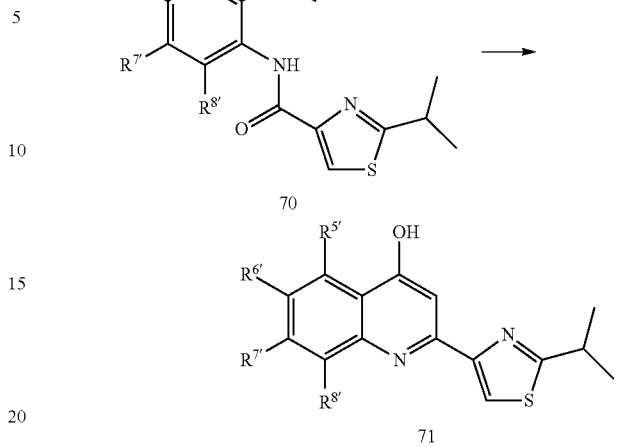

Step B:

Preparation of 8-chloro-2-(2-isopropyl-thiazol-4-yl)-7-methoxy-quinolin-4-ol 244d. Compound 243d (352 mg, 1 mmol) and potassium tert-butoxide (236 mg, 2.1 mmol) in tert-butyl alcohol (10 mL) were stirred in a sealed vessel at 120° C. for 1 hr under microwave radiations. The mixture was then poured into diethyl ether, acidified with 2.5N HCl to pH 5 and extracted with ethyl acetate, and concentrated under reduced pressure to yield compound 244b in 82% yield. $^1$H NMR (CDCl$_3$, 400 MHz) δ (ppm) 1.49 (s, 3H), 1.51 (s, 3H), 3.38-3.45 (quint, J=6.90 Hz, 1H), 4.06 (s, 3H), 6.70 (brs, 1H), 7.05 (d, J=9.35 Hz, 1H), 7.76 (s, 1H).

Example 20

Preparation of Substituted Quinolines 250

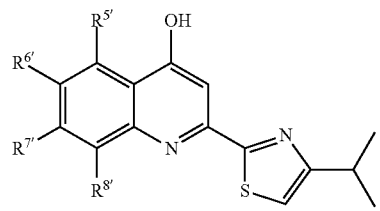

250a: $R^{5'}$ = H, $R^{6'}$ = H, $R^{7'}$ = OCH$_3$, $R^{8'}$ = H
250b: $R^{5'}$ = H, $R^{6'}$ = H, $R^{7'}$ = OCH$_3$, $R^{8'}$ = CH$_3$
250c: $R^{5'}$ = H, $R^{6'}$ = H, $R^{7'}$ = OCH$_3$, $R^{8'}$ = F
250d: $R^{5'}$ = H, $R^{6'}$ = H, $R^{7'}$ = OCH$_3$, $R^{8'}$ = Cl
250e: $R^{5'}$ = OCH$_3$, $R^{6'}$ = H, $R^{7'}$ = OCH$_3$, $R^{8'}$ = H
250f: $R^{5'}$ = H, $R^{6'}$ = OCH$_3$, $R^{7'}$ = H, $R^{8'}$ = CH$_3$
250g: $R^{5'}$ = H, $R^{6'}$ = OCH$_3$, $R^{7'}$ = Cl, $R^{8'}$ = H
250h: $R^{5'}$ = H, $R^{6'}$ = H, $R^{7'}$ = OCH$_3$, $R^{8'}$ = Br

The syntheses of substituted quinolines 250 are illustrated with compound 250d as shown in Scheme 15, where $R^{5'}$, $R^{6'}$, $R^{7'}$, and $R^{8'}$ in compounds 215 and 245 to 249 are the same as defined in compounds 250. The same procedures are also applicable to other compounds 250.

Step A:

Preparation of N-(2-chloro-3-methoxyphenyl)-2-hydroxyimino-acetamide 245d. To a stirred solution of sodium sulfate (58.5 g, 412 mmol) in water (100 mL) was added a solution of chlorahydrate (9.36 g, 56.6 mmol) in water (120 mL). Chloroanisidine 215d (10 g, 51.5 mmol) was added followed by 37% HCl (20 mL). A solution of hydroxylamine (50% in water, 4.7 mL, 154.5 mmol) in 50 mL was then added and the reaction mixture was refluxed for 90 min. The suspended solid was filtered off, and washed with water and ether. Organics were dried over $Na_2SO_4$, filtered, and concentrated under reduced pressure to yield compound 245d as a brown solid. $^1$H NMR (DMSO-$d_6$, 400 MHz) δ (ppm) 3.86 (s, 3H), 6.98 (d, J=8.07 Hz, 1H), 7.31 (t, J=8.07 Hz, 1H), 7.61 (d, J=8.07 Hz, 1H), 7.66 (s, 1H), 9.43 (s, 1H), 12.43 (s, 1H).

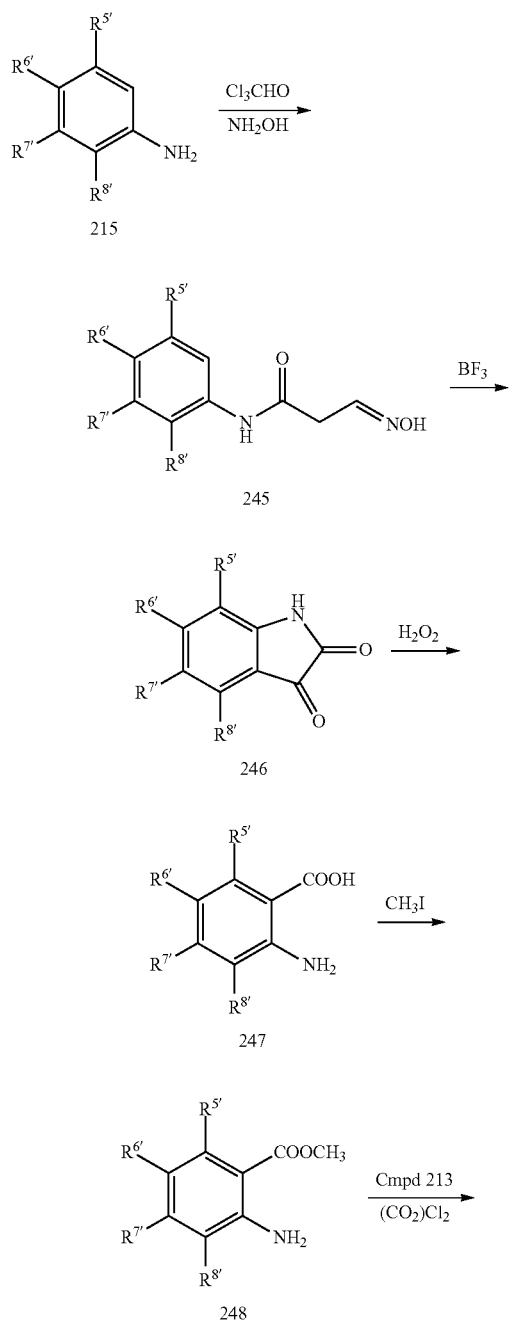

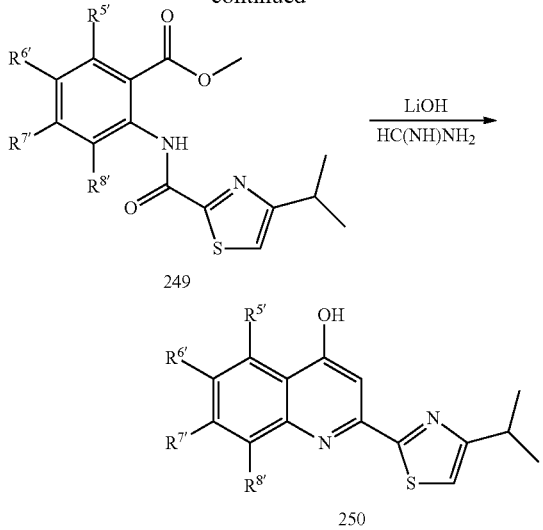

Step B:

Preparation of 7-chloro-6-methoxy-1H-indole-2,3-dione 246d. Compound 245d (10.46 g, 45.74 mmol) was added portionwise to $BF_3 \cdot Et_2O$ at 40° C. The mixture was then heated at 90° C. for 3 hrs. After cooling down to room temperature, the reaction mixture was poured into crushed ice and extracted with EtOAc. Organics were dried over $Na_2SO_4$, filtered, concentrated under reduced pressure, and purified by chromatography on silica gel (petroleum ether/EtOAc). The compound obtained was recrystallised from EtOH to yield compound 246d as a brown solid in 63% yield. $^1$H NMR (DMSO-$d_6$, 400 MHz) δ (ppm) 3.96 (s, 3H), 6.79 (d, J=9.10 Hz, 1H), 7.52 (d, J=9.10 Hz, 1H), 11.40 (s, 1H).

Step C:

Preparation of 2-amino-3-chloro-4-methoxy benzoic acid 247d. A suspension of compound 246d (6.03 g, 28.52 mmol), NaOH (1.25 g, 31.37 mmol), and NaCl (3.49 g, 59.89 mmol) in water (60 mL) was stirred at room temperature for 30 min and was then ice-cooled. $H_2O_2$ was added dropwise. The mixture was stirred at 0° C. for 20 min and at room temperature for 3 hrs. The reaction mixture was quenched with glacial AcOH, filtered, and washed with water. The solid obtained was dissolved in DCM, dried over $Na_2SO_4$, filtered, and concentrated under reduced pressure. The crude material was purified by chromatography on silica gel (DCM/MeOH) to yield compound 247d as an orange solid in 36% yield. $^1$H NMR (DMSO-$d_6$, 400 MHz) δ (ppm) 3.85 (s, 3H), 6.41 (d, J=9.05 Hz, 1H), 6.77 (brs, 2H), 7.74 (d, J=9.05 Hz, 1H), 12.7 (brs, 1H).

Step D:

Preparation of 2-amino-3-chloro-4-methoxy benzoic acid methyl ester 248d. To a stirred solution of compound 247d (1.9 g, 9.6 mmol) in dry DMF (25 mL) was added $K_2CO_3$ (1.32 g, 9.6 mmol) at room temperature. The reaction mixture was stirred for 30 min and methyl iodide (0.77 mL, 12.4 mmol) was added. After 2 hrs at room temperature, 5% aqueous citric acid was added. The mixture was extracted with EtOAc. Organics were washed with water, dried over $Na_2SO_4$, filtered, concentrated under reduced pressure, and purified by chromatography on silica gel (petroleum ether/ EtOAc) to yield compound 248d as beige solid in 50% yield. $^1$H NMR (CDCl$_3$, 400 MHz) δ (ppm) 3.79 (s, 3H), 3.86 (s, 3H), 6.23 (d, J=9.03 Hz, 1H), 7.75 (d, J=9.03 Hz, 1H).

Step E:

Preparation of methyl 3-chloro-2-(4-isopropylthiazole-2-carboxamido)-4-methoxybenzoate 249d. To a stirred solution of compound 213 (758 mg, 4.28 mmol) in dry DCM was added oxalyl chloride (720 µL, 8.56 mmol) and few drops of DMF at 0° C. The reaction mixture was stirred at 0° C. for 30 min and at room temperature for 2 hrs. The mixture was filtered, concentrated under reduced pressure, and dissolved in dioxane (3 mL). Compound 248d (770 mg, 3.56 mmol) in dioxane (6 mL) was then added. The reaction mixture was stirred at room temperature for 16 hrs. Solvent was evaporated. Water was added to the mixture. The reaction mixture was extracted with EtOAc. Organics were dried over $Na_2SO_4$, filtered, concentrated under reduced pressure, and purified by chromatography on silica gel (petroleum ether/EtOAc) to yield compound 249d as a pale yellow solid in 92% yield. $^1$H NMR ($CDCl_3$, 400 MHz) δ (ppm) 1.19 (d, J=6.63 Hz, 6H), 3.09-3.16 (m, 1H), 3.79 (s, 3H), 3.91 (s, 3H), 6.82 (d, J=9.02 Hz, 1H), 7.19 (s, 1H), 7.82 (d, J=9.02 Hz, 1H), 9.97 (s, 1H).

Step F:

Preparation of 8-chloro-2-(4-isopropyl-thiazol-2-yl)-7-methoxy-quinazolin-4-ol 250d. To a stirred solution of compound 249d (1.32 g, 3.58 mmol) in $EtOH/H_2O$ (1/1, 10 mL) was added LiOH (10.3 mg, 4.29 mmol). The reaction mixture was stirred at 60° C. for 2 hrs. An aqueous solution of citric acid (5%) was added and the mixture was extracted with EtOAc. Organic were dried over $Na_2SO_4$, filtered, and concentrated under reduced pressure. The residue was stirred with formamidine (26 mL) at 150° C. for 4 hrs, and the mixture was allowed to cool down to room temperature overnight. The mixture was poured into water, and extracted with DCM. Organics were dried over $Na_2SO_4$, filtered, concentrated under reduced pressure, and purified by chromatography on silica gel (petroleum ether/EtOAc) to yield compound 250d as beige solid in 58% yield. $^1$H NMR (DMSO-$d_6$, 400 MHz) δ (ppm) 1.32 (d, J=6.71 Hz, 6H), 3.09-3.15 (m, 1H), 4.01 (s, 3H), 7.42 (d, J=9.03 Hz, 1H), 7.67 (s, 1H), 8.11 (d, J=9.03 Hz, 1H), 12.42 (s, 1H).

Example 21

Preparation of Substituted Quinolines 255

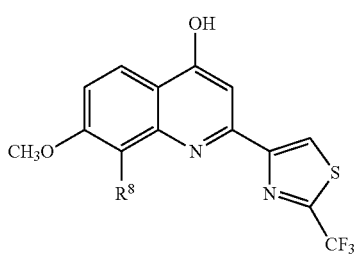

255a: $R^8$ = Cl
255b: $R^8$ = $CH_3$

Substituted quinolines 255 were synthesized as shown in Scheme 16.

Step A:

Preparation of 2-(trifluoromethylthiazole)-4-carboxylic acid ethyl ester 251. A solution of 2,2,2-trifluoroacetamide (14.24 g, 1 eq.) and Lawesson's reagent (30.6 g, 0.6 eq.) in THF (120 mL) was stirred at reflux for 18 hrs. The mixture was cooled, ethyl bromopyruvate (16 mL, 1 eq.) was added and the reaction refluxed for weekend. The reaction was cooled, evaporated in vacuum, and the resulting crude material extracted with dichloromethane and washed with water. The organic layer was dried over $Na_2SO_4$, filtered, and concentrated to give an orange oil. The oil was purified by chromatography on a silica gel (petroleum ether/dichloromethane) to yield compound 251 in 40% yield. $^1$H NMR (DMSO-$d_6$, 400 MHz): δ (ppm) 1.32 (t, J=7.10 Hz, 3H), 4.34 (q, J=7.10 Hz, 2H), 8.9 (s, 114); $^{19}$F NMR (DMSO-$d_6$, 376 MHz): δ (ppm) −60.29 (s, 3F); MS (ESI, EI$^+$): m/z=225.9 (MH$^+$).

Scheme 16

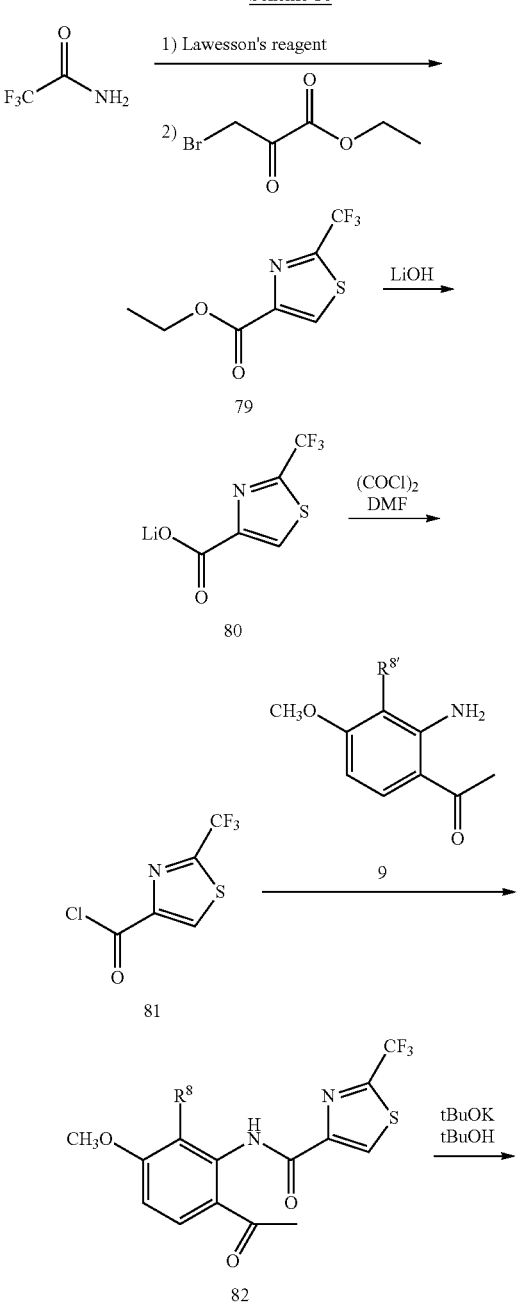

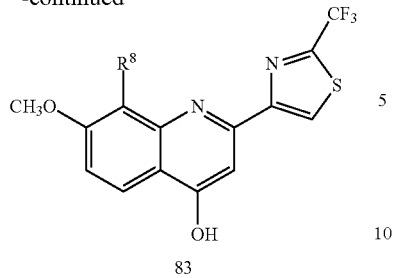

83

Step B:

Preparation of lithium 2-(trifluoromethyl)thiazole-4-carboxylate 252. Compound 252 was synthesized from compound 251 (12.14 g, 1 eq.) as a pink solid in 75% yield, following the procedure as described for compound 213. MS (ESI, EI+): m/z=198 (MH+).

Step C:

Preparation of N-(6-acetyl-2-chloro-3-methoxyphenyl)-2-(trifluoromethyl)thiazole-4-carboxamide 254a. Oxalyl chloride (1.9 mL, 1.4 eq.) was added dropwise under nitrogen at 0° C. to a suspension of compound 252 (4 g, 1.2 eq.) in DCM (120 mL) and DMF (few drops). The reaction mixture was stirred at 0° C. for 30 min and then at room temperature for additional 3 hrs. The solid was removed by filtration under nitrogen and the filtrate was evaporated to give a yellow oil. This oil was solubilised in dioxane (30 mL) and added under nitrogen to a solution of 6-acetyl-2-chloro-3-methoxy aniline 201d (3.26 g, 1 eq.) in 1,4-dioxane (60 mL). The reaction mixture was stirred at room temperature for 3 days. The solvent was removed under reduced pressure, the residue was solubilised in dichloromethane, washed with water, dried over Na$_2$SO$_4$ and concentrated in vacuum. The crude oil was triturated in MeOH/Et$_2$O mixture to give the compound 254a as a white solid in 69% yield. $^1$H NMR (CDCl$_3$, 400 MHz): δ (ppm) 2.59 (s, 3H), 4 (s, 3H), 6.90 (d, J=8.75 Hz, 1H), 7.70 (d, J=8.75 Hz, 1H), 8.44 (s, 1H), 10.28 (s, 1H); $^{19}$F NMR (CDCl$_3$, 376 MHz): δ (ppm) −61.08 (s, 3F).

N-(6-Acetyl-3-methoxy-2-methylphenyl)-4-(2-trifluoromethyl)thiazole-4-carboxamide 254b was synthesized from compound 253 (5.2 g, 1.2 eq.) and 6-acetyl-3-methoxy-2-methyl aniline 201b (3.6 g, 1 eq.) as a white solid in 52% yield, following the procedure as described for compound 254a. $^1$H NMR (DMSO-d$_6$, 400 MHz): δ (ppm) 2.01 (s, 3H), 3.90 (s, 3H), 7.02 (d, J=8.81 Hz, 1H), 7.81 (d, J=8.81 Hz, 1H), 8.82 (s, 1H); MS (ESI, EI+): m/z=381 (MNa+).

Step D:

Preparation of 8-chloro-2-(2-(trifluoromethyl)thiazol-4-yl)-7-methoxyquinolin-4-ol 255a. Compound 255a (white solid) was synthesized from compound 254a (1 g, 1 eq.) in 26% yield, following the procedure as described for compound 209a. $^1$H NMR (CDCl$_3$, 400 MHz): δ (ppm) 4.07 (s, 3H), 6.78 (s, 1H), 7.09 (d, J=9.13 Hz, 1H), 8.14 (s, 1H), 8.30 (d, J=9.13 Hz, 1H), 9.93 (s, 1H); $^{19}$F NMR (CDCl$_3$, 376 MHz): δ (ppm) −61.14 (s, 3F); MS (ESI, EI+): m/z=360.91 (MH+).

7-Methoxy-8-methyl-2-(2-trifluoromethyl-thiazol-4-yl)quinolin-4-ol 255b was synthesized from compound 254b (3.76 g, 1 eq.) as a brown solid in 52% yield, following the procedure as described for compound 209a (80° C. overnight). $^1$H NMR (CDCl$_3$, 400 MHz): δ (ppm) 2.42 (s, 3H), 3.98 (s, 3H), 6.72 (s, 1H), 7.04 (d, J=9.02 Hz, 1H), 8.10 (s, 1H), 8.25 (d, J=9.02 Hz, 1H), 9.45 (br s, 1H); MS (ESI, EI+): m/z=341.06 (MH+).

Example 22

Preparation of 8-chloro-2-(4-cyanothiazol-2-yl)-7-methoxy-quinolin-4-ol 263

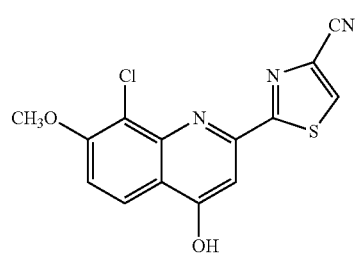

Compound 263 was synthesized as shown in Scheme 17.

Scheme 17

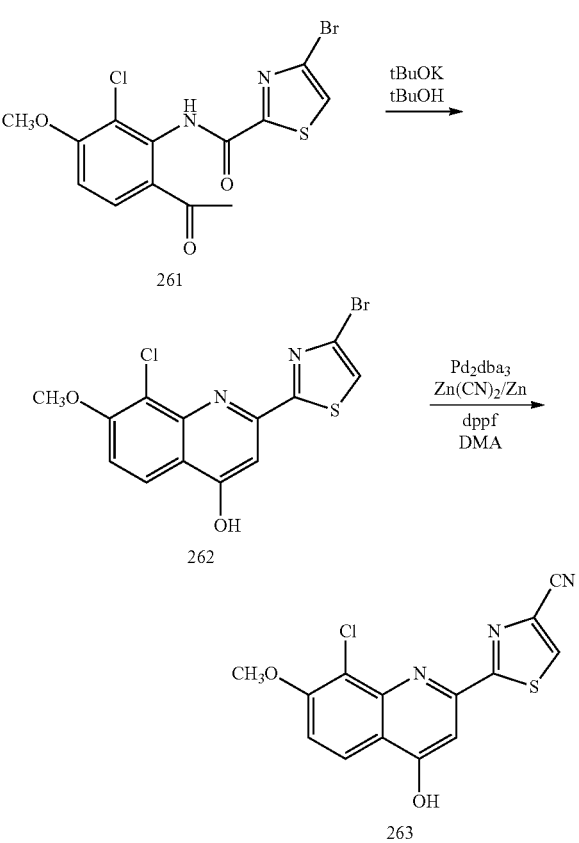

Step A:

Preparation of 2-(4-bromothiazol-2-yl)-8-chloro-7-methoxy-quinolin-4-ol 262. Compound 262 was synthesized from compound 261 (2 g, 1 eq.) as a yellow solid in 92% yield, following the procedure as described for compound 209a (80° C. overnight). $^1$H NMR (CDCl$_3$, 400 MHz) δ (ppm) 4.06 (s, 3H), 6.73 (s, 1H), 7.07 (d, J=9.10 Hz, 1H), 7.46 (s, 1H), 8.27 (d, J=9.10 Hz, 1H), 9.74 (br s, 1H); MS (ESI, EI+): m/z=372.90 (MH+).

Step B:

Preparation of 8-chloro-2-(4-cyanothiazol-2-yl)-7-methoxy-quinolin-4-ol 263. The compound 262 (286 mg, 1 eq.) in degazed dimethylacetamide (10 mL), and Zn (4.5 mg, 0.09 eq.), Zn(CN)$_2$ (84 mg, 0.6 eq.), Pd$_2$dba$_3$ (21 mg, 0.03 eq.), and dppf (26 mg, 0.06 eq.) were heated at 110° C. under microwaves for 30 min. Then, water was added, the precipitate filtered and dissolved in ethyl acetate, dried, and concentrated under vacuum. The residue was purified by chromatography on a silica gel to give compound 263 as a yellow solid in 81% yield. $^1$H NMR (CDCl$_3$, 400 MHz) δ (ppm) 4.07 (s, 3H), 6.79 (br s, 1H), 7.08 (d, J=9.11 Hz, 1H), 8.19 (s, 1H), 8.28 (d, J=9.11 Hz, 1H), 9.74 (br s, 1H); MS (ESI, EI$^+$): m/z=318.15 (MH$^+$).

Example 23

Preparation of Substituted Quinolines 269

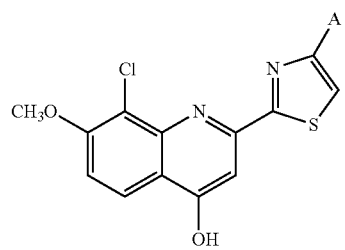

Substituted Quinolines 269 were synthesized as shown in Scheme 18.

Scheme 18

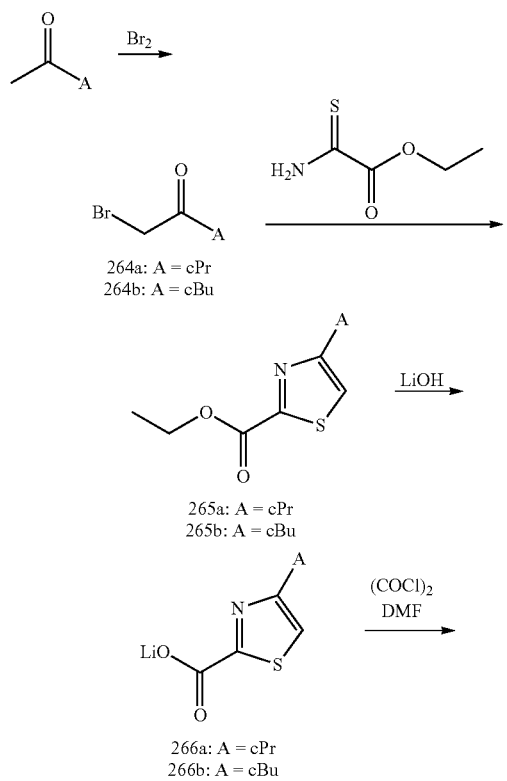

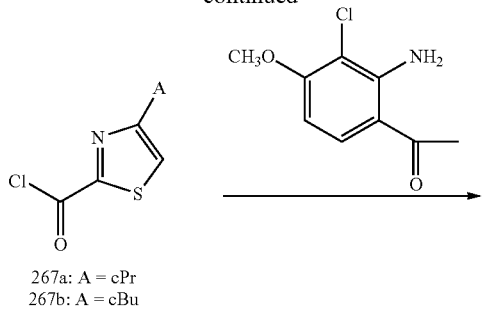

267a: A = cPr
267b: A = cBu

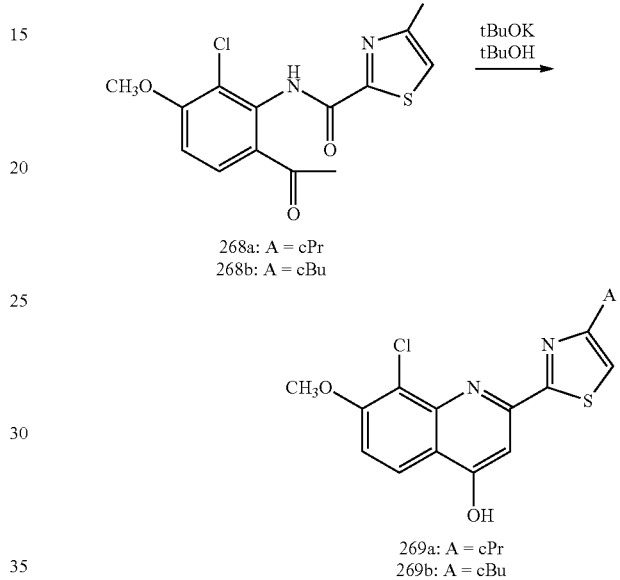

268a: A = cPr
268b: A = cBu

269a: A = cPr
269b: A = cBu

Step A:

Preparation of 2-bromo-1-cyclopropylethanone 264a. To a stirred ice-cooled solution of cyclopropyl methyl ketone (21 g, 1 eq.) in methanol (150 mL) was added dropwise bromine (12.9 ml, 1 eq.). The reaction was allowed to proceed (decolorization) below 10° C. Stirring was continued at room temperature for 1 hr before adding water (75 mL). After an additional 15 min, the mixture was diluted with water (225 mL) and extracted with ethyl ether (two times). Ether layers were washed with 10% Na$_2$CO$_3$ solution and brine. Dried organic layers were evaporated in vacuo to yield a crude orange oil, purified by distillation to yield compound 264a as a colorless oil in 52% yield. $^1$H NMR (CDCl$_3$, 400 MHz): δ (ppm) 0.98-1.02 (m, 2H), 1.09-1.13 (m, 2H), 2.15-2.22 (m, 1H), 4 (s, 2H).

2-Bromo-1-cyclobutylylethanone 264b was synthesized from cyclobutyl methyl ketone (22 g, 1 eq.) and bromine (11.5 mL, 1 eq.) as a yellow oil in 60% yield, following the procedure as described for compound 264a. $^1$H NMR (CDCl$_3$, 400 MHz): δ (ppm) 1.75-1.84 (m, 1H), 1.89-2 (m, 1H), 2.10-2.27 (m, 4H), 3.49-3.57 (m, 1H), 3.82 (s, 2H).

Step B:

Preparation of 4-cyclopropylthiazole-2-carboxylic acid ethyl ester 265a. Compound 265 was synthesized from compound 264a (10 g, 1.25 eq.) as a brown oil in 73% yield, following the procedure as described for compound 212. $^1$H NMR (DMSO-d$_6$, 400 MHz): δ (ppm) 0.80-0.84 (m, 2H), 0.92-0.97 (m, 2H), 1.30 (t, J=7.10 Hz, 3H), 2.13-2.20 (m, 1H), 4.34 (q, J=7.10 Hz, 2H), 7.70 (s, 1H); MS (ESI, EI$^+$): m/z=198 (MH$^+$).

4-Cyclobutylthiazole-2-carboxylic acid ethyl ester 265b was synthesized from compound 264b (23.87 g, 1 eq.) and ethyl thiooxamate (21.41 g, 1 eq.) as a yellow oil in 64% yield, following the procedure as described for compound 212. $^1$H NMR (DMSO-d$_6$, 400 MHz): δ (ppm) 1.32 (t, J=7.12 Hz, 3H), 1.82-1.89 (m, 1H), 1.92-2.02 (m, 1H), 2.15-2.33 (m, 4H), 3.65-3.74 (m, 1H), 4.36 (q, J=7.12 Hz, 2H), 7.76 (d, J=0.64 Hz, 1H); MS (ESI, EI$^+$): m/z=212 (MH$^+$).

Step C:

Preparation of Lithium 4-cyclopropylthiazole-2-carboxylate 266a. Compound 266a was synthesized from compound 265a (6 g, 1 eq.) as a brown solid in 91% yield, following the procedure as described for compound 213. $^1$H NMR (DMSO-d$_6$, 400 MHz): δ (ppm) 0.780-0.80 (m, 2H), 0.81-0.84 (m, 2H), 1.95-2.01 (m, 1H), 7.11 (s, 1H).

Lithium 4-cyclobutylthiazole-2-carboxylate 266b was synthesized from compound 265b (17.5 g, 1 eq.) as a beige solid in 97% yield, following the procedure as described for compound 213. $^1$H NMR (DMSO-d$_6$, 400 MHz): δ (ppm) 1.73-1.85 (m, 1H), 1.88-2 (m, 1H), 2.18-2.24 (m, 4H), 3.50-3.61 (m, 1H), 7.14 (s, 1H); MS (ESI, EI$^+$): m/z=184 (MH$^+$).

Step D:

Preparation of 4-cyclopropylthiazole-2-carbonyl chloride 267a. Compound 267a was synthesized from compound 266a (3 g, 1 eq.) as a brown solid in quantitative yield, following the procedure as described for compound 214. MS (ESI, EI$^+$): m/z=170 (MH$^+$).

4-Cyclobutylthiazole-2-carbonyl chloride 267b was synthesized from compound 266b (5 g, 1 eq.), following the procedure as described for compound 214. MS (ESI, EI$^+$): m/z=198 (MH$^+$).

Step E:

Preparation of N-(6-acetyl-2-chloro-3-methoxyphenyl)-4-cyclopropylthiazole-2-carboxamide 268a. To a solution of compound 267a (3.4 g, 1.2 eq.) in dioxane (60 mL) was added 6-acetyl-2-chloro-3-methoxy aniline 201d (3.01 g, 1 eq.) in dioxane. The mixture was stirred at room temperature overnight. Water was added and the mixture was extracted with ethyl acetate. The organic layer was dried over Na$_2$SO$_4$, filtered, and concentrated under vacuum. The residue was purified by chromatography on silica gel (petroleum ether/ethyl acetate) to yield compound 268a as a brown solid in 66% yield. $^1$H NMR (CDCl$_3$, 400 MHz): δ (ppm) 1-1.06 (m, 4H), 2.08-2.15 (m, 1H), 2.58 (s, 3H), 3.99 (s, 3H), 6.87 (d, J=8.78 Hz, 1H), 7.16 (s, 1H), 7.67 (d, J=8.78 Hz, 1H), 10.27 (br s, 1H); MS (ESI, EI$^+$): m/z=351 (MH$^+$).

N-(6-Acetyl-2-chloro-3-methoxyphenyl)-4-cyclobutylthiazole-2-carboxamide 268b was synthesized from compound 267b (5.48 g, 1.2 eq.) as a white solid in 70% yield, following the procedure as described for compound 268a. $^1$H NMR (CDCl$_3$, 400 MHz): δ (ppm) 1.96-2.12 (m, 2H), 2.34-2.44 (m, 4H), 2.59 (s, 3H), 3.70-3.78 (m, 1H), 3.99 (s, 3H), 6.88 (d, J=8.82 Hz, 1H), 7.20 (s, 1H), 7.68 (d, J=8.76 Hz, 1H), 10.33 (br s, 1H); MS (ESI, EI$^+$): m/z=365 (MH$^+$).

Step F:

Preparation of 8-chloro-7-methoxy-2-(4-cyclopropylthiazol-2-yl)quinolin-4-ol 269a. Compound 269a was synthesized from compound 268a (3.50 g, 1 eq) as an orange solid in 84% yield, following the procedure as described for compound 218a (80° C. overnight). $^1$H NMR (CDCl$_3$, 400 MHz): δ (ppm) 1.04-1.07 (m, 4H), 2.13-2.18 (m, 1H), 4.06 (s, 3H), 6.75 (s, 1H), 7.06 (d, J=9.10 Hz, 1H), 7.09 (s, 1H), 8.27 (d, J=9.10 Hz, 1H), 9.92 (br s, 1H); MS (ESI, EI$^+$): m/z=333.13 (MH$^+$).

8-Chloro-7-methoxy-2-(4-cyclobutylthiazol-2-yl)quinolin-4-ol 269b was synthesized from compound 268b (5.68 g, 1 eq.) as a beige solid in 84% yield, following the procedure as described for compound 218a (80° C. overnight). $^1$H NMR (DMSO-d$_6$, 400 MHz): δ (ppm) 1.87-1.95 (m, 1H), 1.96-2.07 (m, 1H), 2.23-2.35 (m, 4H), 3.67-3.76 (m, 1H), 4.02 (s, 3H), 7.51 (s, 1H), 7.53 (d, J=9.30 Hz, 1H), 7.63 (s, 1H), 8.11 (d, J=9.30 Hz, 1H), 11.89 (br s, 1H); MS (ESI, EI$^+$): m/z=347 (MH$^+$).

Example 24

Preparation of 8-chloro-7-methoxy-2-(4-vinylthiazol-2-yl)quinolin-4-ol 273

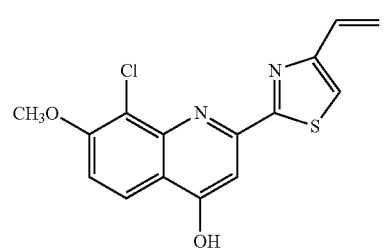

The synthesis of 8-chloro-7-methoxy-2-(4-vinylthiazol-2-yl)quinolin-4-ol 273 is shown in Scheme 19.

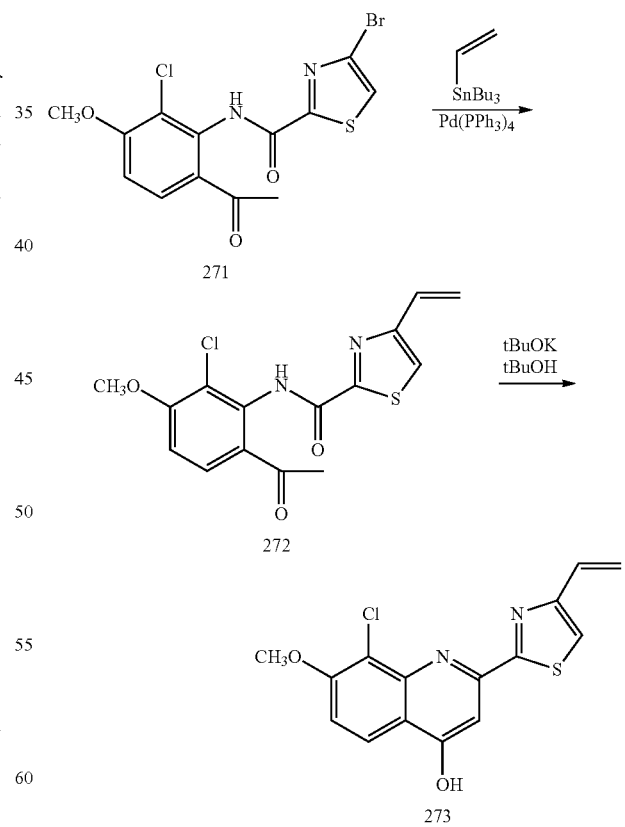

Step A:

Preparation of N-(6-acetyl-2-chloro-3-methoxyphenyl)-4-vinylthiazole-2-carboxamide 272. A solution of compound 271 (2.10 g, 1 eq.) and tributylvinyl tin (2.06 g, 1.2 eq.) in toluene (55 mL) was degazed by bubbling nitrogen during 15 min. Then, triphenylphosphine (250 mg, 4%) was added under nitrogen and the reaction mixture was heated to 100° C. overnight. After cooling, the solvent was concentrated under diminished pressure and the residue was triturated with diethyl ether to yield compound 272 as a beige powder in 88% yield. $^1$H NMR (CDCl$_3$, 400 MHz): δ (ppm) 2.60 (s, 3H), 4 (s, 3H), 5.5 (dd, J=10.85 and 1.24 Hz, 1H), 6.24 (dd, J=17.26 and 1.24 Hz, 1H), 6.79 (dd, J=17.34 and 10.78 Hz, 1H), 6.90 (d, J=8.74 Hz, 1H), 7.40 (s, 1H), 7.71 (d, J=8.74 Hz, 1H), 10.45 (br s, 1H).

Step B:

Preparation of 8-chloro-7-methoxy-2-(4-vinylthiazol-2-yl)quinolin-4-ol 273. Potassium tert-butoxide (2.13 g, 2.2 eq.) was added to a suspension of compound 272 (2.91 g, 1 eq.) in tert-butanol (30 mL). The reaction mixture was heated to 100° C. for 5 hrs. After one night at room temperature, the mixture was diluted with diethyl ether and the precipitate filtered, washed with diethyl ether, and solubilized in water. The pH was adjusted to 6-7 by addition of 1N HCl and the precipitate was filtered, washed with water, and triturated with diethyl ether to yield compound 273 in 73% yield. $^1$H NMR (CDCl$_3$, 400 MHz): δ (ppm) 4.06 (s, 3H), 5.54 (d, J=10.82 Hz, 1H), 6.25 (d, J=17.31 Hz, 1H), 6.74 (s, 1H), 6.79 (dd, J=17.31 and 10.82 Hz, 1H), 7.06 (d, J=9.10 Hz, 1H), 7.32 (s, 1H), 8.28 (d, J=9.10 Hz, 1H), 9.97 (br s, 1H).

Example 25

Preparation of 8-chloro-7-methoxy-2-(4-methylthiazol-2-yl)quinolin-4-ol 276

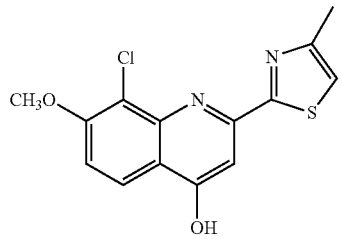

276

The synthesis of 8-chloro-7-methoxy-2-(4-methylthiazol-2-yl)quinolin-4-ol 276 is shown in Scheme 20.

Step A:

Preparation of 4-(4-methoxybenzyloxy)-2,8-dichloro-7-methoxyquinoline 274. Sodium hydride (2.74 g, 1.2 eq.) was added portionwise to a solution of p-methoxybenzyl alcohol (8.55 mL, 1.2 eq.) and 15-crown-5 (13.6 mL, 1.2 eq.) in 35 mL of DMF. The mixture was allowed to stir at room temperature for 30 min, and then added to a solution of 2,4,8-trichloro-7-methoxyquinoline (15 g, 1 eq.) in DMF (75 mL) via cannula. After 18 hrs of stirring at room temperature, the mixture was poured on 500 mL of water and NH$_4$Cl aqueous. Ethyl acetate (200 mL) was added and the precipitate was filtered. The filtrate was purified by chromatography on silica gel to yield compound 274 in 56% yield. $^1$H NMR (CDCl$_3$, 400 MHz) δ (ppm) 3.85 (s, 3H), 4.05 (s, 3H), 5.19 (s, 2H), 6.77 (s, 1H), 6.97 (d, J=8.64 Hz, 2H), 7.23 (d, J=9.25 Hz, 1H), 7.41 (d, J=8.64 Hz, 2H), 8.08 (d, J=9.25 Hz, 1H); MS (ESI, EI$^+$): m/z=386.1 (MNa$^+$).

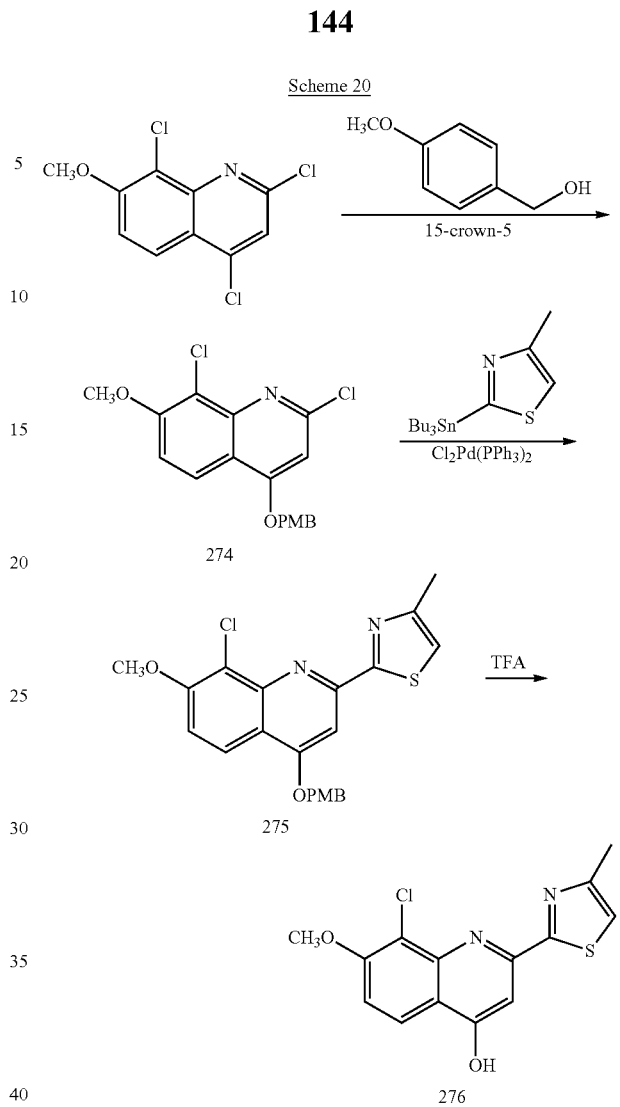

Scheme 20

Step B:

Preparation of 4-(4-methoxybenzyloxy)-8-chloro-7-methoxy-2-(4-methylthiazol-2-yl)quinoline 275. To a solution of compound 274 (1 g, 1 eq.) and 2-(tributylstannyl)-4-methylthiazole (1.28 g, 1.2 eq.) in DMF (14 mL) were added PdCl$_2$(PPh$_3$)$_2$ (193 mg, 10%) and potassium carbonate (455 mg, 1.2 eq.) and the resulting mixture was stirred at 90° C. overnight. DMF was concentrated under vacuum and water and dichloromethane were added. The aqueous layer was extracted with dichloromethane and the combined organic layers washed with water and brine, dried over Na$_2$SO$_4$, filtered, and concentrated. The residue was purified by chromatography on a silica gel to yield compound 275 as a white solid in 65% yield. $^1$H NMR (CDCl$_3$, 400 MHz) δ (ppm) 2.57 (s, 3H), 3.86 (s, 3H), 4.06 (s, 3H), 5.33 (s, 2H), 6.98 (d, J=8.64 Hz, 2H), 7.08 (s, 1H), 7.25 (d, J=9.25 Hz, 1H), 7.46 (d, J=8.64 Hz, 2H), 7.74 (s, 1H), 8.12 (d, J=9.25 Hz, 1H); MS (ESI, EI$^+$): m/z=427.1 (MH$^+$).

Step C:

Preparation of 8-chloro-7-methoxy-2-(4-methylthiazol-2-yl)quinolin-4-ol 276. Compound 275 (750 mg, 1 eq.) in trifluoroacetic acid (5 mL) was stirred at room temperature for 10 min. Then, the acid was evaporated, ethyl acetate added and concentrated again in diminished pressure. The residue was triturated in diethyl ether to give the compound 276 as a white solid in quantitative yield. ¹H NMR (CDCl₃, 400 MHz) δ (ppm) 2.59 (d, J=0.81 Hz, 3H), 4.10 (s, 3H), 7.19 (d, J=9.25 Hz, 1H), 7.22 (d, J=0.81 Hz, 1H), 7.25 (s, 1H), 8.36 (d, J=9.25 Hz, 1H), 10.51 (br s, 1H); MS (ESI, EI⁺): m/z=306.93 (MH⁺).

Example 26

Preparation of (4-chloro-6-(4-methoxy-benzyloxy)-2-(4-trifluoromethyl-thiazol-2-yl)pyrimidine 285

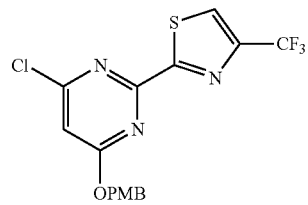

The synthesis of (4-chloro-6-(4-methoxy-benzyloxy)-2-(4-trifluoromethyl-thiazol-2-yl) pyrimidine 285 is shown in Scheme 21.

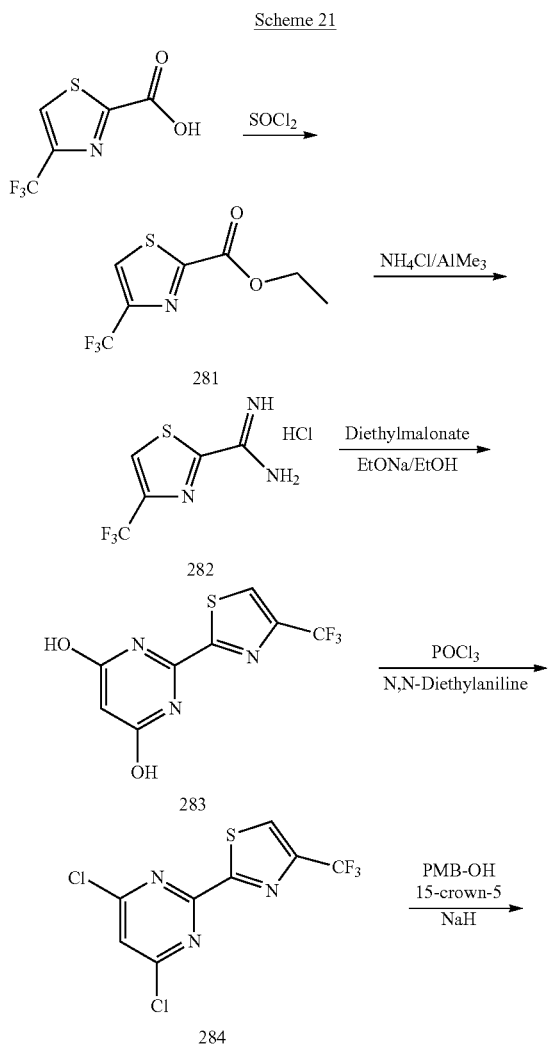

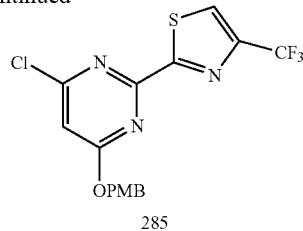

Step A:

Preparation of 4-trifluoromethylthiazole-2-carboxylic acid ethyl ester 281. To a stirred solution of 4-trifluoromethylthiazole-2-carboxylic acid (98 g, 1 eq.) in EtOH (600 mL) was added dropwise SOCl₂ (36 mL, 1 eq.). The mixture was stirred at 40° C. for 8 hrs and then at room temperature for 16 hrs. The reaction mixture was concentrated under reduced pressure and the residue was redissolved in DCM. Organics were washed with saturated aqueous NaHCO₃ solution, dried over Na₂SO₄, filtered, and concentrated under reduced pressure to yield compound 281 as a brown solid in 96% yield. ¹H NMR (CDCl₃, 400 MHz) δ 1.45 (t, J=7.14 Hz, 3H), 4.49-4.54 (q, J=7.10 Hz, 2H), 8.02 (s, 1H).

Step B:

Preparation of 4-trifluoromethylthiazole-2-carboxamidine hydrochloric acid 282. To a suspension of NH₄Cl (19.8 g, 5 eq.) in toluene (250 mL) was added AlMe₃ in toluene (2 M, 185 mL, 5 eq.) dropwise at 0° C. The mixture was stirred at room temperature for 1 hr. A solution of compound 281 (16.8 g, 1 eq.) in toluene (250 mL) was then slowly added and the reaction mixture was stirred at 80° C. for 16 hrs. After cooling at 0° C., MeOH was added and the precipitate obtained was removed by filtration. The filtrate was concentrated under reduced pressure, dissolved in DCM/MeOH mixture, the precipitate obtained was removed by filtration. The filtrate was concentrated under reduced pressure and crystallized from DCM to yield compound 282 as a beige solid in 100% yield. ¹H NMR (DMSO-d₆, 400 MHz) δ 7.44 (s, 1H).

Step C:

Preparation of 2-(4-trifluoromethyl-thiazol-2-yl)-pyrimidin-4,6-diol 283. To a stirred solution of NaOEt (32 g, 5 eq.) in EtOH (200 mL) was slowly added compound 282 (22 g, 1 eq.). The reaction mixture was stirred at room temperature for 30 min and diethyl malonate (11.5 mL, 0.8 eq.) was then added. The suspension was refluxed for 24 hrs. The solvent was removed under reduced pressure. The residue was suspended in H₂O (200 mL) and acidified to pH 5 with 2 N aqueous HCl. The resulting solid was filtered, washed with water, and dried under reduced pressure to yield compound 283 as a brown solid in 98% yield. ¹H NMR (DMSO-d₆, 400 MHz) δ 5.77 (s, 1H), 8.68 (s, 1H).

Step D:

Preparation of 4,6-dichloro-2-(4-trifluoromethyl-thiazol-2-yl)-pyrimidine 284. To a solution of compound 283 (14.41 g, 1 eq.) in POCl₃ (100 mL) was added dropwise N,N-diethylaniline (15 mL, 1.7 eq.) at 0° C. The resulting mixture was stirred at 100° C. for 1 hr. POCl₃ was then removed under reduced pressure. Ice was added to the residue and the mixture was extracted with DCM. The combined organic layers were washed sequentially with H₂O, saturated NaHCO₃, and brine, dried over Na₂SO₄, filtered, and concentrated under reduced pressure. The residue was solubilised in DCM, pentane was added. The solid obtained was removed by filtration and organics were concentrated under reduced pressure to yield compound 284 as an orange solid in 68% yield. MS (ESI, EI⁺): m/z=300 (MH⁺).

147

Step E:

Preparation of 4-chloro-6-(4-methoxy-benzyloxy)-2-(4-trifluoromethyl-thiazol-2-yl) pyrimidine 285. NaH (60% in oil) (1.49 g, 1 eq.) was added portionwise to a stirred solution of compound 284 (11.2 g, 1 eq.) and 4-methoxybenzyl alcohol (5.15 g, 1 eq.). The reaction mixture was stirred at 0° C. for 1 hr and saturated $NaHCO_3$ solution was added. The combined organic layers were dried over $Na_2SO_4$, filtered, and concentrated under reduced pressure. The residue obtained was triturated in pentane to yield compound 285 as a beige solid in 89% yield. MS (ESI, EI+): m/z=402 (MH+).

Alternatively, compound 285 was also prepared as shown in Scheme 22.

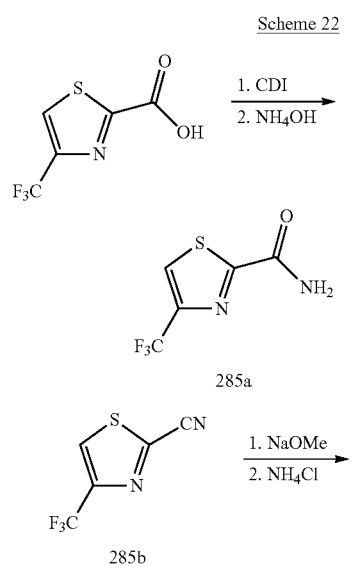

Scheme 22

Step A:

Preparation of 4-trifluoromethyl-thiazole-2-carboxylic acid amide 285a. To a solution of 4-trifluoromethyl-thiazole-2-carboxylic acid (50 g, 1 eq.) in anhydrous THF (480 mL) was added carbodiimidazole (45.2 g, 1.1 eq.) portionwise under nitrogen in an ice/water bath (about 5° C.). The reaction mixture was stirred at room temperature for 16 hrs. $NH_4OH$ (25% in $H_2O$; 1.930 mL) was added. The solution was stirred for 4 hrs, and then partitioned in DCM (500 mL) and $H_2O$ (500 mL). Aqueous layer was further extracted with DCM (500 mL). The combined organic layers were dried over $MgSO_4$, filtered, and concentrated in vacuo to yield compound 285a as an orange solid in 72% yield. MS (ESI, EI+): m/z=197 (MH+).

Step B.

Preparation of 4-trifluoromethyl-thiazole-2-carbonitrile 285b. To a solution of anhydrous DMF (18.5 mL, 1.3 eq.) in acetonitrile (460 mL) was added a 2M solution of oxalyl chloride in DCM (118 mL, 1.3 eq.) dropwise at 0° C. After the mixture was stirred for 30 min at 0° C., a solution of compound 285a (35.5 g, 1.0 eq.) and pyridine (14.5 mL, 1.0 eq.) in acetonitrile (180 mL) was added. The reaction mixture was stirred at room temperature for 3 hrs. The mixture was concentrated in vacuo. The residue obtained was dissolved in EtOAc (400 mL) and washed with $H_2O$ (4×300 mL). Organics were dried over $MgSO_4$, filtered, and concentrated in vacuo to yield compound 285b as a brown oil in 87% yield. $^1$H NMR ($CDCl_3$, 400 MHz) δ 8.15 (s, 1H).

148

Step C:

Preparation of 4-trifluoromethyl-thiazole-2-carboxamidine 285. To a solution of compound 285b (28.12 g, 1.0 eq.) in MeOH (13 mL) in an ice/water bath was added MeONa (853 mg, 0.1 eq.) portionwise. The reaction mixture was stirred in the ice/water bath for 15 min and at room temperature for 1 hr. $NH_4Cl$ (16.88 g, 2.0 eq.) was then added and the mixture was stirred at room temperature for 4 days. Solvent was removed in vacuo. The solid obtained was suspended in DCM (60 mL) and recovered by filtration. The solid was suspended in MeOH (50 mL) and filtered. The filtrate was concentrated under reduced pressure to yield compound 285 as a white solid in 32% yield. MS (ESI, EI+): m/z=196 (MH+).

Example 27

Preparation of 4-chloro-6-methoxy-2-(4-trifluoromethyl-thiazol-2-yl)-pyrimidine 290

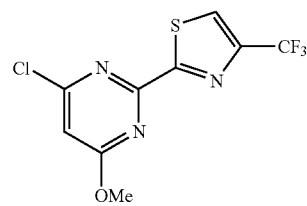

The synthesis of (4-chloro-6-methoxy-2-(4-trifluoromethyl-thiazol-2-yl)-pyrimidine 290 is shown in Scheme 23.

Step A:

Preparation of 4,6-dimethoxy-pyrimidin-2-carboxylic amide 286. Ethyl-4,6-dimethoxy-pyrimidin-2-carboxylate (25 g, 1 eq.) in $NH_3$/MeOH (7 M, 15 mL) was irradiated in a microwave reactor at 100° C. for 15 min. The solution was concentrated in vacuo to yield compound 286 as a beige solid in 100% yield. MS (ESI, EI+): m/z=184 (MH+).

Step B:

Preparation of 4,6-dimethoxy-pyrimidin-2-carbothioic acid amide 287. To a stirred solution of compound 286 (21.86 g, 1 eq.) in dry THF (200 mL) was added Lawesson's reagent (29 g, 0.6 eq.) under nitrogen. The mixture was then stirred at 90° C. for 1 hr and then concentrated in vacuo. The residue obtained was triturated in a DCM/diisopropyl ether mixture to yield compound 287 as an orange solid in 72% yield. MS (ESI, EI+): m/z=200 (MH+).

Scheme 23

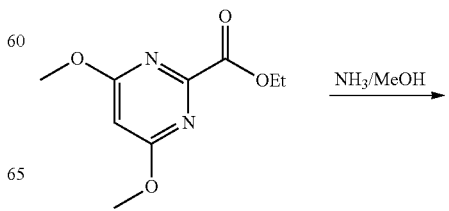

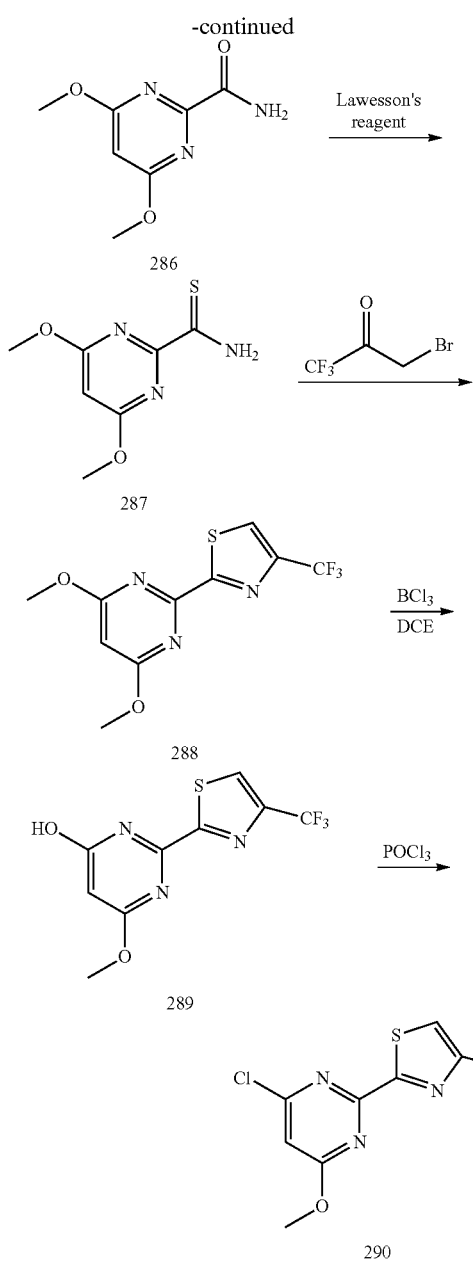

Step C:
Preparation of 4,6-dimethoxy-2-(4-trifluoromethyl-thiazol-2-yl)-pyrimidin-4-ol 288. To a solution of compound 287 (14 g, 1 eq.) in EtOH (140 mL) was added 3-bromo-1,1,1-trifluoroacetone (8.8 mL, 1.2 eq.). The mixture was stirred at 90° C. for 16 hrs and concentrated in vacuo. DCM (20 mL) and water (20 mL) were added. Organics were dried over $Na_2SO_4$, filtered, concentrated under reduced pressure, and flushed on a silica gel column with 5% MeOH/DCM to yield compound 288 as a beige compound in 12% yield. MS (ESI, $EI^+$): m/z=292 ($MH^+$).

Step D:
Preparation of 6-hydroxy-4-methoxy-2-(4-trifluoromethyl-thiazol-2-yl)-pyrimidin-4-ol 289. To a solution of compound 288 (460 mg, 1 eq.) in DCE (10 mL) was added $BCl_3$ (3.16 mL, 2 eq.). The mixture was stirred at 60° C. for 16 hrs. Water and DCM were then added. Organics were separated, dried over $Na_2SO_4$, filtered, and concentrated under reduced pressure. The residue was triturated in a DCM/pentane mixture to yield compound 289 as a beige solid in 38% yield. MS (ESI, $EI^+$): m/z=278 ($MH^+$).

Step D:
Preparation of 4-chloro-6-methoxy-2-(4-trifluoromethyl-thiazol-2-yl)-pyrimidine 290. To a stirred solution of compound 289 (2.38 g, 1 eq.) in $POCl_3$ (7.2 mL) was added N,N-diethylaniline (2.17 g, 1.7 eq.). The mixture was stirred at 110° C. for 16 hrs. The reaction was cooled down to room temperature and poured dropwise into an ice/water mixture. The aqueous solution was extracted with DCM. Organics were dried over $Na_2SO_4$, filtered, concentrated under reduced pressure, and purified by silica gel chromatography to yield compound 290 as an orange solid in 45% yield. MS (ESI, $EI^+$): m/z=296 ($MH^+$).

Example 28

Preparation of 6-substituted-2-(4-trifluoromethyl-thiazol-2-yl)-pyrimidines A1 to AG1

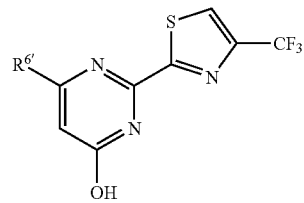

A1 to AG1

The syntheses of pyrimidines A1 to AG1 are shown in Scheme 24.

Scheme 24

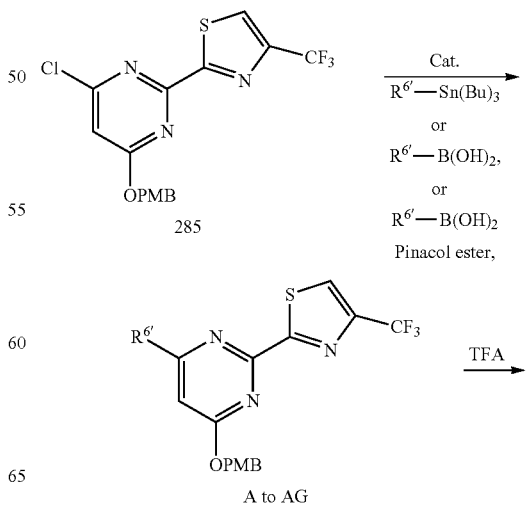

-continued

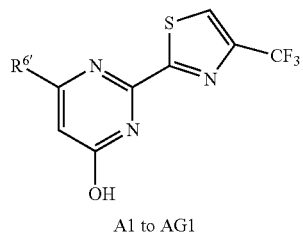

A1 to AG1

Step A:
Preparation of compounds A to AG.

Method 1: Preparation of 6-(4,5-dimethyl-thiazol-2-yl)-4-(4-methoxy-benzyloxy)-2-(4-trifluoromethylthiazol-2-yl)-pyrimidine A

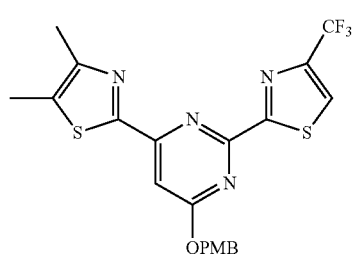

A

Compound 285 (800 mg), K₂CO₃ (331 mg, 1.2 eq.), PdCl₂(PPh₃)₂ (140 mg, 10%), and 4,5-dimethyl-2-(tributylstannyl)thiazole (965 mg, 1.2 eq.) in DMF (8 mL) were irradiated at 100° C. for 1 hr. The reaction mixture was concentrated under reduced pressure. Water and DCM were then added. Organics were separated, concentrated under reduced pressure, and purified by chromatography on silica gel (petroleum ether/EtOAc) to yield compound A as a yellow-brown oil in 92% yield. MS (ESI, EI⁺): m/z=479 (MH⁺).

Compounds B to I were synthesized according to the procedure as described for compound A.

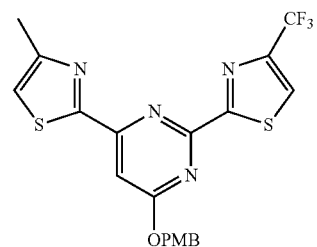

B 4-(4-Methoxy-benzyloxy)-6-(4-methylthiazol-2-yl)-2-(4-trifluoromethyl-thiazol-2-yl)-pyrimidine B was synthesized from 4-methyl-2-(tributylstannyl)thiazole (931 mg, 1.2 eq.) as a pale yellow powder in 87% yield. MS (ESI, EI⁺): m/z=465 (MH⁺).

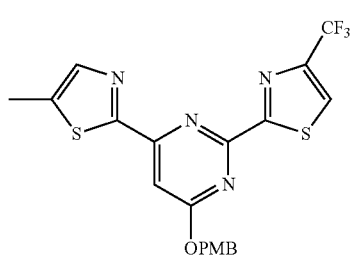

C 4-(4-Methoxy-benzyloxy)-6-(5-methylthiazol-2-yl)-2-(4-trifluoromethyl-thiazol-2-yl)-pyrimidine C was synthesized from 5-methyl-2-(tributylstannyl)thiazole (931 mg, 1.2 eq.) as a pale yellow powder in 39% yield. MS (ESI, EI+): m/z=465 (MH⁺).

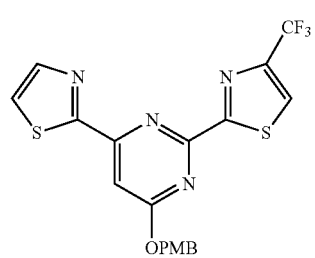

D 4-(4-Methoxy-benzyloxy)-6-(thiazol-2-yl)-2-(4-trifluoromethylthiazol-2-yl)-pyrimidine D was synthesized from 2-(tributylstannyl)thiazole (898 mg, 1.2 eq.) as a pale yellow powder in 79% yield. MS (ESI, EI⁺): m/z=451 (MH⁺).

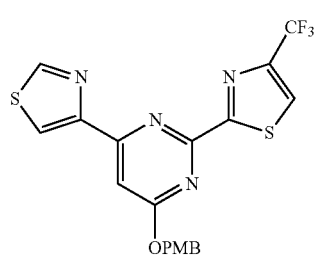

E 4-(4-Methoxy-benzyloxy)-6-(thiazol-4-yl)-2-(4-trifluoromethylthiazol-2-yl)-pyrimidine E was synthesized from 4-(tributylstannyl)thiazole (898 mg, 1.2 eq.) as a pale yellow powder in 77% yield. MS (ESI, EI⁺): m/z=451 (MH⁺).

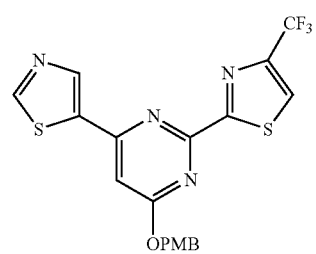

F 4-(4-Methoxy-benzyloxy)-6-(thiazol-5-yl)-2-(4-trifluoromethylthiazol-2-yl)-pyrimidine F was synthesized from 5-(tributylstannyl)thiazole (898 mg, 1.2 eq.) as a pale yellow powder in 31% yield. MS (ESI, EI⁺): m/z=451 (MH⁺).

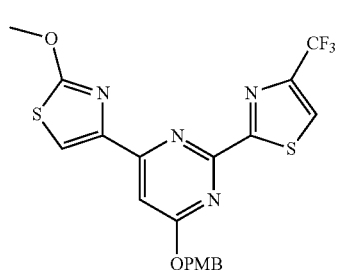

G 4-(4-Methoxy-benzyloxy)-6-(2-methoxy-thiazol-4-yl)-2-(4-trifluoromethyl-thiazol-2-yl)-pyrimidine G was synthesized from 2-methoxy-4-(tributylstannyl)thiazole (970 mg, 1.2 eq.) as a pale yellow powder in 64% yield. MS (ESI, EI⁺): m/z=481 (MH⁺).

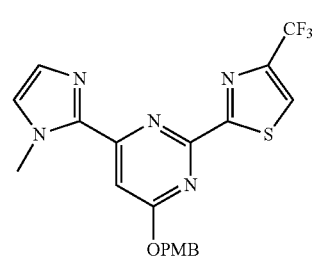

H 4-(4-Methoxy-benzyloxy)-6-(1-methyl-imidazol-2-yl)-2-(4-trifluoromethyl-thiazol-2-yl)-pyrimidine H was synthesized from 1-methyl-2-(tributylstannyl)imidazole (890 mg, 1.2 eq.) as a pale yellow powder in 30% yield. MS (ESI, EI⁺): m/z=448 (MH⁴).

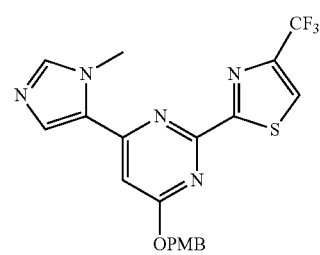

I 4-(4-Methoxy-benzyloxy)-6-(1-methyl-imidazol-5-yl)-2-(4-trifluoromethyl-thiazol-2-yl)-pyrimidine I. Compound I was synthesized from 1-methyl-5-(tributylstannyl)-imidazole (890 mg, 1.2 eq.) as a pale yellow powder in 100% yield. MS (ESI, EI⁺): m/z=448 (MH⁺).

Method 2: Preparation of 4-(4-methoxy-benzyloxy)-6-(5-methyl-thiophen-2-yl)-2-(4-trifluoromethyl-thiazol-2-yl)-pyrimidine J

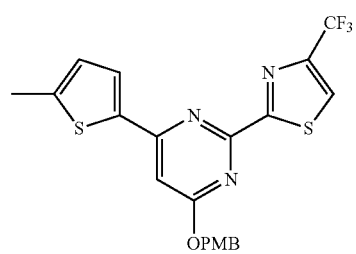

J

A mixture of compound 14 (800 mg, 1 eq.), 5-methylthiophene-2-boronic acid (423 mg, 1.5 eq.), Pd(OAc)₂ (7 mg, 1.5 mol %), PPh₃ (16 mg, 3 mol %), and Na₂CO₃ (422 mg, 2 eq.) in dioxane (8 mL) and water (1 mL) was irradiated at 120° C. for 30 min. The reaction mixture was then vigorously stirred for 10 min in DCM (30 mL) and water (30 mL). Layers were separated and organics were evaporated to yield compound J as an orange solid in 95% yield. MS (ESI, EI⁺): m/z=464 (MH⁺).

Compounds L to AG were synthesized according to the procedure as described for compound J.

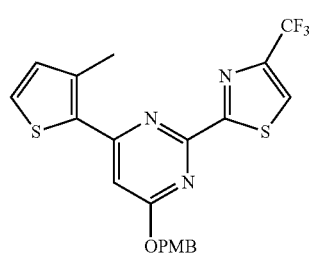

L 4-(4-Methoxy-benzyloxy)-6-(3-methyl-thiophen-2-yl)-2-(4-trifluoromethyl-thiazol-2-yl)-pyrimidine L was synthesized from 3-methylthiophene-2-boronic acid (423 mg, 1.5 eq.) as a yellow solid in 95% yield. MS (ESI, EI⁺): m/z=464 (MH⁺).

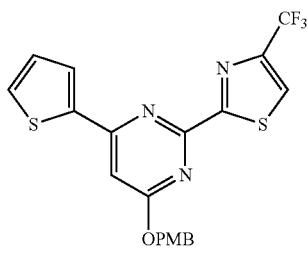

M 4-(4-Methoxy-benzyloxy)-6-(thiophen-2-yl)-2-(4-trifluoromethyl-thiazol-2-yl)-pyrimidine M was synthesized from thiophene-2-boronic acid (509 mg, 1.5 eq.) as a yellow solid in 92% yield. MS (ESI, EI⁺): m/z=450 (MH⁺).

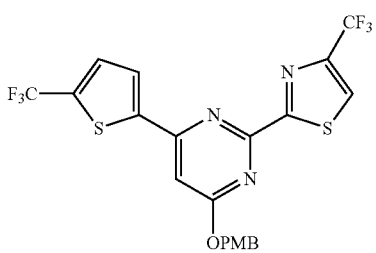

N 4-(4-Methoxy-benzyloxy)-6-(5-trifluoromethyl-thiophen-2-yl)-2-(4-trifluoromethyl-thiazol-2-yl)-pyrimidine N was synthesized from 5-trifluoromethyl-thiophene-2-boronic acid pinacol ester (830 mg, 1.5 eq.) as a yellow solid in 87% yield. MS (ESI, EI$^+$): m/z=518 (MH$^+$).

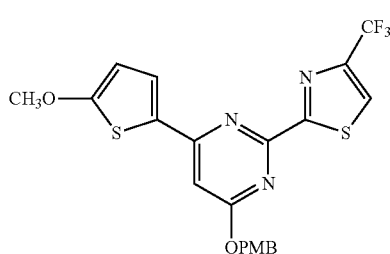

O 4-(4-Methoxy-benzyloxy)-6-(5-methoxy-thiophen-2-yl)-2-(4-trifluoromethyl-thiazol-2-yl)-pyrimidine O was synthesized from 5-methoxy-thiophene-2-boronic acid pinacol ester (716 mg, 1.5 eq.) as an orange solid in 69% yield. MS (ESI, EI$^+$): m/z=480 (MH$^+$).

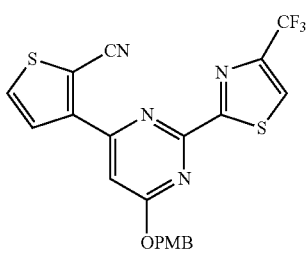

P 4-(4-Methoxy-benzyloxy)-6-(2-cyano-thiophen-3-yl)-2-(4-trifluoromethyl-thiazol-2-yl)-pyrimidine P was synthesized from 2-cyano-thiophene-3-boronic acid pinacol ester (702 mg, 1.5 eq.) as a white foam in 83% yield. MS (ESI, EI$^+$): m/z=497 (M+Na)$^+$.

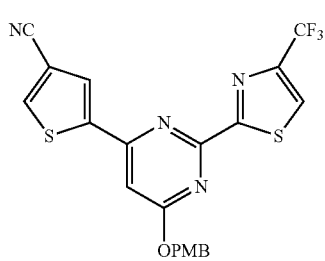

Q 4-(4-Methoxy-benzyloxy)-6-(4-cyano-thiophen-2-yl)-2-(4-trifluoromethyl-thiazol-2-yl)-pyrimidine Q was synthesized from 4-cyano-thiophene-2-boronic acid pinacol ester (702 mg, 1.5 eq.) as a yellow foam in 85% yield. MS (ESI, EI$^+$): m/z=497 (M+Na)$^+$.

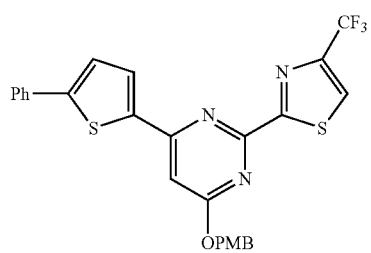

S 4-(4-Methoxy-benzyloxy)-6-(5-phenyl-thiophen-2-yl)-2-(4-trifluoromethyl-thiazol-2-yl)-pyrimidine S was synthesized from 5-phenyl-thiophene-2-boronic acid (609 mg, 1.5 eq.) as a dark green gum in 68% yield. MS (ESI, EI$^+$): m/z=526 (MH$^+$).

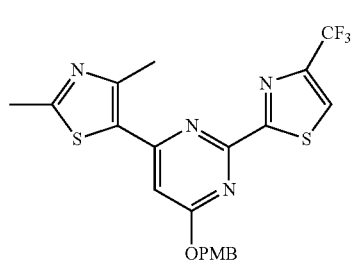

T 4-(4-Methoxy-benzyloxy)-6-(2,4-dimethyl-thiazol-5-yl)-2-(4-trifluoromethyl-thiazol-2-yl)-pyrimidine T was synthesized from 2,4-dimethyl-thiazol-5-boronic acid pinacol ester (739 mg. 1.5 eq.) as a yellow solid in 98% yield. MS (ESI, EI$^+$): m/z=479 (MH$^+$).

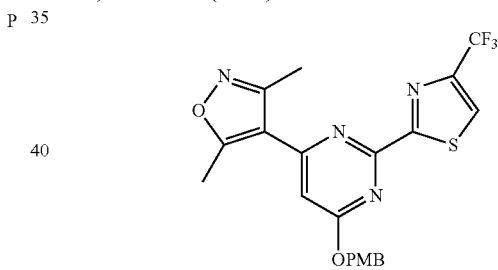

U 4-(4-Methoxy-benzyloxy)-6-(3,5-dimethylisoxazol-4-yl)-2-(4-trifluoromethyl-thiazol-2-yl)-pyrimidine U was synthesized from 3,5-dimethylisoxazol-4-boronic acid (435 mg. 1.5 eq.) as a yellow solid in 57% yield. MS (ESI, EI$^+$): m/z=463 (MH$^+$).

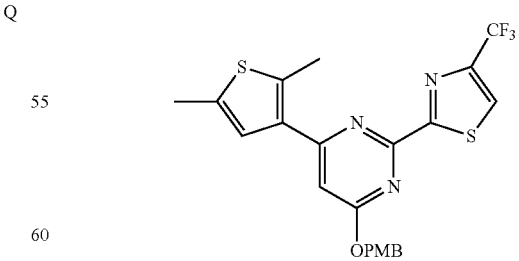

V 4-(4-Methoxy-benzyloxy)-6-(2,5-dimethylthiophen-3-yl)-2-(4-trifluoromethyl-thiazol-2-yl)-pyrimidine V was synthesized from 2,5-dimethylthiophen-3-boronic acid (468 mg, 1.5 eq.) as a beige solid in 100% yield. MS (ESI, EI$^+$): m/z=448 (MH$^+$).

W

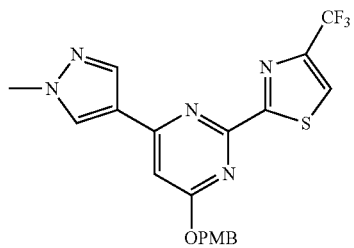

4-(4-Methoxy-benzyloxy)-6-(1-methyl-pyrazol-4-yl)-2-(4-trifluoromethyl-thiazol-2-yl)-pyrimidine W was synthesized from 1-methyl-pyrazole-4-boronic acid (500 mg, 1 eq.) as a brown solid in 92% yield. MS (ESI, EI⁺): m/z=448 (MH⁺).

X

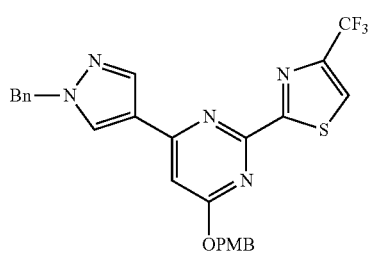

4-(4-Methoxy-benzyloxy)-6-(1-benzyl-pyrazol-4-yl)-2-(4-trifluoromethyl-thiazol-2-yl)-pyrimidine X was synthesized from 1-benzyl-pyrazole-4-boronic acid (460 mg, 1 eq.) as a beige solid in 76% yield. MS (ESI, EI⁺): m/z=524 (MH⁺).

Y

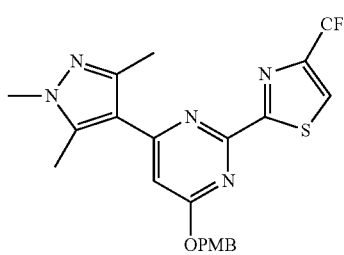

4-(4-Methoxy-benzyloxy)-6-(1,3,5-trimethylpyrazol-4-yl)-2-(4-trifluoromethyl-thiazol-2-yl)-pyrimidine Y was synthesized from 1,3,5-trimethylpyrazole-4-boronic acid (456 mg, 1 eq.) as a beige solid in 56% yield. MS (ESI, EI⁺): m/z=476 (MH⁺).

Z

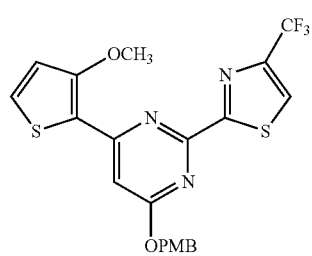

4-(4-Methoxy-benzyloxy)-6-(3-methoxy-thiophen-2-yl)-2-(4-trifluoromethyl-thiazol-2-yl)-pyrimidine Z was synthesized from 3-methoxythiophene-2-boronic acid (720 mg, 1 eq.) as a yellow solid in 76% yield. MS (ESI, EI⁺): m/z=480 (MH⁺).

AA

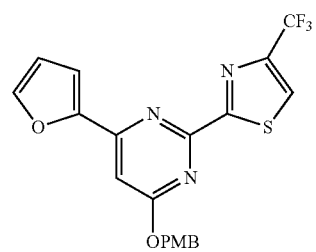

4-(4-Methoxy-benzyloxy)-6-(furan-2-yl)-2-(4-trifluoromethyl-thiazol-2-yl)-pyrimidine AA was synthesized from furan-2-boronic acid (750 mg, 1 eq.) as a beige solid in 92% yield. MS (ESI, EI⁺): m/z=434 (MH⁺).

AB

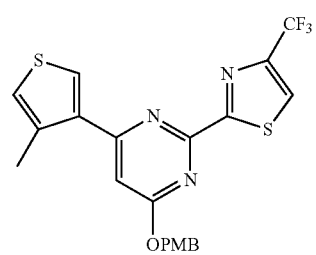

4-(4-Methoxy-benzyloxy)-6-(4-methyl-thiophen-3-yl)-2-(4-trifluoromethyl-thiazol-2-yl)-pyrimidine AB was synthesized from 3-methyl-thiophen-4-boronic acid (426 mg, 1 eq.) as a yellow solid in 90% yield. MS (ESI, EI⁺): m/z=464 (MH⁺).

AC

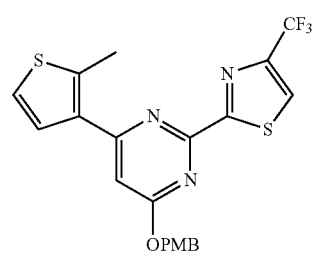

4-(4-Methoxy-benzyloxy)-6-(2-methyl-thiophen-3-yl)-2-(4-trifluoromethyl-thiazol-2-yl)-pyrimidine AC was synthesized from 2-methyl-thiophen-3-boronic acid (672 mg, 1 eq.) as a brown solid in 89% yield. MS (ESI, EI⁺): m/z=464 (MH⁺).

AD

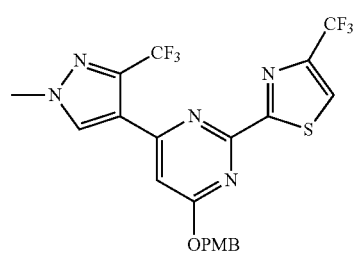

4-(4-Methoxy-benzyloxy)-6-(1-methyl-3-trifluoromethyl-pyrazol-4-yl)-2-(4-trifluoromethyl-thiazol-2-yl)-pyrimidine AD was synthesized from 1-methyl-3-trifluoromethyl-pyrazol-4-yl-boronic acid pinacol ester (414 mg, 1 eq.) as a beige solid in 66% yield. MS (ESI, EI⁺): m/z=516 (MH⁺).

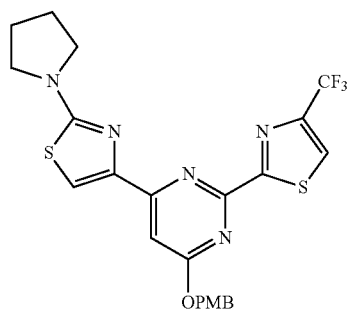

AE 4-(4-Methoxy-benzyloxy)-6-(2-pyrrolidin-1-yl-thiazol-4-yl)-2-(4-trifluoromethylthiazol-2-yl)-pyrimidine AE was synthesized from 2-pyrrolidin-1-yl-thiazol-4-boronic acid pinacol ester (420 mg, 1 eq.) as a yellow solid in 89% yield. MS (ESI, EI⁺): m/z=520 (MH⁺).

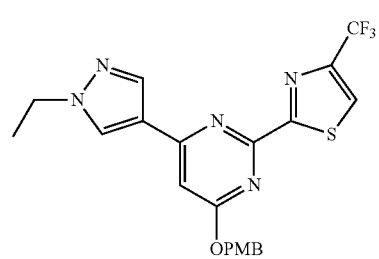

AF 4-(4-Methoxy-benzyloxy)-6-(1-ethyl-pyrazol-4-yl)-2-(4-trifluoromethyl-thiazol-2-yl)-pyrimidine AF was synthesized from 1-ethyl-pyrazole-4-boronic acid pinacol ester (333 mg, 1 eq.) as a beige solid in 96% yield. MS (ESI, EI⁺): m/z=462 (MH⁺).

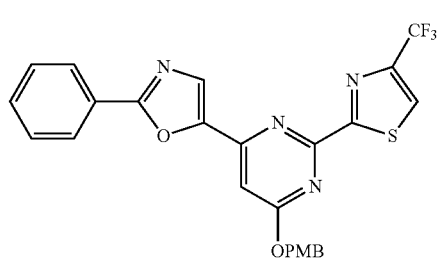

AG 4-(4-Methoxy-benzyloxy)-6-(2-phenyl-oxazol-5-yl)-2-(4-trifluoromethyl-thiazol-2-yl)-pyrimidine AG was synthesized from 2-phenyl-oxazol-5-boronic acid (407 mg, 1 eq.) as a white solid in 68% yield. MS (ESI, EI⁺): m/z=511 (MH⁺).

Step B:
Preparation of compounds A1 to AG1.

Preparation of 6-(4,5-dimethyl-thiazol-2-yl)-2-(4-trifluoromethylthiazol-2-yl)-pyrimidin-4-ol A1

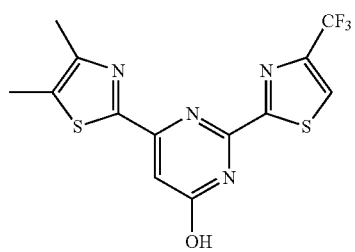

A1

A solution of compound A (881 mg, 1 eq.) in TFA (2 mL) was stirred at room temperature for 2 hrs. DCM was added and the mixture was concentrated under reduced pressure. DCM was added to the residue followed by diisopropylether. The solid obtained was collected by filtration to yield compound A1 as a beige solid in 96% yield. MS (ESI, EI⁺): m/z=359 (MH⁺).

Compounds B1 to AG1 were synthesized according to the procedure as described for compound A1.

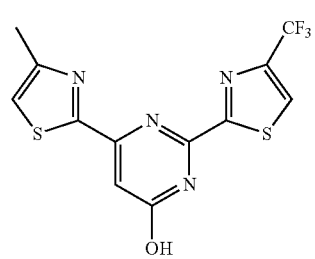

B1

6-(4-Methylthiazol-2-yl)-2-(4-trifluoromethylthiazol-2-yl)-pyrimidin-4-ol B1 was synthesized from compound B (807 mg, 1 eq.) as a pale yellow powder in 91% yield. MS (ESI, EI⁺): m/z=345 (MH⁺).

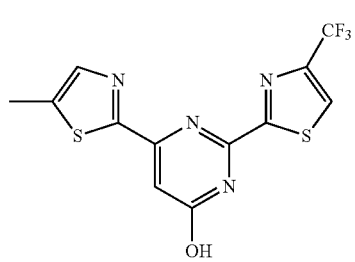

C1

6-(5-Methylthiazol-2-yl)-2-(4-trifluoromethylthiazol-2-yl)-pyrimidin-4-ol C1 was synthesized from compound C (363 mg, 1 eq.) as a pale yellow powder in 98% yield. MS (ESI, EI⁺): m/z=345 (MH⁺).

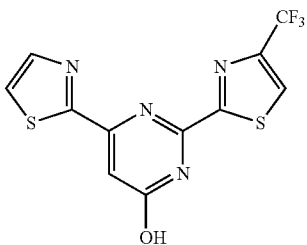

D1

6-(Thiazol-2-yl)-2-(4-trifluoromethylthiazol-2-yl)-pyrimidin-4-ol D1 was synthesized from compound D (715 mg, 1 eq.) as a pale yellow powder in 100% yield. MS (ESI, EI$^+$): m/z=331 (MH$^+$).

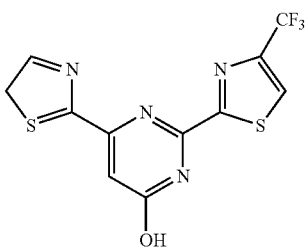

E1

6-(Thiazol-4-yl)-2-(4-trifluoromethylthiazol-2-yl)-pyrimidin-4-ol E1 was synthesized from compound E (695 mg, 1 eq.) as a pale yellow powder in 100% yield. MS (ESI, EI$^+$): m/z=331 (MH$^+$).

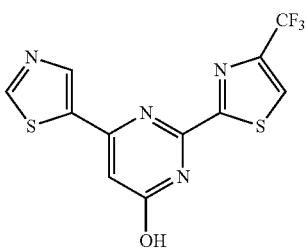

F1

6-(Thiazol-5-yl)-2-(4-trifluoromethylthiazol-2-yl)-pyrimidin-4-ol F1 was synthesized from compound F (280 mg, 1 eq.) as a pale yellow powder in 95% yield. MS (ESI, EI$^+$): m/z=331 (MH$^+$).

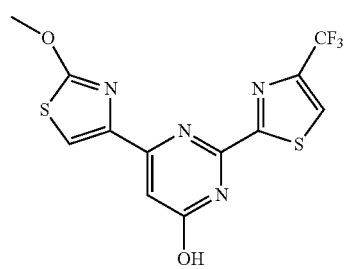

G1

6-(2-Methoxy-thiazol-4-yl)-2-(4-trifluoromethylthiazol-2-yl)-pyrimidin-4-ol G1 was synthesized from compound G (611 mg, 1 eq.) as a pale yellow powder in 97% yield. MS (ESI, EI$^+$): m/z=361 (MH$^+$).

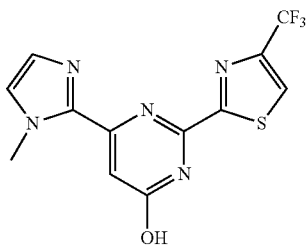

H1

6-(1-Methyl-imidazol-2-yl)-2-(4-trifluoromethylthiazol-2-yl)-pyrimidin-4-ol H1 was synthesized from compound H (270 mg, 1 eq.) as a pale yellow powder in 100% yield. MS (ESI, EI$^+$): m/z=328 (MH$^+$).

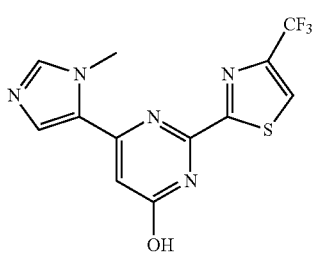

I1

6-(1-Methyl-imidazol-5-yl)-2-(4-trifluoromethylthiazol-2-yl)-pyrimidin-4-ol I1 was synthesized from compound I (915 mg, 1 eq.) as a pale yellow powder in 100% yield. MS (ESI, EI$^+$): m/z=328 (MH$^+$).

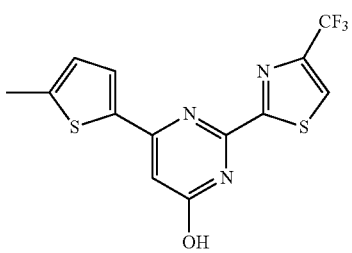

J1

6-(5-Methyl-thiophen-2-yl)-2-(4-trifluoromethyl-thiazol-2-yl)-pyrimidin-4-ol J1 was synthesized from compound J (307 mg, 1 eq.) as white solid in 80% yield. MS (ESI, EI$^+$): m/z=344 (MH$^+$).

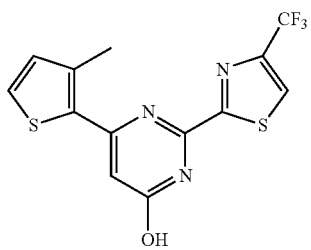

L1

6-(3-Methyl-thiophen-2-yl)-2-(4-trifluoromethyl-thiazol-2-yl)-pyrimidin-4-ol L1 was synthesized from compound L (880 mg, 1 eq.) as a yellow solid in 83% yield. MS (ESI, EI$^+$): m/z=344 (MH$^+$).

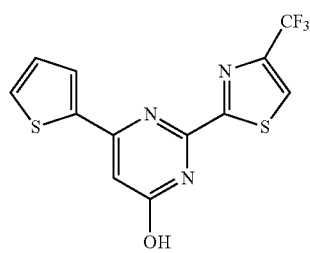
M1

6-(Thiophen-2-yl)-2-(4-trifluoromethyl-thiazol-2-yl)-pyrimidin-4-ol M1 was synthesized from compound M (821 mg, 1 eq.) as a yellow solid in 96% yield. MS (ESI, EI$^+$): m/z=330 (MH$^+$).

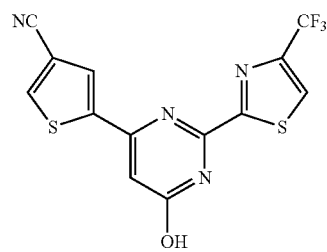
N1

6-(5-Trifluoromethyl-thiophen-2-yl)-2-(4-trifluoromethyl-thiazol-2-yl)-pyrimidin-4-ol N1 was synthesized from compound N (900 mg, 1 eq.) as a yellow solid in 100% yield. MS (ESI, EI$^+$): m/z=398 (MH$^+$).

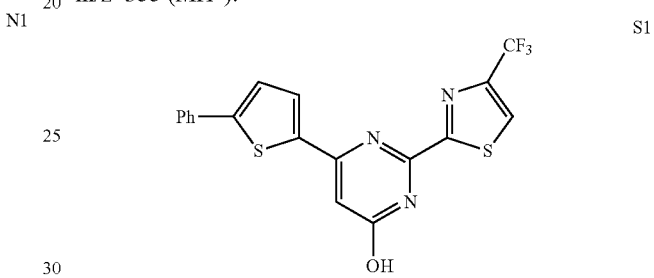
O1

6-(5-Methoxy-thiophen-2-yl)-2-(4-trifluoromethyl-thiazol-2-yl)-pyrimidin-4-ol O1 was synthesized from compound O (657 mg, 1 eq.) as yellow solid in 94% yield. MS (ESI, EI$^+$): m/z=360 (MH$^+$).

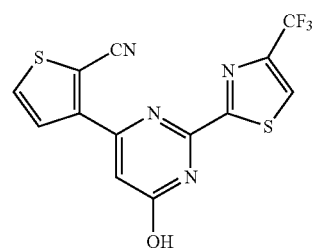
P1

6-(2-Cyano-thiophen-3-yl)-2-(4-trifluoromethyl-thiazol-2-yl)-pyrimidin-4-ol P1 was synthesized from compound P (781 mg, 1 eq.) as a white solid in 100% yield. MS (ESI, EI$^+$): m/z=355 (MH$^+$).

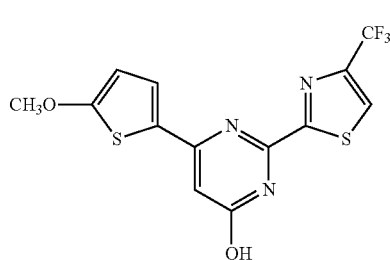
Q1

6-(4-Cyano-thiophen-2-yl)-2-(4-trifluoromethyl-thiazol-2-yl)-pyrimidin-4-ol Q1 was synthesized from compound Q (807 mg, 1 eq.) as a white solid in 94% yield. MS (ESI, EI$^+$): m/z=355 (MH$^+$).

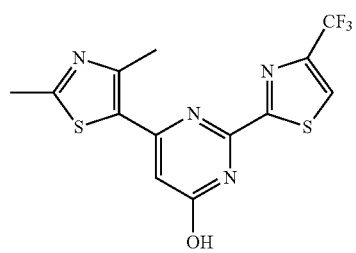
S1

6-(5-Phenyl-thiophen-2-yl)-2-(4-trifluoromethyl-thiazol-2-yl)-pyrimidin-4-ol S1 was synthesized from compound S (719 mg, 1 eq.) as a green solid in 76% yield. MS (ESI, EI$^+$): m/z=406 (MH$^+$).

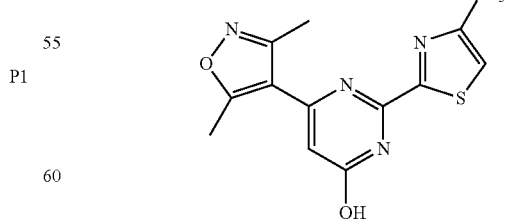
T1

6-(2,4-Dimethyl-thiazol-5-yl)-2-(4-trifluoromethyl-thiazol-2-yl)-pyrimidin-4-ol T1 was synthesized from compound T (685 mg, 1 eq.) as a cream solid in 100% yield. MS (ESI, EI$^+$): m/z=360 (MH$^+$).

U1

6-(3,5-Dimethylisoxazol-4-yl)-2-(4-trifluoromethyl-thiazol-2-yl)-pyrimidin-4-ol U1 was synthesized from compound U (224 mg, 1 eq.) as a white solid in 92% yield. MS (ESI, EI$^+$): m/z=343 (MH$^+$).

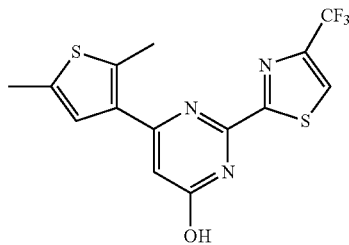
V1

6-(2,5-Dimethylthiophen-3-yl)-2-(4-trifluoromethyl-thiazol-2-yl)-pyrimidin-4-ol V1 was synthesized from compound V (970 mg, 1 eq.) as a beige solid in 46% yield. MS (ESI, EI$^+$): m/z=358 (MH$^+$).

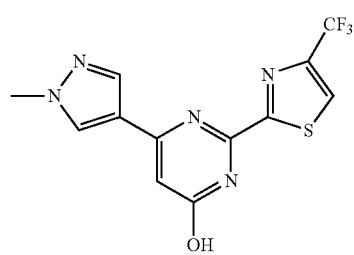
W1

6-(1-Methyl-pyrazol-4-yl)-2-(4-trifluoromethyl-thiazol-2-yl)-pyrimidin-4-ol W1 was synthesized from compound W (826 mg, 1 eq.) as a brown solid in 85% yield. MS (ESI, EI$^+$): m/z=328 (MH$^+$).

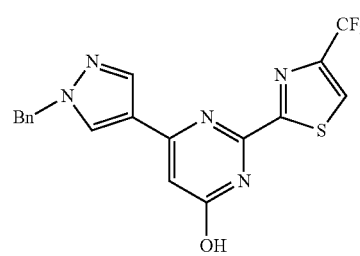
X1

6-(1-Benzyl-pyrazol-4-yl)-2-(4-trifluoromethyl-thiazol-2-yl)-pyrimidin-4-ol X1 was synthesized from compound X (867 mg, 1 eq.) as a beige solid in 100% yield. MS (ESI, EI$^+$): m/z=404 (MH$^+$).

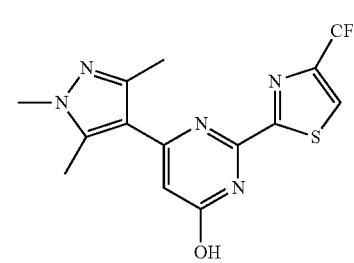
Y1

6-(1,3,5-Trimethyl-pyrazol-4-yl)-2-(4-trifluoromethyl-thiazol-2-yl)-pyrimidin-4-ol Y1 was synthesized from compound Y (489 mg, 1 eq.) as a white solid in 100% yield. MS (ESI, EI$^+$): m/z=356 (MH$^+$).

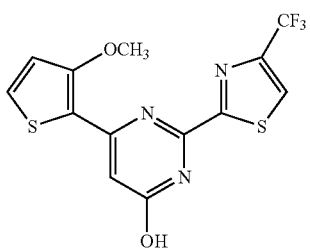
Z1

6-(3-Methoxy-thiophen-2-yl)-2-(4-trifluoromethyl-thiazol-2-yl)-pyrimidin-4-ol Z1 was synthesized from compound Z (744 mg, 1 eq.) as a white solid in 80% yield. MS (ESI, EI$^+$): m/z=360 (MH$^+$).

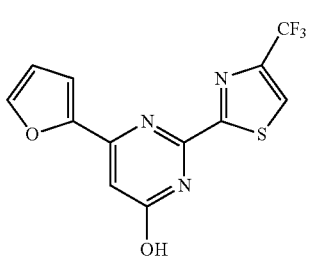
AA1

6-(Furan-2-yl)-2-(4-trifluoromethyl-thiazol-2-yl)-pyrimidin-4-ol AA1 was synthesized from compound AA (791 mg, 1 eq.) as a beige solid in 85% yield. MS (ESI, EI$^+$): m/z=314 (MH$^+$).

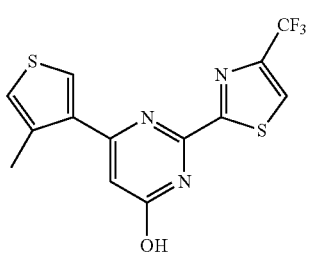
AB1

6-(4-Methyl-thiophen-3-yl)-2-(4-trifluoromethyl-thiazol-2-yl)-pyrimidin-4-ol AB1 was synthesized from compound AB (831 mg, 1 eq.) as a beige solid in 67% yield. MS (ESI, EI$^+$): m/z=344 (MH$^+$).

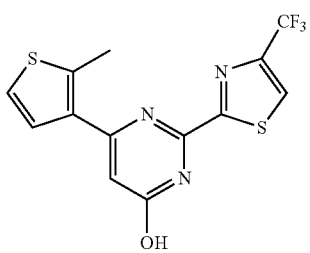
AC1

6-(2-Methyl-thiophen-3-yl)-2-(4-trifluoromethyl-thiazol-2-yl)-pyrimidin-4-ol AC1 was synthesized from compound AC (827 mg, 1 eq.) as a brown solid in 67% yield. MS (ESI, EI$^+$): m/z=344 (MH$^+$).

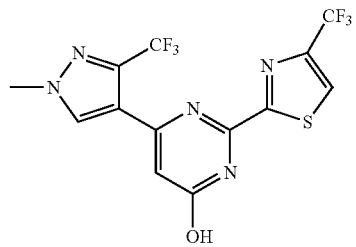
AD1

6-(1-Methyl-3-trifluoromethyl-pyrazol-4-yl)-2-(4-trifluoromethyl-thiazol-2-yl)-pyrimidin-4-ol AD1 was synthesized from compound AD (342 mg, 1 eq.) as a beige solid in 100% yield. MS (ESI, EI$^+$): m/z=396(MH$^+$).

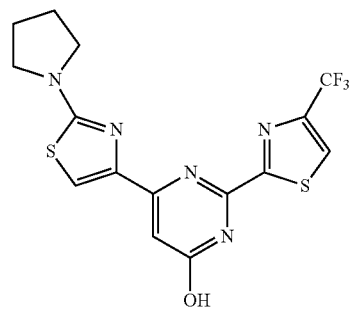
AE1

6-(2-Pyrrolidin-1-yl-thiazol-4-yl)-2-(4-trifluoromethyl-thiazol-2-yl)-pyrimidin-4-ol AE1 was synthesized from compound AE (464 mg, 1 eq.) as a yellow solid in 87% yield. MS (ESI, EI$^+$): m/z=400(MH$^+$).

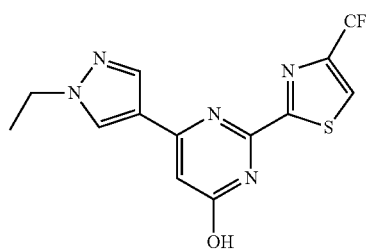
AF1

6-(1-Ethyl-pyrazol-4-yl)-2-(4-trifluoromethyl-thiazol-2-yl)-pyrimidin-4-ol AF1 was synthesized from compound AF (442 mg, 1 eq.) as a beige solid in 93% yield. MS (ESI, EI$^+$): m/z=342(MH$^+$).

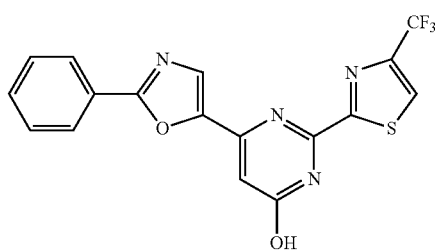
AG1

6-(2-Phenyl-oxazol-5-yl)-2-(4-trifluoromethyl-thiazol-2-yl)-pyrimidin-4-ol AG1 was synthesized from compound AG (346 mg, 1 eq.) as a white solid in 100% yield. MS (ESI, EI$^+$): m/z=391(MH$^+$).

Example 29

Preparation of 6-phenoxy-2-(4-trifluoromethyl-thiazol-2-yl)-pyrimidin-4-ol AH1

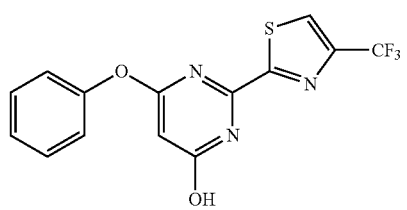
AH1

The synthesis of 6-phenoxy-2-(4-trifluoromethyl-thiazol-2-yl)-pyrimidin-4-ol AH1 is shown in Scheme 25.

Scheme 25

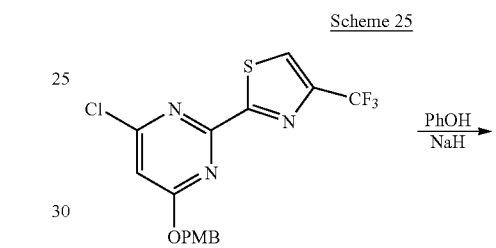
285

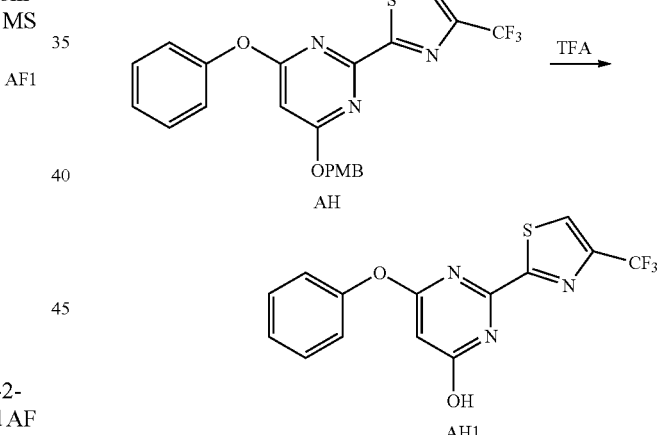
AH

AH1

Step A:

Preparation of 4-(4-methoxy-benzyloxy)-6-phenoxy-2-(4-trifluoromethyl-thiazol-2-yl)-pyrimidine AH. To a stirred solution of compound 285 (246 mg, 1 eq.) in anhydrous DMF (5 mL) was added a solution of phenol (69 mg, 1.2 eq.) and NaH 60% in oil (29 mg, 1.2 eq.) in anhydrous DMF (5 mL). The resulting mixture was stirred at room temperature for 3 hrs and concentrated under reduced pressure. The crude material was solubilized in EtOAc (10 mL), and washed sequentially with water and brine. Organics were dried over MgSO$_4$, filtered, and concentrated under reduced pressure to yield compound AH as a beige solid in 100% yield. $^1$H NMR (CDCl$_3$, 400 MHz) δ 3.82 (s, 3H), 5.48 (s, 2H), 6.01 (s, 1H), 6.83-6.93 (m, 1H), 7.16-7.31 (m; 4H), 4.43 (m, 4H), 7.90 (s, 1H).

Step B.

Preparation of 6-phenoxy-2-(4-trifluoromethyl-thiazol-2-yl)-pyrimidin-4-ol AH1. Compound AH1 was synthesized from compound AH (5 mg, 1 eq.) as beige solid in 60% yield, according to the procedure as described for compound A1. MS (ESI, EI+): m/z=340(MH+).

Example 30

Preparation of 5-phenoxy-2-(4-trifluoromethyl-thiazol-2-yl)-pyrimidin-4-ol AI1

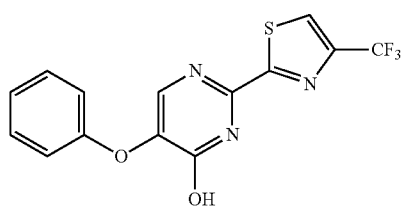

The synthesis of 5-phenoxy-2-(4-trifluoromethyl-thiazol-2-yl)-pyrimidin-4-ol AI1 is shown in Scheme 26.

Scheme 26

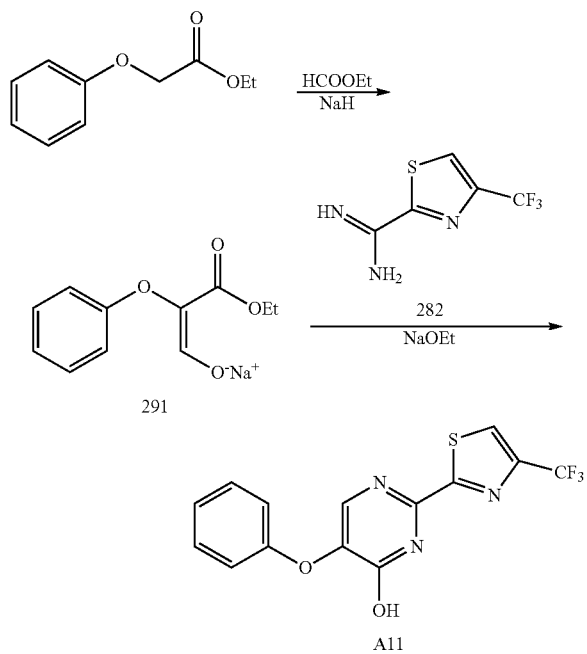

Step A:

Preparation of sodium 2-ethoxycarbonyl-2-phenoxyethenolate 291. To a suspension of NaH (60% in oil) (760 mg, 1.1 eq.) in dry Et$_2$O (8 mL) was added dropwise a solution of ethyl formate (1.4 mL, 1 eq.) and phenoxy ethyl acetate (2.7 mL, 1 eq.) in 2 mL of Et$_2$O at 0° C. The solution was allowed to warm up to room temperature and was stirred for 18 hrs. The suspension obtained was filtered and washed with ether and pentane to yield compound 291 as a white solid in 68% yield. MS (ESI, EI+): m/z=231 (M+Na+).

Step B:

Preparation of 5-phenoxy-2-(4-trifluoromethyl-thiazol-2-yl)-pyrimidin-4-ol AI1. To a solution of compound 282 (280 mg, 1 eq.) in dry EtOH (6 mL) was added compound 291 (1.38 g, 5 eq.) under nitrogen, followed by NaOEt (165 mg, 1 eq.). The reaction mixture was stirred at 90° C. for 2 hrs. EtOH was evaporated and a DCM/water mixture was added. Aqueous layer was acidified to pH 5 with aqueous 1N HCl and was extracted with DCM. The combined organic layers were dried over Na$_2$SO$_4$, filtered, concentrated in vacuo, and purified by chromatography on silica gel (DCM/MeOH) to yield compound AI1 as a beige oil in 81% yield. MS (ESI, EI+): m/z=340 (MH+).

Example 31

Preparation of 6-(thien-3-yl)-2-(4-trifluoromethyl-thiazol-2-yl)-pyrimidin-4-ol AJ1

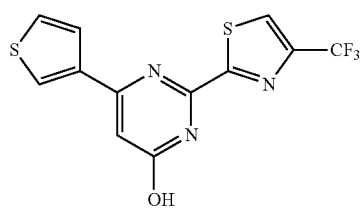

The synthesis of 6-(thien-3-yl)-2-(4-trifluoromethyl-thiazol-2-yl)-pyrimidin-4-ol AJ is shown in Scheme 27.

Scheme 27

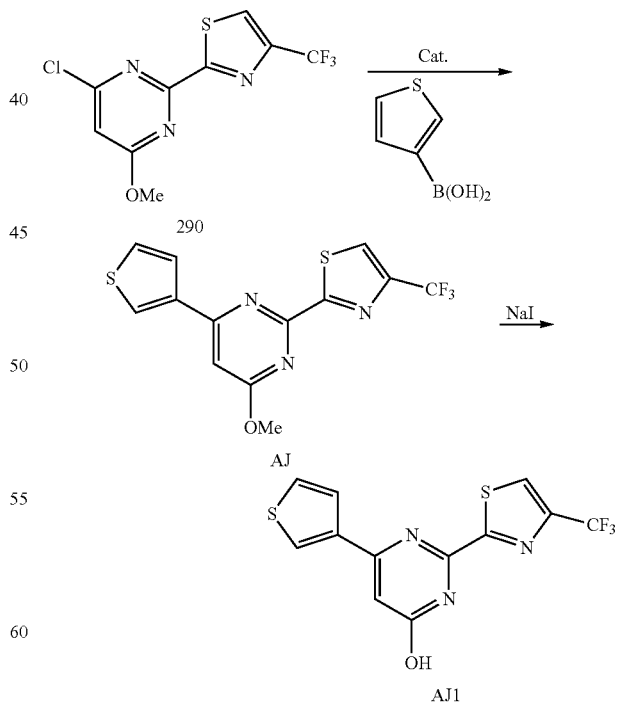

Step A:

Preparation of 4-methoxy-6-thien-3-yl-2-(4-trifluoromethyl-thiazol-2-yl)-pyrimidine AJ. Compound AJ was synthesized from thienyl-3-boronic acid (357 mg, 1.5 eq.) and compound 290 as a white solid in 50% yield according to the procedure as described for compound J. MS (ESI, EI⁺): m/z=344 (MH⁺).

Step B:

Preparation of 6-(thien-3-yl)-2-(4-trifluoromethyl-thiazol-2-yl)-pyrimidin-4-ol AJ1. A mixture of compound AJ (320 mg, 1 eq.) and NaI (557 mg, 4 eq.) in ACN (100 mL) was irradiated for 5 min at room temperature. TMS-Cl (470 µL, 4 eq.) was then added and the mixture was irradiated at 100° C. for 15 min. The mixture was concentrated under reduced pressure. The residue was solubilized in DCM, and washed sequentially with sodium thiosulfate solution and brine. Organics were dried over Na₂SO₄, filtered, and concentrated in vacuo to yield compound AJ1 as a white solid in 100% yield. MS (ESI, EI⁺): m/z=330 (MH⁺).

Example 32

Preparation of Substituted Pyrimidines 308

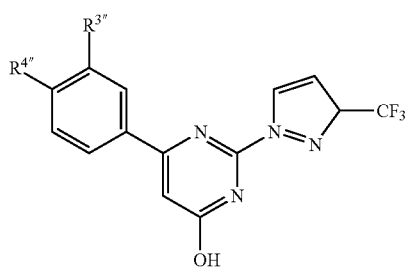

308b: R³″ = H, R⁴″ = H,
308c: R³″ = H, R⁴″ = Me
308d: R³″ = H, R⁴″ = OMe
308e: R³″ = H, R⁴″ = Cl
308f: R³″ = Cl, R⁴″ = H
308g: R³″ = H, R⁴″ = F

The synthesis of compound 308a is shown in Scheme 28.

Step A

Preparation of 4,6-dihydroxy-2-(3-trifluoromethyl-pyrazol-1-yl)-pyrimidine 303. Compound 303 was synthesized from compound 302b (12.3 g, 90.3 mmol), according to the procedure as described for compound 302a, as a white solid in 100% yield. ¹H NMR (DMSO-d₆, 400 MHz) δ (ppm) 5.80 (s, 1H), 7.00 (d. J=2.78 Hz, 1H), 8.62 (dd, J=2.78 Hz and J=1.00 Hz, 1H); ¹⁹F NMR (DMSO-d₆, 376 MHz) δ (ppm) −61.23 (s, 3F).

Step B

Preparation of 4,6-dichloro-2-(3-trifluoromethyl-pyrazol-1-yl)-pyrimidine 304. To compound 303 (8.7 g. 35.15 mmol) were added POCl₃ (16.5 mL) and N,N-diethylaniline (9.56 mL). The resulting mixture was stirred at 110° C. for 2 hrs. The mixture was then cooled down to room temperature and poured dropwise into an ice/water mixture. The precipitate was filtered, washed with water, and dried under reduced pressure to yield compound 304 as a white solid in 90% yield. ¹H NMR (CDCl₃, 400 MHz) δ (ppm) 6.77 (s, 1H), 7.37 (s, 1H), 8.63 (dd, J=2.78 Hz and J=1.00 Hz, 1H); ¹⁹F NMR (CDCl₃, 376 MHz) δ (ppm) −62.78 (s, 3F).

Scheme 28

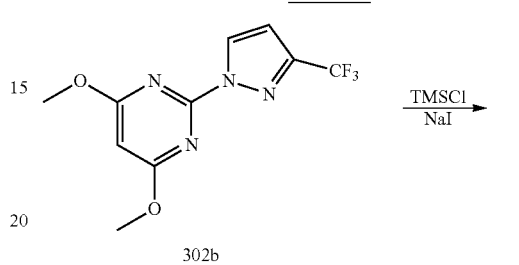

302b

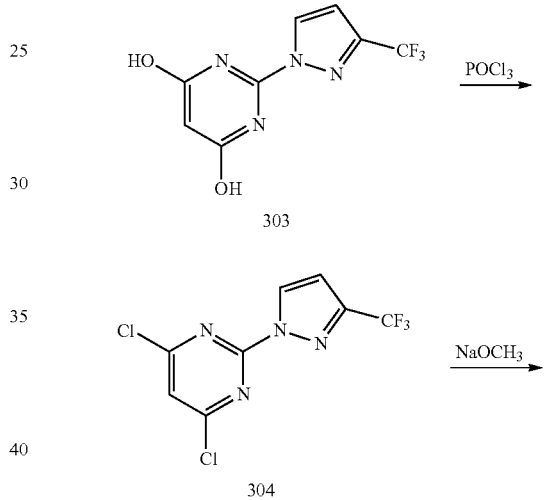

303

304

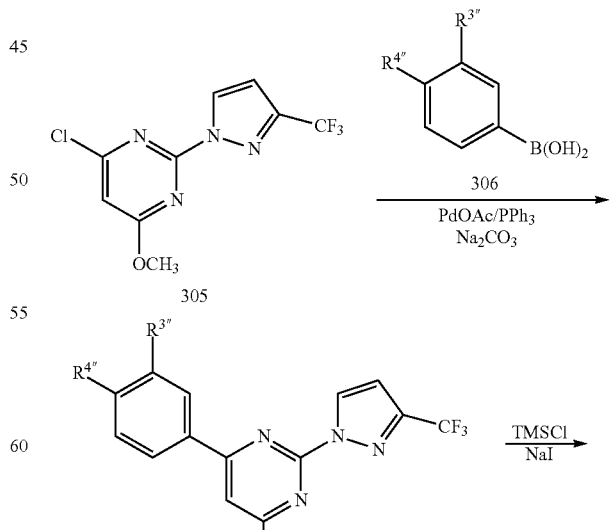

305

306

307

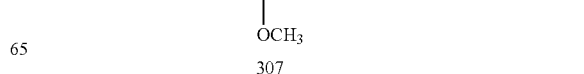

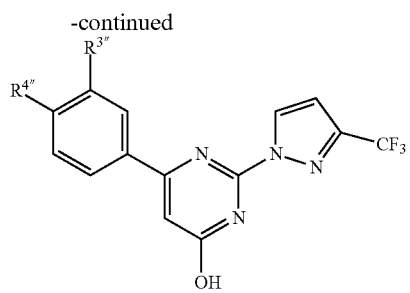

308b: R³" = H, R⁴" = H,
308c: R³" = H, R⁴" = Me
308d: R³" = H, R⁴" = OMe
308e: R³" = H, R⁴" = Cl
308f: R³" = Cl, R⁴"" = H
308g: R³" = H, R⁴" = F

Step C

Preparation of 6-chloro-4-methoxy-2-(3-trifluoromethyl-pyrazol-1-yl)-pyrimidine 305. To a stirred solution of compound 304 (1 g, 3.53 mmol) in MeOH (10 mL) at 0° C. was added NaOMe (760 μL) dropwise. The mixture was stirred at room temperature for 2 hrs. Methanol was evaporated. The residue was dissolved in DCM, washed sequentially with water and brine. Organics were dried over Na₂SO₄ filtered, concentrated under reduced pressure, and purified by silica gel chromatography to yield compound 305 as a white solid in 68% yield. ¹H NMR (CDCl₃, 400 MHz) δ (ppm) 4.11 (s, 3H), 6.71-6.72 (m, 2H), 8.58 (dd, J=2.78 Hz and J=1.00 Hz, 1H); ¹⁹F NMR (CDCl₃, 376 MHz) δ (ppm) −62.54 (s, 3F).

Step D

Preparation of 4-methoxy-6-phenyl-2-(3-trifluoromethyl-pyrazol-1-yl)-pyrimidine 307b

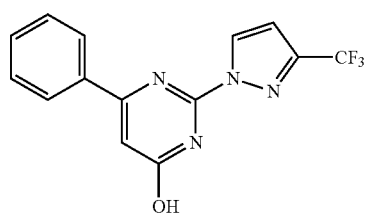

To a solution of compound 305 (670 mg, 2.4 mmol) in dry THF (11 mL) were added phenyl boronic acid 306b (439 mg, 3.6 mmol), palladium acetate (7 mg, 0.03 mmol), triphenyl phosphine (16 mg, 0.06 mmol), and sodium carbonate (4.8 mg). The mixture was stirred at 60° C. for 3 hrs. The solution was then cooled down to room temperature. Water and TBDME were added. Organics were washed with water, dried over Na₂SO₄, filtered, concentrated under reduced pressure, and purified by silica gel chromatography to yield compound 307b as a white solid in 95% yield. ¹H NMR (CDCl₃, 400 MHz) δ (ppm) 4.11 (s, 3H), 6.71-6.72 (m, 2H), 7.54-8.05 (m, 5H), 8.58 (dd, J=2.78 Hz and J=1.00 Hz, 1H); ¹⁹F NMR (CDCl₃, 376 MHz) δ (ppm) −62.45 (s, 3F).

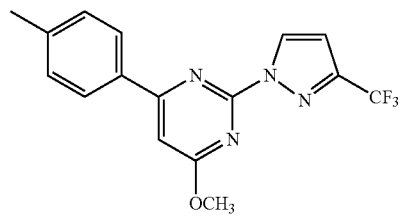

4-Methoxy-6-(4-methyl-phenyl)-2-(3-trifluoromethyl-pyrazol-1-yl)-pyrimidine 307c was synthesized from compound 305 (1 g, 3.59 mmol) and (4-methyl-phenyl)-boronic acid 306c (732 mg, 5.39 mmol), according to the procedure as described for compound 307b, as a white solid in 75% yield. MS (ESI, EI⁺): m/z=335 (MH⁺).

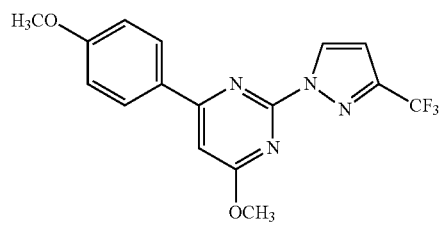

4-Methoxy-6-(4-methoxy-phenyl)-2-(3-trifluoromethyl-pyrazol-1-yl)-pyrimidine 307d was synthesized from compound 305 (1 g, 3.59 mmol) and (4-methoxy-phenyl)-boronic acid 306d (819 mg, 5.39 mmol), according to the procedure as described for compound 307b, as a beige solid in 55% yield. MS (ESI, EI⁺): m/z=351 (MH⁺).

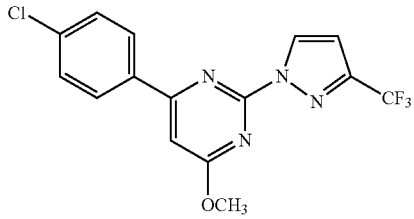

4-Methoxy-6-(4-chloro-phenyl)-2-(3-trifluoromethyl-pyrazol-1-yl)-pyrimidine 307e was synthesized from compound 305 (1 g, 3.59 mmol) and (4-chloro-phenyl)-boronic acid 306e (842 mg, 5.39 mmol), according to the procedure as described for compound 307b, was a beige solid in 45% yield. MS (ESI, EI⁺): m/z=355 (MH⁺).

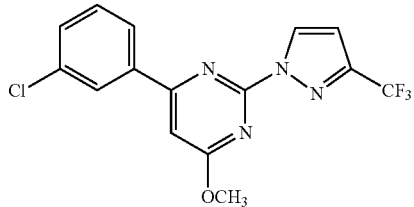

4-Methoxy-6-(3-chloro-phenyl)-2-(3-trifluoromethyl-pyrazol-1-yl)-pyrimidine 307f was synthesized from compound 305 (1 g, 3.59 mmol) and (3-chloro-phenyl)-boronic acid 306f (842 mg, 5.39 mmol), according to the procedure as described for compound 307b as a beige solid in 45% yield. MS (ESI, EI$^+$): m/z=355 (MH$^+$).

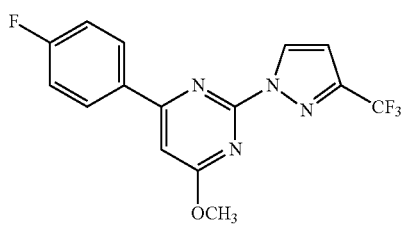

4-Methoxy-6-(4-fluoro-phenyl)-2-(3-trifluoromethyl-pyrazol-1-yl)-pyrimidine 307g was synthesized from compound 100 (760 mg, 3.18 mmol) and compound 27a (650 mg, 4.78 mmol) following the procedure as described for compound 307b, as a yellow solid in 100% yield. MS (ESI, EI$^+$): m/z=339 (MH$^+$).

Step D

Preparation of 4-hydroxy-6-phenyl-2-(3-trifluoromethyl-pyrazol-1-yl)-pyrimidine 308b

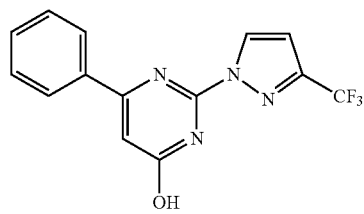

Compound 308b was synthesized from compound 307b (720 mg, 2.25 mmol), according to the procedure as described for compound 308a, as a white solid in 20% yield. $^1$H NMR (DMSO-d$_6$, 400 MHz) δ (ppm) 7.06 (d, J=2.65 Hz, 1H), 7.26 (s, 1H), 7.51-7.56 (m, 3H), 8.24-8.27 (m, 2H), 8.99 (dd, J=2.70 Hz and J=0.97 Hz, 1H).

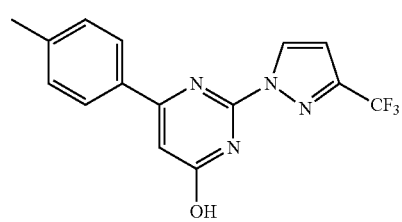

4-Hydroxy-6-(4-methyl-phenyl)-2-(3-trifluoromethyl-pyrazol-1-yl)-pyrimidine 308c was synthesized from compound 307c, according to the procedure as described for compound 308a, as a white solid in 50% yield. MS (ESI, EI$^+$): m/z=321 (MH$^+$).

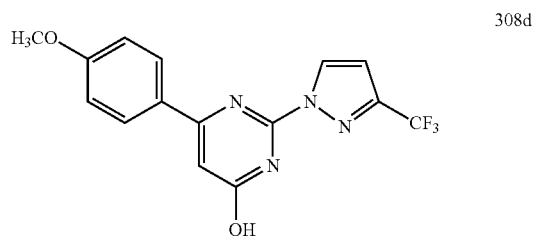 [SMILES: COc1ccc(-c2cc(O)nc(-n3ccc(C(F)(F)F)n3)n2)cc1]

4-Hydroxy-6-(4-methoxy-phenyl)-2-(3-trifluoromethyl-pyrazol-1-yl)-pyrimidine 308d was synthesized from compound 307d, according to the procedure as described for compound 308a, as a beige solid in 60% yield. MS (ESI, EI$^+$): m/z=337 (MH$^+$).

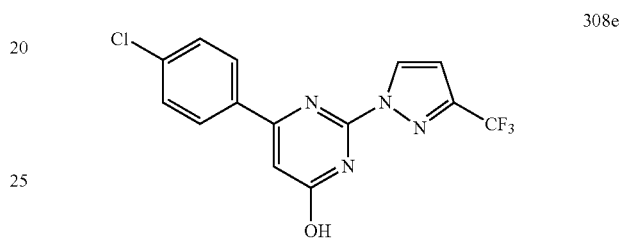

4-Hydroxy-6-(4-chloro-phenyl)-2-(3-trifluoromethyl-pyrazol-1-yl)-pyrimidine 308e was synthesized from compound 307e, according to the procedure as described for compound 308a, as a beige solid in 42% yield. MS (ESI, EI$^+$): m/z=341 (MH$^+$).

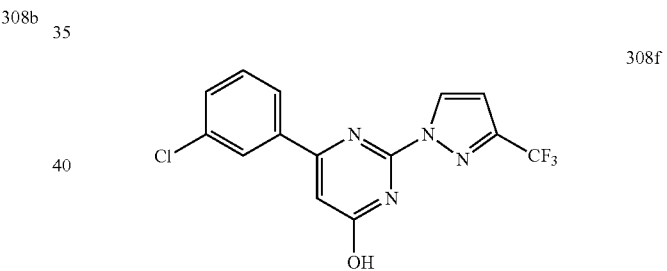

4-Hydroxy-6-(3-chloro-phenyl)-2-(3-trifluoromethyl-pyrazol-1-yl)-pyrimidine 308f was synthesized from compound 307f, according to the procedure as described for compound 308a, as a beige solid in 90% yield. MS (ESI, EI$^+$): m/z=341 (MH$^+$).

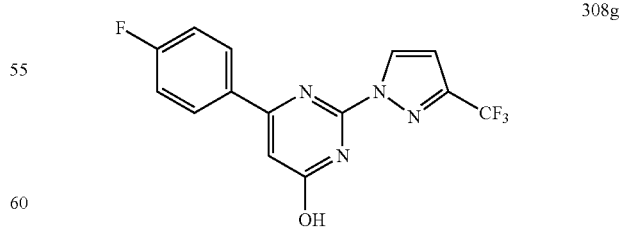

4-Hydroxy-6-(4-fluoro-phenyl)-2-(3-trifluoromethyl-pyrazol-1-yl)-pyrimidine 308g was synthesized from compound 307g, according to the procedure as described for compound 308a, as a yellow solid in 43% yield. MS (ESI, EI$^+$): m/z=325 (MH$^+$).

Example 30

Preparation of 4-hydroxy-6-(4-isopropyl-thiazol-2-yl)-2-(3-trifluoromethyl-pyrazol-1-yl)-pyrimidine 308h

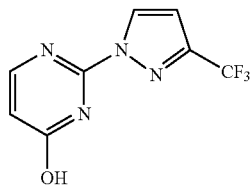

308h

The synthesis of compound 308h is shown in Scheme 29.

Step A:

Preparation of 4-methoxy-6-(4-isopropyl-thiazol-2-yl)-2-(3-trifluoromethyl-pyrazol-1-yl)-pyrimidine 307h. To a solution of compound 305 (892 mg, 3.2 mmol) in dry DMF (15 mL) were added tributyl(4-isopropyl-thiazole)-stannane (2 g, 4.8 mmol), PdCl$_2$(PPh$_3$)$_2$ (224 mg, 0.32 mmol), and potassium carbonate (530 mg, 3.84 mmol). The mixture was stirred at 90° C. for 48 hrs, and the concentrated under reduced pressure. Water and ethyl acetate were added. Organics were washed with water, dried over Na$_2$SO$_4$, filtered, concentrated under reduced pressure, and purified by silica gel chromatography to yield compound 307h as a beige solid in 76% yield. MS (ESI, EI$^+$): m/z=370 (MH$^+$).

Scheme 29

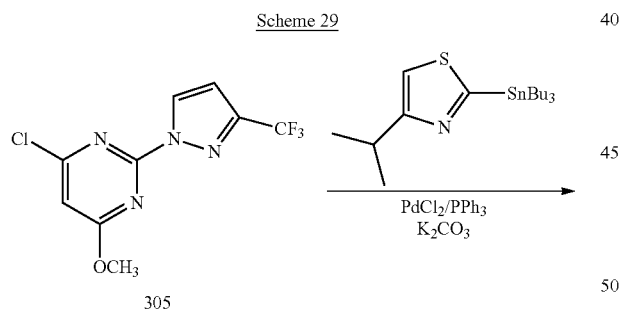

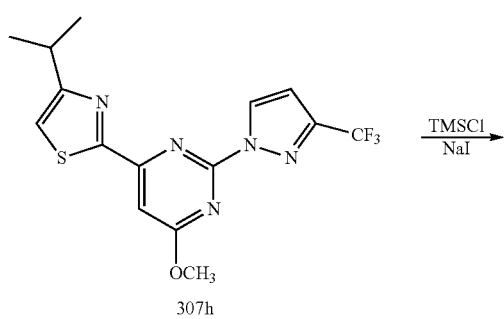

Step B:

Preparation of 4-hydroxy-6-(4-isopropyl-thiazol-2-yl)-2-(3-trifluoromethyl-pyrazol-1-yl)-pyrimidine 308h. Compound 308h was synthesized from compound 307h (900 mg, 2.44 mmol), according to the procedure as described for compound 308a, as a beige solid in 30% yield. MS (ESI, EI$^+$): m/z=356 (MH$^+$).

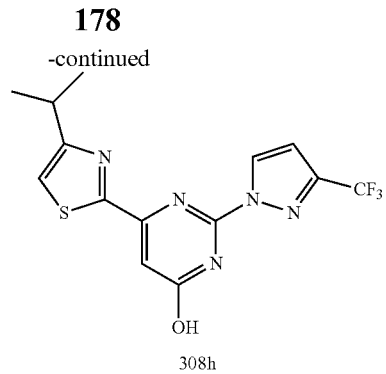

Example 33

Preparation of Compound 52

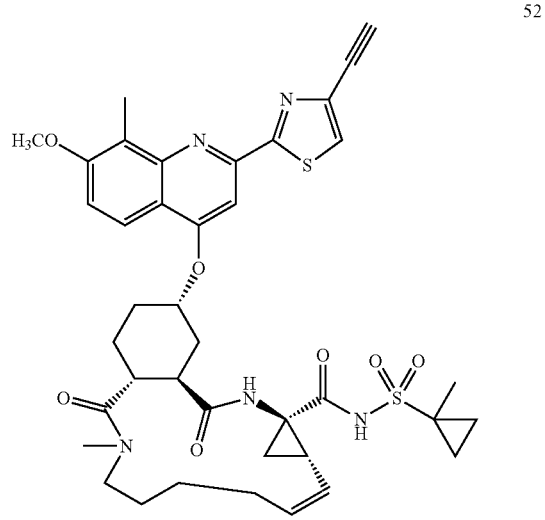 [SMILES: C#Cc1csc(-c2cc(O[C@H]3CC[C@H]4C(=O)N(C)CCCC/C=C\[C@@H]5C[C@@]5(C(=O)NS(=O)(=O)C5(C)CC5)NC(=O)[C@@H]4C3)c3ccc(OC)c(C)c3n2)n1]

Compound 52 was synthesized according to Schemes 30 and 31.

Step A.

Preparation of (1R,2R,4R)-2-benzyl 1-methyl 4-(tert-butyldiphenylsilyloxy)cyclohexane-1,2-dicarboxylate 35. To a solution of compound 34d (10.9 mmol) in DMF (35 mL) were added TBDPSCl (24.0 mmol) and imidazole (32.7 mmol). The reaction mixture was stirred at room temperature for 16 hrs. The reaction mixture was then diluted with DCM (140 mL) and washed sequentially with 1N HCl (140 mL) and H$_2$O (140 mL). Organics were dried, concentrated, and purified by silica gel chromatography (PE/EtOAc) to yield compound 35 as a colourless oil in 65% yield.

Step B.

Preparation of (1R,2R,5R)-5-(tert-butyldiphenylsilyloxy)-2-(methoxycarbonyl)cyclohexanecarboxylic acid 36. To a solution of compound 35 (12.2 mmol) in anhydrous EtOH (50 mL) was added Pd/C 10% (20% w/w). The vessel was flushed with nitrogen and $H_2$ was added. The reaction mixture was stirred under hydrogen atmosphere for 16 hrs. The catalyst was filtered off and washed several times with EtOH. The filtrate was concentrated in vacuo to yield compound 36 as a colourless oil in a quantitative yield.

Scheme 30

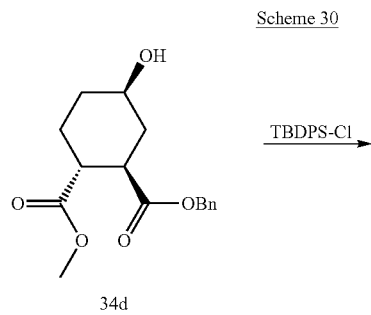

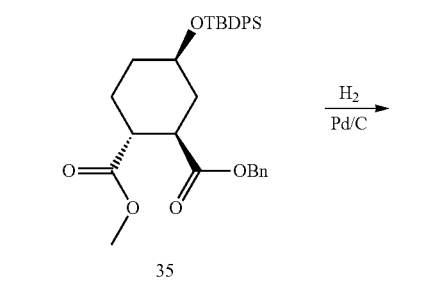

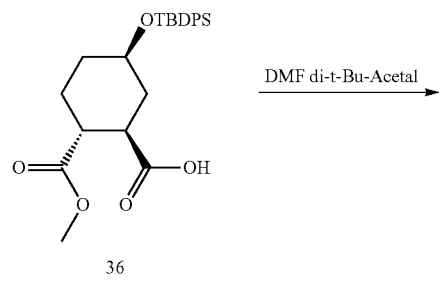

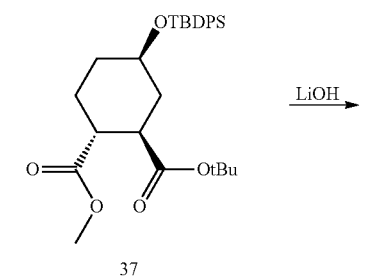

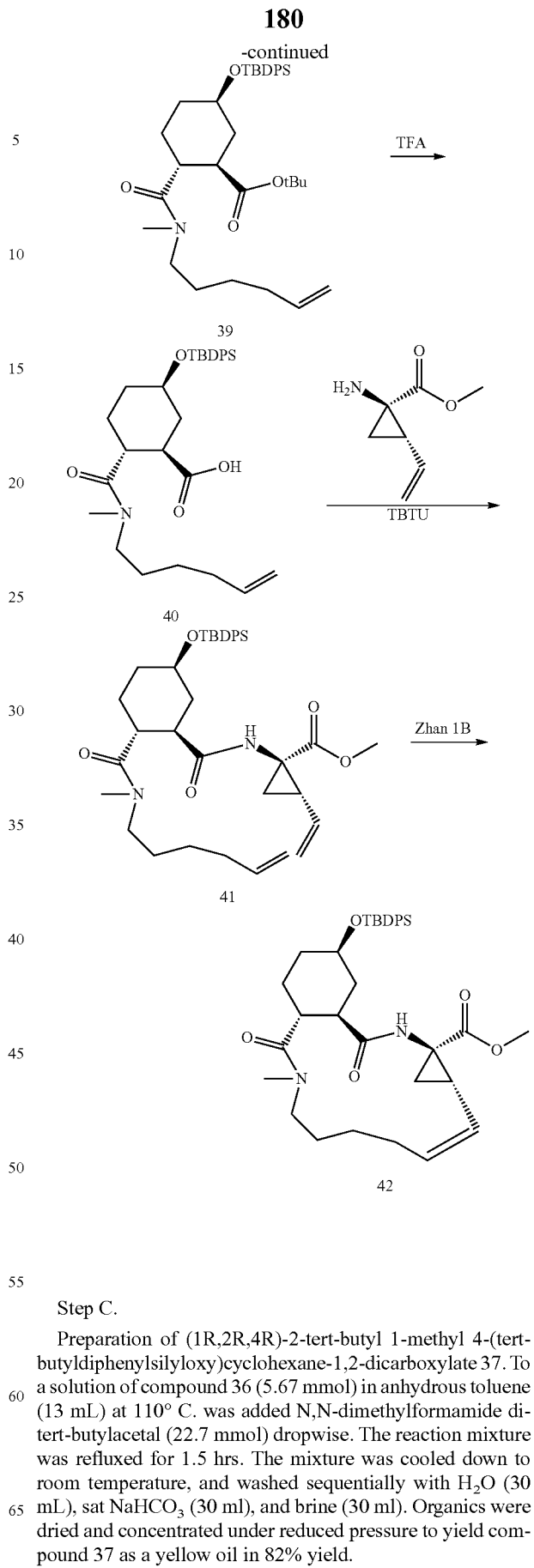

Step C.

Preparation of (1R,2R,4R)-2-tert-butyl 1-methyl 4-(tert-butyldiphenylsilyloxy)cyclohexane-1,2-dicarboxylate 37. To a solution of compound 36 (5.67 mmol) in anhydrous toluene (13 mL) at 110° C. was added N,N-dimethylformamide di-tert-butylacetal (22.7 mmol) dropwise. The reaction mixture was refluxed for 1.5 hrs. The mixture was cooled down to room temperature, and washed sequentially with $H_2O$ (30 mL), sat $NaHCO_3$ (30 ml), and brine (30 ml). Organics were dried and concentrated under reduced pressure to yield compound 37 as a yellow oil in 82% yield.

Scheme 31

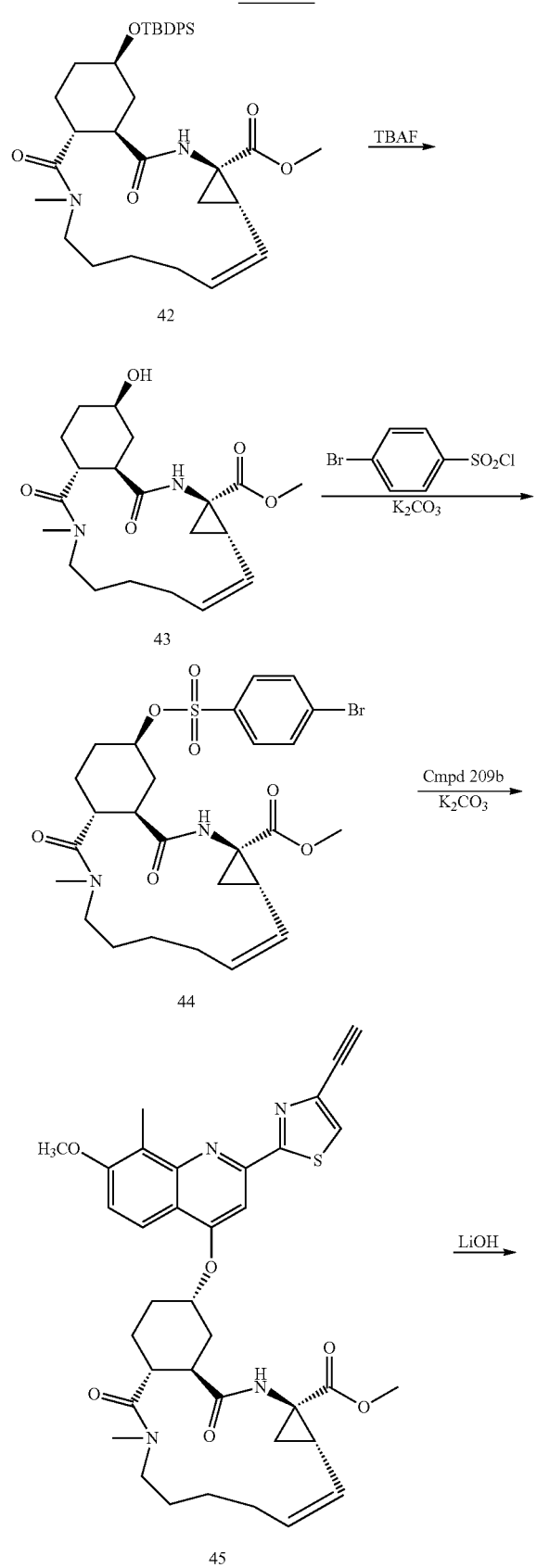

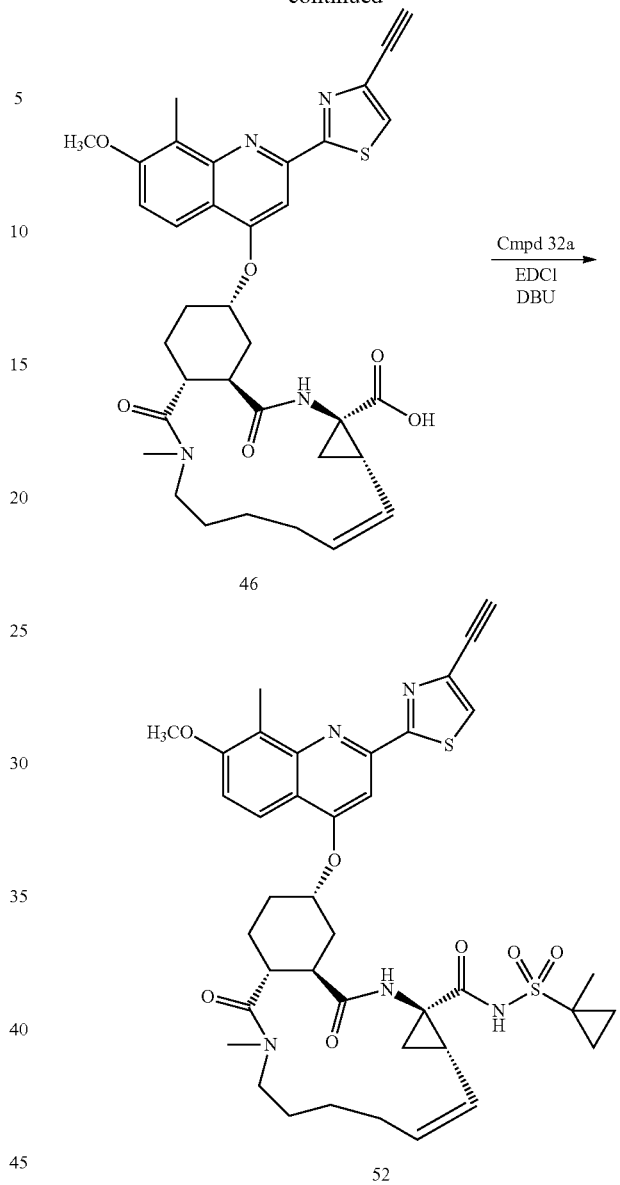

Step D.

Preparation of (1R,2R,4R)-2-(tert-butoxycarbonyl)-4-(tert-butyldiphenylsilyloxy)cyclohexanecarboxylic acid 38. A solution of compound 37 (4.2 mmol) and LiOH (16.8 mmol) in THF/H$_2$O 1/1 (40 mL) was stirred at room temperature for 16 hrs. The reaction mixture was neutralized with 1N HCl to pH 2, and then extracted with DCM (100 mL). Organics were concentrated under reduced pressure and purified by chromatography on silica gel (Cyclohexane/EtOAc) to yield compound 38 as pale yellow oil in 63% yield.

Step E.

Preparation of (1R,2R,5R)-tert-butyl 5-(tert-butyldiphenylsilyloxy)-2-(hex-5-enyl(methyl)carbamoyl)cyclohexanecarboxylate 39. To a cold solution of compound 38 (1.80 mmol), TBTU (2.17 mmol), and N-methylhex-5-en-1-amine tosylate salt 31a (2.17 mmol) in DMF (100 mL) was added diisopropyl ethyl amine (5.4 mmol) dropwise under nitrogen at 0° C. The reaction mixture was stirred overnight at room temperature, then quenched with water and extracted with diethyl ether. The organic layer was washed with brine, then dried on magnesium sulphate, concentrated under reduced pressure, and purified by chromatography on silica gel to yield compound 39 as a beige solid in 85% yield. MS (ESI, EI$^+$): m/z=578 (MH$^+$).

Step F.

Preparation of (1R,2R,5R)-5-(tert-butyldiphenylsilyloxy)-2-(hex-5-enyl(methyl)carbamoyl)cyclohexanecarboxylic acid 40. To a solution of compound 39 (1.07 mmol) in anhydrous DCM (70 mL) was added TFA (42.6 mmol) slowly. The reaction mixture was stirred at room temperature for 16 hrs. The reaction mixture was concentrated and purified by silica gel chromatography (DCM/MeOH) to yield compound 40 as a yellow oil in 48% yield. MS (ESI, EI$^+$): m/z=522 (MH$^+$).

Step G.

Preparation of (1R,2S)-methyl 1-((1R,2R,5R)-5-(tert-butyldiphenylsilyloxy)-2-(hex-5-enyl(methyl)carbamoyl)cyclohexanecarboxamido)-2-vinylcyclopropanecarboxylate 41. Compound 41 was synthesized from compound 40 and (1R,2S)-methyl 1-amino-2-vinylcyclopropanecarboxylate as described for compound 39 to yield compound 41 as a yellow oil in 76% yield. MS (ESI, EI$^+$): m/z=645 (MH$^+$)

Step H.

Preparation of (1aR,3aR,5R,7aR,15aS,Z)-methyl 5-(tert-butyldiphenylsilyloxy)-9-methyl-3,8-dioxo-1a,2,3,3a,4,5,6,7,7a,8,9,10,11,12,13,15a-hexadecahydro-1H-benzo[c]cyclopropa[g][1,6]diazacyclotetradecine-1a-carboxylate 42. To a solution of compound 41 (0.74 mmol) in dichloroethane (700 mL), degassed for 45 min by bubbling nitrogen, was Zhan 1B (4%, 22 mg) at 80° C. under continuous degassing with nitrogen. After the reaction was refluxed for 1 hr, a second portion of Zhan 1B (22 mg) was added. After heating for 1.5 hr, the reaction mixture was cooled down to room temperature, poured onto a silica pad, and eluted with DCM. The crude material was purified by chromatography on silica gel (DCM/MeOH) to yield compound 42 as a brown solid in 81% yield. MS (ESI, EI$^+$): m/z=617 (MH$^+$).

Step I.

Preparation of (1aR,3aR,5R,7aR,15aS,Z)-methyl 5-hydroxy-9-methyl-3,8-dioxo-1a,2,3,3a,4,5,6,7,7a,8,9,10,11,12,13,15a-hexadecahydro-1H-benzo[c]cyclopropa[g][1,6]diazacyclotetradecine-1a-carboxylate 43. To a solution of compound 42 (0.6 mmol) in dry THF (12 mL) was added dropwise a solution of tetrabutylammonium fluoride (1M in THF, 12 mL). The reaction was stirred at room temperature overnight, and then concentrated. The residue was dissolved in MeOH and purified by semi preparative HPLC (RP18) to yield compound 43, which was used without further purification directly in the next step. MS (ESI, EI$^+$): m/z=379 (MH$^+$).

Step J.

Preparation of (1aR,3aR,5R,7aR,15aS,Z)-methyl 5-(4-bromophenylsulfonyloxy)-9-methyl-3,8-dioxo-1a,2,3,3a,4,5,6,7,7a,8,9,10,11,12,13,15a-hexadecahydro-1H-benzo[c]cyclopropa[g][1,6]diazacyclotetradecine-1a-carboxylate 44. To a mixture of compound 43 (0.13 mmol), TEA (0.39 mmol), and DMAP (0.009 mmol) in anhydrous DCM (0.3 mL) was added 4-bromobenzenesulfonyl chloride (0.17 mmol) in DCM (0.15 mL) dropwise. The reaction mixture was stirred at room temperature under nitrogen for 16 hrs. The crude material was washed sequentially with 0.5N HCl and 2.5% NaHCO$_3$. The organics were concentrated to yield compound 44 as a yellow oil in a quantitative yield. MS (ESI, EI$^+$): m/z=598 (MH$^+$).

Step K.

Preparation of (1aR,3aR,5S,7aR,15aS,Z)-methyl 5-(2-(4-ethynylthiazol-2-yl)-7-methoxy-8-methyl-quinolin-4-yloxy)-9-methyl-3,8-dioxo-1a,2,3,3a,4,5,6,7,7a,8,9,10,11,12,13,15a-hexadecahydro-1H-benzo[c]cyclopropa[g][1,6]diazacyclotetradecine-1a-carboxylate 45. Compound 44 (0.13 mmol) and 2-(4-ethynyl-thiazol-2-yl)-7-methoxy-8-methyl-quinolin-4-ol (0.14 mmol) 209b were dissolved in NMP (0.5 mL). K$_2$CO$_3$ (0.19 mmol) was added and the reaction mixture was heated at 70° C. for 2 days. The crude material was purified by silica gel chromatography (PE/EtOAc) to yield compound 45 as a beige solid. MS (ESI, EI$^+$): m/z=657 (MH$^+$).

Step L.

Preparation of (1aR,3aR,5S,7aR,15aS,Z)-5-(2-(4-ethynylthiazol-2-yl)-7-methoxy-8-methylquinolin-4-yloxy)-9-methyl-3,8-dioxo-1a,2,3,3a,4,5,6,7,7a,8,9,10,11,12,13,15a-hexadecahydro-1H-benzo[c]cyclopropa[g][1,6]diazacyclotetradecine-1a-carboxylic acid 46. Compound 46 was synthesized from compound 45 as described for compound 38 to yield compound 46 as a beige solid. MS (ESI, EI$^+$): m/z=643 (MH$^+$).

Step M.

Preparation of (1aR,3aR,5S,7aR,15aS,Z)-5-(2-(4-ethynylthiazol-2-yl)-7-methoxy-8-methylquinolin-4-yloxy)-9-methyl-N-(1-methylcyclopropylsulfonyl)-3,8-dioxo-1a,2,3,3a,4,5,6,7,7a,8,9,10,11,12,13,15a-hexadecahydro-1H-benzo[c]cyclopropa[g][1,6]diazacyclotetradecine-1a-carboxamide 52. To compound 46 (0.00003 mmol) in DCM (2 mL) under nitrogen was added EDCI (0.000062 mmol). The reaction mixture was stirred at room temperature for 2 hrs. Methyl-cyclopropylsulfonamide (0.00012 mmol) and DBU (0.00012 mmol) were then added and the reaction was stirred at room temperature for 16 hrs. DCM was then added, the mixture was washed with water and brine. Solvent was evaporated and the crude material was purified by silica gel chromatography (DCM/MeOH) to yield compound 52 as a white solid. MS (ESI, EI$^+$): m/z=760 (MH$^+$).

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula Ia or Ib:

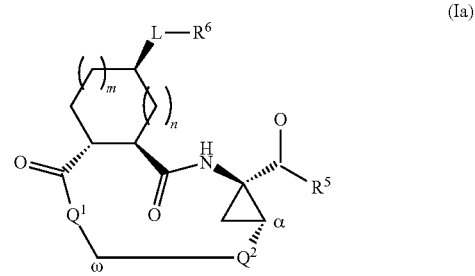

-continued

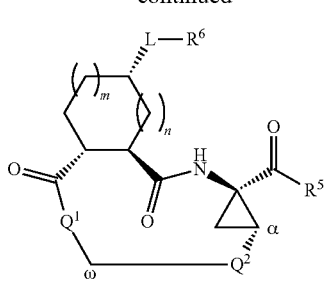

(Ib)

or a single enantiomer, a racemic mixture, a mixture of diastereomers, or an isotopic variant thereof; or a pharmaceutically acceptable salt thereof;
wherein:
$R^5$ is —NHS(O)$_2$R$^8$; wherein R$^8$ is 1-methylcyclopropyl or 1-ethynylcyclopropyl;
L is —O— or —OC(O)NH—;
$R^6$ is methoxy-fluoro-(isopropylthiazolyl)quinolinyl, methoxy-chloro-(isopropyl-thiazolyl)quinolinyl, methoxy-bromo-(isopropylthiazolyl)quinolinyl, methoxy-methyl-(isopropylthiazolyl)quinolinyl, dimethoxy-(isopropylthiazolyl)quinolinyl, difluoromethyl-chloro-(isopropylthiazolyl)quinolinyl, difluoromethyl-methyl-(isopropylthiazolyl)quinolinyl, trifluoromethyl-methyl-(isopropyl-thiazolyl)quinolinyl, methanesulfonamido-chloro-(isopropylthiazolyl)quinolinyl, methanesulfonamido-methyl-(isopropylthiazolyl)quinolinyl, methoxy-fluoro-(trifluoromethylthiazolyl)-quinolinyl, methoxy-chloro-(trifluoro-methylthiazolyl)quinolinyl, methoxy-bromo-(trifluoromethylthiazolyl)quinolinyl, methoxy-methyl-(trifluoromethylthiazolyl)quinolinyl, dimethoxy-(trifluoromethylthiazolyl)quinolinyl, methanesulfonamido-methyl-(trifluoromethylthiazolyl)quinolinyl, methoxy-chloro-(ethenyl-thiazolyl)quinolinyl, methoxy-chloro-(ethynylthiazolyl)quinolinyl, methoxy-methyl-(ethynyl-thiazolyl)quinolinyl, methoxy-chloro-(cyanothiazolyl)quinolinyl, methoxy-chloro-(methyl-thiazolyl)quinolinyl, methoxy-chloro-(cyclopropylthiazolyl)quinolinyl, methoxy-chloro-(cyclobutylthiazolyl)quinolinyl, chloro-methoxy-(isopropyl-1H-pyrazolyl)quinolinyl, methyl-methoxy-(isopropyl-1H-pyrazolyl)quinolinyl, chloro-methoxy-(trifluoromethyl-1H-pyrazolyl)-quinolinyl, methyl-methoxy-(trifluoromethyl-1H-pyrazolyl)quinolinyl, methoxy-fluoro-(isopropylisoxazolyl)quinolinyl, methoxy-chloro-(isopropyl-isoxazolyl)quinolinyl, methoxy-bromo-(isopropylisoxazolyl)quinolinyl, methoxy-methyl-(isopropylisoxazolyl)quinolinyl, dimethoxy-(isopropylisoxazolyl)quinolinyl; and
$Q^1$ is —N(R$^{17}$)—; wherein R$^{17}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;
$Q^2$ has the structure of:

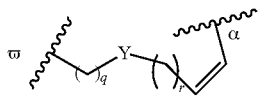

wherein:
Y is a bond, —O—, —S—, —S(O)—, —S(O)$_2$—, or —N(R$^Y$)—, wherein R$^Y$ is hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, —C(O)R$^{Ya}$, —C(O)OR$^{Ya}$, —C(O)NR$^{Yb}$R$^{Yc}$, —S(O)$_2$NR$^{Yb}$R$^{Yc}$, or —S(O)$_2$R$^{Ya}$; where each R$^{Ya}$, R$^{Yb}$, and R$^{Yc}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;
q is an integer of 0, 1, 2, 3, or 4;
r is an integer of 0, 1, 2, 3, or 4; and
m is an integer of 0 or 1; and n is an integer of 1 or 2; with the proviso that the sum of m and n is 2.

2. The compound of claim 1, wherein R$^{17}$ is hydrogen or methyl.

3. The compound of claim 1, wherein R$^6$ is 7-methoxy-8-fluoro-2-(4-isopropylthiazol-2-yl)quinolin-4-yl, 7-methoxy-8-chloro-2-(4-isopropylthiazol-2-yl)quinolin-4-yl, 7-methoxy-8-bromo-2-(4-isopropylthiazol-2-yl)quinolin-4-yl, 7-methoxy-8-methyl-2-(4-isopropylthiazol-2-yl)quinolin-4-yl, 5,7-dimethoxy-2-(4-isopropylthiazol-2-yl)quinolin-4-yl, 6-chloro-7-methoxy-2-(4-isopropyl-thiazol-2-yl)quinolin-4-yl, 6-methoxy-7-chloro-2-(4-isopropylthiazol-2-yl)quinolin-4-yl, 6-methoxy-8-methyl-2-(4-isopropylthiazol-2-yl)quinolin-4-yl, 6-methoxy-8-chloro-2-(4-isopropylthiazol-2-yl)quinolin-4-yl, 7-difluoromethyl-8-methyl-2-(4-isopropylthiazol-2-yl)quinolin-4-yl, 7-difluoromethyl-8-chloro-2-(4-isopropylthiazol-2-yl)quinolin-4-yl, 6-trifluoromethyl-8-methyl-2-(4-isopropylthiazol-2-yl)quinolin-4-yl, 7-trifluoromethyl-8-methyl-2-(4-isopropylthiazol-2-yl)quinolin-4-yl, 7-trifluoromethyl-8-chloro-2-(4-isopropyl-thiazol-2-yl)quinolin-4-yl, 7-methanesulfonamido-8-methyl-2-(4-isopropylthiazol-2-yl)-quinolin-4-yl, 7-methanesulfonamido-8-chloro-2-(4-isopropylthiazol-2-yl)quinolin-4-yl, 6-methyl-8-difluoromethyl-2-(4-isopropylthiazol-2-yl)quinolin-4-yl, 7-methoxy-8-fluoro-2-(4-trifluoromethylthiazol-2-yl)quinolin-4-yl, 7-methoxy-8-chloro-2-(4-trifluoromethylthiazol-2-yl)quinolin-4-yl, 7-methoxy-8-bromo-2-(4-trifluoromethylthiazol-2-yl)quinolin-4-yl, 7-methoxy-8-methyl-2-(4-trifluoromethylthiazol-2-yl)quinolin-4-yl, 5,7-dimethoxy-2-(4-trifluoromethylthiazol-2-yl)quinolin-4-yl, 6-methoxy-7-chloro-2-(4-trifluoromethylthiazol-2-yl)quinolin-4-yl, 6-methoxy-8-methyl-2-(4-trifluoromethylthiazol-2-yl)quinolin-4-yl, 7-methanesulfonamido-8-methyl-2-(4-trifluoromethylthiazol-2-yl)quinolin-4-yl, 7-methoxy-8-chloro-2-(4-ethenylthiazol-2-yl)quinolin-4-yl, 7-methoxy-8-chloro-2-(4-ethynylthiazol-2-yl)quinolin-4-yl, 7-methoxy-8-methyl-2-(4-ethynylthiazol-2-yl)quinolin-4-yl, 7-methoxy-8-chloro-2-(4-cyanothiazol-2-yl)quinolin-4-yl, 7-methoxy-8-chloro-2-(4-methylthiazol-2-yl)quinolin-4-yl, 7-methoxy-8-chloro-2-(4-cyclopropylthiazol-2-yl)quinolin-4-yl, 7-methoxy-8-chloro-2-(4-cyclobutylthiazol-2-yl)quinolin-4-yl, 7-methoxy-8-fluoro-2-(2-isopropylthiazol-4-yl)quinolin-4-yl, 7-methoxy-8-chloro-2-(2-isopropylthiazol-4-yl)quinolin-4-yl, 7-methoxy-8-bromo-2-(2-isopropylthiazol-4-yl)quinolin-4-yl, 7-methoxy-8-methyl-2-(2-isopropylthiazol-4-yl)quinolin-4-yl, 5,7-dimethoxy-2-(2-isopropylthiazol-4-yl)quinolin-4-yl, 6-methoxy-7-chloro-2-(2-isopropylthiazol-4-yl)quinolin-4-yl, 6-methoxy-8-methyl-2-(2-isopropylthiazol-4-yl)quinolin-4-yl, 7-methoxy-8-chloro-2-(2-trifluoromethylthiazol-4-yl)quinolin-4-yl, 7-methoxy-8-methyl-2-(2-trifluoromethylthiazol-4-yl)quinolin-4-yl, 8-chloro-7-methoxy-2-(3-isopropyl-1H-pyrazol-1-yl)quinolin-4-yl, 8-methyl-7-methoxy-2-(3-isopropyl-1H-pyrazol-1-yl)-quinolin-4-yl, 8-chloro-7-methoxy-2-(3-trifluoromethyl-1H-pyrazol-1-yl)quinolin-4-yl, 8-methyl-7-methoxy-2-(3-trifluoromethyl-1H-pyrazol-1-yl)quinolin-4-yl, 7-methoxy-8-fluoro-2-(5-isopropylisoxazol-3-yl)-quinolin-4-yl, 7-methoxy-8-chloro-2-(5-isopropylisoxazol-3-yl)quinolin-4-yl, 7-methoxy-8-bromo-2-(5-isopropylisoxazol-3-yl)quinolin-4-yl, 7-methoxy-8-methyl-2-(5-isopropyl-isoxazol-3-yl)quinolin-4-yl, 5,7-dimethoxy-2-(5-isopropylisoxazol-3-yl)quinolin-4-yl, 6-methoxy-7-chloro-2-(5-isopropylisoxazol-3-yl)quinolin-4-yl, or 6-methoxy-8-methyl-2-(5-isopropylisoxazol-3-yl)quinolin-4-yl.

4. The compound of claim 1, wherein m is 0.
5. The compound of claim 1, wherein m is 1.
6. The compound of claim 1, wherein n is 1.
7. The compound of claim 1, wherein n is 2.

8. The compound of claim 1, wherein $R^8$ is 1-methylcyclopropyl.

9. The compound of claim 1, wherein the compound is:

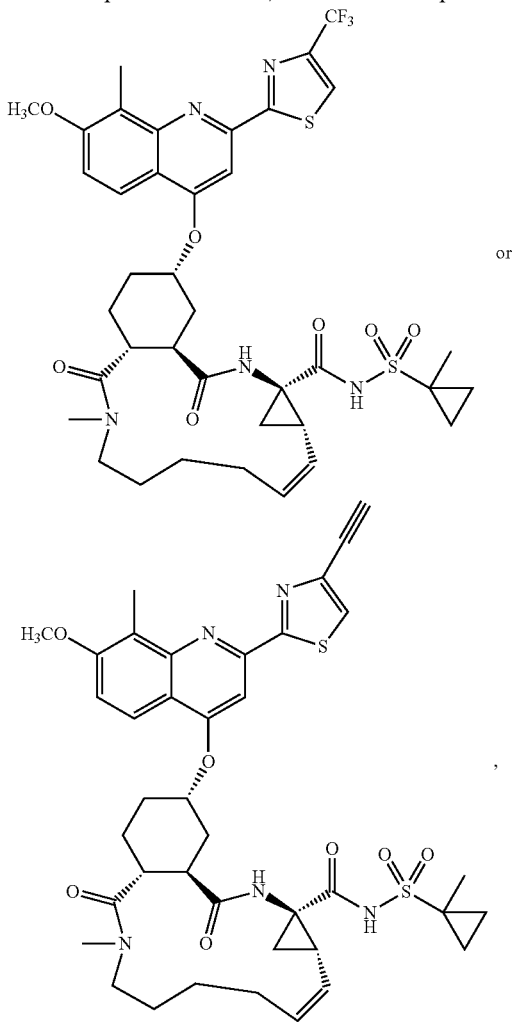

or a single enantiomer, a racemic mixture, a mixture of diastereomers, or an isotopic variant thereof or a pharmaceutically acceptable salt thereof.

10. A pharmaceutical composition comprising the compound of claim 1, and one or more pharmaceutically acceptable carriers.

11. The pharmaceutical composition of claim 10, further comprising a second antiviral agent.

12. The pharmaceutical composition of claim 11, wherein the second antiviral agent is selected from an interferon, ribavirin, an interleukin, an NS3 protease inhibitor, a cysteine protease inhibitor, a phenathrenequinone, a thiazolidine, a benzanilide, a helicase inhibitor, a polymerase inhibitor, a nucleotide analogue, a liotoxin, acerulenin, an antisense phosphorothioate oligodeoxynucleotide, an inhibitor of IRES-dependent translation, or a ribozyme.

13. The pharmaceutical composition of claim 11, wherein the second antiviral agent is an interferon.

14. The pharmaceutical composition of claim 13, wherein the interferon is selected from pegylated interferon alpha 2a, interferon alfahcon-1, natural interferon, albuferon, interferon beta-1a, omega interferon, interferon alpha, interferon gamma, interferon tau, interferon delta, or interferon gamma-1b.

15. The pharmaceutical composition of claim 10, wherein the composition is formulated for single dose administration.

16. The pharmaceutical composition of claim 10, wherein the composition is formulated as oral, parenteral, or intravenous dosage form.

17. The pharmaceutical composition of claim 16, wherein the oral dosage form is a tablet or capsule.

18. The pharmaceutical composition of claim 10, wherein the compound is administered in a dose of about 0.5 milligram to about 1,000 milligram daily.

* * * * *